(12) United States Patent
Hsieh et al.

(10) Patent No.: US 9,120,870 B2
(45) Date of Patent: Sep. 1, 2015

(54) DUAL SPECIFIC BINDING PROTEINS DIRECTED AGAINST IL-13 AND IL-17

(71) Applicant: AbbVie Inc., North Chicago, IL (US)

(72) Inventors: Chung-Ming Hsieh, Newton, MA (US); Tariq Ghayur, Holliston, MA (US); Carrie L. Goodreau, Ludlow, MA (US)

(73) Assignee: AbbVie Inc., North Chicago, IL (US)

( * ) Notice: Subject to any disclaimer, the term of this patent is extended or adjusted under 35 U.S.C. 154(b) by 115 days.

(21) Appl. No.: 13/729,645

(22) Filed: Dec. 28, 2012

(65) Prior Publication Data
US 2013/0236458 A1 Sep. 12, 2013

Related U.S. Application Data

(60) Provisional application No. 61/581,964, filed on Dec. 30, 2011.

(51) Int. Cl.
| | | |
|---|---|---|
| *A61K 39/395* | (2006.01) | |
| *C07K 16/46* | (2006.01) | |
| *A61K 45/06* | (2006.01) | |
| *G01N 33/68* | (2006.01) | |
| *C07K 16/24* | (2006.01) | |

(52) U.S. Cl.
CPC ........... *C07K 16/468* (2013.01); *A61K 39/3955* (2013.01); *A61K 45/06* (2013.01); *C07K 16/244* (2013.01); *G01N 33/6854* (2013.01); *C07K 2317/24* (2013.01); *C07K 2317/31* (2013.01); *C07K 2317/565* (2013.01); *C07K 2317/567* (2013.01); *C07K 2317/64* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | |
|---|---|---|
| 4,526,938 A | 7/1985 | Churchill et al. |
| 4,699,784 A | 10/1987 | Shih et al. |
| 4,753,894 A | 6/1988 | Frankel et al. |
| 4,816,567 A | 3/1989 | Cabilly et al. |
| 4,943,533 A | 7/1990 | Mendelsohn et al. |
| 4,946,778 A | 8/1990 | Ladner et al. |
| 4,980,286 A | 12/1990 | Morgan et al. |
| 5,128,326 A | 7/1992 | Balazs et al. |
| 5,223,409 A | 6/1993 | Ladner et al. |
| 5,225,539 A | 7/1993 | Winter |
| 5,258,498 A | 11/1993 | Huston et al. |
| 5,290,540 A | 3/1994 | Prince et al. |
| 5,403,484 A | 4/1995 | Ladner et al. |
| 5,427,908 A | 6/1995 | Dower et al. |
| 5,500,362 A | 3/1996 | Robinson et al. |
| 5,516,637 A | 5/1996 | Huang et al. |
| 5,530,101 A | 6/1996 | Queen et al. |
| 5,558,864 A | 9/1996 | Bendig et al. |
| 5,565,332 A | 10/1996 | Hoogenboom et al. |
| 5,565,352 A | 10/1996 | Hochstrasser et al. |
| 5,571,698 A | 11/1996 | Ladner et al. |
| 5,580,717 A | 12/1996 | Dower et al. |
| 5,585,089 A | 12/1996 | Queen et al. |
| 5,624,821 A | 4/1997 | Winter et al. |
| 5,627,052 A | 5/1997 | Schrader |
| 5,641,870 A | 6/1997 | Rinderknecht et al. |
| 5,648,260 A | 7/1997 | Winter et al. |
| 5,658,727 A | 8/1997 | Barbas et al. |
| 5,677,171 A | 10/1997 | Hudziak et al. |
| 5,679,377 A | 10/1997 | Bernstein et al. |
| 5,693,762 A | 12/1997 | Queen et al. |
| 5,698,426 A | 12/1997 | Huse |
| 5,714,350 A | 2/1998 | Co et al. |
| 5,714,352 A | 2/1998 | Jakobovits |
| 5,723,323 A | 3/1998 | Kauffman et al. |
| 5,733,743 A | 3/1998 | Johnson et al. |
| 5,736,137 A | 4/1998 | Anderson et al. |
| 5,763,192 A | 6/1998 | Kauffman et al. |
| 5,766,886 A | 6/1998 | Studnicka et al. |
| 5,776,456 A | 7/1998 | Anderson et al. |
| 5,780,225 A | 7/1998 | Wigler et al. |
| 5,789,554 A | 8/1998 | Leung et al. |
| 5,795,965 A | 8/1998 | Tsuchiya et al. |
| 5,814,476 A | 9/1998 | Kauffman et al. |
| 5,817,483 A | 10/1998 | Kauffman et al. |
| 5,821,047 A | 10/1998 | Garrard et al. |
| 5,824,514 A | 10/1998 | Kauffman et al. |
| 5,846,765 A | 12/1998 | Matthews et al. |
| 5,849,500 A | 12/1998 | Breitling et al. |
| 5,855,913 A | 1/1999 | Hanes et al. |
| 5,863,765 A | 1/1999 | Berry et al. |
| 5,874,064 A | 2/1999 | Edwards et al. |
| 5,891,996 A | 4/1999 | Mateo de Acosta del Rio et al. |
| 5,912,015 A | 6/1999 | Bernstein et al. |
| 5,916,597 A | 6/1999 | Lee et al. |
| 5,916,771 A | 6/1999 | Hori et al. |
| 5,929,212 A | 7/1999 | Jolliffe et al. |
| 5,934,272 A | 8/1999 | Lloyd et al. |
| 5,939,598 A | 8/1999 | Kucherlapati et al. |
| 5,959,083 A | 9/1999 | Bosslet et al. |
| 5,969,108 A | 10/1999 | McCafferty et al. |
| 5,976,862 A | 11/1999 | Kauffman et al. |

(Continued)

FOREIGN PATENT DOCUMENTS

| | | |
|---|---|---|
| CN | 1276428 A | 12/2000 |
| CN | 101058609 A | 10/2007 |

(Continued)

OTHER PUBLICATIONS

Lajoie et al. Complement-mediated regulation of the IL-17A axis is a central genetic determinant of the severity of experimental allergic asthma. Nat Immunol. Oct. 2010;11(10):928-35.*

(Continued)

*Primary Examiner* — Dong Jiang
(74) *Attorney, Agent, or Firm* — Finnegan, Henderson, Farabow, Garrett & Dunner, LLP

(57) ABSTRACT

Engineered multivalent and multispecific binding proteins that bind IL-13 and/or IL-17 are provided, along with methods of making and uses in the prevention, diagnosis, and/or treatment of disease.

16 Claims, 1 Drawing Sheet

(56) References Cited

U.S. PATENT DOCUMENTS

| | | |
|---|---|---|
| 5,985,309 A | 11/1999 | Edwards et al. |
| 5,985,320 A | 11/1999 | Edwards et al. |
| 5,985,588 A | 11/1999 | Breitling et al. |
| 5,985,615 A | 11/1999 | Jakobovits et al. |
| 5,989,463 A | 11/1999 | Tracy et al. |
| 5,989,830 A | 11/1999 | Davis et al. |
| 5,998,209 A | 12/1999 | Jokobovits et al. |
| 6,019,968 A | 2/2000 | Platz et al. |
| 6,054,297 A | 4/2000 | Carter et al. |
| 6,057,098 A | 5/2000 | Buechler et al. |
| 6,066,719 A | 5/2000 | Zapata |
| 6,075,181 A | 6/2000 | Kucherlapati et al. |
| 6,090,382 A | 7/2000 | Salfeld et al. |
| 6,091,001 A | 7/2000 | Jakobovits et al. |
| 6,114,598 A | 9/2000 | Kucherlapati et al. |
| 6,127,132 A | 10/2000 | Breitling et al. |
| 6,130,364 A | 10/2000 | Jakobovits et al. |
| 6,180,370 B1 | 1/2001 | Queen et al. |
| 6,204,023 B1 | 3/2001 | Robinson et al. |
| 6,214,984 B1 | 4/2001 | Zapata |
| 6,235,883 B1 | 5/2001 | Jakobovits et al. |
| 6,239,259 B1 | 5/2001 | Davis et al. |
| 6,258,562 B1 | 7/2001 | Salfeld et al. |
| 6,350,861 B1 | 2/2002 | Co et al. |
| 6,387,627 B1 | 5/2002 | Breitling et al. |
| 6,491,916 B1 | 12/2002 | Bluestone et al. |
| 6,506,883 B2 | 1/2003 | Meteo de Acosta del Rio et al. |
| 6,509,015 B1 | 1/2003 | Salfeld et al. |
| 6,639,055 B1 | 10/2003 | Carter et al. |
| 6,660,843 B1 | 12/2003 | Feige et al. |
| 6,699,473 B2 | 3/2004 | Raisch et al. |
| 6,699,658 B1 | 3/2004 | Wittrup et al. |
| 6,730,483 B2 | 5/2004 | Breitling et al. |
| 6,818,392 B2 | 11/2004 | Lou et al. |
| 6,884,879 B1 | 4/2005 | Baca et al. |
| 6,914,128 B1 | 7/2005 | Salfeld et al. |
| 6,986,890 B1 | 1/2006 | Shitara et al. |
| 7,060,269 B1 | 6/2006 | Baca et al. |
| 7,060,808 B1 | 6/2006 | Goldstein et al. |
| 7,070,775 B2 | 7/2006 | Le et al. |
| 7,179,892 B2 | 2/2007 | Basi et al. |
| 7,202,343 B2 | 4/2007 | Gudas et al. |
| 7,247,301 B2 | 7/2007 | van de Winkel et al. |
| 7,247,304 B2 | 7/2007 | van de Winkel et al. |
| 7,258,857 B2 | 8/2007 | Stern et al. |
| 7,262,028 B2 | 8/2007 | Van Berkel et al. |
| 7,317,091 B2 | 1/2008 | Lazar et al. |
| 7,419,821 B2 | 9/2008 | Davis et al. |
| 7,429,486 B2 | 9/2008 | Van Berkel et al. |
| 7,438,911 B2 | 10/2008 | Shitara et al. |
| 7,446,175 B2 | 11/2008 | Gram et al. |
| 7,446,179 B2 | 11/2008 | Jensen et al. |
| 7,449,616 B2 | 11/2008 | Pons et al. |
| 7,491,516 B2 | 2/2009 | Collinson et al. |
| 7,528,236 B2 | 5/2009 | Fong et al. |
| 7,566,772 B2 | 7/2009 | Green et al. |
| 7,592,429 B2 | 9/2009 | Paszty et al. |
| 7,612,181 B2 | 11/2009 | Wu et al. |
| 7,682,833 B2 | 3/2010 | Miller et al. |
| 7,727,527 B2 | 6/2010 | Shelton |
| 7,790,858 B2 | 9/2010 | Presta |
| 7,863,419 B2 | 1/2011 | Taylor et al. |
| 7,928,205 B2 | 4/2011 | Dillon et al. |
| 8,258,268 B2 | 9/2012 | Wu et al. |
| 8,389,237 B2 | 3/2013 | Skerry et al. |
| 8,586,714 B2 | 11/2013 | Ghayur et al. |
| 8,716,450 B2 | 5/2014 | Ghayur et al. |
| 8,722,855 B2 | 5/2014 | Ghayur et al. |
| 8,735,546 B2 | 5/2014 | Ghayur et al. |
| 8,822,645 B2 | 9/2014 | Ghayur et al. |
| 8,835,610 B2 | 9/2014 | Hsieh et al. |
| 2002/0004587 A1 | 1/2002 | Miller et al. |
| 2002/0127231 A1 | 9/2002 | Schneck et al. |
| 2002/0136719 A1 | 9/2002 | Shenoy et al. |
| 2002/0137134 A1 | 9/2002 | Gerngross |
| 2003/0039645 A1 | 2/2003 | Adair et al. |
| 2003/0091561 A1 | 5/2003 | van de Winkel et al. |
| 2003/0092059 A1 | 5/2003 | Salfeld et al. |
| 2003/0118583 A1 | 6/2003 | Emery et al. |
| 2003/0165496 A1 | 9/2003 | Basi et al. |
| 2003/0186374 A1 | 10/2003 | Hufton et al. |
| 2003/0206898 A1 | 11/2003 | Fischkoff et al. |
| 2004/0018577 A1 | 1/2004 | Emerson Campbell et al. |
| 2004/0018590 A1 | 1/2004 | Gerngross et al. |
| 2004/0038339 A1 | 2/2004 | Kufer et al. |
| 2004/0133357 A1 | 7/2004 | Zhong et al. |
| 2004/0162411 A1 | 8/2004 | Lanzavecchia |
| 2004/0219144 A1 | 11/2004 | Shelton |
| 2004/0237124 A1 | 11/2004 | Pons et al. |
| 2004/0241745 A1 | 12/2004 | Honjo et al. |
| 2005/0026881 A1 | 2/2005 | Robinson et al. |
| 2005/0038231 A1 | 2/2005 | Fahrner et al. |
| 2005/0042664 A1 | 2/2005 | Wu et al. |
| 2005/0095246 A1 | 5/2005 | Shafer |
| 2005/0118643 A1 | 6/2005 | Burgess et al. |
| 2005/0147610 A1 | 7/2005 | Ghayur et al. |
| 2005/0215769 A1 | 9/2005 | Breece et al. |
| 2005/0260204 A1 | 11/2005 | Allan |
| 2006/0002923 A1 | 1/2006 | Uede et al. |
| 2006/0024300 A1 | 2/2006 | Adams et al. |
| 2006/0041058 A1 | 2/2006 | Yin et al. |
| 2006/0067930 A1 | 3/2006 | Adams et al. |
| 2006/0078967 A1 | 4/2006 | Medlock et al. |
| 2006/0093599 A1 | 5/2006 | Gazit-Bornstein et al. |
| 2006/0104968 A1 | 5/2006 | Bookbinder et al. |
| 2006/0134105 A1 | 6/2006 | Lazar et al. |
| 2006/0160164 A1 | 7/2006 | Miller et al. |
| 2006/0233791 A1 | 10/2006 | Tedder et al. |
| 2006/0246071 A1 | 11/2006 | Green et al. |
| 2006/0253100 A1 | 11/2006 | Burright et al. |
| 2006/0280747 A1 | 12/2006 | Fuh et al. |
| 2007/0041905 A1 | 2/2007 | Hoffman et al. |
| 2007/0042458 A1 | 2/2007 | DeFrees et al. |
| 2007/0071675 A1 | 3/2007 | Wu et al. |
| 2007/0071745 A1 | 3/2007 | Umana et al. |
| 2007/0072225 A1 | 3/2007 | Alving |
| 2007/0092507 A1 | 4/2007 | Balthasar et al. |
| 2007/0092520 A1 | 4/2007 | Dennis et al. |
| 2007/0110747 A1 | 5/2007 | Paszty et al. |
| 2007/0123479 A1 | 5/2007 | Kufer et al. |
| 2007/0196376 A1 | 8/2007 | Raeber et al. |
| 2007/0232556 A1 | 10/2007 | Montine et al. |
| 2007/0286858 A1 | 12/2007 | Clancy et al. |
| 2007/0292420 A1 | 12/2007 | Giles-Komar et al. |
| 2008/0014196 A1 | 1/2008 | Yan |
| 2008/0015194 A1 | 1/2008 | Errico et al. |
| 2008/0038257 A1 | 2/2008 | Han et al. |
| 2008/0112888 A1 | 5/2008 | Wang |
| 2008/0118506 A1 | 5/2008 | An et al. |
| 2008/0118978 A1 | 5/2008 | Sato et al. |
| 2008/0171014 A1 | 7/2008 | Wu et al. |
| 2008/0175847 A1 | 7/2008 | Yan et al. |
| 2008/0187966 A1 | 8/2008 | Simmons |
| 2008/0193455 A1 | 8/2008 | Stassen et al. |
| 2008/0219971 A1 | 9/2008 | Smith et al. |
| 2008/0241163 A1 | 10/2008 | Burkly et al. |
| 2009/0028851 A1 | 1/2009 | Stuhmer et al. |
| 2009/0030308 A1 | 1/2009 | Bradford et al. |
| 2009/0035308 A1 | 2/2009 | Gill et al. |
| 2009/0042214 A1 | 2/2009 | Cooke et al. |
| 2009/0048122 A1 | 2/2009 | Glaser et al. |
| 2009/0053243 A1 | 2/2009 | Kurosawa et al. |
| 2009/0068195 A1 | 3/2009 | Vugmeyster et al. |
| 2009/0081234 A1 | 3/2009 | Heavner et al. |
| 2009/0148513 A1 | 6/2009 | Fraunhofer et al. |
| 2009/0155257 A1 | 6/2009 | Adams et al. |
| 2009/0155275 A1 | 6/2009 | Wu et al. |
| 2009/0191225 A1 | 7/2009 | Chang et al. |
| 2009/0208490 A1 | 8/2009 | Pavone et al. |
| 2009/0215992 A1 | 8/2009 | Wu et al. |
| 2009/0239259 A1 | 9/2009 | Hsieh |
| 2009/0259026 A1 | 10/2009 | Tomlinson et al. |
| 2009/0304693 A1 | 12/2009 | Ghayur et al. |
| 2009/0311253 A1 | 12/2009 | Ghayur et al. |

(56) References Cited

U.S. PATENT DOCUMENTS

| | | |
|---|---|---|
| 2010/0028340 A1 | 2/2010 | Mueller et al. |
| 2010/0040537 A1 | 2/2010 | Gu et al. |
| 2010/0047239 A1 | 2/2010 | Wu et al. |
| 2010/0056762 A1 | 3/2010 | Old |
| 2010/0074900 A1 | 3/2010 | Ghayur et al. |
| 2010/0076178 A1 | 3/2010 | Ghayur et al. |
| 2010/0104573 A1 | 4/2010 | Burkly et al. |
| 2010/0105569 A1 | 4/2010 | Hsieh et al. |
| 2010/0158901 A1 | 6/2010 | Tedder et al. |
| 2010/0190247 A1 | 7/2010 | Lazar et al. |
| 2010/0233079 A1 | 9/2010 | Jakob et al. |
| 2010/0260668 A1 | 10/2010 | Ghayur et al. |
| 2010/0266531 A1 | 10/2010 | Hsieh et al. |
| 2011/0008766 A1 | 1/2011 | Ghayur et al. |
| 2011/0044980 A1 | 2/2011 | Ghayur et al. |
| 2011/0091372 A1 | 4/2011 | Ghayur et al. |
| 2011/0091463 A1 | 4/2011 | Ghayur et al. |
| 2011/0117079 A1 | 5/2011 | Benatuil et al. |
| 2011/0142761 A1 | 6/2011 | Wu et al. |
| 2011/0150870 A1 | 6/2011 | Rader et al. |
| 2011/0212094 A1 | 9/2011 | Ghayur et al. |
| 2011/0217237 A1 | 9/2011 | Chen et al. |
| 2011/0229476 A1 | 9/2011 | Liu et al. |
| 2011/0263827 A1 | 10/2011 | Ghayur et al. |
| 2011/0318349 A1 | 12/2011 | Ghayur et al. |
| 2012/0014957 A1 | 1/2012 | Ghayur et al. |
| 2012/0034160 A1 | 2/2012 | Ghayur et al. |
| 2012/0087858 A1 | 4/2012 | Ghayur et al. |
| 2012/0258108 A1 | 10/2012 | Ghayur et al. |
| 2012/0263722 A1 | 10/2012 | Ghayur et al. |
| 2013/0004416 A1 | 1/2013 | Wu et al. |
| 2013/0171059 A1 | 7/2013 | Ghayur et al. |
| 2013/0171096 A1 | 7/2013 | Hsieh et al. |
| 2013/0195871 A1 | 8/2013 | Ghayur et al. |
| 2014/0093521 A1 | 4/2014 | Benatuil at al. |
| 2014/0134171 A1 | 5/2014 | Ghayur et al. |
| 2014/0134172 A1 | 5/2014 | Gu et al. |
| 2014/0213772 A1 | 7/2014 | Ghayur et al. |
| 2014/0219912 A1 | 8/2014 | Ghayur et al. |
| 2014/0234208 A1 | 8/2014 | Ghayur et al. |
| 2014/0271457 A1 | 9/2014 | Ghayur et al. |
| 2014/0271458 A1 | 9/2014 | Ghayur et al. |
| 2014/0308286 A1 | 10/2014 | Ghayur et al. |
| 2014/0348835 A1 | 11/2014 | Gu et al. |
| 2014/0356281 A1 | 12/2014 | Ghayur et al. |

FOREIGN PATENT DOCUMENTS

| | | |
|---|---|---|
| EP | 0 148 075 A2 | 7/1985 |
| EP | 0 517 024 A2 | 12/1992 |
| EP | 0 592 106 A1 | 4/1994 |
| EP | 0 239 400 B1 | 8/1994 |
| EP | 1 176 195 A1 | 1/2002 |
| EP | 1 454 917 A2 | 9/2004 |
| EP | 0 592 106 B1 | 11/2004 |
| EP | 0 519 596 B1 | 2/2005 |
| RU | 2 273 664 C2 | 4/2006 |
| WO | WO 89/06692 A1 | 7/1989 |
| WO | WO 90/02809 A1 | 3/1990 |
| WO | WO 90/05144 A1 | 5/1990 |
| WO | WO 90/05183 A1 | 5/1990 |
| WO | WO 90/14424 A1 | 11/1990 |
| WO | WO 90/14430 A1 | 11/1990 |
| WO | WO 90/14443 A1 | 11/1990 |
| WO | WO 91/05548 A1 | 5/1991 |
| WO | WO 91/09967 A1 | 7/1991 |
| WO | WO 91/10737 A1 | 7/1991 |
| WO | WO 91/10741 A1 | 7/1991 |
| WO | WO 91/17271 A1 | 11/1991 |
| WO | WO 91/18983 A1 | 12/1991 |
| WO | WO 92/01047 A1 | 1/1992 |
| WO | WO 92/02551 A1 | 2/1992 |
| WO | WO 92/03461 A1 | 3/1992 |
| WO | WO 92/09690 A2 | 6/1992 |
| WO | WO 92/11272 A1 | 7/1992 |
| WO | WO 92/15679 A1 | 9/1992 |
| WO | WO 92/16553 A1 | 10/1992 |
| WO | WO 92/18619 A1 | 10/1992 |
| WO | WO 92/19244 A2 | 11/1992 |
| WO | WO 92/20791 A1 | 11/1992 |
| WO | WO 92/22324 A1 | 12/1992 |
| WO | WO 92/22653 A1 | 12/1992 |
| WO | WO 93/01288 A1 | 1/1993 |
| WO | WO 93/06213 A1 | 4/1993 |
| WO | WO 93/11161 A1 | 6/1993 |
| WO | WO 93/11236 A1 | 6/1993 |
| WO | WO 94/02602 A1 | 2/1994 |
| WO | WO 94/11026 A1 | 5/1994 |
| WO | WO 94/18219 A1 | 8/1994 |
| WO | WO 95/01997 A1 | 1/1995 |
| WO | WO 95/09917 A1 | 4/1995 |
| WO | WO 95/14780 A2 | 6/1995 |
| WO | WO 95/15982 A2 | 6/1995 |
| WO | WO 95/16026 A1 | 6/1995 |
| WO | WO 95/20045 A1 | 7/1995 |
| WO | WO 95/20401 A1 | 8/1995 |
| WO | WO 95/24918 A1 | 9/1995 |
| WO | WO 95/25167 A1 | 9/1995 |
| WO | WO 96/20698 A2 | 7/1996 |
| WO | WO 96/33735 A1 | 10/1996 |
| WO | WO 96/34096 A1 | 10/1996 |
| WO | WO 96/40210 A1 | 12/1996 |
| WO | WO 97/20032 A1 | 6/1997 |
| WO | WO 97/29131 A1 | 8/1997 |
| WO | WO 97/32572 A2 | 9/1997 |
| WO | WO 97/44013 A1 | 11/1997 |
| WO | WO 98/16654 A1 | 4/1998 |
| WO | WO 98/24893 A2 | 6/1998 |
| WO | WO 98/31346 A1 | 7/1998 |
| WO | WO 98/31700 A1 | 7/1998 |
| WO | WO 98/45331 A2 | 10/1998 |
| WO | WO 98/50433 A2 | 11/1998 |
| WO | WO 99/06834 A2 | 2/1999 |
| WO | WO 99/15154 A1 | 4/1999 |
| WO | WO 99/20253 A1 | 4/1999 |
| WO | WO 99/23221 A2 | 5/1999 |
| WO | WO 99/45031 A2 | 9/1999 |
| WO | WO 99/53049 A1 | 10/1999 |
| WO | WO 99/54342 A1 | 10/1999 |
| WO | WO 99/57134 A1 | 11/1999 |
| WO | WO 99/66903 A2 | 12/1999 |
| WO | WO 00/09560 A2 | 2/2000 |
| WO | WO 00/37504 A2 | 6/2000 |
| WO | WO 00/56772 A1 | 9/2000 |
| WO | WO 00/78815 A1 | 12/2000 |
| WO | WO 01/00244 A2 | 1/2001 |
| WO | WO 01/32712 A2 | 5/2001 |
| WO | WO 01/58956 A2 | 8/2001 |
| WO | WO 01/62300 A2 | 8/2001 |
| WO | WO 01/62931 A2 | 8/2001 |
| WO | WO 01/71005 A2 | 9/2001 |
| WO | WO 01/77342 A1 | 10/2001 |
| WO | WO 01/83525 A2 | 11/2001 |
| WO | WO 01/88138 A1 | 11/2001 |
| WO | WO 02/02773 A2 | 1/2002 |
| WO | WO 02/02781 A1 | 1/2002 |
| WO | WO 02/16436 A2 | 2/2002 |
| WO | WO 02/053596 A2 | 7/2002 |
| WO | WO 02/072636 A2 | 9/2002 |
| WO | WO 02/097048 A2 | 12/2002 |
| WO | WO 03/016466 A2 | 2/2003 |
| WO | WO 03/035835 A2 | 5/2003 |
| WO | WO 03/039486 A2 | 5/2003 |
| WO | WO 03/068801 A2 | 8/2003 |
| WO | WO 03/086458 A1 | 10/2003 |
| WO | WO 03/089614 A2 | 10/2003 |
| WO | WO 03/100008 A2 | 12/2003 |
| WO | WO 03/102132 A2 | 12/2003 |
| WO | WO 2004/016286 A2 | 2/2004 |
| WO | WO 2004/024866 A2 | 3/2004 |
| WO | WO 2004/050683 A2 | 6/2004 |
| WO | WO 2004/058184 A2 | 7/2004 |
| WO | WO 2004/078140 A2 | 9/2004 |

(56) References Cited

FOREIGN PATENT DOCUMENTS

| | | |
|---|---|---|
| WO | WO 2005/016970 A2 | 2/2005 |
| WO | WO 2005/017107 A2 | 2/2005 |
| WO | WO 2005/044853 A2 | 5/2005 |
| WO | WO 2005/061540 A2 | 7/2005 |
| WO | WO 2005/061547 A2 | 7/2005 |
| WO | WO 2005/100584 A2 | 10/2005 |
| WO | WO 2005/118635 A2 | 12/2005 |
| WO | WO 2005/120557 A2 | 12/2005 |
| WO | WO 2006/013107 A1 | 2/2006 |
| WO | WO 2006/015373 A2 | 2/2006 |
| WO | WO 2006/020258 A2 | 2/2006 |
| WO | WO 2006/024867 A2 | 3/2006 |
| WO | WO 2006/031370 A2 | 3/2006 |
| WO | WO 2006/044908 A2 | 4/2006 |
| WO | WO 2006/047350 A2 | 5/2006 |
| WO | WO 2006/066171 A2 | 6/2006 |
| WO | WO 2006/089133 A2 | 8/2006 |
| WO | WO 2006/099698 A2 | 9/2006 |
| WO | WO 2006/110883 A2 | 10/2006 |
| WO | WO 2006/116269 A2 | 11/2006 |
| WO | WO 2006/122187 A2 | 11/2006 |
| WO | WO 2006/130374 A2 | 12/2006 |
| WO | WO 2006/130429 A2 | 12/2006 |
| WO | WO 2006/131951 A2 | 12/2006 |
| WO | WO 2006/136159 A2 | 12/2006 |
| WO | WO 2007/005955 A2 | 1/2007 |
| WO | WO 2007/024715 A9 | 3/2007 |
| WO | WO 2007/042261 A2 | 4/2007 |
| WO | WO 2007/048849 A1 | 5/2007 |
| WO | WO 2007/053447 A2 | 5/2007 |
| WO | WO 2007/056470 A2 | 5/2007 |
| WO | WO 2007/059136 A2 | 5/2007 |
| WO | WO 2007/062037 A2 | 5/2007 |
| WO | WO 2007/062852 A2 | 6/2007 |
| WO | WO 2007/077028 A2 | 7/2007 |
| WO | WO 2007/117749 A2 | 10/2007 |
| WO | WO 2007/120828 A1 | 10/2007 |
| WO | WO 2007120651 A2 | 10/2007 |
| WO | WO 2007/124299 A2 | 11/2007 |
| WO | WO 2007/143098 A2 | 12/2007 |
| WO | WO 2007/147901 A1 | 12/2007 |
| WO | WO 2008/011348 A2 | 1/2008 |
| WO | WO 2008/022152 A2 | 2/2008 |
| WO | WO 2008/024188 A2 | 2/2008 |
| WO | WO 2008/042236 A2 | 4/2008 |
| WO | WO 2008/057240 A2 | 5/2008 |
| WO | WO 2008/079326 A2 | 7/2008 |
| WO | WO 2008/100624 A2 | 8/2008 |
| WO | WO 2008/145338 A2 | 12/2008 |
| WO | WO 2008/150841 A1 | 12/2008 |
| WO | WO 2009/020654 A1 | 2/2009 |
| WO | WO 2009/052400 A1 | 4/2009 |
| WO | WO 2009/077993 A2 | 6/2009 |
| WO | WO 2009/089004 A1 | 7/2009 |
| WO | WO 2009/136382 A2 | 11/2009 |
| WO | WO 2009/155324 A2 | 12/2009 |
| WO | WO 2010/096434 A2 | 8/2010 |
| WO | WO 2010/102251 A2 | 9/2010 |
| WO | WO 2011/039370 A1 | 4/2011 |
| WO | WO 2011/084714 A2 | 7/2011 |
| WO | WO 2011/143562 A2 | 11/2011 |
| WO | WO 2012/061374 A2 | 5/2012 |

OTHER PUBLICATIONS

Wynn et al. Distinct roles for IL-13 and IL-17 in chronic inflammation and fibrosis. meeting abstract, J. Immunol., 2010, 184, 134.8.*
"Rituximab," in *The Merck Index*. 14th Ed., John Wiley & Sons, 2006; p. 1422.
Arimura et al., "Prevention of Allergic Inflammation by a Novel Prostaglandin Receptor Antagonist, S-5751," *J. Pharmacol. Exper. Therapeut.*, 298(2): 411-419 (2001).
Aroonrerk et al., "A sensitive direct ELISA for detection of prostaglandin E2" *J. Immunoassay & Immunochem.*, 28:319-330 (2007).
Boado et al., "Fusion Antibody for Alzheimer's Disease with Bidirectional Transport Across the Blood-Brain Barrier and Aβ Fibril Disaggregation," *Bioconj. Chem.*, 18(2): 447-455 (2007).
Caron et al., "Chondroprotective Effect of Intraarticular Injections of Interleukin-1 Receptor Antagonist in Experimental Osteoarthritis," *Arthritis Rheum.*, 39: 1535-1544 (1996).
Dayer et al., "Collagenase Production by Rheumatoid Synovial Cells: Stimulation by a Human Lymphocyte Factor," *Science*, 195: 181-183 (1977).
Dayer et al., "Effects of Prostaglandin E2, Indomethacin, Trifluoperazine and Drugs Affecting the Cytoskeleton on Collagenase Production by Cultured Adherent Rheumatoid Synovial Cells," *Biochem. Pharmacol.*, 33(18): 2893-2899 (1984).
Desplat-Jego et al., "Anti-TWEAK monoclonal antibodies reduce immune cell infiltration in the central nervous system and severity of experimental autoimmune encephalomyelitis," *Clin. Immunol.*, 117(1): 15-23 (2005).
Dinarello et al., "Immunological and Inflammatory Functions of the Interleukin-1 Family," *Annu. Rev. Immunol.*, 27: 519-550 (2009).
Dohi et al., "Effect of combination Treatment with TNF-Inhibitor and Anti-TWEAK Antibody in Mouse Colitis Model," *Gastroenterology*, 138(5): S-413, Abstract M1758 (2010).
European Patent Application No. 10814433.8: Supplementary European Search Report and Search Opinion, dated Apr. 18, 2013 (11 pages).
European Patent Application No. 10825739.5: Supplementary European Search Report and Search Opinion, dated Apr. 29, 2013 (13 pages).
European Patent Application No. 10830460.1: Supplementary European Search Report and Search Opinion, dated Apr. 29, 2013 (15 pages).
European Patent Application No. 11798923.6: Supplementary European Search Report and Search Opinion, dated Jan. 2, 2014 (10 pages).
European Patent Application No. 11804385.0: Supplementary European Search Report and Search Opinion, dated Nov. 20, 2013 (16 pages).
European Patent Application No. 11815172.9: Partial Supplementary European Search Report, dated Nov. 12, 2014 (10 pages).
European Patent Application No. 11820654.9: Supplementary European Search Report and Search Opinion, dated Dec. 17, 2013 (17 pages).
European Patent Application No. 14176206.2 by AbbVie Inc.: Extended European Search Report and Opinion, dated Nov. 12, 2014 (7 pages).
Ewert et al., "Stability improvement of antibodies for extracellular and intracellular applications: CDR grafting to stable frameworks and structure-based framework engineering," *Methods*, 34: 184-199 (2004).
Fernandes et al., "In Vivo Transfer of Interleukin-1 Receptor Antagonist Gene in Osteoarthritic Rabbit Knee Joints," *Am. J. Pathol.*, 154(4): 1159-1169 (1999).
Flierl et al., "Adverse functions of IL-17A in experimental sepsis," *FASEB J.*, 22: 2198-2205 (2008).
GENBANK Accession No. BAL50004, "Anti-prostaglandin E2 antibody kappa light chain [*Mus musculus*]," Feb. 4, 2012 (2 pages).
Goldring et al., "Interleukin 1 Suppresses Expression of Cartilage-specific Types II and IX Collagens and Increases Types I and III Collagens in Human Chondrocytes," *J. Clin. Investig.*, 82: 2026-2037 (1988).
Goldring et al., "Modulation by Recombinant Interleukin 1 of Synthesis of Types I and III Collagens and Associated Procollagen mRNA Levels in Cultured Human Cells," *J. Biol. Chem.*, 262: 16724-16729 (1987).
Gu et al., "Generation of Dual-Vanable-Domain Immunoglobulin Molecules for Dual-Specific Targeting," *Methods in Enzymology*, 502: 25-41 (2012).
Hart et al., "Suppression of Ongoing Disease in a Nonhuman Primate Model of Multiple Sclerosis by a Human-Anti-Human IL-12p40 Antibody," *J. Immunol.*, 175(7): 4761-4768 (2005).
Hill et al., "Interleukin-17 deficiency improves locomotor recovery and tissue sparing after spinal cord contusion injury in mice," *Neurosci. Lett.*, 487(3): 363-367 (2011).

(56) References Cited

OTHER PUBLICATIONS

Hindawi et al., "The development and application of a direct radioimmunoassay for prostaglandin E2 utilising a α-labelled ligand," *Prostaglandins, Leukotrienes and Medicine*, 18: 81-94 (1985).

Honegger et al., "Yet Another Numbering Scheme for Immunoglobulin Variable Domains: An Automatic Modeling and Analysis Tool," *J. Mol. Biol.*, 309(3): 657-670 (2001).

Inter Partes Reexamination (Control No. 95/001,380) of U.S. Patent No. 7,612,181 (U.S. Appl. No. 11/507,050): Reexamination Non-Final Office Action ("Action Closing Prosecution"), dated Sep. 1, 2011.

Inter Partes Reexamination (Control No. 95/001,380) of U.S. Patent No. 7,612,181 (U.S. Appl. No. 11/507,050): Patent Owner Comments After Action Closing Prosecution ("Response Pursuant to 37 CFR § 1.951(a)"), dated Oct. 31, 2011.

Inter Partes Reexamination (Control No. 95/001,380) of U.S. Patent No. 7,612,181 (U.S. Appl. No. 11/507,050): Third Party Requester Comments after Action Closing Prosecution ("Sanofi's Comments Pursuant to 37 CFR §1.951(a)"), dated Nov. 30, 2011.

Inter Partes Reexamination (Control No. 95/001,380) of U.S. Patent No. 7,612,181 (U.S. Appl. No. 11/507,050): Right of Appeal Notice (37 CFR 1.953), dated Mar. 7, 2012.

Inter Partes Reexamination (Control No. 95/001,380) of U.S. Patent No. 7,612,181 (U.S. Appl. No. 11/507,050): Decision on Appeal, dated Mar. 24, 2014.

International Patent Application No. PCT/US2009/049953 by Abbott Laboratories: International Search Report and Written Opinion, mailed Oct. 29, 2009 (10 pages).

International Patent Application No. PCT/US2012/071929: International Search Report and Written Opinion, dated Sep. 11, 2013 (29 pages).

International Patent Application No. PCT/US2013/067873: International Search Report and Written Opinion, dated May 8, 2014 (23 pages).

International Patent Application No. PCT/US2014/028618: Invitation to Pay Additional Fees and Communication Relating to the Results of the Partial International Search, dated Aug. 13, 2014 (8 pages).

International Patent Application No. PCT/US2014/028646: International Search Report and Written Opinion, Oct. 17, 2014 (18 pages).

International Patent Application No. PCT/US2014/028646: Invitation to Pay Additional Fees and Communication Relating to the Results of the Partial International Search, dated Aug. 14, 2014 (10 pages).

International Patent Application No. PCT/US2014/028618: International Search Report and Written Opinion, Oct. 28, 2014 (25 pages).

Jakubowski et al., "Dual role for TWEAK in angiogenic regulation," *J. Cell Sci.*, 115(2): 267-274 (2002).

Kim and Moalem-Taylor, "Interleukin-17 Contributes to Neuroinflammation and Neuropathic Pain Following Peripheral Nerve Injury in Mice," *J. Pain*, 12(3): 370-383 (2010).

Kyte et al., "A Simple Method for Displaying the Hydropathic Character of a Protein," *J. Mol. Biol.*, 157: 105-132 (1982).

Malfait et al., "ADAMTS-5 deficient mice do not develop mechanical allodynia associated with osteoarthritis following medial meniscal destabilization," *Osteoarthritis Cartilage*, 18: 572-580 (2010).

McGuire-Goldring et al., "In Vitro Activation of Human Chondrocytes and Synoviocytes by a Human Interleukin-1-Like Factor," *Arthritis Rheum.*, 27(6): 654-662 (1984).

Michaelson, J., "Dual Targeting of TNF and TWEAK in inflammatory Bowel Disease: The Promise of a Bispecific Antibody," Conference, Cytokines & Inflammation, Jan. 28, 2011; Agenda, p. 11. Retrieved from the Internet: http://www.cytokinesandinflammation.com/Index.php?option=com_content&view=article&id=50&itemid=54.

Miossec et al., "Targeting IL-17 and TH17 cells in chronic inflammation," *Nat. Rev. Drug. Disc.*, 11(10): 763-776 (2012).

Morgan et al., "Dissociation of hyperalgesia from fever following intracerebroventricular administration of interleukin-1β in the rat," *Brain Res.*, 1022(1-2): 96-100 (2004).

Morimoto et al., "The Increased interleukin-13 in Patients with Systemic Lupus Erythematosus: Relations to Other Th1-, Th2-Related Cytokines and Clinical Findings," *Autoimmunity*, 34(1): 19-25 (2001).

Nalbandian et al., "Interleukin-17 and systemic lupus erythematosus: current concepts," *Clin. Exp. Immunol.*, 157(2): 209-215 (2009).

Neuman et al., "An ELISA for PGE2 utilizing monoclonal antibody," *J. Immunoassay & Immunochem.*, 9(2):159-177 (1988).

Parikh et al., "Urine NGAL and IL-18 are predictive biomarkers for delayed graft function following kidney transplantation," *Am. J. Transplant.*, 6(7): 1639-1645 (2006).

Park and Lee, "Interleukin-17 regulation: an attractive therapeutic approach for asthma," *Respir. Res.*, 11: 78 (2010).

Pelletier et al., "In Vivo Suppression of Early Experimental Osteoarthritis by Interleukin-1 Receptor Antagonist Using Gene Therapy," *Arthritis Rheum.*, 40(6): 1012-1019 (1997).

Pettiphar et al., "Interleukin 1 induces leukocyte infiltration and cartilage proteoglycan degradation in the synovial joint," *Proc. Natl. Acad. Sci. USA*, 83: 8749-8753 (1986).

PIR (Protein Information Resource) Accession No. PC4203, "Ig kappa chain (monoclonal antibody MabA34)—mouse (fragment)," Jan. 11, 2000 (2 pages).

Portanova et al., "Selective Neutralization of Prostaglandin $E_2$ Blocks inflammation, Hyperalgesia, and Interleukin 6 Production in Vivo," *J. Exp. Med.*, 184(3): 883-891 (1996).

Qi et al, "A bispecific antibody against IL-1β and IL-17A is beneficial for experimental rheumatoid arthritis," *Internat'l. Immunopharm.*, 14:770-778 (2012).

Shukla et al., "HER2 specific delivery of methotrexate by dendrimer conjugated anti-Her2 mAB," *Nanotechnology*, 19: 295102 (2008) (7 pages).

Streppel et al., "Focal application of neutralizing antibodies to soluble neurotrophic factors reduces collateral axonal branching after peripheral nerve lesion," *Eur. J. Neurosci.*, 15(8): 1327-1342 (2002).

Tarsca et al. "Dual-Variable Domain Immunoglobulin (DVD-Ig™ Technology: A Versatile, Novel Format for the Next Generation of Dual-Targeting Biologics," Chapter 10 in *Bispecific Antibodies*. Roland E. Kontermann (ed.), Springer, New York, 2011; pp. 171-185.

Torisu et al., "Discovery of a new class of potent, selective, and orally active prostaglandin $D_2$ receptor antagonists," *Bioorg. Med. Chem.*, 12: 5361-5378 (2004).

U.S. Appl. No. 12/431,460, filed Apr. 28, 2009 by Ghayur et al.: Final Office Action, Aug. 7, 2014.

U.S. Appl. No. 12/431,460, filed Apr. 28, 2009 by Ghayur et al.: Non-Final Office Action, Apr. 4, 2014.

U.S. Appl. No. 12/477,668, filed Jun. 3, 2009 by Ghayur et al.: Non-Final Office Action, Mar. 10, 2014.

U.S. Appl. No. 12/477,711, filed Jun. 3, 2009 by Ghayur et al.: Non-Final Office Action, Jul. 29, 2014.

U.S. Appl. No. 12/477,711, filed Jun. 3, 2009 by Ghayur et al.: Final Office Action, Feb. 7, 2014.

U.S. Appl. No. 12/477,711, filed Jun. 3, 2009 by Ghayur et al.: Non-Final Office Action, Jul. 17, 2013.

U.S. Appl. No. 12/499,652, filed Jul. 8, 2009 by Ghayur et al.: Notice of Allowance, Apr. 10, 2014.

U.S. Appl. No. 12/631,483, filed Dec. 4, 2009 by Jakob et al.: Non-Final Office Action, May 27, 2014.

U.S. Appl. No. 12/771,871, filed Apr. 30, 2010 by Ghayur et al.: Non-Final Office Action, Apr. 15, 2014.

U.S. Appl. No. 12/771,871, filed Apr. 30, 2010 by Ghayur et al.: Final Office Action, May 28, 2013.

U.S. Appl. No. 12/846,317, filed Jul. 29, 2010 by Ghayur et al.: Final Office Action, Nov. 6, 2013.

U.S. Appl. No. 12/846,317, filed Jul. 29, 2010 by Ghayur et al.: Final Office Action, May 23, 2013.

U.S. Appl. No. 12/873,926, filed Sep. 1, 2010 by Ghayur et al.: Notice of Allowance, Jul. 24, 2013.

U.S. Appl. No. 12/905,474, filed Oct. 15, 2010 by Ghayur et al.: Notice of Allowance, Jan. 10, 2014.

U.S. Appl. No. 12/914,614, filed Oct. 28, 2010 by Ghayur et al.: Notice of Allowance, Jan. 10, 2014.

(56) References Cited

OTHER PUBLICATIONS

U.S. Appl. No. 12/914,614, filed Oct. 28, 2010 by Ghayur et al.: Non-Final Office Action, Jun. 6, 2013.
U.S. Appl. No. 13/196,138, filed Aug. 2, 2011 by Ghayur et al.: Notice of Allowance, Jan. 16, 2014.
U.S. Appl. No. 13/286,707, filed Nov. 1, 2011 by Ghayur et al.: Final Office Action, Aug. 29, 2014.
U.S. Appl. No. 13/286,707, filed Nov. 1, 2011 by Ghayur et al.: Non-Final Office Action, Jan. 29, 2014.
Winkles, J., "The TWEAK-Fn14 cytokine-receptor axis: discovery, biology and therapeutic targeting," *Nature Reviews. Drug Disc.*, 7(5): 411-425 (2008).
Witkowski et al., "Interleukin-17: A mediator of inflammatory responses," *Cell. Mol. Life Sci.*, 61: 567-579 (2004).
Wong et al., "Hyperproduction of IL-23 and IL-17 in patients with systemic lupus erythematosus: Implications for Th17-mediated inflammation in autoimmunity," *Clin. Immunol.*, 127(3): 385-393 (2008).
Yao et al., "Human IL-17: A Novel Cytokine Derived from T Cells," *J. Immunol.*, 155: 5483-5486 (1995).
Yao et al., "Molecular characterization of the human interleukin (IL)-17 receptor," *Cytokine.* 9(11): 794-800 (1997).
Zhang et al., "Direct chitosan-mediated gene delivery to the rabbit knee joints in vitro and in vivo," *Biochem. Biophys. Res. Commun.*, 341: 202-208 (2006).
Andrew et al., "Fragmentation of Immunoglobulin G," *Current Protocols in Cell Biology*, 16.4.1-16.4.10 (2000).
Andrew et al., "Fragmentation of Immunoglobulin G," *Current Protocols in Cell Biology*, 2.8.1-2.8.10 (1997).
David et al., "Characterization of monoclonal antibodies against prostaglandin $E_2$: Fine specificity and neuralization of biological effects," *Mol. Immunol.*, 22(3):339-346 (1985).
Digiammarino et al., "Ligand association rates to the inner-variable-domain of a dual-variable-domain immunoglobulin are significantly impacted by linker design," *mAbs*, 3(5): 487-494 (2011).
European Patent Application No. 09831213.5: Supplementary European Search Report and Search Opinion, dated Oct. 21, 2013 (6 pages).
European Patent Application No. 10770441.3 Supplementary European Search Report and Search Opinion, dated Sep. 23, 2013 (16 pages).
Fuh et al., "Structure-Function Studies of Two Synthetic Anti-vascular Endothelial Growth Factor Fabs and Comparison with the Avastin™ Fab," *J. Biol. Chem.*, 281(10):6625-6631 (2006).
International Patent Application No. PCT/US2012/071897: International Search Report and Written Opinion, dated Sep. 3, 2013 (17 pages).
Kwong et al., "Generation, affinity maturation, and characterization of a human anti-human NKG2D monoclonal antibody with dual antagonistic and agonistic activity," *J. Mol. Biol.*, 384(5): 1143-1156 (2008).
Liu et al., "Heterogeneity of Monoclonal Antibodies," *J. Pharm. Sci.*, 97(7):2426-2447 (2008).
Lo, B., "Antibody Humanization by CDR Grafting," *Methods Mol. Biol.*, 248: 135-159 (2004).
Pham, V. et al., "De novo proteomic sequencing of a monoclonal antibody raised against OX40 ligand," *Analytical Biochemistry*, 352: 77-86 (2006).
U.S. Appl. No. 12/771,874, filed Apr. 30, 2010 by Ghayur et al.; Final Office Action, Nov. 12, 2013.
U.S. Appl. No. 13/167,323, filed Jun. 23, 2011 by Ghayur et al.: Final Office Action, Nov. 20, 2013.
Voller et al., "Enzyme immunoassays with special reference to ELISA techniques," *J. Clin. Pathol.*, 31:507-520 (1978).
"Adalimumab," in *The Merck Index.* 14th Ed., John Wiley & Sons, 2006; pp. 26-27.
"Cetuximab," in *The Merck Index.* 14th Ed., John Wiley & Sons, 2006; p. 335.
"Inflixmab," in *The Merck Index.* 14th Ed., John Wiley & Sons, 2006; p. 863.
"Trastuzumab," in *The Merck Index.* 14th Ed., John Wiley & Sons, 2006; p. 1646.
T Hart et al., "Suppression of Ongoing Disease in a Nonhuman Primate Model of Multiple Sclerosis by a Human-Anti-Human IL-12p40 Antibody," *J. Immunol.*, 175(7): 4761-4768 (2005).
Alderson et al., "Regulation of apoptosis and T cell activation by Fas-specific mAb," *Int. Immunol.*, 6(11): 1799-1806 (1994).
Alegre et al., "An Anti-Murine CD3 Monoclonal Antibody with a Low Affinity for Fcγ Receptors Suppresses Transplantation Responses While Minimizing Acute Toxicity and Immunogenicity," *J. Immunol.*, 155: 1544-1555 (1995).
Alt et al., "Novel tetravalent and bispecific IgG-like antibody molecules combing single-chain diabodies with the immunoglobulin g1 Fc or CH3 region," *FEBS Letters*, 454: 90-94 (1999).
Ames et al., "Conversion of murine Fabs isolated from a combinatorial phage display library to full length immunoglobulins," *J. Immunol. Methods*, 184: 177-186 (1995).
Aoki et al., "Endothelial Progenitor Cell Capture by Stents Coated with Antibody Against CD34," *J. Am. Coll. Cardiol.*, 45(10): 1574-1579 (2005).
Arancio et al., "RAGE potentiates Aβ-induced perturbation of neuronal function in transgenic mice," *EMBO J.*, 23: 4096-4105 (2004).
Arndt et al., "Bispecific Diabodies for Cancer Therapy," *Methods Mol. Biol.*, 207: 305-321 (2003).
Azzazy et al., "Phage display technology: clinical applications and recent innovations," *Clin. Biochem.*, 35: 425-445 (2002).
Babcook et al., "A novel strategy for generating monoclonal antibodies from single, isolated lymphocytes producing antibodies of defined specificities," *Proc. Natl. Acad. Sci. USA*, 93:7843-7848 (1996).
Bäckström et al., "Signaling Efficiency of the T Cell Receptor Controlled by a Single Amino Acid in the b Chain Constant Region," *J. Exp. Med.*, 186 (11): 1933-1938 (1997).
Balthasar et al., "High-affinity rabbit antibodies directed against methotrexate: Production, purification, characterization, and pharmacokinetics in the rat," *J. Pharm. Sci.*, 84(1): 2-6 (1995) (Abstract only) (1 page).
Balthasar et al., "Inverse Targeting of Peritoneial Tumors: Selective Alteration of the Disposition of Methotrexate through the Use of Anti-Methotrexate Antibodies and Antibody Fragments," *J. Pharm. Sci.*, 85(10): 1035-1043 (1996).
Barbas et al., "Assembly of combinatorial antibody libraries on phage surfaces: The gene III site," *Proc. Natl. Acad. Sci. USA*, 88: 7978-7982 (1991).
Barbas et al., "In vitro evolution of a neutralizing human antibody to human immunodeficiency virus type 1 to enhance affinity and broaden strain cross-reactivity," *Proc. Natl. Acad. Sci. USA*, 91:3809-3813 (1984).
Barrios et al., "Length of the antibody heavy chain complementarity determining region 3 as a specificity-determining factor," *J. Mol. Recog.*, 17: 332-338 (2004).
Baslund et al., "Targeting interleukin-15 in patients with rheumatoid arthritis," *Arthritis Rheum.*, 52(9): 2686-2692 (2005).
Baumgartner et al., "Double blind, placebo controlled trial of tumor necrosis factor receptor fusion protein (TNFR:Fc) in active rheumatoid arthritis," Biomedicine '96. Medical Research from Bench to Bedside. Washington, DC, May 3-6, 1996. *J. Invest. Med.*, 44(3):235A (Mar. 1996) (Abstract) (1 page).
Berzofsky et al., "Immunogenicity and Antigen Structure," in *Fundamental Immunology.* (Paul, W.E. ed.), New York, NY: Raven Press, 1993; Chapter 8, p. 242 (1 page).
Bessis et al., "Use of hollow fibers filled with cells engineered to secrete IL-4 or IL-13 for treatment of experimental arthritis," (Abstract No. 1681), *Arthritis Rheum.*, 39(9Suppl.): S308 (1996) (1 page).
Better et al., "*Escherichia coli* Secretion of an Active Chimeric Antibody Fragment," *Science*, 240: 1041-1043 1988).
Biewenga et al., "IgA1 half molecules in human multiple myeloma and the in vitro production of similar fragments from intact IgA1 molecules," *Clin. Exp. Immunol.*, 51: 395-400 (1983).
Bird et al., "Single-Chain Antigen-Binding Proteins," *Science*, 242: 423-426 (1988).

(56) References Cited

OTHER PUBLICATIONS

Bornemann et al., "Aβ-induced Inflammatory Processes in Microglia Cells of APP23 Transgenic Mice," *Am. J. Pathol.*, 158(1): 63-73 (2001).
Boyce et al., "No audible wheezing: Nuggets and conundrums from mouse asthma models," *J. Exp. Med.*, 201(12): 1869-1873 (2005).
Brand, D.D., "Rodent Models of Rheumatoid Arthritis," *Comparative Medicine*, 55(2): 114-122 (2005).
Bree et al., "IL-13 blockade reduces lung inflammation after *Ascaris suum* challenge in cynomolgus monkeys," *J. Allergy Clin. Immunol.*, 119(5): 1251-1257 (2007).
Brennan et al., "Preparation of Bispecific Antibodies by Chemical Recombination of Monoclonal Immunoglobulin $G_1$ Fragments," *Science*, 229: 81-83 (1985).
Brinkmann et al., "Phage display of disulfide-stabilized Fv fragments," *J. Immunol. Methods*, 182: 41-50 (1995).
Bruncko et al., "Studies leading to potent, dual inhibitors of Bcl-2 and Bcl-xL," *J. Med. Chem.*, 50(4): 641-662 (2007).
Brüsselbach et al., "Enzyme recruitment and tumor cell killing in vitro by a secreted bispecific single-chain diabody," *Tumor Targeting*, 4. 115-123 (1999).
Buchwald et al., "Long-term, continuous intravenous heparin administration by an implantable infusion pump in ambulatory patients with recurrent venous thrombosis" *Surgery*, 88: 507-516 (1980).
Buras et al., "Animal Models of Sepsis: Setting the Stage," *Nat. Rev. Drug. Discovery*, 4: 854-865 (2005).
Burke et al., "Zotarolimus (ABT-578) eluting stents," *Adv. Drug Del. Rev.*, 58: 437-446 (2006).
Burton et al., "Human Antibodies from Combinatorial Libraries," *Adv. Immunol.*, 57: 191-280 (1994).
Calandra et al., "Protection from septic shock by neutralization of macrophage migration inhibitory factor," *Nature Med.*, 6(2): 164-170 (2000).
Carroll et al., "The selection of high-producing cell lines using flow cytometry and cell sorting," *Expert Opin. Biol. Ther.*, 4: 1821-1829 (2004).
Carter et al., "Humanization of an anti-p185$^{HER2}$ antibody for human cancer therapy," *Proc. Natl. Acad. Sci. USA*, 89: 4285-4289 (1992).
Casset et al., "A peptide mimetic of an anti-CD4 monoclonal antibody by rational design," *Biochem. Biophys. Res. Commun.*, 307: 198-205 (2003).
Chayen, N.E., "Turning protein crystallisation from an art into a science" *Curr. Opin. Struct. Biol.*, 14:577-583 (2004).
Chayen et al., "Protein crystallization: from purified protein to diffraction-quality crystal," *Nature Methods*,5(2): 147-153 (2008).
Chen et al., "Selection and analysis of an optimized anti-VEGF antibody: Crystal structure of an affinity matured Fab in complex with antigen," *J. Mol. Biol.*, 293: 865-881 (1999).
Chikanza et al., "Treatment of patients with rheumatoid arthritis with RP73401 phosphodiesterase Type IV inhibitor," (Abstract No. 1527), *Arthritis Rheum.*, 39(9 Suppl.): S282 (1996) (1 page).
Choi et al., "Recombinant chimeric OKT3 scfv IgM antibodies mediate immune suppression while reducing T cell activation in vitro," *Eur. J. Immunol.*, 31(1): 94-106 (2001).
Chothia et al., "Canonical Structures for the Hypervariable Regions of Immunoglobulins," *J. Mol. Biol.*, 196: 901-917 (1987).
Chothia et al., "Conformations of immunoglobulin hypervariable regions," *Nature*, 342: 877-883 (1989).
Clackson et al., "Making antibody fragments using pahge display libraries," *Nature*, 352: 624-628 (1991).
Cleek et al., "Biodegradable Polymeric Carriers for a bFGF Antibody for Cardiovascular Application," *Proceed. Intl. Symp. Control. Rel. Bioact. Mater.*, 24: 853-854 (1997).
Co et al., "Genetically Engineered Deglycosylation of the Variable Domain increases the Affinity of an Anti-CD33 Monoclonal Antibody," *Mol. Immunol.*, 30(15): 1361-1367 (1993).
Coffman et al., "Nonhuman primate models of asthma," *J. Exp. Med.*, 201(12): 1875-1879 (2005).
Colman, "Effects of amino acid sequence changes on antibody-antigen interactions," *Research in Immunology*, 145:33-36 (1994).
Coloma et al., "Design and production of novel tetravalent bispecific antibodies," *Nature Biotechnol.*, 15: 159-163 (1997).
Cot et al., "Production and characterization of highly specific anti-methotrexate monoclonal antibodies," *Hybridoma*, 6(1): 87-95 (1987).
Cox et al., "Measurement of cytokine release at the single cell level using the ELISPOT assay," *Methods*, 38(4): 274-282 (2006).
D'Andrea et al., "Production of Natural Killer Cell Stimulatory Factor (Interleukin 12) by Peripheral Blood Mononuclear Cells," *J. Exp. Med.*, 176: 1387-1398 (1992).
Dall'Acqua et al., "Contribution of Domain Interface Residues to the Stability of Antibody $C_H3$ Domain Homodimers," *Biochemistry*, 37: 9266-9273 (1998).
Dall'Acqua et al., "Increasing the affinity of a human IgG1 for the neonatal Fc receptor: Biological consequences," *J. Immunol.*, 169(9): 5171-5180 (2002).
Dall'Acqua et al., "Properties of human IgG1s: engineered for enhanced binding to the neonatal Fc receptor (FcRn)," *J. Biol. Chem.*, 281: 23514-23524 (2006).
De Pascalis et al., "Grafting of 'Abbreviated' Complementarity-Determining Regions Containing Specificity-Determining Residues Essential for Ligand Contact to Engineer a Less Immunogenic Humanized Monoclonal Antibody," *J. Immunol.*, 169: 3076-3084 (2002).
Deane et al., "RAGE mediates amyloid-β peptide transport across the blood-brain barrier and accumulation in brain," *Nature Med.*, 9(7): 907-913 (2003).
Deluca et al., "Marine and botanical lipids as immunomodulatory and therapeutic agents in the treatment of rheumatoid arthritis," *Rheum. Dis. Clin. North Am.*, 21: 759-777 (1995).
Descotes, J., "Immunotoxicology of Immunomodulators," *Develop. Biol. Standard*, 77: 99-102 (1992).
Desmet et al., "Anchor profiles of HLA-specific peptides: analysis by a novel affinity scoring method and experimental validation," *Proteins*, 58: 53-69 (2005).
Dickson, B.J., "Molecular Mechanisms of Axon Guidance," *Science*, 298: 1959-1964 (2002).
Dinarello et al., "Measurement of soluble and membrane-bound interleukin 1 using a fibroblast bioassay," Unit 6.2, in *Current Protocols in Immunology*, pp 6.21-6.27 (2000) (7 pages).
Domeniconi et al., "Overcoming inhibitors in myelin to promote axonal regeneration," *J. Neurological Sciences*, 233: 43-47 (2005).
During et al., "Controlled Release of Dopamine from a Polymeric Brain Implant: In Vivo Characterization," *Ann. Neurol.*, 25(4): 351-356 (1989).
Durocher et al., "High-level and high-throughput recombinant protein production by transient transfection of suspension-growing human 293-EBNA1 cells," *Nucl. Acids Res.*, 30(2): e9, (9 pages) (2002).
Economides et al., "Cytokine traps: multi-component, high-affinity blockers of cytokine action," *Nature Med.*, 9(1): 47-52 (2003).
Ehrich et al., "Demonstration of selective COX-2 inhibition by MK-966 in humans," (Abstract No. 328), *Arthritis Rheum.*, 39 (9 Suppl.): S81 (1996) (1 page).
Ehrich et al., "Efficacy of MK-966, a highly selective inhibitor of COX-2, in the treatment of postoperative dental pain," (Abstract No. 329), *Arthritis Rheum.*, 39(9Suppl.): S81 (1996) (1 page).
European Patent Application No. 06813554.0: Supplementary European Search Report and Search Opinion, dated Sep. 21, 2009 (11 pages).
European Patent Application No. 07811045.9: Supplementary European Search Report and Search Opinion, dated Sep. 21, 2009 (7 pages).
European Patent Application No. 09739578.4: Supplementary European Search Report and Search Opinion, dated Mar. 28, 2012 (21 pages).
European Patent Application No. 09759344.6: Supplementary European Search Report and Search Opinion, dated Jun. 13, 2012 (12 pages).
European Patent Application No. 09759348.7: Supplementary European Search Report and Search Opinion, dated Jul. 4, 2012 (11 pages).

(56) References Cited

OTHER PUBLICATIONS

European Patent Application No. 09795128.9: Supplementary European Search Report and Search Opinion, dated May 22, 2013 (10 pages).
European Patent Application No. 10805046.9: Supplementary European Search Report and Search Opinion, dated Mar. 26, 2013 (7 pages).
European Patent Application No. 10824164.7: Supplementary European Search Report and Search Opinion, dated May 22, 2013 (11 pages).
Evans et al., "Efficacy of tumor necrosis factor binding protein (TNF-bp) in the streptococcal cell wall-induced reactivation model of arthritis," (Abstract No. 1540), *Arthritis Rheum.*, 39(9 Suppl.): S284 (1996) (1 page).
Farr et al., "Sulphasalazine (SASP) in rheumatoid arthritis (RA): A 5 year prospective study," (Abstract No. 1519), *Arthritis Rheum.*, 39(9 Suppl.): S281 (1996) (1 page).
Fiebich et al., "Effects of NSAIDs on IL-1-beta-induced IL-6 mRNA and protein synthesis in human astrocytoma cells," *NeuroReport*, 7: 1209-1213 (1996).
Finnegan et al., "Leflunomide inhibits immunoglobulin production by two separate mechanisms," (Abstract No. 627), *Arthritis Rheum.*, 39(9 (Suppl.): S131 (1996) (1 page).
Finotto, et al., "Asthmatic changes in mice lacking T-bet are mediated by 1L-13," *Int. Immunol.*, 17(8): 993-1007 (2005).
Fuchs et al., "Targeting Recombinant Antibodies to the Surface of *Escherichia coli*: Fusion to a Peptidoglycan Associated Lipoprotein," *Bio/Technology*, 9: 1369-1372 (1991).
Garrard et al., "$F_{AB}$ Assembly and Enrichment in a Monovalent Phage Display System," *Bio/Technology*, 9: 1373-1377 (1991).
Gavilondo et al., "Antibody Engineering at the Millennium," *Biotechniques*, 29: 128-145 (2000).
Genain et al., "Creation of a model for multiple sclerosis in *Callithrix jacchus* marmosets,"*J. Mol. Med.*, 75(3): 187-197 (1997).
GENBANK Accession No. U17870, "*Cricetulus migratorius* 145.2c11 kappa light chain mRna, complete cds," ROD Feb. 7, 1996 (2 pages).
GENBANK Accession No. U17871, "*Cricetulus migratorius* 145.2c11 heavy chain mRNA, partial cds," Feb. 7, 1996 (2 pages).
GENBANK Accession No. X99230, "*M.musculus* mRNA for immunoglobulin heavy chain variable domain, subgroup IIb," ROD Oct. 8, 1996 (2 pages).
GENBANK Accession No. X99232, "*M.musculus* mRNA for immunoglobulin light chain variable domain, subgroup III," ROD Oct. 8, 1996 (2 pages).
GENBANK Accession No. Y14283, "*Mus musculus* mRNA for immunoglobulin heavy chain variable region, subunits VH, DH and JH" ROD May 26, 1998 (2 pages).
GENBANK Accession No. Y14284, "*Mus musculus* mRNA for irnmunoglobulin light chain variable region, subunits VL and JL," ROD May 26, 1998 (2 pages).
Genovese et al., "Abatacept for Rheumatoid Arthritis Refractory to Tumor Necrosis Factor α Inhibition," *N. Engl. J. Med.*, 353: 1114-1123 (2005).
Germain et al., "Redirecting NK cells mediated tumor cell lysis by a new recombinant bifunctional protein," *Protein Engineering Design and Selection*, 21(11):665-672 (2008).
Ghetie et al., "Increasing the serum persistence of an IgG fragment by random mutagenesis," *Nature Biotechnol.*, 15(7): (637-640 (1997).
Giegé et al., Chapter 1, in *Crystallization of Nucleic Acids and Proteins, a Practical Approach*, 2nd ed., (Ducruix and Giegé, eds.) (Oxford University Press, New York, 1999) pp. 1-16.
Glennie et al., "Preparation and Performance of Bispecific $F(ab'\gamma)_2$ Antibody Containing Thioether-Linked Fab'γ Fragments," *J. Immunol.*, 139(7): 2367-2375 (1987).
Goldspiel et al., "Human Gene Therapy," *Clin. Pharm.*, 12: 488-505 (1993).

Goodson, J.M., "Dental Applications," Chapter 6, In Medical Applications of Controlled Release, vol. II, Applications and Evaluation, (Langer and Wise, eds.) (CRC Press, Inc., Boca Raton, 1984), pp. 115-138.
Gracie et al., "A proinflammatory role for IL-18 in rheumatoid arthritis," *J. Clin. Invest.*, 104(10): 1393-1401 (1999).
Gram et al., "In vitro selection and affinity maturation of antibodies from a naive combinatorial immunoglobulin library," *Proc. Natl. Acad. Sci. USA*, 89: 3576-3580 (1992).
Green et al., "Antigen-specific human monoclonal antibodies from mice engineered with human Ig heavy and light chain YACs," *Nature Genetics*, 7: 13-21 (1994).
Green et al., "Regulation of B Cell Development by Variable Gene Complexity in Mice Reconstituted with Human Immunoglobulin Yeast Artificial Chromosomes," *J. Exp. Med.*, 188(3): 483-495 (1998).
Griffin et al., "Blockade of T Cell Activation Using a Surface-Linked Single Chain Antibody to CTLA-4 (CD152)," *J. Immunol.*, 164: 4433-4442 (2000).
Griffiths et al., "Human anti-self antibodies with high specificity from phage display libraries," *EMBO J.*, 12(2): 725-734 (1993).
Güssow et al., "Humanization of Monoclonal Antibodies," *Methods Enzymol.*, 203: 99-121 (1991).
Guttadauria, M., "Tenidap in Rheumatoid Arthritis Collaborative International Study (TRACIS): a 6-month interim analysis," (Abstract No 1516), *Arthritis Rheum.*, 39(9 Suppl.): S280 (1996) (1 page).
Hammerling et al., eds., "Appendix: Production of Antibody-Producing Hybridomas in the Rodent Systems," In *Monoclonal Antibodies and T-Cell Hybridomas. Research Monographs in Immunology*, vol. 3. (J.L. Turk, General Editor) (Elsevier, New York, 1981), pp. 563-587.
Hanasaki et al., "Binding of Human Plasma Sialoglycoproteins by the B Cell-specific Lectin CD22," *J. Biol. Chem.*, 270(13): 7543-7550 (1995).
Hara et al., "Therapeutic effect of T-614, a new anti-arthritic agent, on rheumatoid arthritis," (Abstract No. 1526) *Arthritis Rheum.*, 39(9 Suppl.): S282 (1996) (1 page).
Harriman et al., "Summary of clinical trials in rheumatoid arthritis using infliximab, an anti-TNFα treatment," *Ann. Rheum. Dis.*, 58(Suppl. I): I61-I64 (1999) (4 pages).
Hart et al., "Preclinical efficacy and safety of mepolizumab (SB-240563), a humanized monoclonal antibody to IL-5, in cynomolgus monkeys," *J. Allergy Clin. Immunol.*, 108(2): 250-257 (2001).
Hawkins et al., "Selection of Phage Antibodies by Binding Affinity Mimicking Affinity Maturation," *J. Mol. Biol.*, 226: 889-896 (1992).
Hay et al., "Bacteriophage cloning and *Escherichia coli* expression of a human IgM Fab," *Hum. Antibod. Hybridomas*, 3: 81-85 (1992).
Henry et al., "A Prostate-Specific Membrane Antigen Targeted Monoclonal Antibody-Chemotherapeutic Conjugate Designed for the Treatment of Prostate Cancer," *Cancer Res.*, 64: 7995-8001 (2004).
Hickey et al., "The Rheumatoid Arthritis Azathioprine Registry (RAAR)—interim analysis of malignancy and mortality," (Abstract No. 1521), *Arthritis Rheum.*, 39(9 Suppl.): S281 (1996) (1 page).
Hildebrand et al., "Surface coatings for biological activation and functionalization of medical devices," *Surface & Coatings Technology*, 200: 6318-6324 (2006).
Hinton et al., "Engineered human IgG antibodies with longer serum half-lives in primates," *J. Biol. Chem.* 279(8): 6213-6216 (2004).
Holliger et al., "'Diabodies': Small bivalent and bispecific antibody fragments," *Proc. Natl. Acad. Sci. USA*, 90: 6444-6448 (1993).
Holliger et al., "Diabodies: Small bispecific antibody fragments," *Cancer Immunol. Immunother.*, 45: 128-130 (1997).
Holm et al., "Functional mapping and single chain construction of the anti-cytokeratin 8 monoclonal antibody TS1," *Mol. Immunol.*, 44: 1075-1084 (2007).
Hoogenboom et al., "Multi-subunit proteins on the surface of filamentous phage: Methodologies for displaying antibody (Fab) heavy and light chains." *Nucl. Acids Res.*, 19(15): 4133-4137 (1991).
Hoogenboom et al., "Natural and designer binding sites made by phage display technology," *Immunol. Today*, 21(8): 371-378 (2000).

(56) References Cited

OTHER PUBLICATIONS

Hoogenboom, H.R., "Designing and optimizing library selection strategies for generating high-affinity antibodies," *Trends Biotechnol.*, 15: 62-70 (1997).
Hoogenboom, H.R., "Mix and match: Building manifold binding sites, " *Nature Biotechnol.*, 15: 125-126 (1997).
Howard et al., "Intracerebral drug delivery in rats with lesion-induced memory deficits," *J. Neurosurg.*, 71: 105-112 (1989).
Huber et al., "Crystallographic structure studies of an IgG molecule and an Fc fragment," *Nature*, 264: 415-420 (1976).
Huse et al., "Generation of a Large Combinatorial Library of the Immunoglobulin Repertoire in Phage Lambda," *Science*, 246: 1275-1281 (1989).
Huston et al., "Protein engineering of antibody binding sites: Recovery of specific activity in an anti-digoxin single-chain Fv analogue produced to *Escherichia coli*," *Proc. Natl. Acad. Sci. USA*, 85: 5879-5883 (1988).
Huston et al., "Protein Engineering of Single-Chain Fv Analogs and Fusion Proteins," *Methods Enzymol.*, 203: 46-88 (1991).
Hwang et al., "Cutting Edge: Targeted Ligation of CTLA-4 In Vivo by Membrane-Bound Anti-CTLA-4 Antibody Prevents Rejection of Allogeneic Cells," *J. Immunol.*, 163: 633-637 (2002).
Inter Partes Reexamination (Control No. 95/001,380) of U.S. Patent No. 7,612,181 (U.S. Appl. No. 11/507,050): Replacement Request, dated Jun. 24, 2010 (62 pages).
Inter Partes Reexamination (Control No. 95/001,380) of U.S. Patent No. 7,612,181 (U.S. Appl. No. 11/507,050): Order Granting Request for Inter Partes Reexamination, issued Sep. 1, 2010 (18 pages).
Inter Partes Reexamination (Control No. 95/001,380) of U.S. Patent No. 7,612,181 (U.S. Appl. No. 11/507,050): Reexamination Non-Final Office Action, dated Sep. 1, 2010 (13 pages).
Inter Partes Reexamination (Control No. 95/001,380) of U.S. Patent No. 7,612,181 (U.S. Appl. No. 11/507,050): Third Party Requester Comments After Non-Final Action ("Sanofi's Comments Pursuant to 37 CFR § 1.947"), dated Dec. 1, 2010 (81 pages).
Inter Partes Reexamination (Control No. 95/001,380) of U.S. Patent No. 7,612,181(U.S. Appl. No. 11/507,050): Response After Non-Final Action—Owner Timely ("Patent Owner's Response Pursuant to 37 CFR § 1.945"), dated Nov. 1, 2010 (71 pages).
International Patent Application No. PCT/US2006/032398: International Preliminary Report on Patentability, dated Jul. 6, 2010 (14 pages).
International Patent Application No. PCT/US2006/032398: International Search Report and Written Opinion, dated Aug. 18, 2008 (14 pages).
International Patent Application No. PCT/US2007/017340: International Preliminary Report on Patentability, dated Nov. 14, 2008 (3 pages).
International Patent Application No. PCT/US2007/017340: International Search Report and Written Opinion, dated Jun. 24, 2008 (5 pages).
International Patent Application No. PCT/US2009/041945: International Preliminary Report on Patentability, dated Aug. 9, 2010 (12 pages).
International Patent Application No. PCT/US2009/041945: International Search Report and Written Opinion, dated Nov. 2, 2009 (12 pages).
International Patent Application No. PCT/US2009/046130: International Preliminary Report on Patentability, dated Aug. 21, 2010 (13 pages).
International Patent Application No. PCT/US2009/046130: International Search Report and Written Opinion, dated Jan. 11, 2010 (17 pages).
International Patent Application No. PCT/US2009/046137: International Preliminary Report on Patentability, dated Jun. 18, 2010 (14 pages).
International Patent Application No. PCT/US2009/046137: International Search Report and Written Opinion, dated Jan. 12, 2010 (18 pages).
International Patent Application No. PCT/US2009/049954: International Preliminary Report on Patentability, dated Jul. 2, 2011 (11 pages).
International Patent Application No. PCT/US2009/049954: International Search Report and Written Opinion, dated Mar. 31, 2010 (14 pages).
International Patent Application No. PCT/US2009/066815: International Preliminary Report on Patentability, dated Jan. 6, 2011 (13 pages).
International Patent Application No. PCT/US2009/066815: International Search Report and Written Opinion, dated Mar. 23, 2010 (14 pages).
International Patent Application No. PCT/US2010/033231: International Preliminary Report on Patentability, dated Apr. 27, 2011 (10 pages).
International Patent Application No. PCT/US2010/033231: International Search Report and Written Opinion, dated Nov. 22, 2010 (10 pages).
International Patent Application No. PCT/US2010/033246: International Preliminary Report on Patentability, dated May 4, 2011 (28 pages).
International Patent Application No. PCT/US2010/033246: International Search Report and Written Opinion, dated Nov. 24, 2010 (18 pages).
International Patent Application No. PCT/US2010/043716: International Preliminary Report on Patentability, dated Aug. 31, 2012 (24 pages).
International Patent Application No. PCT/US2010/043716: International Search Report and Written Opinion, dated Feb. 28, 2011 (17 pages).
International Patent Application No. PCT/US2010/047543: International Search Report and Written Opinion, dated Feb. 24, 2011 (14 pages).
International Patent Application No. PCT/US2010/052843: International Search Report and Written Opinion, dated Jul. 1, 2011 (21 pages).
International Patent Application No. PCT/US2010/053730: International Preliminary Report on Patentability, dated Nov. 21, 2011 (12 pages).
International Patent Application No. PCT/US2010/053730: International Search Report and Written Opinion, dated May 6, 2011 (13 pages).
International Patent Application No. PCT/US2010/054521: International Preliminary Report on Patentability, dated Feb. 8, 2012 (12 pages).
International Patent Application No. PCT/US2010/054521: International Search Report and Written Opinion, dated May 26, 2011 (12 pages).
International Patent Application No. PCT/US2011/041633: International Search Report and Written Opinion, dated Mar. 13, 2012 (16 pages).
International Patent Application No. PCT/US2011/043297: International Search Report and Written Opinion, dated Feb. 28, 2012 (19 pages).
International Patent Application No. PCT/US2011/046233: International Search Report and Written Opinion, dated Apr. 3, 2012 (17 pages).
International Patent Application No. PCT/US2011/049147: International Search Report and Written Opinion, dated Mar. 21, 2012 (16 pages).
International Patent Application No. PCT/US2011/058769: International Search Report and Written Opinion, dated Jun. 15, 2012 (15 pages).
International Patent Application No. PCT/US2011/059074: International Search Report and Written Opinion, dated Jun. 15, 2012 (18 pages).
International Patent Application No. PCT/US2012/072017: International Search Report and Written Opinion, dated Jul. 17, 2013 (24 pages).
Ito et al., "Transfer of Severe Experimental Autoimmune Encephalomyelitis by IL-12- and IL-18-Potentiated T Cells is Estrogen Sensitive" *J Immunol.*, 170(9): 4802-4809 (2003).

(56) References Cited

OTHER PUBLICATIONS

Jackson et al., "In Vitro Antibody Maturation, Improvement of a High Affinity, Neutralizing Antibody Against IL-1β," *J. Immunol.*, 154(7): 3310-3319 (1995).

Janelsins et al., "Early correlation of microglial activation with enhanced tumor necrosis factor-alpha and monocyte chemoattractant protein-I expression specifically within the entorhinal cortex of triple transgenic Alzheimer's disease mice," *J. Neuroinflammation*, 2(23): 1-12 (2005).

Janeway et al., *Immunobiology. The immune System in Health and Disease*. 3rd Ed. Current Biology Ltd./Garland Publishing Inc., 1997; Chapter 3, pp. 1-11.

Jefferis, R., "Glycosylation of Recombinant Antibody Therapeutics," *Biotechnol. Prog.*, 21: 11-16 (2005).

Jendreyko et al., "Intradiabodies, Bispecific, Tetravalent Antibodies for the Simultaneous Functional Knockout of Two Cell Surface Receptors," *J. Biol. Chem.*, 278(48):47812-47819 (2003).

Jiang et al., "Regulation of recombinant monoclonal antibody production in Chinese hamster ovary cells: A comparative study of gene copy number, mRNA level, and protein expression," *Biotechnol. Prog.*, 22(1): 313-318 (2006).

Jin et al., "Pharmacokinetic and Pharmacodynamic Effects of High-Dose Monoclonal Antibody Therapy in a Rat Model of Immune Thrombocytopenia." *The AAPS Journal*, 7(4):Article 87, E895-E902 (2006) [online]. Retrieved from: http://www.springerlink.com/content/v6n04672761n9313/fulltext.pdf.

Joachimiak, "High-throughput crystallography for structural genomics" *Curr. Opin. Struct. Biol.*, 19:573-584 (2009).

Johnsson et al., "Comparison of Methods for Immobilization to Carboxymethyl Dextran Sensor Surfaces by Analysis of the Specific Activity of Monoclonal Antibodies," *J. Mol. Recognit.*, 8: 125-131 (1995).

Johnsson et al., "Immobilization of Proteins to a Carboxymethyldextran-Modified Gold Surface for Biospecific Interaction Analysis in Surface Plasmon Resonance Sensors," *Anal. Biochem.*, 198: 268-277 (1991).

Joliot et al., "Antennapedia homeobox peptide regulates neural morphogenesis," *Proc. Natl. Acad. Sci. USA*, 88: 1864-1868 (1991).

Jones et al., "Replacing the complementarity-determining regions in a human antibody with those from a mouse," *Nature*, 321: 522-525 (1986).

Jones, A.G., "Particle formation and separation in suspension crystallization processes," Chapter 4, in *Process. Solid-Liq. Suspensions*, (P. Ayazi Shamlou, ed.) (Butterworth-Heinemann, Oxford, UK, 1993) pp. 93-117.

Jones, A.J.S., "Analytical methods for the assessment of protein formulations and delivery systems," Chapter 2, in *Formulation and Delivery of Proteins and Peptides*, 1st ed., (Cleland and Langer, eds.) (American Chemical Society, Washington, D.C., 1994) pp. 22-45.

Jones, R., "Rovelizumab—ICOS Corp," *IDrugs*, 3(4): 442-446 (2000).

Jönsson et al., "Introducing a biosensor based technology for real-time biospecific interaction analysis," *Ann. Biol. Clin.*, 51: 19-26 (1993).

Jönsson, et al., "Real-Time Biospecific Interaction Analysis Using Surface Plasmon Resonance and a Sensor Chip Technology," *BioTechniques*, 11(5): 620-627 (1991).

Joosten et al., "Anticytokine Treatment of Established Type II Collagen-Induced Arthritis in DBA/I Mice," *Arthritis Rheum.*, 39(5): 797-809 (1996).

Ju et al., "Inhibitory effects of nardostachin on nitric oxide, prostaglandin E2, and tumor necrosis factor-alpha production in lipopolysaccharide activated macrophages," *Biol. Pharm. Bull.* 26: 1375-1378 (2003).

Jungbluth et al., "A monoclonal antibody recognizing human cancers with amplification/overexpression of the human epidermal growth factor receptor," *Proc. Natl. Acad. Sci. USA*, 100(2): 639-644 (2003).

Kabat et al., "Attempts to Located Complementarity-Determining Residues in the Variable Position of Light and Heavy Chains," *Ann. NY Acad. Sci.*, 190: 382-391 (1971).

Kaine et al., "Results of a multi-dose protocol 7002 using an immunomodulating, non-depleting Primatized™ anti-CD4 monoclonal antibody in rheumatoid arthritis (RA)," (Abstract No. 195), *Arthritis Rheum.*, 38: S185 (1995) (1 page).

Kanda et al., "Establishment of a GDP-mannose 4,6-dehydratase (GMD) knockout host cell line: A new strategy for generating completely non-fucosylated recombinant therapeutics," *J. Biotechnol.*, 130(3): 300-310 (2007).

Kapadia et al., "Soluble TNF binding proteins modulate the negative inotropic properties of TNF-alpha in vitro," *Am. J. Physiol. Heart Circ. Physiol.* 268 (2 Pt. 2): H517-H525 (1995).

Karnezis et al., "The neurite outgrowth inhibitor Nogo A is involved in autoimmune-mediated demyelination," *Nature Neurosci.*, 7: 736-744 (2004).

Karni et al., "IL-18 is linked to raised IFN-γ in multiple sclerosis and is induced by activated $CD4^+$ T cells via CD40-CD40 ligand interactions," *J. Neuroimmunol.*, 125: 134-140 (2002).

Kashmiri et al., "SDR grafting—a new approach to antibody humanization," *Methods*, 36(1): 25-34 (2005).

Kaufman and Sharp, "Amplification and expression of sequences cotransfected with a modular dihydrofolate reductase complementary DNA gene," *J. Mol. Biol.*, 159(4): 601-621 (1982).

Keith Jr., et al., "Recombinant human interleukin eleven decreases arthritis in HLA-B27 transgenic rats," (Abstract No. 1613), *Arthritis Rheum.*, 39(9 Suppl.): S296 (1996) (1 page).

Kellerman et al., "Antibody discovery: The use of transgenic mice to generate human monoclonal antibodies for therapeutics," *Curr. Opin. Biotechnol.*, 13: 593-597 (2002).

Kettleborough et al., "Humanization of a mouse monoclonal antibody by CDR-grafting: the importance of framework residues on loop conformation," *Protein Eng.*, 4(7): 773-783 (1991).

Kettleborough et al., "Isolation of tumor cell-specific single-chain Fv from immunized mice using phage-antibody libraries and the reconstruction of whole antibodies from these antibody fragments," *Eur. J. Immunol.*, 24: 952-958 (1994).

Kim et al., "Identifying amino acid residues that influence plasma clearance of murine IgG1 fragments by site-directed mutagenesis," *Eur. J. Immunol.*, 24: 542-548 (1994).

Kipriyanov et al., "Bispecific CD3×CD19 Diabody for T Cell Mediated Lysis of Malignant Human B Cells," *Int. J. Cancer*, 77: 763-772 (1998).

Kipriyanov et al., "Generation of recombinant antibodies," *Mol. Biotechnol.*, 12: 173-201 (1999).

Klein, W.L., "Aβ toxicity in Alzheimer's disease: Globular oligomers (ADDLs) as new vaccine and drug targets," *Neurochem. Int.*, 41: 345-352 (2002).

Klyubin et al., "Amyloid β protein immunotherapy neutralizes Aβ oligomers that disrupt synaptic plasticity in vivo," *Nature Med.*, 11: 556-561 (2005).

Köhler and Milstein, "Continuous cultures of fused cells secreting antibody of predefined specificity," *Nature*, 256, 495-497 (1975).

Konishi et al., "A simple and sensitive bioassay for the detection of human interleukin-18/ interferon-γ-inducing factor using human myelomonocytic KG-1 cells," *J. Immunol. Methods*, 209: 187-191 (1997).

Kontermann, R.E., "Recombinant bispecific antibodies for cancer therapy," *Acta Pharmacologica Sinica*, 26(1): 1-9 (2005).

Kostelny et al., "Formation of a Bispecific Antibody by the Use of Leucine Zippers," *J. Immunol.*, 148(5): 1547-1553 (1992).

Kriangkum et al., "Bispecific and bifunctional single chain recombinant antibodies" *Biomol. Eng.*, 18: 31-40 (2001).

Krop et al., "Self-renewal of B-1 lymphocytes is dependent on CD19," *Eur. J. Immunol.*, 26: 238-242 (1996).

Kuby, *Immunology*, 2nd ed., (W.H. Freeman and Company, New York, 1994), p. 115, Fig. 5-6 (1 page).

Lam et al., "Microencapsulation of Recombinant Humanized Monoclonal Antibody for Local Delivery," *Proceed. Intl. Symp. Control Rel. Bioact. Mater.*, 24: 759-760 (1997).

Langer and Peppas, "Chemical and Physical Structure of Polymers as Carriers for Controlled Release of Bioactive Agents: A Review," *J. Macromol. Sci. RMC*, C23(1): 61-126 (1983).

Langer, R., "New Methods of Drug Delivery," *Science*, 249: 1527-1533 (1990).

(56) References Cited

OTHER PUBLICATIONS

Laue, T., "Analytical centrifugation: equilibrium approach," In *Current Protocols in Protein Science*, (John Wiley & Sons, Inc., New York, 1999), Supplement 18, Unit 20.3, pp. 20.3.1-20.3.13 (13 pages).

Le Gall et al., "Di-, tri- and tetrameric, single chain Fv antibody fragments against human CD19: Effect of valency on cell binding," *FEBS Letters*, 453: 164-163 (1989).

Le Gall et al., "Immunosuppressive properties of anti-CD3 single-chain Fv and diabody," *J. Immunol. Methods*, 285: 111-127 (2004).

Lee et al., "BiP and imunoglobulin light chain cooperate to control the folding of heavy chain and ensure the fidelity of immunoglobulin assembly," *Mol. Biol. Cell*, 10: 2209-2219 (1999).

Lee et al., "Treatment of rheumatoid arthritis (RA) with thalidomide," (Abstract No. 1524), *Arthritis Rheum.*, 39(9 Suppl.) S282 (1996) (1 page).

Legros et al., "Characterization of an anti-*Borrelia burgdorferi* OspA conformational epitope by limited proteolysis of monoclonal antibody-bound antigen and mass spectrometric peptide mapping," *Protein Science*, 9: 1002-1010 (2000).

Leung et al., "Combined Effects of IL-12 and IL-18 on the Induction of Collagen-induced Arthritis," *J. Immunol.*, 164(12):.6495-6502 (2000).

Levy et al., "Inhibition of Calcification of Bioprosthetic Heart Valves by Local Controlled-Release Diphosphonate," *Science*, 228: 190-192 (1985).

Li et al., "Structural mutations in the constant region of the T-cell antigen receptor (TCR)β chain and their effect on TCRα and β chain interaction," *Immunology*, 88: 524-530 (1996).

Li et al., "Synergistic effects of IL-12 and IL-18 in skewing tumor-reactive 7-cell responses towards a type I pattern." *Cancer Res.*, 66(3): 1063-1070 (2005).

Li et al., "Genetically engineered brain drug delivery vectors: Cloning, expression and in vivo application of an anti-transferrin receptor single chain antibody-streptavidin fusion gene and protein," *Protein Eng.*, 12(9): 787-796 (1999).

Little et al., "Of mice and men: hybridoma and recombinant antibodies," *Immunol. Today.* 21(8): 64-370 (2000).

Lloyd et al., "Mouse Models of Allergic Airway Disease," *Adv. Immunol.*, 77: 263-295 (2001).

Lobo, "Anti-Methotrexate Fab Fragments for Optimization of Intraperitoneal Methotrexate Chemotherapy," Dissertation, University of New York at Buffalo, Dept. of Pharmaceutical Sciences, Aug. 2002, pp. 1-243. Available online at: http://www.acsu.buffalo.edu/~jb/Thesis%20080802.pdf.

Lobo et al., "Application of anti-methotrexate Fab fragments for the optimization of intraperitoneal methotrexate therapy in a murine model of peritoneal cancer," *J. Pharma. Sci.*, 94(9): 1957-1964 (2005) (Abstract only) (1 page).

Lotz et al., "IL-17 promotes cartilage degradation," (Abstract No. 559), *Arthritis Rheum.*, 39(9 Suppl.): S120 (1996) (1 page).

Lu et al.. "A Fully Human Recombinant IgG-like Bispecific Antibody to Both the Epidermal Growth Factor Receptor and the Insulin-like Growth Factor Receptor for Enhanced Antitumor Activity," *J. Biol. Chem.*, 280 (20): 19665-19672 (2005).

Lu et al., "Fab-scFv fusion protein: an efficient approach to production of bispecific antibody fragments," *J. Immunol. Methods*, 267:213-226 (2002).

Lu et al., "Di-diabody: A novel tetravalent bispecific antibody molecule by design," *J. Immunol. Methods*, 279: 219-232 (2003).

Lu et al., "Simultaneous Blockade of Both the Epidermal Growth Factor Receptor and the Insulin-like Growth Factor Receptor Signaling Pathways in Cancer Cells with a Fully Human Recombinant Bispecific Antibody," *J. Biol. Chem.*, 279(4): 2856-2865 (2004).

Lublin, F.D., "Relapsing Experimental Allergic Encephalomyelitis. An Autoimmune Model of Multiple Sclerosis," *Springer Semin. Immunopathol.*, 8: 197-208 (1985).

Lund et al., "Human Fc gamma RI and Fc gamma RII interact with distinct but overlapping sites on human IgG," *J. Immunol.*, 147: 2657-2662 (1991).

Luster et al., "Use of animal studies in risk assessment for immunotoxicology," *Toxicology*, 92(1-3): 229-243 (1994).

MacCallum et al., "Antibody-antigen Interactions: Contact Analysis and Binding Site Topography," *J. Mol. Biol.*, 262: 732-745 (1996).

Mack et al., "A small bispecific antibody construct expressed as a functional single-chain molecule with high tumor cell cytotoxicity," *Proc. Natl. Acad. Sci. USA*, 92: 7021-7025 (1995).

Madhusudan et al., "A phase II study of etanercept (Enbrel), a tumor necrosis factor alpha inhibitor in patients with metastatic breast cancer," *Clin. Cancer Res.*, 10(19): 6528-6534 (2004).

Makwana et al., "Molecular mechanisms in successful peripheral regeneration," *FEBS J.*, 272: 2628-2638 (2005).

Malik-Hall et al., "Primary afferent nociceptor mechanisms mediating NGF-induced mechanical hyperalgesia," *Eur. J. Neurosci.*, 21(12): 3387-3394 (2005).

Marchalonis et al., "Evolutionary Factors in the Emergence of the Combinatorial Germline Antibody Repertoire," *Adv. Exp. Med. Biol.*, 484: 13-30 (2001).

Margolin et al., "Protein crystals as novel catalytic materials," *Angew. Chem. Int. Ed.*, 40: 2204-2222 (2001).

Mariuzza et al., "The Structural Basis of Antigen-Antibody Recognition," *Annu. Rev. Biophys. Biophys. Chem.*, 16: 139-159 (1987).

Marks et al., "By-Passing Immunization: Building High Affinity Human Antibodies by Chain Shuffling," *BioTechnology*, 10: 779-783 (1992).

Marques et al., "Mediation of the Cytokine Network in the Implantation of Orthopedic Devices," Chapter 21, In *Biodegradable Systems in Tissue Engineering and Regenerative Medicine*, (Reis et al., eds.) (CRC Press LLC, Boca Raton, 2005) pp. 377-397.

Marquina et al., "Inhibition of B cell death causes the development of an IgA nephropathy in (New Zealand White x C57BL/6)F1-bcl-2 transgenic mice," *J. Immunol.*, 172(11): 7177-7185 (2004).

Martin, A.C.R., "Protein Sequence and Structure Analysis of Antibody Variable Domains," Chapter 31, In *Antibody Engineering*, Kontenmann and Dübel, eds. ), (Springer-Verlag, Berlin, 2001), pp. 422-439.

Marvin and Zhu, "Recombinant approaches to IgG-like bispecific antibodies," *Acta Pharmacologica Sinica*, 26(6): 649-658 (2005).

Masliah et al., "Effects of α-Synuclein Immunization in a Mouse Model of Parkinson's Disease," *Neuron*, 46: 857-868 (2005).

Mateo et al., "Humanization of a mouse monoclonal antibody that blocks the epidermal growth factor receptor: recovery of antagonistic activity," *Immunotechnology*, 3: 71-81 (1997).

McCafferty et al., "Phage antibodies: Filamentous phage displaying antibody variable domains," *Nature*, 348: 552-554 (1990).

McDonnell et al., "TNF Antagonism," In *New Drugs for Asthma, Allergy and COPD. Prog Respir Res.*, vol. 31. (Hansel et al., eds.) (Karger, Basel, 2001) pp. 247-250.

McGee et al., "The Nogo-66 receptor: Focusing myelin inhibition of axon regeneration," *Trends in Neurosciences*, 26(4): 193-198 (2003).

McIntosh et al., "In Vivo induction of IL-6 by Administration of Exogenous Cytokines and Detection of De Novo Serum Levels of IL-6 in Tumor-Bearing Mice," *J. Immunol.* 143(1): 162-167 (1989).

McMahon et al., "Does Anti-TNF-Alpha Have a Role in the Treatment of Osteoporosis?" *Bulletin of the NYU Hospital for Joint Diseases*, 66: 280-281 (2008).

Mendez et al., "Functional transplant of megabase human immunoglobulin loci recapitulates human antibody response in mice," *Nature Genet.*, 15: 146-156 (1997).

Merchant et al., "An efficient route to human bispecific IgG," *Nature Biotechnol.*, 16: 677-681 (1998).

Miller et al., "Design, Construction, and In Vitro Analyses of Multivalent Antibodies," *J. Immunol.*, 170: 4854-4861 (2003).

Milstein et al., "Hybrid hybridomas and their use in immunohistochemistry," *Nature*, 305: 537-540 (1983).

Mizushima et al., "pEF-BOS, a powerful mammalian expression vector," *Nucl. Acids Res.*, 18(17): 5322 (1990).

Mnich et al., "Characterization of a monoclonal antibody that neutralizes the activity of prostaglandin $E_2$," *J. Immunol.*, 155: 4437-4444 (1995).

(56) References Cited

OTHER PUBLICATIONS

Modjtahedi et al., "Antitumor Activity of Combinations of Antibodies Directed Against Different Epitopes on the Extracellular Domain of the Human EGF Receptor," *Cell Biophys.*, 22(1-3): 129-146 (1993).
Modjtahedi et al., "Phase I trial and tumour localisation of the anti-EGFR monoclonal antibody 1CR62 in head and neck or lung cancer," *Br. J. Cancer*, 73:228-235 (1996).
Modjtahedi et al., "Targeting of Cells Expressing Wild-Type EGFR and Type-III Mutant EGFR (EGFRVIII) by Anti-EGFR MAB ICR62: A Two-Pronged Attack for Tumour Therapy," *Int. J. Cancer*, 105: 273-280 (2003).
Modjtahedi et al., "The human EGF receptor as a target for cancer therapy: Six new rat mAbs against the receptor on the breast carcinoma MDA-MB 468", *Br. J. Cancer*, 67: 247-253 (1993).
Moreland et al., "Soluble tumor necrosis factor receptors (sTNFR): Results of a phase I dose-escalation study in patients with rheumatoid arthritis," (Abstract No. 813), *Arthritis Rheum.*, 37: S295 (1994) (1 page).
Morgan and Anderson, "Human Gene Therapy," *Ann. Rev. Biochem.*, 62: 191-217 (1993).
Moriuchi et al., "Treatment of established collagen-induced arthritis with PGE1 incorporated in lipid microspheres," (Abstract No. 1526), *Arthritis Rheum.*, 39(9 Suppl.): S282 (1996) (1 page).
Morrison and Schlom, "Recombinant Chimeric Monoclonal Antibodies," Chapter 1, In *Important Advances in Oncology* 1990 (J.B. Lippincott Company, Philadelphia, 1990), pp. 3-18.
Morrison et al., "Genetically Engineered Antibody Molecules," *Advances in Immunology*, 44:65-92 (1989).
Morrison, S., "Two heads are better than one," *Nature Biotech.*, 25(11): 1233-1234 (2007).
Müller et al., "The first constant domain ($C_H1$ and $C_L$) of an antibody used as heterodimerization domain for bispecific miniantibodies," *FEBS Lett.*, 422: 259-264 (1998).
Mulligan, R.C., "The Basic Science of Gene Therapy," *Science*, 260: 926-932 (1993).
Mullinax et al., "Expression of a Heterodimeric Fab Antibody Protein in One Cloning Step," *BioTechniques*, 12(6): 864-869 (1992).
Murthy et al., "Binding of an Antagonistic Monoclonal Antibody to an Intact and Fragmented EGF-Receptor Polypeptide," *Arch. Biochem. Biophys.*, 252(2): 549-560 (1987).
Nakanishi et al., "Interleukin-18 Regulates Both TH1 and TH2 Responses," *Ann. Rev. Immunol.*, 19: 423-474 (2001).
National Center for Biotechnology Information (NCBI), Protein Database, "Chain H, Vascular Endothelial Growth Factor in Complex with a Neutralizing Antibody." Accession No. 1BJ1_H, ROD Jun. 30, 1998 [online]. Retrieved from the Internet: http://www.ncbi.nlm.nih.gov/protein/1BJ1_H (3 pages).
National Center for Biotechnology Information (NCBI), Protein Database, "Chain L, Vascular Endothelial Growth Factor in Complex with a Neutralizing Antibody," Accession No. 1BJ1_L, ROD Jun. 30, 1998 [online]. Retrieved from the Internet: http://www.ncbi.nlm.nih.gov/protein/4389276?sat=11&satkey=3623907 (3 pages).
National Center for Biotechnology Information (NCBI), Protein Database, "Chain H, Structure of the G6 Fab, a Phage Derived Vegf Binding Fab," Accession No. 2FJF_H, PRI Jan. 2, 2006 [online]. Retrieved from the Internet: http://www.ncbi.nlm.nih.gov/protein/90109456?sat=34&satkey=11061854 (2 pages).
National Center for Biotechnology Information (NCBI), Protein Database, "Chain L, Structure of the G6 Fab, a Phage Derived Vegf Binding Fab," Accession No. 2FJF_L, PRI Jan. 2, 2006 [online]. Retrieved from the Internet: http://www.ncbi.nlm.nih.gov/protein/90109455?sat=34&satkey=11061854 (2 pages).
National Center for Biotechnology Information (NCBI), Protein Database, "Chain H, Structure of the B20-4 Fab, a Phage Derived Fab Fragment, in Complex with Vegf," Accession No. 2FJH_H, PRI Jan. 2, 2006 [online]. Retrieved from the Internet: http://www.ncbi.nlm.nih.gov/protein/90109487?sat=34&satkey=11061856 (2 pages).
National Center for Biotechnology Information (NCBI), Protein Database, "Chain L, Structure of the B20-4 Fab, a Phage Derived Fab fragment, in Complex with Vegf," Accession No. 2FJH_L, PRI Jan. 2, 2006 [online]. Retrieved from the Internet: http://www.ncbi.nlm.nih.gov/protein/90109486?sat=34&satkey=11061856 (2 pages).
Nelson, R.B. "The Dualistic Nature of Immune Modulation in Alzheimer's Disease: Lessons from the Transgenic Models," *Curr. Pharm. Des.*, 11: 3335-3352 (2005).
Ning et al., "Intratumoral radioimmunotherapy of a human colon cancer xenograft using a sustained-release gel," *Radiotherapy Oncol.*, 39: 179-189 (1996).
Nishimoto et al., "Treatment of rheumatoid arthritis with humanized anti-interleukin-6 receptor antibody," *Arthritis Rheum.*, 50(6): 1761-1769 (2004).
O'Connor et al., "Requirement of multiple phage displayed peptide libraries for optimal mapping of a conformational antibody epitope on CCR5," *J. Immunol. Methods*, 299: 21-35 (2005).
Okamoto et al., "Rituximab for Rheumatoid Arthritis," *N. Engl. J. Med.*, 351: 1909 (2004) (1 page).
Owens et al., "The Immunology of Multiple Sclerosis and its Animal Model, Experimental Allergic Encephalomyelitis," *Neurol. Clin.*, 13(1): 51-73 (1995).
Pack and Plückthun, "Miniantibodies: Use of Amphipathic Helices to Produce Functional, Flexibly Linked Dimeric $F_v$ Fragments with High Avidity in *Escherichia coli*," *Biochemistry*,31: 1579-1584 (1992).
Padilla et al., "IL-13 Regulates the Immune Response to Inhaled Antigens," *J. Immunol.*, 174(12): 8097-8105 (2005).
Padlan et al., "Identification of specificity-determining residues in antibodies," *FASEB J.*, 9: 133-139 (1995).
Padlan, E.A., "A Possible Procedure for Reducing the Immunogenicity of Antibody Variable Domains While Preserving Their Ligand-Binding Properties," *Mol. Immunol.*, 28(4/5): 489-498 (1991).
Park et al., "Generation and characterization of a novel tetravalent bispecific antibody that binds to hepatitis B virus surface antigens," *Molecular Immunol.*, 37: 1123-1130 (2000).
Pearlman and Nguyen, "Analysis of protein drugs," Chapter 6, In *Peptide and Protein Drug Delivery. Advances in Parenteral Sciences*, vol. 4, 1st ed. (Lee, ed.) Marcel Dekker, Inc., New York, 1991), pp. 247-301.
Peipp et al., "Bispecific antibodies targeting cancer cells," *Biochem. Soc. Trans.*, 30(4): 507-511 (2002).
Peng et al., "Experimental Use of Murine Lupus Models," *Methods Mol. Med.*, 102: 227-272 (2004).
Persic et al., "An integrated vector system for the eukaryotic expression of antibodies or their fragments after seletion from phage display libraries," *Gene*, 187: 9-18 (1997).
Petkova et al., "Enhanced half-life of genetically engineered human IgG1 antibodies in a humanized FcRn mouse model: Potential application in humorally mediated autoimmune disease," *Int. Immunol.*, 18: 1759-1769 (2006).
Petrey et al., "Using multiple structure alignments, fast model building, and energetic analysis in fold recognition and homology modeling." *Proteins*, 53: 430-435 (2003).
Piatesi et al., "Immunological Optimization of a Generic Hydrophobic Pocket for High Affinity Hapten Binding and Diels-Alder Activity," *ChemBioChem*, 5: 460-466 (2004).
Pimm et al., "A bispecific monoclonal antibody against methotrexate and a human tumour associated antigen augments cytotoxicity of methotrexate-carrier conjugate," *Br. J. Cancer*, 61: 503-513 (1990).
Plückthun et al., "New protein engineering approaches to multivalent and bispecific antibody fragments," *Immunotechnology*, 3: 83-105 (1997).
Poljak, R.J., "Production and structure of diabodies," *Structure*, 2: 1121-1123 (1994).
Portolano et al., "Lack of promiscuity in autoantigen-specific H and L chain combinations as revealed by human H and L chain 'roulette,'" *J. Immunol.*, 150:880-887 (1993).
Presta et al., "Humanization of an Antibody Directed Against IgE," *J. Immunol.*, 151(5): 2623-2632 (1993).
Presta, L.G., "Engineering of therapeutic antibodies to minimize immunogenicity and optimize function," *Adv. Drug. Del. Rev.*, 58: 640-656 (2006).
Presta, L.G., "Molecular engineering and design of therapeutic antibodies, " *Curr Opin. Immunol.*, 20: 460-470 (2008).

(56) References Cited

OTHER PUBLICATIONS

Presta, L.G., "Selection, design, and engineering of therapeutic antibodies," *J. Allergy Clin. Immunol.*, 116: 731-736 (2005).
Qu et al., "Bispecific anti-CD20/22 antibodies inhibit B-cell lymphoma proliferation by a unique mechanism of action," *Blood*, 111(4): 2211-2219 (2007).
*Remington: The Science and Practice of Pharmacy.* 21$^{st}$ ed. (Lippincott Williams & Wilkins, Philadelphia, 2005), pp. 745-747, 802-804, 838, 879-883, 889-890, and 1079-1082 (14 pages).
Reusch et al., "Anti-CD3 x Anti-Epidermal Growth Factor Receptor (EGFR) Bispecific Antibody Redirects T Cell Cytolytic Activity to EGFR-Positive Cancers In vitro and in an Animal Model," *Clin. Cancer Res.*, 12(1): 183-190 (2006).
Ridgway et al., "'Knobs-into-holes'engineering of antibody $C_H3$ domains for heavy chain heterodimerization," *Protein Eng.*, 9(7): 617-621 (1996).
Riechmann et al., "Reshaping human antibodies for therapy," *Nature*, 332: 323-327 (1988).
Riemer et al., "Matching of trastuzumab (Herceptin®) epitope mimics onto the surface of Her-2/neu—a new method of epitope definition" *Mol. Immunol.*, 42: 1121-1124 (2005).
Roberts et al., "RNA-peptide fusions for the in vitro selection of peptides and proteins," *Proc. Natl. Acad. Sci. USA*, 94: 12297-12302 (1997).
Robinson, C., "Gene therapy—proceeding from laboratory to clinic," *Trends Biotechnol.*, 11(5): 155 (1993) (1 page).
Rodeck et al., "Interations Between Growth Factor Receptors and Corresponding Monoclonal Antibodies in Human Tumors," *J. Cell Biochem.*, 35: 315-320 (1987).
Roguska et al., "A comparison of two murine monoclonal antibodies humanized by CDR-grafting and variable domain resurfacing," *Protein Eng.*, 9(10): 895-904 (1996).
Roguska et al., "Humanization of murine monoclonal antibodies through variable domain resurfacing," *Proc. Natl. Acad. Sci. USA*, 91: 969-973 (1994).
Ronday et al., "Tranexamic acid (TEA), an inhibitor of plasminogen activation reduces collagen crosslink excretion in arthritis," (Abstract No. 1541), *Arthritis Rheum.*, 39(9 Suppl.): S284 (1996) (1 page).
Ross, J.M., "Sulfasalazine (SSZ) toxicity: An assessment of American College of Rheumatology (ACR) 1 monitering guidelines for SSZ," (Abstract No. 1520), *Arthritis Rheum.*, 39(9 Suppl.): S281 (1996) (1 page).
Rudikoff et al., "Single amino acid substitution altering antigen binding specificity," *Proc. Natl. Acad. Sci. USA*, 79: 1979-1983 (1982).
Sambrook and Russell (eds.), *Molecular Cloning: A Laboratory Manual.* 3$^{rd}$ Ed. Cold Spring Harbor Laboratory Press, Cold Spring Harbor, NY, 2001; pp. 1.10-1.15, 1.84-1.87, 8.18-8.24, 15.54-15.59, and 16.47-16.55 (18 pages).
Santos et al., "Generation and Characterization of a Single Gene-encoded Single-Chain-Tetravalent Antitumor Antibody," *Clin. Cancer Res.*, 5 (Suppl.): 3118s-3123s (1999).
Satoh et al., "Non-fucosylated therapeutic antibodies as next-generation therapeutic antibodies," *Expert Opin. Biol. Ther.*, 6(11): 1161-1173 (2006).
Saudek et al., "A Preliminary Trial of the Programmable Implantable Medication System for insulin Delivery, " *N. Engl. J. Med.*, 321: 574-579 (1989).
Sawai et al., "Direct Production of the Fab Fragment Derived From the Sperm Immobilizing Antibody Using Polymerase Chain Reaction and cDNA Expression Vectors," *Am. J. Reprod. Immunol.*, 34: 26-34 (1995).
Schier et al., "Identification of functional and structural amino-acid residues by parsimonious mutagenesis," *Gene*, 169: 147-155 (1995).
Scholz, P., "Inhibition of the production and effect of TNF-alpha by iloprost: possible impact for treatment of rheumatoid arthritis," (Abstract No. 336), *Arthritis Rheum.*, 39(9Suppl.): S82 (1996).
Sefton, M.V., "Implantable Pumps," *CRC Crit. Rev. Biomed. Eng.*, 14(3): 201-240 (1987).
Seligmann et al., "Immunochemical Study of a Human Myeloma IgG1 Half Molecule," *Ann. Immunol.*, 129 C: 855-870 (1978).

Sewell et al., "$DAB_{486}IL$-2 fusion toxin in refractory rheumatoid arthritis," *Arthritis Rheum.*, 36(9): 1223-1233 (Sep. 1993).
Sfikakis et al., "Rituximab anti-B-cell therapy in systemic lupus erythematosus: Pointing to the future," *Curr. Opin. Rheumatol.*, 17: 550-557 (2005).
Shalaby et al., "Development of Humanized Bispecific Antibodies Reactive with Cytotoxic Lymphocytes and Tumor Cells Overexpressing the *HER2* Protooncogene," *J. Exp. Med.*, 175: 217-225 (1992).
Shapiro et al., "DNA Target Motifs of Somatic Mutagenesis in Antibody Genes," *Crit. Rev. Immunol.*, 22(3): 183-200 (2002).
Shepherd et al., "Novel 'inflammatory plague' pathology in presenilin-1 Alzheimer's disease," *Neuropathol. Appl. Neurobiol.*, 31: 503-511 (2005).
Shields et al., "Lack of Fucose on Human IgG1 N-Linked Oligosaccharide Improves Binding to Human FcγRIII and Antibody-dependent Cellular Toxicity," *J. Biol. Chem.*, 277(30): 26733-26740 (2002).
Shu et al., "Secretion of a single-gene-encoded immunoglobulin from myeloma cells," *Proc. Natl. Acad. Sci. USA*, 90: 7995-7999 (1993).
Sims et al., "A Humanized CD18 Antibody Can Block Function without Cell Destruction," *J. Immunol.*, 151(4): 2296-2308 (1993).
Skerra et al., "Assembly of a Functional Immunoglobulin $F_v$Fragment in *Escherichia coli*," *Science*, 240: 1038-1041 (1988).
Smith and Morrison, "Recombinant Polymeric IgG: An Approach to Engineering More Potent Antibodies" *Bio/Technology*, 12: 683-688 (1994).
Snibson et al., "Airway remodelling and inflammation in sheep lungs after chronic airway challenge with house dust mite," *Clin. Exp. Allergy*, 35: 146-152 (2005).
Soloman, B., "Alzheimer's Disease and Immunotherapy," *Curr. Alzheimer. Res.*, 1: 149-163 (2004).
Song et al., "Antibody Mediated Lung Targeting of Long-Circulating Emulsions," *PDA J. Pharm. Sci. Technol.*, 50: 372-377 (1996).
Staerz et al., "Hybrid antibodies can target sites for attack by T cells," *Nature*, 314: 628-631 (1985).
Stamper et al., "Crystal structure of the B7-1/CTLA-4 complex that inhibits human immune responses," *Nature*, 410: 606-611 (2001).
Stancovski et al., "Mechanistic aspects of the opposing effects of monoclonal antibodies to the ERBB2 receptor on tumor growth," *Proc. Natl. Acad. Sci. USA*, 88: 8691-8695 (1991).
Steffen et al., "Basic studies on enzyme therapy of immune complex diseases" *Wien Klin. Wochenschr.*, 97(8): 376-385 (1985) (Abstract only) (1 page).
Steinman et al., "Virtues and pitfalls of EAE for the development of therapies for multiple sclerosis," *Trends Immunol.*, 26(11): 565-571 (2005).
Stickler et al., "CD4+ T-cell epitope determination using unexposed human donor peripheral blood mononuclear cells," *J. Immunotherapy*, 23: 654-660 (2000).
Stolk et al., "Are severe non-hematologic side-effects on azathioprine treatment caused by altered purine enzyme activities?" (Abstract No. 1522), *Arthritis Rheum.*, 39(9 Suppl.): S281 (1996) (1 page).
Studnicka et al., "Human-engineered monoclonal antibodies retain full specific binding activity by preserving non-CDR complementarity-modulating residues," *Protein Eng.*, 7(6): 805-814 (1994).
Taiwan Patent Application No. 095130565: Taiwan Patent Office Search Report, dated Apr. 24, 2009.
Taylor et al., "A transgenic mouse that expresses a diversity of human sequence heavy and light chain immunoglobulins," *Nucl. Acids Res.*, 20: 6287-6295 (1992).
Teng et al., "Nogo Signaling and Non-Physical Injury-Induced Nervous System Pathology," *J. Neuroscience Research*, 79: 273-278 (2005).
Thies et al., "Folding and Association of the Antibody Domain $C_H3$: Prolyl Isomerization Preceeds Dimerization," *J. Mol. Biol.*, 293: 67-79 (1999).
Thoss et al., "Immunomodulation of rat antigen-induced arthritis by leflunomide alone and in combination with cyclosporin A," *Inflamm. Res.*, 45: 103-107 (1996).
Tol et al., "Chemotherapy, Bevacizumab, and Cetuximab in Metastatic Colorectal Cancer," *N. Engl. J. Med.*, 360(6): 563-572 (2009).

(56) References Cited

OTHER PUBLICATIONS

Tolstoshev, P., "Gene Therapy, Concepts, Current Trials and Future Directions," *Ann. Rev. Pharmacol. Toxicol.*, 32: 573-596 (1993).
Tuohy et al., "Spontaneous Regression of Primary Autoreactivity during Chronic Progression of Experimental Autoimmune Encephalomyelitis and Multiple Sclerosis," *J. Exp. Med.*, 189(7): 1033-1042 (1999).
Umana et al., "Engineered glycoforms of an antineuroblastoma IgG1 with optimized antibody-dependent cellular cytotoxic activity," *Nature Biotechnol.*, 17: 176-180 (1999).
Urlaub et al., "Isolation of Chinese hamster cell mutants deficient in dihydrofolate reductase activity," *Proc. Natl. Acad Sci. USA*, 77: 4216-4220 (1980).
U.S. Appl. No. 12/431,460, filed Apr. 28, 2009 by Ghayur et al.: Non-Final Office Action, Mar. 16, 2011.
U.S. Appl. No. 12/431,460, filed Apr. 28, 2009 by Ghayur et al.: Final Office Action, Nov. 2, 2011.
U.S. Appl. No. 12/477,668, filed Jun. 3, 2009 by Ghayur et al.: Non-Final Office Action, Sep. 8, 2011.
U.S. Appl. No. 12/477,668, filed Jun. 3, 2009 by Ghayur et al.: Final Office Action, May 3, 2012.
U.S. Appl. No. 12/477,711, filed Jun. 3, 2009 by Ghayur et al.: Non-Final Office Action, Aug. 11, 2011.
U.S. Appl. No. 12/477,711, filed Jun. 3, 2009 by Ghayur et al.: Final Office Action, Dec. 30, 2011.
U.S. Appl. No. 12/499,652, filed Jul. 8, 2009 by Ghayur et al.: Non-Final Office Action, May 10, 2011.
U.S. Appl. No. 12/499,652, filed Jul. 8, 2009 by Ghayur et al.: Final Office Action, Nov. 3, 2011.
U.S. Appl. No. 12/605,094, filed Oct. 23, 2009 by Ghayur et al.: Non-Final Office Action, Jun. 29, 2011.
U.S. Appl. No. 12/605,094, filed Oct. 23, 2009 by Ghayur et al.: Final Office Action, Nov. 30, 2011.
U.S. Appl. No. 12/631,483, filed Dec. 4, 2009 by Jakob et al.: Non-Final Office Action, Nov. 23, 2011.
U.S. Appl. No. 12/631,483, filed Dec. 4, 2009 by Jakob et al.: Final Office Action, Jul. 6, 2012.
U.S. Appl. No. 12/771,871, filed Apr. 30, 2010 by Ghayur et al.: Non-Final Office Action, May 16, 2012.
U.S. Appl. No. 12/771,874, filed Apr. 30, 2010 by Ghayur et al.: Non-Final Office Action, Sep. 7, 2012.
U.S. Appl. No. 12/771,874, filed Apr. 30, 2010 by Ghayur et al.: Final Office Action, Apr. 18, 2013.
U.S. Appl. No. 12/873,926, filed Sep. 1, 2010 by Ghayur et al.: Non-Final Office Action, Aug. 28, 2012.
U.S. Appl. No. 12/873,926, filed Sep. 1, 2010 by Ghayur et al.: Final Office Action, Mar. 12, 2013.
U.S. Appl. No. 12/905,474, filed Oct. 15, 2010 by Ghayur et al.: Non-Final Office Action, May 29, 2013.
U.S. Appl. No. 13/167,323, filed Jun. 23, 2011 by Ghayur et al.: Non-Final Office Action, Jun. 4, 2013.
U.S. Appl. No. 13/196,138, filed Aug. 2, 2011 by Ghayur et al.: Non-Final Office Action, Nov. 27, 2012.
U.S. Appl. No. 13/217,937, filed Aug. 25, 2011 by Ghayur et al.: Non-Final Office Action, Sep. 6, 2012.
U.S. Appl. No. 13/217,937, filed Aug. 25, 2011 by Ghayur et al.: Final Office Action, Mar. 20, 2013.
U.S. Appl. No. 13/286,707, filed Nov. 1, 2011 by Ghayur et al.: Non-Final Office Action, Feb. 25, 2013.
U.S. Appl. No. 13/286,707, filed Nov. 1, 2011 by Ghayur et al.: Final Office Action, Jul. 17, 2013.
Vaccaro et al., "Divergent activities of an engineered antibody in murine and human systems have implications for therapeutic, antibodies" *Proc. Natl. Acad. Sci. USA*, 103: 18709-18714 (2006).
Vajdos et al., "Comprehensive functional maps of the antigen-binding site of an anti-ErbB2 antibody obtained with shotgun scanning mutagenesis," *J. Mol. Biol.*, 320: 415-428 (2002).
Verhoeyen et al., "Reshaping Human Antibodies: Grafting an Antilysozyme Activity," *Science*, 239: 1534-1536 (1986).
Voet et al. (Eds.), *Biochemistry*, John Wiley & Sons, Inc., 1999; p. 1100.
Von Mehren et al., "Monoclonal Antibody Therapy for Cancer," *Ann. Rev. Med.*, 54: 343-369 (2003).
Wallick et al., "Glycosylation of a $V_H$ Residue of a Monoclonal Antibody Against α(1→6) Dextran Increases It Affinity for Antigen," *J. Exp. Med.*, 168: 1099-1109 (1988).
Wang et al., "Antibody Structure, Instability, and Formulation," *J. Pharm. Sci.*, 96(1): 1-26 (2007).
Ward et al., "Binding activities of a repertoire of single immunoglobulin variable domains secreted from *Escheria coli*," *Nature*, 341: 544-546 (1989).
West Jr. et al., "Crystal Structure and Immunoglobulin G Binding Properties of the Human Major Histocompatibility Complex-Related Fc Receptor," *Biochemistry*, 39: 9698-9708 (2000).
Wileman et al., "Association between Subunit Ectodomains Promote T Cell Antigen Receptor Assembly and Protect against Degradation in the ER," *J. Cell Biol.*, 122(1): 67-78 (1993).
Wing et al., "Ex-vivo whole blood cultures for predicting cytokine-release syndrome: Dependence on target antigen and antibody isotype," *Therapeutic Immunol.*, 2(4): 183-190 (1995).
Wooldridge et al., "Tricks with tetramers: How to get the most from muitimeric peptide-MHC," *Immunology*, 126: 147-164 (2009).
Wright et al., "Antibody variable region glycosylation: Position effects on antigen binding and carbohydrate structure," *EMBO J.*, 10(10): 2717-2723 (1991).
Wu and Grainger, "Drug/device combinations for local drug therapies and infection prophylaxis," *Biomaterials*, 27: 2450-2467 (2006).
Wu and Wu, "Delivery systems for gene therapy," *Biotherapy*, 3: 87-95 (1991).
Wu and Wu, "Receptor-mediated in Vitro Gene Transformation by a Soluble DNA Carrier System," *J. Biol. Chem.*, 262(10): 4429-4432 (1987).
Wu et al., "Humanization of a murine monoclonal antibody by simultaneous optimization of framework and CDR residues", *J. Mol. Biol.*, 294: 151-162 (1999).
Wu et al., "IL-18 receptor β-induced changes in the presentation of IL-18 binding sites affect ligand binding and signal transduction." *J. Immunol.*, 170: 5571-5577 (2003).
Wu et al., "Simultaneous targeting of multiple disease mediators by a dual-variable-domain immunoglobulin," *Nature Biotechnol.*, 25(11): 1290-1297 (2007).
Wu et al., "Simultaneous targeting of multiple disease mediators by a dual-variable-domain immunoglobulin," *Nature Biotechnology* (advance online publication, http://www.nature.com/naturebiotechnology), pp. 1-8 (published online Oct. 14, 2007).
Wu et al., "Tumor localization of anti-CEA single-chain Fvs: Improved targeting by non-covalent dimers," *Immunotechnology*, 2(1):21-36 (1996).
Wu et al., "Molecular construction and optimization of anti-human IL-1α/β dual variable domain immunoglobulin (DVD-lg™) molecules" *mAbs*, 1(4): 339-347 (2009).
Wu et al., "Generation and Characterization of a Dual Variable Domain Immunoglobulin (DVD-lg™) Molecule," in *Antibody Engineering*, vol. 2, R. Kontermann and S Dübel (Eds.), Springer-Verlag, 2010; pp. 239-250.
Wurm, F.M.. "Production of recombinant protein therapeutics in cultivated mammalian cells," *Nature Biotechnol.*, 22(11): 1393-1398 (2004).
Xu et al., "Recombinant DNA vaccine encoding multiple domains related to inhibition of neurite outgrowth: A potential strategy for axonal regeneration," *J. Neurochem.*, 91: 1018-1023 (2004).
Yelton et al., "Affinity Maturation of the BR96 Anti-Carcinoma Antibody by Codon-Based Mutagenesis," *J. Immunol.*, 155: 1994-2004 (1995).
Yonehara et al., "Involvement of apoptosis antigen Fas in clonal deletion of human thymocytes," *Int. Immunol.*, 6(12): 1849-1856 (1994).
Zapata et al., "Engineering linear F(ab')₂ fragments for efficient production in *Escherchia coli* and enhanced antiproliferative activity," *Protein Eng.*, 8(10): 1057-1062 (1995).

(56) References Cited

OTHER PUBLICATIONS

Zhang et al., "Inhibition of Cyclooxygenase-2 Rapidly Reverses Inflammatory Hyperalgesia and Prostaglandin $E_2$ Production," *J. Pharmacol. Exp. Ther.*, 283(3): 1069-1075 (1997).

Zola et al., "CD Molecules 2005: Human cell differentiation molecules," *Blood*, 106: 3123-3126 (2005).

Zuo et al., "An efficient route to the production of an IgG-like bispecific antibody," *Protein Eng.*, 13(5): 361-367 (2000).

* cited by examiner

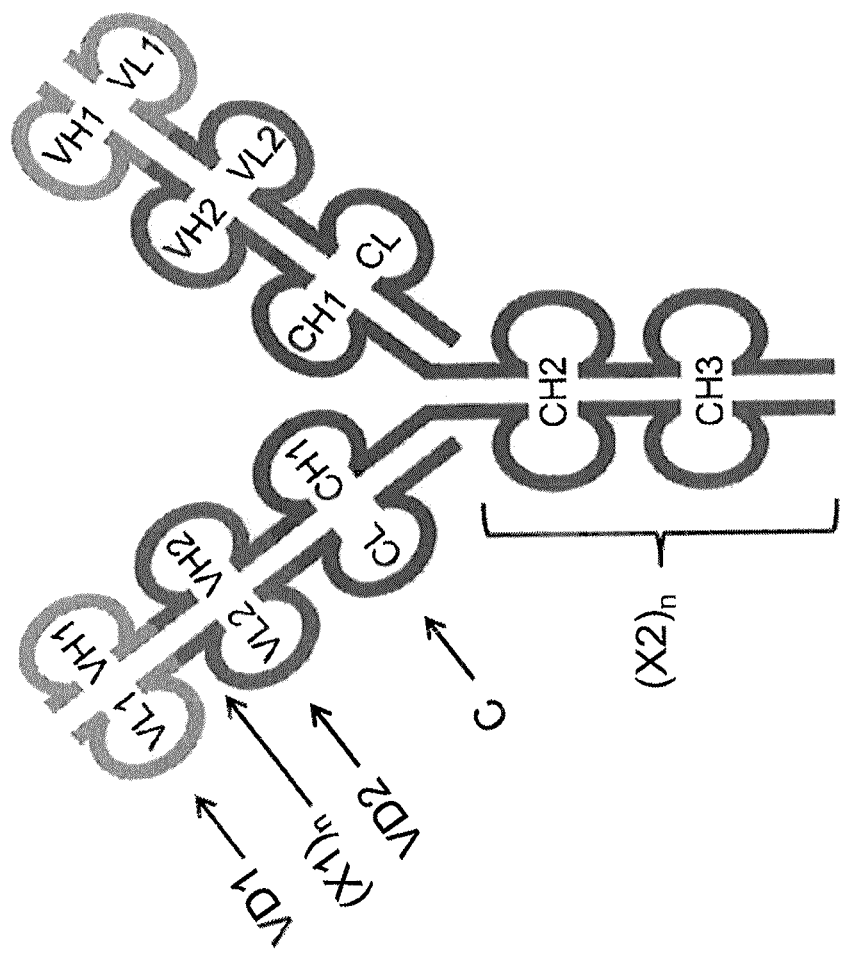

SEQUENCE LISTING

```
<160> NUMBER OF SEQ ID NOS: 56

<210> SEQ ID NO 1
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 1

Ala Lys Thr Thr Pro Lys Leu Glu Glu Gly Glu Phe Ser Glu Ala Arg
1               5                   10                  15

<210> SEQ ID NO 2
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Ala Lys Thr Thr Pro Lys Leu Glu Glu Gly Glu Phe Ser Glu Ala Arg
1               5                   10                  15
Val

<210> SEQ ID NO 3
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Ala Lys Thr Thr Pro Lys Leu Gly Gly
1               5

<210> SEQ ID NO 4
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Ser Ala Lys Thr Thr Pro Lys Leu Gly Gly
1               5                   10

<210> SEQ ID NO 5
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Ser Ala Lys Thr Thr Pro
1               5

<210> SEQ ID NO 6
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Arg Ala Asp Ala Ala Pro
1               5

<210> SEQ ID NO 7
```

```
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Arg Ala Asp Ala Ala Pro Thr Val Ser
1               5

<210> SEQ ID NO 8
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Arg Ala Asp Ala Ala Ala Ala Gly Gly Pro Gly Ser
1               5                   10

<210> SEQ ID NO 9
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Arg Ala Asp Ala Ala Ala Ala Gly Gly Gly Gly Ser Gly Gly Gly Gly
1               5                   10                  15

Ser Gly Gly Gly Gly Ser Gly Gly Gly Gly Ser
            20                  25

<210> SEQ ID NO 10
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Ser Ala Lys Thr Thr Pro Lys Leu Glu Glu Gly Glu Phe Ser Glu Ala
1               5                   10                  15

Arg Val

<210> SEQ ID NO 11
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Ala Asp Ala Ala Pro
1               5

<210> SEQ ID NO 12
<211> LENGTH: 12
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 12

Ala Asp Ala Ala Pro Thr Val Ser Ile Phe Pro Pro
1               5                   10

<210> SEQ ID NO 13
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Thr Val Ala Ala Pro
1               5

<210> SEQ ID NO 14
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Thr Val Ala Ala Pro Ser Val Phe Ile Phe Pro Pro
1               5                   10

<210> SEQ ID NO 15
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Gln Pro Lys Ala Ala Pro
1               5

<210> SEQ ID NO 16
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Gln Pro Lys Ala Ala Pro Ser Val Thr Leu Phe Pro Pro
1               5                   10

<210> SEQ ID NO 17
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Ala Lys Thr Thr Pro Pro
1               5
```

```
<210> SEQ ID NO 18
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Ala Lys Thr Thr Pro Pro Ser Val Thr Pro Leu Ala Pro
1               5                   10

<210> SEQ ID NO 19
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Ala Lys Thr Thr Ala Pro
1               5

<210> SEQ ID NO 20
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Ala Lys Thr Thr Ala Pro Ser Val Tyr Pro Leu Ala Pro
1               5                   10

<210> SEQ ID NO 21
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Ala Ser Thr Lys Gly Pro
1               5

<210> SEQ ID NO 22
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Ala Ser Thr Lys Gly Pro Ser Val Phe Pro Leu Ala Pro
1               5                   10

<210> SEQ ID NO 23
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23
```

```
Gly Gly Gly Gly Ser Gly Gly Gly Gly Ser Gly Gly Gly Gly Ser
1               5                   10                  15

<210> SEQ ID NO 24
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Gly Glu Asn Lys Val Glu Tyr Ala Pro Ala Leu Met Ala Leu Ser
1               5                   10                  15

<210> SEQ ID NO 25
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Gly Pro Ala Lys Glu Leu Thr Pro Leu Lys Glu Ala Lys Val Ser
1               5                   10                  15

<210> SEQ ID NO 26
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Gly His Glu Ala Ala Ala Val Met Gln Val Gln Tyr Pro Ala Ser
1               5                   10                  15

<210> SEQ ID NO 27
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Thr Val Ala Ala Pro Ser Val Phe Ile Phe Pro Pro Thr Val Ala Ala
1               5                   10                  15

Pro Ser Val Phe Ile Phe Pro Pro
            20

<210> SEQ ID NO 28
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Ala Ser Thr Lys Gly Pro Ser Val Phe Pro Leu Ala Pro Ala Ser Thr
1               5                   10                  15

Lys Gly Pro Ser Val Phe Pro Leu Ala Pro
            20                  25
```

```
<210> SEQ ID NO 29
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Gly Gly Gly Gly Ser
1               5

<210> SEQ ID NO 30
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Glu Val Thr Leu Arg Glu Ser Gly Pro Gly Leu Val Lys Pro Thr Gln
1               5                   10                  15

Thr Leu Thr Leu Thr Cys Thr Leu Tyr Gly Phe Ser Leu Ser Thr Ser
            20                  25                  30

Asp Met Gly Val Asp Trp Ile Arg Gln Pro Pro Gly Lys Gly Leu Glu
        35                  40                  45

Trp Leu Ala His Ile Trp Trp Asp Asp Val Lys Arg Tyr Asn Pro Ala
    50                  55                  60

Leu Lys Ser Arg Leu Thr Ile Ser Lys Asp Thr Ser Lys Asn Gln Val
65                  70                  75                  80

Val Leu Lys Leu Thr Ser Val Asp Pro Val Asp Thr Ala Thr Tyr Tyr
                85                  90                  95

Cys Ala Arg Thr Val Ser Ser Gly Tyr Ile Tyr Tyr Ala Met Asp Tyr
            100                 105                 110

Trp Gly Gln Gly Thr Leu Val Thr Val Ser Ser
        115                 120

<210> SEQ ID NO 31
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Asp Ile Gln Met Thr Gln Ser Pro Ser Ser Leu Ser Ala Ser Val Gly
1               5                   10                  15

Asp Arg Val Thr Ile Ser Cys Arg Ala Ser Gln Asp Ile Arg Asn Tyr
            20                  25                  30

Leu Asn Trp Tyr Gln Gln Lys Pro Gly Lys Ala Pro Lys Leu Leu Ile
        35                  40                  45

Phe Tyr Thr Ser Lys Leu His Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Ile Ala Thr Tyr Tyr Cys Gln Gln Gly Leu Thr Pro Pro Leu
                85                  90                  95
```

Thr Phe Gly Gly Gly Thr Lys Val Glu Ile Lys Arg
            100                 105

<210> SEQ ID NO 32
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Thr Tyr
            20                  25                  30

Gly Val Ser Trp Val Arg Gln Ala Pro Gly Gln Gly Leu Glu Trp Met
        35                  40                  45

Gly Glu Ile Tyr Pro Gly Asn Tyr Asn Thr Tyr Asn Glu Lys Phe
    50                  55                  60

Arg Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Trp Arg Thr Ser Tyr Ser Asp Tyr Gly Tyr Phe Asp Tyr
            100                 105                 110

Trp Gly Gln Gly Thr Thr Val Thr Val Ser Ser
        115                 120

<210> SEQ ID NO 33
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val His Ser
            20                  25                  30

His Gly Asn Thr Tyr Leu His Trp Tyr Gln Gln Arg Pro Gly Gln Ser
        35                  40                  45

Pro Arg Leu Leu Ile Tyr Thr Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Val Pro Tyr Thr Phe Gly Gly Gly Thr Lys Val Glu Ile Lys
            100                 105                 110

Arg

<210> SEQ ID NO 34
<211> LENGTH: 119
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 34

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met His Trp Val Arg Gln Ala Pro Gly Gln Gly Leu Glu Trp Ile
        35                  40                  45

Gly Asn Ile Asn Pro Lys Gly Gly Ser Asn Ile Tyr Asn Glu Lys Phe
50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Leu Asp Tyr Phe Gly Asp Ser Phe Asp Leu Trp Gly Gln Gly
            100                 105                 110

Thr Thr Val Thr Val Ser Ser
        115

<210> SEQ ID NO 35
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Tyr
            20                  25                  30

Leu Asn Trp Tyr Gln Gln Lys Pro Gly Lys Ala Pro Lys Leu Leu Ile
        35                  40                  45

Tyr Tyr Ala Ser Asn Leu Glu Val Gly Val Pro Ser Arg Phe Ser Gly
50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Asp Asn Arg Phe Pro Tyr
                85                  90                  95

Thr Phe Gly Gly Gly Thr Lys Val Glu Ile Lys Arg
            100                 105

<210> SEQ ID NO 36
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Glu Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asp Tyr
            20                  25                  30

Glu Ile His Trp Val Arg Gln Ala Pro Gly Gln Gly Leu Glu Trp Met
        35                  40                  45

Gly Val Asn Asp Pro Glu Ser Gly Gly Thr Phe Tyr Asn Gln Lys Phe
            50                  55                  60

Asp Gly Arg Val Thr Leu Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Tyr Ser Lys Trp Asp Ser Phe Asp Gly Met Asp Tyr Trp Gly
            100                 105                 110

Gln Gly Thr Thr Val Thr Val Ser Ser
            115                 120

<210> SEQ ID NO 37
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Asp Ile Gln Met Thr Gln Ser Pro Ser Ser Leu Ser Ala Ser Val Gly
1               5                   10                  15

Asp Arg Val Thr Ile Thr Cys Arg Ala Ser Ser Gly Ile Ile Ser Tyr
            20                  25                  30

Ile Asp Trp Phe Gln Gln Lys Pro Gly Lys Ala Pro Lys Arg Leu Ile
        35                  40                  45

Tyr Ala Thr Phe Asp Leu Ala Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Arg Gln Val Gly Ser Tyr Pro Glu
                85                  90                  95

Thr Phe Gly Gln Gly Thr Lys Leu Glu Ile Lys Arg
            100                 105

<210> SEQ ID NO 38
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Glu Val Gln Leu Val Gln Ser Gly Ala Glu Val Lys Lys Pro Gly Ser
1               5                   10                  15

Ser Val Lys Val Ser Cys Lys Ala Ser Gly Gly Ser Phe Gly Gly Tyr
            20                  25                  30

Gly Ile Gly Trp Val Arg Gln Ala Pro Gly Gln Gly Leu Glu Trp Met
        35                  40                  45

Gly Gly Ile Thr Pro Phe Phe Gly Phe Ala Asp Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Gly Leu Thr Ser Asp Asp Thr Ala Val Tyr Tyr Cys
                85                  90                  95

Ala Arg Asp Pro Asn Glu Phe Trp Asn Gly Tyr Tyr Ser Thr His Asp
            100                 105                 110

```
Phe Asp Ser Trp Gly Gln Gly Thr Thr Val Thr Val Ser Ser
            115                 120                 125

<210> SEQ ID NO 39
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Glu Ile Val Leu Thr Gln Ser Pro Asp Phe Gln Ser Val Thr Pro Lys
1               5                   10                  15

Glu Lys Val Thr Ile Thr Cys Arg Ala Ser Gln Asp Ile Gly Ser Glu
            20                  25                  30

Leu His Trp Tyr Gln Gln Lys Pro Asp Gln Pro Pro Lys Leu Leu Ile
        35                  40                  45

Lys Tyr Ala Ser His Ser Thr Ser Gly Val Pro Ser Arg Phe Ser Gly
50                  55                  60

Ser Gly Ser Gly Thr Asp Phe Thr Leu Thr Ile Asn Gly Leu Glu Ala
65                  70                  75                  80

Glu Asp Ala Gly Thr Tyr Tyr Cys His Gln Thr Asp Ser Leu Pro Tyr
                85                  90                  95

Thr Phe Gly Pro Gly Thr Lys Val Asp Ile Lys Arg
            100                 105

<210> SEQ ID NO 40
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Glu Val Gln Leu Val Gln Ser Gly Ala Glu Val Lys Lys Pro Gly Glu
1               5                   10                  15

Ser Val Lys Ile Ser Cys Lys Ala Ser Gly Gly Ser Phe Arg Ser Tyr
            20                  25                  30

Gly Ile Ser Trp Val Arg Gln Ala Pro Gly Gln Gly Leu Glu Trp Met
        35                  40                  45

Gly Gly Ile Thr His Phe Phe Gly Ile Thr Asp Tyr Ala Gln Lys Phe
50                  55                  60

Gln Gly Arg Val Thr Ile Thr Ala Asp Glu Ser Thr Thr Thr Ala Tyr
65                  70                  75                  80

Met Glu Leu Ser Gly Leu Thr Ser Asp Asp Thr Ala Val Tyr Tyr Cys
                85                  90                  95

Ala Arg Glu Pro Asn Asp Phe Trp Asn Gly Tyr Tyr Asp Thr His Asp
            100                 105                 110

Phe Asp Ser Trp Gly Gln Gly Thr Thr Val Thr Val Ser Ser
            115                 120                 125

<210> SEQ ID NO 41
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 41

Glu Ile Val Leu Thr Gln Ser Pro Asp Phe Gln Ser Val Thr Pro Lys
1               5                   10                  15

Glu Lys Val Thr Ile Thr Cys Arg Ala Ser Gln Asn Ile Gly Ser Glu
            20                  25                  30

Leu His Trp Tyr Gln Gln Lys Pro Asp Gln Ser Pro Lys Leu Leu Ile
        35                  40                  45

Lys Tyr Ala Ser His Ser Ile Ser Gly Val Pro Ser Arg Phe Ser Gly
    50                  55                  60

Ser Gly Ser Gly Thr Asp Phe Thr Leu Thr Ile Asn Gly Leu Glu Ala
65                  70                  75                  80

Glu Asp Ala Ala Thr Tyr Tyr Cys His Gln Ser Asp Thr Leu Pro His
                85                  90                  95

Thr Phe Gly Gln Gly Thr Lys Val Asp Ile Lys Arg
            100                 105

<210> SEQ ID NO 42
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Glu Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asp Tyr
            20                  25                  30

Glu Ile His Trp Val Arg Gln Ala Pro Gly Gln Gly Leu Glu Trp Ile
        35                  40                  45

Gly Val Asn Asp Pro Glu Ser Gly Gly Thr Phe Tyr Asn Gln Lys Phe
    50                  55                  60

Asp Gly Arg Ala Thr Leu Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Tyr Tyr Arg Tyr Glu Ser Phe Tyr Gly Met Asp Tyr Trp Gly
            100                 105                 110

Gln Gly Thr Thr Val Thr Val Ser Ser
        115                 120

<210> SEQ ID NO 43
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Glu Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Asp Asp Tyr
            20                  25                  30

Glu Ile His Trp Val Arg Gln Ala Pro Gly Gln Gly Leu Glu Trp Ile
        35                  40                  45

Gly Val Asn Asp Pro Glu Ser Gly Gly Thr Phe Tyr Asn Gln Lys Phe
        50                  55                  60

Asp Gly Arg Ala Thr Leu Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Thr Arg Tyr Asp Lys Trp Asp Ser Phe Tyr Gly Met Asp Tyr Trp Gly
                100                 105                 110

Gln Gly Thr Thr Val Thr Val Ser Ser
            115                 120

<210> SEQ ID NO 44
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Glu Val Gln Leu Val Gln Ser Gly Ala Glu Val Lys Lys Pro Gly Ser
 1               5                  10                  15

Ser Val Lys Val Ser Cys Lys Ala Ser Gly Tyr Thr Phe Thr Asp Tyr
                 20                  25                  30

Glu Ile His Trp Val Arg Gln Ala Pro Gly Gln Gly Leu Glu Trp Met
             35                  40                  45

Gly Val Asn Asp Pro Glu Ser Gly Gly Thr Phe Tyr Asn Gln Lys Phe
        50                  55                  60

Asp Gly Arg Val Thr Leu Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Thr Arg Tyr Ser Lys Trp Asp Ser Phe Asp Gly Met Asp Tyr Trp Gly
                100                 105                 110

Gln Gly Thr Thr Val Thr Val Ser Ser
            115                 120

<210> SEQ ID NO 45
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

Glu Val Gln Leu Val Gln Ser Gly Ala Glu Val Lys Lys Pro Gly Ser
 1               5                  10                  15

Ser Val Lys Val Ser Cys Lys Ala Ser Gly Tyr Thr Phe Thr Asp Tyr
                 20                  25                  30

Glu Ile His Trp Val Arg Gln Ala Pro Gly Gln Gly Leu Glu Trp Ile
             35                  40                  45

Gly Val Asn Asp Pro Asp Ser Gly Gly Thr Leu Tyr Asn Gln Lys Phe
        50                  55                  60

Asp Gly Arg Val Thr Leu Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

```
Thr Arg Tyr Asp Lys Trp Tyr Ser Phe Glu Gly Met Asp Ile Trp Gly
                100                 105                 110

Gln Gly Thr Thr Val Thr Val Ser Ser
        115                 120

<210> SEQ ID NO 46
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

Glu Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asp Tyr
            20                  25                  30

Glu Ile His Trp Val Arg Gln Ala Pro Gly Gln Gly Leu Glu Trp Ile
        35                  40                  45

Gly Val Asn Asp Pro Glu Ser Gly Gly Thr Phe Tyr Asn Gln Lys Phe
    50                  55                  60

Asp Gly Arg Val Thr Leu Ser Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Tyr Asp Lys Trp Tyr Ser Phe Glu Gly Met Asp Tyr Trp Gly
                100                 105                 110

Gln Gly Thr Thr Val Thr Val Ser Ser
        115                 120

<210> SEQ ID NO 47
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

Glu Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Ser Asp Tyr
            20                  25                  30

Glu Ile His Trp Val Arg Gln Ala Pro Gly Gln Gly Leu Glu Trp Met
        35                  40                  45

Gly Val Asn Asp Pro Glu Ser Gly Gly Thr Phe Tyr Asn Gln Lys Phe
    50                  55                  60

Asp Gly Arg Val Thr Leu Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Tyr Asp Lys Trp Tyr Ser Phe Glu Gly Met Asp Ile Trp Gly
                100                 105                 110

Gln Gly Thr Thr Val Thr Val Ser Ser
        115                 120

<210> SEQ ID NO 48
<211> LENGTH: 121
```

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

Glu Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Ser Asp Tyr
                20                  25                  30

Glu Ile His Trp Val Arg Gln Ala Pro Gly Gln Gly Leu Glu Trp Met
            35                  40                  45

Gly Val Asn Asp Pro Glu Ser Gly Gly Thr Phe Tyr Asn Gln Lys Phe
    50                  55                  60

Asp Gly Arg Val Thr Leu Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Tyr Asp Lys Tyr Trp Ser Phe Glu Gly Met Asp Tyr Trp Gly
                100                 105                 110

Gln Gly Thr Thr Val Thr Val Ser Ser
            115                 120

<210> SEQ ID NO 49
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

Glu Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asp Tyr
                20                  25                  30

Glu Ile His Trp Val Arg Gln Ala Pro Gly Gln Gly Leu Glu Trp Met
            35                  40                  45

Gly Val Asn Asp Pro Glu Ser Gly Gly Thr Phe Tyr Asn Gln Lys Phe
    50                  55                  60

Asp Gly Arg Val Thr Leu Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Tyr Asp Lys Trp Tyr Ser Phe Glu Gly Met Asp Ile Trp Gly
                100                 105                 110

Gln Gly Thr Thr Val Thr Val Ser Ser
            115                 120

<210> SEQ ID NO 50
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

Asp Ile Gln Met Thr Gln Ser Pro Ser Ser Leu Ser Ala Ser Val Gly
```

```
1               5                   10                  15
Asp Arg Val Thr Ile Thr Cys Ser Ala Ser Ser Gly Ser Ile Ser Tyr
                20                  25                  30

Ile Asp Trp Phe Gln Gln Lys Pro Gly Lys Ala Pro Lys Arg Leu Ile
                35                  40                  45

Tyr Ala Thr Phe Glu Leu Ala Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys His Gln Leu Gly Ser Tyr Pro Asp
                85                  90                  95

Thr Phe Gly Gln Gly Thr Lys Leu Glu Ile Lys
                100                 105
```

<210> SEQ ID NO 51
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Ser Gly Ile Ile Ser Tyr
                20                  25                  30

Ile Asp Trp Phe Gln Gln Lys Pro Gly Lys Ala Pro Lys Arg Leu Ile
                35                  40                  45

Tyr Ala Thr Phe Asp Leu Ala Ser Gly Val Pro Ser Arg Phe Ser Gly
        50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Arg Gln Val Gly Ser Tyr Pro Glu
                85                  90                  95

Thr Phe Gly Gln Gly Thr Lys Leu Glu Ile Lys
                100                 105
```

<210> SEQ ID NO 52
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 52

```
Asp Ile Gln Met Thr Gln Ser Pro Ser Ser Leu Ser Ala Ser Val Gly
1               5                   10                  15

Asp Arg Val Thr Ile Thr Cys Ser Ala Ser Ser Gly Ile Ile Ser Ser
                20                  25                  30

Ile Asp Trp Phe Gln Gln Lys Pro Gly Lys Ala Pro Lys Arg Leu Ile
                35                  40                  45

Tyr Ala Thr Phe Ala Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Ser Gln Met Ser Ser Tyr Pro His
```

Thr Phe Gly Gln Gly Thr Lys Leu Glu Ile Lys
            100                 105

<210> SEQ ID NO 53
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 53

Asp Ile Gln Met Thr Gln Ser Pro Ser Ser Leu Ser Ala Ser Val Gly
1               5                   10                  15

Asp Arg Val Thr Ile Thr Cys Ser Ala Ser Ser Asp Ile Ser Ser Tyr
            20                  25                  30

Leu Asn Trp Phe Gln Gln Lys Pro Gly Lys Ser Pro Lys Arg Leu Ile
        35                  40                  45

Tyr Arg Thr Ser Glu Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Trp Ser Ser Tyr Pro Trp
                85                  90                  95

Thr Phe Gly Gln Gly Thr Lys Leu Glu Ile Lys
            100                 105

<210> SEQ ID NO 54
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 54

Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Gly Ile Arg Ser Tyr
            20                  25                  30

Ile Asp Trp Phe Gln Gln Lys Pro Gly Lys Ser Pro Lys Arg Leu Ile
        35                  40                  45

Tyr Ala Thr Phe Asp Leu Ala Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Arg Gln Val Gly Asn Tyr Pro Gly
                85                  90                  95

Thr Phe Gly Gln Gly Thr Lys Leu Glu Ile Lys
            100                 105

<210> SEQ ID NO 55
<211> LENGTH: 121
<212> TYPE: PRT
<213> ORGANISM: Artificial Sequence
<220> FEATURE:
<223> OTHER INFORMATION: Description of Artificial Sequence: Synthetic
      consensus sequence
<220> FEATURE:
<221> NAME/KEY: MOD_RES

```
<222> LOCATION: (16)..(16)
<223> OTHER INFORMATION: Ser, Asp, Ala, Glu, Asn or Pro
<220> FEATURE:
<221> NAME/KEY: MOD_RES
<222> LOCATION: (17)..(17)
<223> OTHER INFORMATION: Ser or Glu
<220> FEATURE:
<221> NAME/KEY: MOD_RES
<222> LOCATION: (26)..(26)
<223> OTHER INFORMATION: Gly or Met
<220> FEATURE:
<221> NAME/KEY: MOD_RES
<222> LOCATION: (28)..(28)
<223> OTHER INFORMATION: Thr or Ile
<220> FEATURE:
<221> NAME/KEY: MOD_RES
<222> LOCATION: (30)..(30)
<223> OTHER INFORMATION: Thr or Asp
<220> FEATURE:
<221> NAME/KEY: MOD_RES
<222> LOCATION: (31)..(31)
<223> OTHER INFORMATION: Asp, Ile or Met
<220> FEATURE:
<221> NAME/KEY: MOD_RES
<222> LOCATION: (33)..(33)
<223> OTHER INFORMATION: Glu or Ser
<220> FEATURE:
<221> NAME/KEY: MOD_RES
<222> LOCATION: (34)..(34)
<223> OTHER INFORMATION: Ile or Leu
<220> FEATURE:
<221> NAME/KEY: MOD_RES
<222> LOCATION: (66)..(66)
<223> OTHER INFORMATION: Gly, Val or Ile
<220> FEATURE:
<221> NAME/KEY: MOD_RES
<222> LOCATION: (68)..(68)
<223> OTHER INFORMATION: Ala or Ile
<220> FEATURE:
<221> NAME/KEY: MOD_RES
<222> LOCATION: (82)..(82)
<223> OTHER INFORMATION: Glu, Trp, Phe or Asn
<220> FEATURE:
<221> NAME/KEY: MOD_RES
<222> LOCATION: (83)..(83)
<223> OTHER INFORMATION: Leu, Ser or Phe
<220> FEATURE:
<221> NAME/KEY: MOD_RES
<222> LOCATION: (84)..(84)
<223> OTHER INFORMATION: Ser, Asp, Met, Tyr, Val or Asn
<220> FEATURE:
<221> NAME/KEY: MOD_RES
<222> LOCATION: (85)..(85)
<223> OTHER INFORMATION: Ser, Lys, Phe, Ala, Arg, Met or His
<220> FEATURE:
<221> NAME/KEY: MOD_RES
<222> LOCATION: (86)..(86)
<223> OTHER INFORMATION: Leu, Trp, Ser or Gln
<220> FEATURE:
<221> NAME/KEY: MOD_RES
<222> LOCATION: (87)..(87)
<223> OTHER INFORMATION: Arg or Asp
<220> FEATURE:
<221> NAME/KEY: MOD_RES
<222> LOCATION: (88)..(88)
<223> OTHER INFORMATION: Ser, Gly, Tyr, His or Ala
<220> FEATURE:
<221> NAME/KEY: MOD_RES
<222> LOCATION: (89)..(89)
<223> OTHER INFORMATION: Glu, Leu, Asn, Ser or Phe
<220> FEATURE:
<221> NAME/KEY: MOD_RES
<222> LOCATION: (90)..(90)
<223> OTHER INFORMATION: Asp or Glu
<220> FEATURE:
<221> NAME/KEY: MOD_RES
<222> LOCATION: (92)..(92)
<223> OTHER INFORMATION: Ala or Cys
<220> FEATURE:
```

<221> NAME/KEY: MOD_RES
<222> LOCATION: (93)..(93)
<223> OTHER INFORMATION: Val or Ile

<400> SEQUENCE: 55

Glu Val Gln Leu Val Gln Ser Gly Ala Glu Val Lys Lys Pro Gly Xaa
1               5                   10                  15

Xaa Val Lys Val Ser Cys Lys Ala Ser Xaa Tyr Xaa Phe Xaa Xaa Tyr
            20                  25                  30

Xaa Xaa His Trp Val Arg Gln Ala Pro Gly Gln Gly Leu Glu Trp Ile
        35                  40                  45

Gly Val Asn Asp Pro Glu Ser Gly Gly Thr Phe Tyr Asn Gln Lys Phe
50                  55                  60

Asp Xaa Arg Xaa Thr Leu Thr Ala Asp Lys Ser Thr Ser Thr Ala Tyr
65              70                  75                  80

Met Xaa Xaa Xaa Xaa Xaa Xaa Xaa Thr Xaa Xaa Tyr Tyr Cys
            85                  90                  95

Thr Arg Tyr Tyr Arg Tyr Glu Ser Phe Tyr Gly Met Asp Tyr Trp Gly
            100                 105                 110

Gln Gly Thr Thr Val Thr Val Ser Ser
        115                 120

<210> SEQ ID NO 56
<211> LENGTH: 107
<212> TYPE: PRT
<213> ORGANISM: Artificial Sequence
<220> FEATURE:
<223> OTHER INFORMATION: Description of Artificial Sequence: Synthetic
      consensus sequence
<220> FEATURE:
<221> NAME/KEY: MOD_RES
<222> LOCATION: (3)..(3)
<223> OTHER INFORMATION: Gln or Met
<220> FEATURE:
<221> NAME/KEY: MOD_RES
<222> LOCATION: (13)..(13)
<223> OTHER INFORMATION: Ala or Lys
<220> FEATURE:
<221> NAME/KEY: MOD_RES
<222> LOCATION: (14)..(14)
<223> OTHER INFORMATION: Ser or Arg
<220> FEATURE:
<221> NAME/KEY: MOD_RES
<222> LOCATION: (15)..(15)
<223> OTHER INFORMATION: Val, Asp, Gln, Ala, Ile, Thr or Glu
<220> FEATURE:
<221> NAME/KEY: MOD_RES
<222> LOCATION: (16)..(16)
<223> OTHER INFORMATION: Gly, Gln, Ser, Leu or Met
<220> FEATURE:
<221> NAME/KEY: MOD_RES
<222> LOCATION: (17)..(17)
<223> OTHER INFORMATION: Asp, Gly, Val, Asn, Phe, Leu, Pro or Lys
<220> FEATURE:
<221> NAME/KEY: MOD_RES
<222> LOCATION: (18)..(18)
<223> OTHER INFORMATION: Arg, Ile, Ser, Gly, Thr, Pro, Leu, Asp or Cys
<220> FEATURE:
<221> NAME/KEY: MOD_RES
<222> LOCATION: (19)..(19)
<223> OTHER INFORMATION: Val, Arg, Asn, Asp, Pro, Ile, Phe or Ala
<220> FEATURE:
<221> NAME/KEY: MOD_RES
<222> LOCATION: (20)..(20)
<223> OTHER INFORMATION: Thr, Arg or Ser
<220> FEATURE:
<221> NAME/KEY: MOD_RES
<222> LOCATION: (21)..(21)
<223> OTHER INFORMATION: Ile, Cys, Val, Phe, Ser, Gln or Gly
<220> FEATURE:

-continued

```
<221> NAME/KEY: MOD_RES
<222> LOCATION: (22)..(22)
<223> OTHER INFORMATION: Thr, Leu or Asn
<220> FEATURE:
<221> NAME/KEY: MOD_RES
<222> LOCATION: (23)..(23)
<223> OTHER INFORMATION: Cys or Asp
<220> FEATURE:
<221> NAME/KEY: MOD_RES
<222> LOCATION: (25)..(25)
<223> OTHER INFORMATION: Ala or Tyr
<220> FEATURE:
<221> NAME/KEY: MOD_RES
<222> LOCATION: (28)..(28)
<223> OTHER INFORMATION: May or may not be present
<220> FEATURE:
<221> NAME/KEY: MOD_RES
<222> LOCATION: (29)..(29)
<223> OTHER INFORMATION: Ser, Ala, Gln or Pro
<220> FEATURE:
<221> NAME/KEY: MOD_RES
<222> LOCATION: (30)..(30)
<223> OTHER INFORMATION: Ile, Asp, Ser, Gly or Thr
<220> FEATURE:
<221> NAME/KEY: MOD_RES
<222> LOCATION: (31)..(31)
<223> OTHER INFORMATION: Ser, Glu, Leu or His
<220> FEATURE:
<221> NAME/KEY: MOD_RES
<222> LOCATION: (32)..(32)
<223> OTHER INFORMATION: Tyr, Leu, Gly, Gln or Trp
<220> FEATURE:
<221> NAME/KEY: MOD_RES
<222> LOCATION: (33)..(33)
<223> OTHER INFORMATION: Ile or Ala
<220> FEATURE:
<221> NAME/KEY: MOD_RES
<222> LOCATION: (34)..(34)
<223> OTHER INFORMATION: Tyr or Arg
<220> FEATURE:
<221> NAME/KEY: MOD_RES
<222> LOCATION: (36)..(36)
<223> OTHER INFORMATION: Phe or Ser
<220> FEATURE:
<221> NAME/KEY: MOD_RES
<222> LOCATION: (37)..(37)
<223> OTHER INFORMATION: Gln or Asp
<220> FEATURE:
<221> NAME/KEY: MOD_RES
<222> LOCATION: (39)..(39)
<223> OTHER INFORMATION: Lys or Gln
<220> FEATURE:
<221> NAME/KEY: MOD_RES
<222> LOCATION: (76)..(76)
<223> OTHER INFORMATION: Ser, Arg, Gln, Leu, Asn, Tyr, Val or Ala
<220> FEATURE:
<221> NAME/KEY: MOD_RES
<222> LOCATION: (77)..(77)
<223> OTHER INFORMATION: Ser, Gln, Ile, Thr or Asp
<220> FEATURE:
<221> NAME/KEY: MOD_RES
<222> LOCATION: (78)..(78)
<223> OTHER INFORMATION: Leu, Val, Trp, Met, Lys, Phe, Pro or Gly
<220> FEATURE:
<221> NAME/KEY: MOD_RES
<222> LOCATION: (79)..(79)
<223> OTHER INFORMATION: Gln, Gly, Thr, Met, Asn, Arg, Lys, Ala, Asp,
      Trp or His
<220> FEATURE:
<221> NAME/KEY: MOD_RES
<222> LOCATION: (80)..(80)
<223> OTHER INFORMATION: Pro, Asn, Ile, Arg, Phe, Thr, Tyr, Leu, Met or
      Cys
<220> FEATURE:
<221> NAME/KEY: MOD_RES
<222> LOCATION: (81)..(81)
<223> OTHER INFORMATION: Glu, Arg, His, Gln or Asn
<220> FEATURE:
<221> NAME/KEY: MOD_RES
```

```
<222> LOCATION: (82)..(82)
<223> OTHER INFORMATION: Asp, Glu, Leu, Gly, Phe, Tyr, Pro or Ile

<400> SEQUENCE: 56

Asp Ile Xaa Leu Thr Gln Ser Pro Ser Ser Leu Ser Xaa Xaa Xaa Xaa
1               5                   10                  15

Xaa Xaa Xaa Xaa Xaa Xaa Ser Xaa Ser Ser Met Xaa Xaa Xaa Xaa
            20                  25                  30

Xaa Xaa Trp Xaa Xaa Gln Xaa Pro Gly Lys Ser Pro Lys Arg Trp Ile
        35                  40                  45

Tyr Ala Thr Phe Glu Leu Ala Ser Gly Val Pro Ser Arg Phe Ser Gly
    50                  55                  60

Ser Gly Ser Gly Thr Asp Tyr Thr Leu Thr Ile Xaa Xaa Xaa Xaa Xaa
65                  70                  75                  80

Xaa Xaa Phe Ala Thr Tyr Tyr Cys His Gln Arg Ser Ser Tyr Pro Trp
            85                  90                  95

Thr Phe Gly Gln Gly Thr Lys Leu Glu Ile Lys
            100                 105
```

DUAL SPECIFIC BINDING PROTEINS DIRECTED AGAINST IL-13 AND IL-17

RELATED APPLICATIONS

This application claims benefit of U.S. Provisional Application No. 61/581,964, filed Dec. 30, 2011, the complete disclosure of which is hereby incorporated by reference.

SEQUENCE LISTING

The instant application contains a Sequence Listing which has been submitted in ASCII format via EFS-Web and is hereby incorporated by reference in its entirety. Said ASCII copy, created on Jan. 21, 2013, is named 11664000.txt and is 42,118 bytes in size.

FIELD

Multivalent and multispecific binding proteins that bind IL-13 and/or IL-17, methods of making, and their uses in the diagnosis, prevention, and/or treatment of acute and chronic inflammatory diseases, cancer, and other diseases are provided.

BACKGROUND

Engineered proteins, such as multispecific binding proteins capable of binding two or more antigens, are known in the art. Such multispecific binding proteins can be generated using cell fusion, chemical conjugation, or recombinant DNA techniques. There are a variety of multispecific binding protein structures known in the art and many structures and methods have distinct disadvantages.

Bispecific antibodies have been produced using quadroma technology. However, the presence of mis-paired by-products and significantly reduced production yields with this technology means that sophisticated purification procedures are required. Bispecific antibodies can also be produced by chemical conjugation of two different mAbs. However, this approach does not yield homogeneous preparations.

Other approaches used previously include coupling of two parental antibodies with a hetero-bifunctional crosslinker, production of tandem single-chain Fv molecules, diabodies, bispecific diabodies, single-chain diabodies, and di-diabodies. However, each of these approaches have disadvantages. In addition, a multivalent antibody construct comprising two Fab repeats in the heavy chain of an IgG and capable of binding four antigen molecules has been described (see PCT Publication No. WO 0177342 and Miller et al. (2003) J. Immunol. 170(9): 4854-61).

U.S. Pat. No. 7,612,181 provides a novel family of binding proteins capable of binding two or more antigens with high affinity, which are called dual variable domain binding proteins (DVD binding protein) or dual variable domain immunoglobulins (DVD-Ig™).

While a variety of structures are provided in the art, some with advantages and disadvantages, specific constructs are required for preparing multivalent binding proteins with specific properties and which bind to specific targets. Additionally, new variable domain sequences can further improve the properties of the binding proteins.

Interleukin 13 (IL-13) is a 17-kDa glycoprotein produced by activated T cells of the Th2 lineage. The function of IL-13 includes immunoglobulin isotype switching to IgE in human B cells and suppressing inflammatory cytokine production. IL-13 is associated primarily with the induction of airway inflammation such as asthma. It has also been linked to other allergic diseases, fibrotic conditions, cancer and infectious diseases.

Interleukin-17 (IL-17, also referred to as IL-17A) is a 20-30 kD homodimeric glycoprotein secreted by activated T cells at the site of inflammation. IL-17 acts as a proinflammatory cytokine by inducing the production of multiple adhesion molecules, inflammatory cytokines and chemokines in various tissues to recruit monocytes and neutrophils to the site of inflammation. IL-17 also plays an important role in the maturation of hematopoietic progenitor cells. Inappropriate or excessive production of IL-17 is associated with the pathology of various diseases or disorders including rheumatoid arthritis, asthma, lupus, allograft rejection, other inflammatory or autoimmune diseases and cancer.

There is a need in the art for improved multivalent binding proteins capable of binding IL-13 and/or IL-17. Novel binding proteins that bind IL-13 and IL-17 are provided herein.

SUMMARY

Binding proteins capable of binding IL-13 and/or IL-17 are provided. In an embodiment, binding proteins capable of binding IL-13 and/or IL-17 with high affinity are provided.

In one embodiment, binding proteins comprising a polypeptide chain that binds IL-13 and/or IL-17, wherein the polypeptide chain comprises VD1-(X1)n-VD2-C—(X2)n, wherein VD1 is a first variable domain, VD2 is a second variable domain, C is a constant domain, X1 represents an amino acid or polypeptide, X2 represents an Fc region and n is 0 or 1, are provided. In an embodiment, the VD1 and VD2 in the binding protein are heavy chain variable domains. In another embodiment, VD1 and VD2 are capable of binding the same antigen. In another embodiment, VD1 and VD2 are capable of binding different antigens. In still another embodiment, C is a heavy chain constant domain. For example, X1 is a linker with the proviso that X1 is not CH1.

In an embodiment, the binding protein disclosed herein comprises a polypeptide chain that binds IL-13 and/or IL-17, wherein the polypeptide chain comprises VD1-(X1)n-VD2-C—(X2)n, wherein VD1 is a first heavy chain variable domain, VD2 is a second heavy chain variable domain, C is a heavy chain constant domain, X1 is a linker, and X2 is an Fc region. In an embodiment, X1 is a linker with the proviso that it is not CH1.

In an embodiment, the binding protein disclosed herein comprises a polypeptide chain that binds IL-13 and/or IL-17, wherein the polypeptide chain comprises VD1-(X1)n-VD2-C—(X2)n, wherein VD1 is a first light chain variable domain, VD2 is a second light chain variable domain, C is a light chain constant domain, X1 is a linker, and X2 does not comprise an Fc region. In an embodiment, X1 is a linker with the proviso that it is not CL.

In another embodiment, a binding protein that binds IL-13 and/or IL-17 comprising two polypeptide chains, wherein the first polypeptide chain comprises VD1-(X1)n-VD2-C—(X2) n, wherein VD1 is a first heavy chain variable domain, VD2 is a second heavy chain variable domain, C is a heavy chain constant domain, X1 is a first linker, and X2 is an Fc region; and the second polypeptide chain comprises VD1-(X1)n-VD2-C—(X2)n, wherein VD1 is a first light chain variable domain, VD2 is a second light chain variable domain, C is a light chain constant domain, X1 is a second linker, and X2 does not comprise an Fc region is provided. In some embodiments, the first and second X1 are the same. In other embodiments, the first and second X1 are different. In some embodiments the first X1 is not a CH1 domain and/or the second X1 is not a CL domain. In one embodiment, the first X1 and the second X1 are short (e.g., 6 amino acid) linkers. In another embodiment, the first X1 and the second X1 are long (e.g., greater than 6 amino acid) linkers. In another embodiment, the first X1 is a short linker and the second X1 is a long linker. In another embodiment, the first X1 is a long linker and the second X1 is a short linker.

In an embodiment, the Dual Variable Domain (DVD) binding protein comprises four polypeptide chains, wherein each of the first two polypeptide chains comprises VD1-(X1)n-VD2-C—(X2)n, wherein VD1 is a first heavy chain variable domain, VD2 is a second heavy chain variable domain, C is a heavy chain constant domain, X1 is a first linker, and X2 is an Fc region; and each of the second two polypeptide chain comprises VD1-(X1)n-VD2-C—(X2)n, wherein VD1 is a first light chain variable domain, VD2 is a second light chain variable domain, C is a light chain constant domain, X1 is a second linker, and X2 does not comprise an Fc region. Such a DVD binding protein has four antigen binding sites. In some embodiments, the first and second X1 are the same. In other embodiments, the first and second X1 are different. In some embodiments, the first X1 is not a CH1 domain and/or the second X1 is not a CL domain. In another embodiment, the binding proteins disclosed herein are capable of binding IL-13 and IL-17. Accordingly, in some embodiments, the binding proteins comprise at least two variable domain sequences (e.g., VD1 and VD2) capable of binding IL-13 and IL-17, in any orientation. In some embodiments, VD1 and VD2 are independently chosen. Therefore, in some embodiments, VD1 and VD2 comprise the same SEQ ID NO and, in other embodiments, VD1 and VD2 comprise different SEQ ID NOS.

In an embodiment,
(a) the binding protein binds IL-13 and IL-17;
(b) VD1 or VD2 heavy chain variable domain comprises three CDRs from SEQ ID NO: 42, 43, 44, 45, 46, 47, 48 or 49;
(c) VD1 and VD2 heavy chain variable domains independently comprise three CDRs from SEQ ID NO: 42, 43, 44, 45, 46, 47, 48 or 49; (d) VD1 heavy chain variable domain comprises three CDRs from SEQ ID NO: 36, 38, 40, 42, 43, 44, 45, 46, 47, 48 or 49, and VD2 heavy chain variable domain comprises three CDRs from SEQ ID NO: 30, 32 or 34; or
(e) VD2 heavy chain variable domain comprises three CDRs from SEQ ID NO: 36, 38, 40, 42, 43, 44, 45, 46, 47, 48 or 49, and VD1 heavy chain variable domain comprises three CDRs from SEQ ID NO: 30, 32 or 34.

In another embodiment,
(a) VD1 or VD2 heavy chain variable domain comprises SEQ ID NO: 42, 43, 44, 45, 46, 47, 48 or 49;
(b) VD1 and VD2 heavy chain variable domains independently comprise SEQ ID NO: 42, 43, 44, 45, 46, 47, 48 or 49;
(c) VD1 heavy chain variable domain comprises SEQ ID NO: 36, 38, 40, 42, 43, 44, 45, 46, 47, 48 or 49, and VD2 heavy chain variable domain comprises SEQ ID NO: 30, 32 or 34; or
(d) VD2 heavy chain variable domain comprises SEQ ID NO: 36, 38, 40, 42, 43, 44, 45, 46, 47, 48 or 49, and VD1 heavy chain variable domain comprises SEQ ID NO: 30, 32 or 34.

In an embodiment,
(a) the binding protein binds IL-13 and IL-17;
(b) VD1 or VD2 light chain variable domain comprises three CDRs from SEQ ID NO: 50, 51, 52, 53 or 54;
(c) VD1 and VD2 light chain variable domains independently comprise three CDRs from SEQ ID NO: 50, 51, 52, 53 or 54;
(d) VD1 light chain variable domain comprises three CDRs from SEQ ID NO: 37, 39, 41, 50, 51, 52, 53 or 54, and VD2 light chain variable domain comprises three CDRs from SEQ ID NO: 31, 33 or 35; or
(e) VD2 light chain variable domain comprises three CDRs from SEQ ID NO: 37, 39, 41, 50, 51, 52, 53 or 54, and VD1 light chain variable domain comprises three CDRs from SEQ ID NO: 31, 33 or 35.

In another embodiment,
(a) VD1 or VD2 light chain variable domain comprises SEQ ID NO: 50, 51, 52, 53 or 54;
(b) VD1 and VD2 light chain variable domains independently comprise SEQ ID NO: 50, 51, 52, 53 or 54;
(c) VD1 light chain variable domain comprises SEQ ID NO: 37, 39, 41, 50, 51, 52, 53 or 54, and VD2 light chain variable domain comprises SEQ ID NO: 31, 33 or 35; or
(d) VD2 light chain variable domain comprises SEQ ID NO: 37, 39, 41, 50, 51, 52, 53 or 54, and VD1 light chain variable domain comprises SEQ ID NO: 31, 33 or 35.

In another embodiment, the binding protein comprises a heavy chain and a light chain sequence as shown in the Table 1 herein.

A further embodiment, of any of the heavy chain, light chain, two chain, or four chain embodiments, includes at least one X1 linker comprising AKTTPKLEEGEFSEAR (SEQ ID NO: 1); AKTTPKLEEGEFSEARV (SEQ ID NO: 2); AKTTPKLGG (SEQ ID NO: 3); SAKTTPKLGG (SEQ ID NO: 4); SAKTTP (SEQ ID NO: 5); RADAAP (SEQ ID NO: 6); RADAAPTVS (SEQ ID NO: 7); RADAAAAGGPGS (SEQ ID NO: 8); RADAAAA(G$_4$S)$_4$ (SEQ ID NO: 9); SAKTTP-KLEEGEFSEARV (SEQ ID NO: 10); ADAAP (SEQ ID NO: 11); ADAAPTVSIFPP (SEQ ID NO: 12); TVAAP (SEQ ID NO: 13); TVAAPSVFIFPP (SEQ ID NO: 14); QPKAAP (SEQ ID NO: 15); QPKAAPSVTLFPP (SEQ ID NO: 16); AKTTPP (SEQ ID NO: 17); AKTTPPSVTPLAP (SEQ ID NO: 18); akttap (SEQ ID NO: 19); akttapsvyplap (SEQ ID NO: 20); ASTKGP (SEQ ID NO: 21); ASTKGPSVFPLAP (SEQ ID NO: 22), GGGGSGGGGSGGGGS (SEQ ID NO: 23); GENKVEYAPALMALS (SEQ ID NO: 24); GPAKELT-PLKEAKVS (SEQ ID NO: 25); or GHEAAAVMQVQYPAS (SEQ ID NO: 26); TVAAPSVFIFPPTVAAPSVFIFPP (SEQ ID NO: 27); ASTKGPSVFPLAPASTKGPSVFPLAP (SEQ ID NO: 28); or G/S based sequences (e.g., G4S (SEQ ID NO: 29) and G4S (SEQ ID NO: 29) repeats). In an embodiment, X2 is an Fc region. In another embodiment, X2 is a variant Fc region.

In still another embodiment, the Fc region, if present in the first polypeptide, is a native sequence Fc region or a variant sequence Fc region. In yet another embodiment, the Fc region is an Fc region from an IgG1, an Fc region from an IgG2, an Fc region from an IgG3, an Fc region from an IgG4, an Fc region from an IgA, an Fc region from an IgM, an Fc region from an IgE, or an Fc region from an IgD.

A method of making a binding protein that binds IL-13 and/or IL-17 is provided. In an embodiment, the method of making a binding protein that binds IL-13 and/or IL-17 comprises the steps of a) obtaining a first parent antibody, or antigen binding portion thereof, that binds IL-13; b) obtaining a second parent antibody, or antigen binding portion thereof, that binds IL-17; c) preparing construct(s) encoding any of the binding proteins described herein; and d) expressing the polypeptide chains, such that a binding protein that binds the first and the second antigen is generated.

In any of the embodiments herein, the VD1 heavy chain variable domain, if present, and light chain variable domain, if present, can be from a first parent antibody or antigen binding portion thereof; the VD2 heavy chain variable domain, if present, and light chain variable domain, if present, can be from a second parent antibody or antigen binding portion thereof. The first and second parent antibodies can be the same or different.

In one embodiment, the first parent antibody or antigen binding portion thereof, binds a first antigen, and the second parent antibody or antigen binding portion thereof, binds a second antigen. In an embodiment, the first and second antigens are the same antigen. In another embodiment, the parent antibodies bind different epitopes on the same antigen. In another embodiment, the first and second antigens are different antigens. In another embodiment, the first parent antibody or antigen binding portion thereof, binds the first antigen with a potency different from the potency with which the second parent antibody or antigen binding portion thereof, binds the second antigen. In yet another embodiment, the first parent antibody or antigen binding portion thereof, binds the first antigen with an affinity different from the affinity with which the second parent antibody or antigen binding portion thereof, binds the second antigen.

In another embodiment, the first parent antibody or antigen binding portion thereof, and the second parent antibody or antigen binding portion thereof, are a human antibody, CDR grafted antibody, humanized antibody, and/or affinity matured antibody.

In another embodiment, the binding protein possesses at least one desired property exhibited by the first parent antibody or antigen binding portion thereof, or the second parent antibody or antigen binding portion thereof. Alternatively, the first parent antibody or antigen binding portion thereof and the second parent antibody or antigen binding portion thereof possess at least one desired property exhibited by the binding protein. In an embodiment, the desired property is one or more antibody parameters. In another embodiment, the antibody parameters are antigen specificity, affinity to antigen, potency, biological function, epitope recognition, stability, solubility, production efficiency, immunogenicity, pharmacokinetics, bioavailability, tissue cross reactivity, or orthologous antigen binding. In an embodiment, the binding protein is multivalent. In another embodiment, the binding protein is multispecific. The multivalent and or multispecific binding proteins described herein have desirable properties particularly from a therapeutic standpoint. For instance, the multivalent and or multispecific binding protein may (1) be internalized (and/or catabolized) faster than a bivalent antibody by a cell expressing an antigen to which the antibodies bind; (2) be an agonist binding protein; and/or (3) induce cell death and/or apoptosis of a cell expressing an antigen to which the multivalent binding protein is capable of binding. The "parent antibody", which provides at least one antigen binding specificity of the multivalent and or multispecific binding protein, may be one that is internalized (and/or catabolized) by a cell expressing an antigen to which the antibody binds; and/or may be an agonist, cell death-inducing, and/or apoptosis-inducing antibody, and the multivalent and or multispecific binding protein as described herein may display improvement(s) in one or more of these properties. Moreover, the parent antibody may lack any one or more of these properties, but may acquire one or more of them when constructed as a multivalent binding protein as described herein.

In another embodiment, the binding protein has an on rate constant ($K_{on}$) to one or more targets of at least about $10^2 M^{-1} s^{-1}$; at least about $10^3 M^{-1} s^{-1}$; at least about $10^4 M^{-1} s^{-1}$; at least about $10^5 M^{-1} s^{-1}$; or at least about $10^6 M^{-1} s^{-1}$, as measured by surface plasmon resonance. In an embodiment, the binding protein has an on rate constant ($K_{on}$) to one or more targets from about $10^2 M^{-1} s^{-1}$ to about $10^3 M^{-1} s^{-1}$; from about $10^3 M^{-1} s^{-1}$ to about $10^4 M^{-1} s^{-1}$; from about $10^4 M^{-1} s^{-1}$ to about $10^5 M^{-1} s^{-1}$; or from about $10^5 M^{-1} s^{-1}$ to about $10^6 M^{-1} s^{-1}$, as measured by surface plasmon resonance.

In another embodiment, the binding protein has an off rate constant ($K_{off}$) for one or more targets of at most about $10^{-3} s^{-1}$; at most about $10^{-4} s^{-1}$; at most about $10^{-5} s^{-1}$; or at most about $10^{-6} s^{-1}$, as measured by surface plasmon resonance. In an embodiment, the binding protein has an off rate constant ($K_{off}$) to one or more targets of about $10^{-3} s^{-1}$ to about $10^{-4} s^{-1}$; of about $10^{-4} s^{-1}$ to about $10^{-5} s^{-1}$; or of about $10^{-5} s^{-1}$ to about $10^{-6} e$, as measured by surface plasmon resonance.

In another embodiment, the binding protein has a dissociation constant ($K_d$) to one or more targets of at most about $10^{-7} M$; at most about $10^{-8} M$; at most about $10^{-9} M$; at most about $10^{-10} M$; at most about $10^{-11} M$; at most about $10^{-12} M$; or at most $10^{-13} M$. In an embodiment, the binding protein has a dissociation constant ($K_d$) to its targets of about $10^{-7} M$ to about $10^{-8} M$; of about $10^{-8} M$ to about $10^{-9} M$; of about $10^{-9} M$ to about $10^{-19} M$; of about $10^{-19} M$ to about $10^{-11} M$; of about $10^{-11} M$ to about $10^{-12} M$; or of about $10^{12}$ to M about $10^{-13} M$.

In another embodiment, the binding protein is a conjugate further comprising an agent. In an embodiment, the agent is an immunoadhesion molecule, an imaging agent, a therapeutic agent, or a cytotoxic agent. In an embodiment, the imaging agent is a radiolabel, an enzyme, a fluorescent label, a luminescent label, a bioluminescent label, a magnetic label, or biotin. In another embodiment, the radiolabel is $^3H$, $^{14}C$, $^{35}S$, $^{90}Y$, $^{99}Tc$, $^{111}In$, $^{125}I$, $^{131}I$, $^{177}Lu$, $^{166}Ho$, or $^{153}Sm$. In yet another embodiment, the therapeutic or cytotoxic agent is an anti-metabolite, an alkylating agent, an antibiotic, a growth factor, a cytokine, an anti-angiogenic agent, an anti-mitotic agent, an anthracycline, toxin, or an apoptotic agent.

In another embodiment, the binding protein is a crystallized binding protein and exists as a crystal. In an embodiment, the crystal is a carrier-free pharmaceutical controlled release crystal. In another embodiment, the crystallized binding protein has a greater half life in vivo than the soluble counterpart of the binding protein. In yet another embodiment, the crystallized binding protein retains biological activity.

In another embodiment, the binding protein described herein is glycosylated. For example, the glycosylation pattern is a human glycosylation pattern.

An isolated nucleic acid encoding any one of the binding proteins disclosed herein is also provided. A further embodiment provides a vector comprising the isolated nucleic acid disclosed herein wherein the vector is pcDNA; pTT (Durocher et al. (2002) Nucleic Acids Res. 30(2); pTT3 (pTT with additional multiple cloning site; pEFBOS (Mizushima and Nagata (1990) Nucleic Acids Res. 18(17); pBV; pJV; pcDNA3.1 TOPO; pEF6 TOPO; pBOS; pHybE; or pBJ. In an embodiment, the vector is a vector disclosed in US Patent Publication No. 20090239259.

In another aspect, a host cell is transformed with the vector disclosed herein. In an embodiment, the host cell is a prokaryotic cell, for example, E. coli. In another embodiment, the host cell is a eukaryotic cell, for example, a protist cell, an animal cell, a plant cell, or a fungal cell. In an embodiment, the host cell is a mammalian cell including, but not limited to, CHO, COS, NS0, SP2, PER.C6, or a fungal cell, such as Saccharomyces cerevisiae, or an insect cell, such as Sf9. In an embodiment, two or more binding proteins, e.g., with different specificities, are produced in a single recombinant host cell. For example, the expression of a mixture of antibodies has been called Oligoclonics™ (Merus B. V., The Netherlands) U.S. Pat. Nos. 7,262,028 and 7,429,486.

A method of producing a binding protein disclosed herein comprising culturing any one of the host cells disclosed herein in a culture medium under conditions sufficient to produce the binding protein is provided. In an embodiment, 50%-75% of the binding protein produced by this method is a dual specific tetravalent binding protein. In another embodiment, 75%-90% of the binding protein produced by this method is a dual specific tetravalent binding protein. In another embodiment, 90%-95% of the binding protein produced is a dual specific tetravalent binding protein.

One embodiment provides a composition for the release of a binding protein wherein the composition comprises a crystallized binding protein, an ingredient, and at least one polymeric carrier. In an embodiment, the polymeric carrier is poly (acrylic acid), a poly (cyanoacrylate), a poly (amino acid), a poly (anhydride), a poly (depsipeptide), a poly (ester), poly (lactic acid), poly (lactic-co-glycolic acid) or PLGA, poly (b-hydroxybutryate), poly (caprolactone), poly (dioxanone), poly (ethylene glycol), poly ((hydroxypropyl) methacrylamide, poly [(organo)phosphazene], a poly (ortho ester), poly (vinyl alcohol), poly (vinylpyrrolidone), a maleic anhydride-alkyl vinyl ether copolymer, a pluronic polyol, albumin, alginate, cellulose, a cellulose derivative, collagen, fibrin, gelatin, hyaluronic acid, an oligosaccharide, a glycaminoglycan, a sulfated polysaccharide, or blends and copolymers thereof. In an embodiment, the ingredient is albumin, sucrose, trehalose, lactitol, gelatin, hydroxypropyl-β-cyclodextrin, methoxypolyethylene glycol, or polyethylene glycol.

Another embodiment provides a method for treating a mammal comprising the step of administering to the mammal an effective amount of a composition disclosed herein.

A pharmaceutical composition comprising a binding protein disclosed herein and a pharmaceutically acceptable carrier is provided. In a further embodiment, the pharmaceutical composition comprises at least one additional therapeutic agent for treating a disorder. For example, the additional agent may be a therapeutic agent, an imaging agent, a cytotoxic agent, an angiogenesis inhibitor (including but not limited to an anti-VEGF antibody or a VEGF-trap), a kinase inhibitor (including but not limited to a KDR and a TIE-2 inhibitor), a co-stimulation molecule blocker (including but not limited to anti-B7.1, anti-B7.2, CTLA4-Ig, anti-CD20), an adhesion molecule blocker (including but not limited to an anti-LFA-1 antibody, an anti-E/L selectin antibody, a small molecule inhibitor), an anti-cytokine antibody or functional fragment thereof (including but not limited to an anti-IL-18, an anti-TNF, and an anti-IL-6/cytokine receptor antibody), methotrexate, cyclosporin, rapamycin, FK506, a detectable label or reporter, a TNF antagonist, an antirheumatic, a muscle relaxant, a narcotic, a non-steroid anti-inflammatory drug (NSAID), an analgesic, an anesthetic, a sedative, a local anesthetic, a neuromuscular blocker, an antimicrobial, an antipsoriatic, a corticosteriod, an anabolic steroid, an erythropoietin, an immunization, an immunoglobulin, an immunosuppressive, a growth hormone, a hormone replacement drug, a radiopharmaceutical, an antidepressant, an antipsychotic, a stimulant, an asthma medication, a beta agonist, an inhaled steroid, an epinephrine or analog, a cytokine, or a cytokine antagonist.

A method for treating a human subject suffering from a disorder in which the target, or targets, capable of being bound by the binding protein disclosed herein is detrimental, comprising administering to the human subject a binding protein disclosed herein such that the activity of the target, or targets, in the human subject is inhibited and one or more symptoms is alleviated or treatment is achieved is provided. The binding proteins provided herein can be used to treat humans suffering from autoimmune diseases such as, for example, those associated with inflammation. In an embodiment, the binding proteins provided herein or antigen-binding portions thereof, are used to treat asthma, allergies, allergic lung disease, allergic rhinitis, atopic dermatitis, chronic obstructive pulmonary disease (COPD), fibrosis, cystic fibrosis (CF), fibrotic lung disease, idiopathic pulmonary fibrosis, liver fibrosis, lupus, hepatitis B-related liver diseases and fibrosis, sepsis, systemic lupus erythematosus (SLE), glomerulonephritis, inflammatory skin diseases, psoriasis, diabetes, insulin dependent diabetes mellitus, infectious diseases caused by HIV, inflammatory bowel disease (IBD), ulcerative colitis (UC), Crohn's disease (CD), rheumatoid arthritis (RA), osteoarthritis (OA), multiple sclerosis (MS), graft-versus-host disease (GVHD), transplant rejection, ischemic heart disease (IHD), celiac disease, contact hypersensitivity, alcoholic liver disease, Behcet's disease, atherosclerotic vascular disease, occular surface inflammatory diseases, or Lyme disease.

In another embodiment, the disorder or condition to be treated comprises the symptoms caused by viral infection in a human which is caused by, for example, HIV, the human rhinovirus, an enterovirus, a coronavirus, a herpes virus, an influenza virus, a parainfluenza virus, a respiratory syncytial virus or an adenovirus.

The binding proteins provided herein can be used to treat neurological disorders. In an embodiment, the binding proteins provided herein, or antigen-binding portions thereof, are used to treat neurodegenerative diseases and conditions involving neuronal regeneration and spinal cord injury.

In an embodiment, diseases that can be treated or diagnosed with the compositions and methods disclosed herein include, but are not limited to, primary and metastatic cancers, including carcinomas of breast, colon, rectum, lung, oropharynx, hypopharynx, esophagus, stomach, pancreas, liver, gallbladder and bile ducts, small intestine, urinary tract (including kidney, bladder and urothelium), female genital tract (including cervix, uterus, and ovaries as well as choriocarcinoma and gestational trophoblastic disease), male genital tract (including prostate, seminal vesicles, testes and germ cell tumors), endocrine glands (including the thyroid, adrenal, and pituitary glands), and skin, as well as hemangiomas, melanomas, sarcomas (including those arising from bone and soft tissues as well as Kaposi's sarcoma), tumors of the brain, nerves, eyes, and meninges (including astrocytomas, gliomas, glioblastomas, retinoblastomas, neuromas, neuroblastomas, Schwannomas, and meningiomas), solid tumors arising from hematopoietic malignancies such as leukemias, and lymphomas (both Hodgkin's and non-Hodgkin's lymphomas).

Another embodiment provides for the use of the binding protein in the treatment of a disease or disorder, wherein said disease or disorder is rheumatoid arthritis, osteoarthritis, juvenile chronic arthritis, septic arthritis, Lyme arthritis, psoriatic arthritis, reactive arthritis, spondyloarthropathy, systemic lupus erythematosus, Crohn's disease, ulcerative colitis, inflammatory bowel disease, insulin dependent diabetes mellitus, thyroiditis, asthma, allergic diseases, psoriasis, dermatitis scleroderma, graft versus host disease, organ transplant rejection, acute or chronic immune disease associated with organ transplantation, sarcoidosis, atherosclerosis, disseminated intravascular coagulation, Kawasaki's disease, Grave's disease, nephrotic syndrome, chronic fatigue syndrome, Wegener's granulomatosis, Henoch-Schoenlein purpurea, microscopic vasculitis of the kidneys, chronic active hepatitis, uveitis, septic shock, toxic shock syndrome, sepsis syndrome, cachexia, infectious diseases, parasitic diseases, acquired immunodeficiency syndrome, acute transverse myelitis, Huntington's chorea, Parkinson's disease, Alzheimer's disease, stroke, primary biliary cirrhosis, hemolytic anemia, malignancies, heart failure, Addison's disease, sporadic, polyglandular deficiency type I and polyglandular deficiency type II, Schmidt's syndrome, adult (acute) respiratory distress syndrome, alopecia, alopecia greata, arthropathy, Reiter's disease, psoriatic arthropathy, ulcerative colitic arthropathy, enteropathic synovitis, chlamydia, yersinia and salmonella associated arthropathy, atheromatous disease/arteriosclerosis, atopic allergy, autoimmune bullous disease, pemphigus vulgaris, pemphigus foliaceus, pemphigoid, linear IgA disease, autoimmune haemolytic anaemia, Coombs positive haemolytic anaemia, acquired pernicious anaemia, juvenile pernicious anaemia, myalgic encephalitis/Royal Free Disease, chronic mucocutaneous candidiasis, giant cell arteritis, primary sclerosing hepatitis, cryptogenic autoimmune hepatitis, acquired immunodeficiency related diseases, hepatitis B, hepatitis C, common varied immunodeficiency (common variable hypogammaglobulinaemia), dilated cardiomyopathy, female infertility, ovarian failure, premature ovarian failure, fibrotic lung disease, cryptogenic fibrosing alveolitis, post-inflammatory interstitial lung disease, interstitial pneumonitis, connective tissue disease associated interstitial lung disease, mixed connective tissue disease associated lung disease, systemic sclerosis associated interstitial lung disease, rheumatoid arthritis associated interstitial lung disease, systemic lupus erythematosus associated lung disease, dermatomyositis/polymyositis associated lung disease, Sjögren's disease associated lung disease, ankylosing spondylitis associated lung disease, vasculitic diffuse lung disease, haemosiderosis associated lung disease, drug-induced interstitial lung disease, fibrosis, radiation fibrosis, bronchiolitis obliterans, chronic eosinophilic pneumonia, lymphocytic infiltrative lung disease, postinfectious interstitial lung disease, gouty arthritis, autoimmune hepatitis, type-1 autoimmune hepatitis (classical autoimmune or lupoid hepatitis), type-2 autoimmune hepatitis (anti-LKM antibody hepatitis), autoimmune mediated hypoglycaemia, type B insulin resistance with acanthosis nigricans, hypoparathyroidism, acute immune disease associated with organ transplantation, chronic immune disease associated with organ transplantation, osteoarthrosis, primary sclerosing cholangitis, psoriasis type 1, psoriasis type 2, idiopathic leucopaenia, autoimmune neutropaenia, renal disease NOS, glomerulonephritides, microscopic vasulitis of the kidneys, lyme disease, discoid lupus erythematosus, male infertility idiopathic or NOS, sperm autoimmunity, multiple sclerosis (all subtypes), sympathetic ophthalmia, pulmonary hypertension secondary to connective tissue disease, Goodpasture's syndrome, pulmonary manifestation of polyarteritis nodosa, acute rheumatic fever, rheumatoid spondylitis, Still's disease, systemic sclerosis, Sjorgren's syndrome, Takayasu's disease/arteritis, autoimmune thrombocytopaenia, idiopathic thrombocytopaenia, autoimmune thyroid disease, hyperthyroidism, goitrous autoimmune hypothyroidism (Hashimoto's disease), atrophic autoimmune hypothyroidism, primary myxoedema, phacogenic uveitis, primary vasculitis, vitiligo acute liver disease, chronic liver diseases, alcoholic cirrhosis, alcohol-induced liver injury, choleosatatis, idiosyncratic liver disease, drug-induced hepatitis, non-alcoholic steatohepatitis, allergy and asthma, group B streptococci (GBS) infection, mental disorders, depression, schizophrenia, Th2 Type and TM Type mediated diseases, acute and chronic pain, different forms of pain, cancers, lung cancer, breast cancer, stomach cancer, bladder cancer, colon cancer, pancreatic cancer, ovarian cancer, prostate cancer, rectal cancer, hematopoietic malignancies, leukemia, lymphoma, Abetalipoprotemia, acrocyanosis, acute and chronic parasitic or infectious processes, acute leukemia, acute lymphoblastic leukemia (ALL), acute myeloid leukemia (AML), acute or chronic bacterial infection, acute pancreatitis, acute renal failure, adenocarcinomas, aerial ectopic beats, AIDS dementia complex, alcohol-induced hepatitis, allergic conjunctivitis, allergic contact dermatitis, allergic rhinitis, allograft rejection, alpha-1-antitrypsin deficiency, amyotrophic lateral sclerosis, anemia, angina pectoris, anterior horn cell degeneration, anti cd3 therapy, antiphospholipid syndrome, anti-receptor hypersensitivity reactions, aortic and peripheral aneuryisms, aortic dissection, arterial hypertension, arteriosclerosis, arteriovenous fistula, ataxia, atrial fibrillation (sustained or paroxysmal), atrial flutter, atrioventricular block, B cell lymphoma, bone graft rejection, bone marrow transplant (BMT) rejection, bundle branch block, Burkitt's lymphoma, burns, cardiac arrhythmias, cardiac stun syndrome, cardiac tumors, cardiomyopathy, cardiopulmonary bypass inflammation response, cartilage transplant rejection, cerebellar cortical degenerations, cerebellar disorders, chaotic or multifocal atrial tachycardia, chemotherapy associated disorders, chronic myelocytic leukemia (CML), chronic alcoholism, chronic inflammatory pathologies, chronic lymphocytic leukemia (CLL), chronic obstructive pulmonary disease (COPD), chronic salicylate intoxication, colorectal carcinoma, congestive heart failure, conjunctivitis, contact dermatitis, cor pulmonale, coronary artery disease, Creutzfeldt-Jakob disease, culture negative sepsis, cystic fibrosis, cytokine therapy associated disorders, dementia pugilistica, demyelinating diseases, dengue hemorrhagic fever, dermatitis, dermatologic conditions, diabetes, diabetes mellitus, diabetic ateriosclerotic disease, diffuse Lewy body disease, dilated congestive cardiomyopathy, disorders of the basal ganglia, Down's syndrome in middle age, drug-induced movement disorders induced by drugs which block CNS dopamine receptors, drug sensitivity, eczema, encephalomyelitis, endocarditis, endocrinopathy, epiglottitis, epstein-barr virus infection, erythromelalgia, extrapyramidal and cerebellar disorders, familial hematophagocytic lymphohistiocytosis, fetal thymus implant rejection, Friedreich's ataxia, functional peripheral arterial disorders, fungal sepsis, gas gangrene, gastric ulcer, glomerular nephritis, graft rejection of any organ or tissue, gram negative sepsis, gram positive sepsis, granulomas due to intracellular organisms, hairy cell leukemia, Hallervorden-Spatz disease, Hashimoto's thyroiditis, hay fever, heart transplant rejection, hemachromatosis, hemodialysis, hemolytic uremic syndrome/thrombolytic thrombocytopenic purpura, hemorrhage, hepatitis A, His bundle arrythmias, HIV infection/HIV neuropathy, Hodgkin's disease, hyperkinetic movement disorders, hypersensitivity reactions, hypersensitivity pneumonitis, hypertension, hypokinetic movement disorders, hypothalamic-pituitary-adrenal axis evaluation, idiopathic Addison's disease, idiopathic pulmonary fibrosis, antibody mediated cytotoxicity, Asthenia, infantile spinal muscular atrophy, inflammation of the aorta, influenza a, ionizing radiation exposure, iridocyclitis/uveitis/optic neuritis, ischemia-reperfusion injury, ischemic stroke, juvenile rheumatoid arthritis, juvenile spinal muscular atrophy, Kaposi's sarcoma, kidney transplant rejection, legionella, leishmaniasis, leprosy, lesions of the corticospinal system, lipedema, liver transplant rejection, lymphederma, malaria, malignant lymphoma, malignant histiocytosis, malignant melanoma, meningitis, meningococcemia, metabolic/idiopathic, migraine headache, mitochondrial multi.system disorder, mixed connective tissue disease, monoclonal gammopathy, multiple myeloma, multiple systems degenerations (Mencel Dejerine-Thomas Shi-Drager and Machado-Joseph), mycobacterium avium intracellulare, mycobacterium tuberculosis, myelodyplastic syndrome, myocardial infarction, myocardial ischemic disorders, nasopharyngeal carcinoma, neonatal chronic lung disease, nephritis, nephrosis, neurodegenerative diseases, neurogenic muscular atrophies, neutropenic fever, non-hodgkins lymphoma, occlusion of the abdominal aorta and its branches, occulsive arterial disorders, okt3 therapy, orchitis/epidydimitis, orchitis/vasectomy reversal procedures, organomegaly, osteoporosis, pancreas transplant rejection, pancreatic carcinoma, paraneoplastic syndrome/hypercalcemia of malignancy, parathyroid transplant rejection, pelvic inflammatory disease, perennial rhinitis, pericardial disease, peripheral atherlosclerotic disease, peripheral vascular disorders, peritonitis, pernicious anemia, pneumocystis carinii pneumonia, pneumonia, POEMS syndrome (polyneuropathy, organomegaly, endocrinopathy, monoclonal gammopathy, and skin changes syndrome), post perfusion syndrome, post pump syndrome, post-MI cardiotomy syndrome, preeclampsia, progressive supranucleo palsy, primary pulmonary hypertension, radiation therapy, Raynaud's phenomenon and disease, Raynoud's disease, Refsum's disease, regular narrow QRS tachycardia, renovascular hypertension, reperfusion injury, restrictive cardiomyopathy, sarcomas, scleroderma, senile chorea, senile dementia of Lewy body type, seronegative arthropathies, shock, sickle cell anemia, skin allograft rejection, skin changes syndrome, small bowel transplant rejection, solid tumors, specific arrythmias, spinal ataxia, spinocerebellar degenerations, streptococcal myositis, structural lesions of the cerebellum, subacute sclerosing panencephalitis, syncope, syphilis of the cardiovascular system, systemic anaphalaxis, systemic inflammatory response syndrome, systemic onset juvenile rheumatoid arthritis, T-cell or FAB ALL telangiectasia, thromboangitis obliterans, thrombocytopenia, toxicity, transplants, trauma/hemorrhage, type III hypersensitivity reactions, type IV hypersensitivity, unstable angina, uremia, urosepsis, valvular heart diseases, varicose veins, vasculitis, venous diseases, venous thrombosis, ventricular fibrillation, viral and fungal infections, vital encephalitis/aseptic meningitis, vital-associated hemaphagocytic syndrome, Wernicke-Korsakoff syndrome, Wilson's disease, xenograft rejection of any organ or tissue, acute coronary syndromes, acute idiopathic polyneuritis, acute inflammatory demyelinating polyradiculoneuropathy, acute ischemia, adult Still's disease, anaphylaxis, anti-phospholipid antibody syndrome, aplastic anemia, atopic eczema, atopic dermatitis, autoimmune dermatitis, autoimmune disorder associated with streptococcus infection, autoimmune enteropathy, autoimmune hearing loss, autoimmune lymphoproliferative syndrome (ALPS), autoimmune myocarditis, autoimmune premature ovarian failure, blepharitis, bronchiectasis, bullous pemphigoid, cardiovascular disease, catastrophic antiphospholipid syndrome, celiac disease, cervical spondylosis, chronic ischemia, cicatricial pemphigoid, clinically isolated syndrome (cis) with risk for multiple sclerosis, childhood onset psychiatric disorder, dacryocystitis, dermatomyositis, diabetic retinopathy, disk herniation, disk prolaps, drug induced immune hemolytic anemia, endometriosis, endophthalmitis, episcleritis, erythema multiforme, erythema multiforme major, gestational pemphigoid, Guillain-Barré syndrome (GBS), Hughes syndrome, idiopathic Parkinson's disease, idiopathic interstitial pneumonia, IgE-mediated allergy, immune hemolytic anemia, inclusion body myositis, infectious ocular inflammatory disease, inflammatory demyelinating disease, inflammatory heart disease, inflammatory kidney disease, IPF/UIP, iritis, keratitis, keratojuntivitis sicca, Kussmaul disease or Kussmaul-Meier disease, Landry's paralysis, Langerhan's cell histiocytosis, livedo reticularis, macular degeneration, microscopic polyangiitis, morbus bechterev, motor neuron disorders, mucous membrane pemphigoid, multiple organ failure, myasthenia gravis, myelodysplastic syndrome, myocarditis, nerve root disorders, neuropathy, non-A non-B hepatitis, optic neuritis, osteolysis, pauciarticular JRA, peripheral artery occlusive disease (PAOD), peripheral vascular disease (PVD), peripheral artery, disease (PAD), phlebitis, polyarteritis nodosa (or periarteritis nodosa), polychondritis, poliosis, polyarticular JRA, polyendocrine deficiency syndrome, polymyositis, polymyalgia rheumatica (PMR), primary Parkinsonism, prostatitis, pure red cell aplasia, primary adrenal insufficiency, recurrent neuromyelitis optica, restenosis, rheumatic heart disease, sapho (synovitis, acne, pustulosis, hyperostosis, and osteitis), secondary amyloidosis, shock lung, scleritis, sciatica, secondary adrenal insufficiency, silicone associated connective tissue disease, sneddon-wilkinson dermatosis, spondilitis ankylosans, Stevens-Johnson syndrome (SJS), temporal arteritis, toxoplasmic retinitis, toxic epidermal necrolysis, transverse myelitis, TRAPS (tumor necrosis factor receptor, type 1 allergic reaction, type II diabetes, urticaria, usual interstitial pneumonia (UIP), vasculitis, vernal conjunctivitis, viral retinitis, Vogt-Koyanagi-Harada syndrome (VKH syndrome), wet macular degeneration, or wound healing.

In an embodiment, the binding proteins, or antigen-binding portions thereof, are used to treat cancer or in the prevention or inhibition of metastases from the tumors described herein either when used alone or in combination with radiotherapy and/or chemotherapeutic agents.

In another aspect, methods of treating a patient suffering from a disorder comprising the step of administering any one of the binding proteins disclosed herein before, concurrently, or after the administration of a second agent, are provided. In an embodiment, the second agent is budenoside, epidermal growth factor, a corticosteroid, cyclosporin, sulfasalazine, an aminosalicylate, 6-mercaptopurine, azathioprine, metronidazole, a lipoxygenase inhibitor, mesalamine, olsalazine, balsalazide, an antioxidant, a thromboxane inhibitor, an IL-1 receptor antagonist, an anti-IL-1β mAbs, an anti-IL-6 or IL-6 receptor mAb, a growth factor, an elastase inhibitor, a pyridinyl-imidazole compound, an antibody or agonist of TNF, LT, IL-1, IL-2, IL-6, IL-7, IL-8, IL-12, IL-13, IL-15, IL-16, IL-18, IL-23, EMAP-II, GM-CSF, FGF, or PDGF, an antibody to CD2, CD3, CD4, CD8, CD-19, CD25, CD28, CD30, CD40, CD45, CD69, CD90 or a ligand thereof, methotrexate, cyclosporin, FK506, rapamycin, mycophenolate mofetil, leflunomide, an NSAID, ibuprofen, prednisolone, a phosphodiesterase inhibitor, an adenosine agonist, an antithrombotic agent, a complement inhibitor, an adrenergic agent, IRAK, NIK, IKK, p38, a MAP kinase inhibitor, an IL-1β converting enzyme inhibitor, a TNFα-converting enzyme inhibitor, a T-cell signalling inhibitor, a metalloproteinase inhibitor, sulfasalazine, azathioprine, a 6-mercaptopurine, an angiotensin converting enzyme inhibitor, a soluble cytokine receptor, a soluble p55 TNF receptor, a soluble p75 TNF receptor, sIL-1RI, sIL-1RII, sIL-6R, an antiinflammatory cytokine, IL-4, IL-10, IL-11, IL-13, or TG93. In a particular embodiment, the pharmaceutical compositions disclosed herein are administered to a patient by parenteral, subcutaneous, intramuscular, intravenous, intrarticular, intrabronchial, intraabdominal, intracapsular, intracartilaginous, intracavitary, intracelial, intracerebellar, intracerebroventricular, intracolic, intracervical, intragastric, intrahepatic, intramyocardial, intraosteal, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravesical, bolus, vaginal, rectal, buccal, sublingual, intranasal, or transdermal administration.

Anti-idiotype antibodies to the binding proteins disclosed herein are also provided. An anti-idiotype antibody includes any protein or peptide-containing molecule that comprises at least a portion of an immunoglobulin molecule such as, but not limited to, at least one complementarily determining region (CDR) of a heavy or light chain or a ligand binding portion thereof, a heavy chain or light chain variable region, a heavy chain or light chain constant region, a framework region, or any portion thereof, that can be incorporated into a binding protein provided herein.

A method of determining the presence, amount or concentration of IL-13 and/or IL-17, or fragment thereof, in a test sample is provided. The method comprises assaying the test sample for the antigen, or fragment thereof, by an immunoassay. The immunoassay (i) employs at least one binding protein and at least one detectable label and (ii) comprises comparing a signal generated by the detectable label as a direct or indirect indication of the presence, amount or concentration of the antigen, or fragment thereof, in the test sample to a signal generated as a direct or indirect indication of the presence, amount or concentration of the antigen, or fragment thereof, in a control or a calibrator. The calibrator is optionally part of a series of calibrators in which each of the calibrators differs from the other calibrators in the series by the concentration of the antigen, or fragment thereof. The method can comprise (i) contacting the test sample with at least one capture agent, which binds to an epitope on the antigen, or fragment thereof, so as to form a capture agent/antigen, or fragment thereof, complex, (ii) contacting the capture agent/antigen, or fragment thereof, complex with at least one detection agent, which comprises a detectable label and binds to an epitope on the antigen, or fragment thereof, that is not bound by the capture agent, to form a capture agent/antigen, or fragment thereof/detection agent complex, and (iii) determining the presence, amount or concentration of the antigen, or fragment thereof, in the test sample based on the signal generated by the detectable label in the capture agent/antigen, or fragment thereof/detection agent complex formed in (ii), wherein at least one capture agent and/or at least one detection agent is the at least one binding protein.

Alternatively, the method can comprise (i) contacting the test sample with at least one capture agent, which binds to an epitope on the antigen, or fragment thereof, so as to form a capture agent/antigen, or fragment thereof, complex, and simultaneously or sequentially, in either order, contacting the test sample with detectably labeled antigen, or fragment thereof, which can compete with any antigen, or fragment thereof, in the test sample for binding to the at least one capture agent, wherein any antigen, or fragment thereof, present in the test sample and the detectably labeled antigen compete with each other to form a capture agent/antigen, or fragment thereof, complex and a capture agent/detectably labeled antigen, or fragment thereof, complex, respectively, and (ii) determining the presence, amount or concentration of the antigen, or fragment thereof, in the test sample based on the signal generated by the detectable label in the capture agent/detectably labeled antigen, or fragment thereof, complex formed in (ii), wherein at least one capture agent is the at least one binding protein and wherein the signal generated by the detectable label in the capture agent/detectably labeled antigen, or fragment thereof, complex is inversely proportional to the amount or concentration of antigen, or fragment thereof, in the test sample.

The test sample can be from a patient, in which case the method can further comprise diagnosing, prognosticating, or assessing the efficacy of therapeutic/prophylactic treatment of the patient. If the method further comprises assessing the efficacy of therapeutic/prophylactic treatment of the patient, the method optionally further comprises modifying the therapeutic/prophylactic treatment of the patient as needed to improve efficacy. The method can be adapted for use in an automated system or a semi-automated system. Accordingly, the methods described herein also can be used to determine whether or not a subject has or is at risk of developing a given disease, disorder or condition. Specifically, such a method can comprise the steps of:

(a) determining the concentration or amount in a test sample from a subject of analyte, or fragment thereof, (e.g., using the methods described herein, or methods known in the art); and (b) comparing the concentration or amount of analyte, or fragment thereof, determined in step (a) with a predetermined level, wherein, if the concentration or amount of analyte determined in step (a) is favorable with respect to a predetermined level, then the subject is determined not to have or be at risk for a given disease, disorder or condition. However, if the concentration or amount of analyte determined in step (a) is unfavorable with respect to the predetermined level, then the subject is determined to have or be at risk for a given disease, disorder or condition.

Additionally, provided herein is method of monitoring the progression of disease in a subject. Optimally the method comprising the steps of:

(a) determining the concentration or amount in a test sample from a subject of analyte;

(b) determining the concentration or amount in a later test sample from the subject of analyte; and (c) comparing the concentration or amount of analyte as determined in step (b) with the concentration or amount of analyte determined in step (a), wherein if the concentration or amount determined in step (b) is unchanged or is unfavorable when compared to the concentration or amount of analyte determined in step (a), then the disease in the subject is determined to have continued, progressed or worsened. By comparison, if the concentration or amount of analyte as determined in step (b) is favorable when compared to the concentration or amount of analyte as determined in step (a), then the disease in the subject is determined to have discontinued, regressed or improved.

Optionally, the method further comprises comparing the concentration or amount of analyte as determined in step (b), for example, with a predetermined level. Further, optionally the method comprises treating the subject with one or more pharmaceutical compositions for a period of time if the comparison shows that the concentration or amount of analyte as determined in step (b), for example, is unfavorably altered with respect to the predetermined level.

Also provided is a kit for assaying a test sample for IL-13 and/or IL-17, or fragment thereof. The kit comprises at least one component for assaying the test sample for an antigen, or fragment thereof, and instructions for assaying the test sample for an antigen, or fragment thereof, wherein the at least one component includes at least one composition comprising the binding protein disclosed herein, wherein the binding protein is optionally detectably labeled.

BRIEF DESCRIPTION OF THE DRAWINGS

FIG. 1 is a schematic representation of Dual Variable Domain (DVD) binding protein constructs.

DETAILED DESCRIPTION

Multivalent and/or multispecific binding proteins capable of binding IL13 and/or IL-17 are provided. Dual variable domain binding proteins (DVD binding proteins) or dual variable domain immunoglobulins (DVD-Ig™), and pharmaceutical compositions thereof, as well as nucleic acids, recombinant expression vectors and host cells for making such DVD binding proteins are also provided. Methods of using the DVD binding proteins to detect specific antigens, either in vitro or in vivo are also provided.

Unless otherwise defined herein, scientific and technical terms used herein have the meanings that are commonly understood by those of ordinary skill in the art. In the event of any latent ambiguity, definitions provided herein take precedent over any dictionary or extrinsic definition. Unless otherwise required by context, singular terms shall include pluralities and plural terms shall include the singular. The use of "or" means "and/or" unless stated otherwise. The use of the term "including", as well as other forms, such as "includes" and "included", is not limiting.

Generally, nomenclatures used in connection with cell and tissue culture, molecular biology, immunology, microbiology, genetics and protein and nucleic acid chemistry and hybridization described herein are those well known and commonly used in the art. The methods and techniques provided herein are generally performed according to conventional methods well known in the art and as described in various general and more specific references that are cited and discussed throughout the present specification unless otherwise indicated. Enzymatic reactions and purification techniques are performed according to manufacturer's specifications, as commonly accomplished in the art or as described herein. The nomenclatures used in connection with, and the laboratory procedures and techniques of, analytical chemistry, synthetic organic chemistry, and medicinal and pharmaceutical chemistry described herein are those well known and commonly used in the art. Standard techniques are used for chemical syntheses, chemical analyses, pharmaceutical preparation, formulation, and delivery, and treatment of patients.

That the disclosure may be more readily understood, select terms are defined below.

The term "antibody" refers to an immunoglobulin (Ig) molecule, which is generally comprised of four polypeptide chains, two heavy (H) chains and two light (L) chains, or a functional fragment, mutant, variant, or derivative thereof, that retains the epitope binding features of an Ig molecule. Such fragment, mutant, variant, or derivative antibody formats are known in the art. In an embodiment of a full-length antibody, each heavy chain is comprised of a heavy chain variable region (VH) and a heavy chain constant region (CH). The CH is comprised of three domains, CH1, CH2 and CH3. Each light chain is comprised of a light chain variable region (VL) and a light chain constant region (CL). The CL is comprised of a single CL domain. The VH and VL can be further subdivided into regions of hypervariability, termed complementarity determining regions (CDRs), interspersed with regions that are more conserved, termed framework regions (FRs). Generally, each VH and VL is composed of three CDRs and four FRs, arranged from amino-terminus to carboxy-terminus in the following order: FR1, CDR1, FR2, CDR2, FR3, CDR3, and FR4. Immunoglobulin molecules can be of any type (e.g., IgG, IgE, IgM, IgD, IgA and IgY), class (e.g., IgG1, IgG2, IgG3, IgG4, IgA1 and IgA2), or subclass.

The term "bispecific antibody" refers to an antibody that binds one antigen (or epitope) on one of its two binding arms (one pair of HC/LC), and binds a different antigen (or epitope) on its second binding arm (a different pair of HC/LC). A bispecific antibody has two distinct antigen binding arms (in both specificity and CDR sequences), and is monovalent for each antigen to which it binds. Bispecific antibodies include those generated by quadroma technology (Milstein and Cuello (1983) Nature 305(5934): 537-40), by chemical conjugation of two different monoclonal antibodies (Staerz et al. (1985) Nature 314(6012): 628-31), or by knob-into-hole or similar approaches which introduces mutations in the Fc region (Holliger et al. (1993) Proc. Natl. Acad. Sci. USA 90(14): 6444-6448).

An "affinity matured" antibody is an antibody with one or more alterations in one or more CDRs thereof which result an improvement in the affinity of the antibody for antigen, compared to a parent antibody which does not possess those alteration(s). Exemplary affinity matured antibodies will have nanomolar or even picomolar affinities for the target antigen. Affinity matured antibodies are produced by procedures known in the art. Marks et al. (1992) BioTechnology 10:779-783 describes affinity maturation by VH and VL domain shuffling. Random mutagenesis of CDR and/or framework residues is described by Barbas et al. (1994) Proc. Nat. Acad. Sci. USA 91:3809-3813; Schier et al. (1995) Gene 169:147-155; Yelton et al. (1995) J. Immunol. 155:1994-2004; Jackson et al. (1995) J. Immunol. 154(7):3310-9; Hawkins et al. (1992) J. Mol. Biol. 226:889-896 and mutation at selective mutagenesis positions, contact or hypermutation positions with an activity enhancing amino acid residue as described in U.S. Pat. No. 6,914,128.

The term "CDR-grafted antibody" refers to an antibody that comprises heavy and light chain variable region sequences in which the sequences of one or more of the CDR regions of VH and/or VL are replaced with CDR sequences of another antibody. For example, the two antibodies can be from different species, such as antibodies having murine heavy and light chain variable regions in which one or more of the murine CDRs has been replaced with human CDR sequences.

The term "humanized antibody" refers to an antibody from a non-human species that has been altered to be more "human-like", i.e., more similar to human germline sequences. One type of humanized antibody is a CDR-grafted antibody, in which non-human CDR sequences are introduced into human VH and VL sequences to replace the corresponding human CDR sequences. A "humanized antibody" is also an antibody or a variant, derivative, analog or fragment thereof that comprises framework region (FR) sequences having substantially (e.g., at least 80%, at least 85%, at least 90%, at least 95%, at least 98% or at least 99% identity to) the amino acid sequence of a human antibody and at least one CDR having substantially the amino acid sequence of a non-human antibody. A humanized antibody may comprise substantially all of at least one, and typically two, variable domains (Fab, Fab', F(ab')2, FabC, Fv) in which the sequence of all or substantially all of the CDR regions correspond to those of a non-human immunoglobulin (i.e., donor antibody) and the sequence of all or substantially all of the FR regions are those of a human immunoglobulin. The humanized antibody also may include the CH1, hinge, CH2, CH3, and CH4 regions of the heavy chain. In an embodiment, a humanized antibody also comprises at least a portion of a human immunoglobulin Fc region. In some embodiments, a humanized antibody only contains a humanized light chain. In some embodiments, a humanized antibody only contains a humanized heavy chain. In some embodiments, a humanized antibody only contains a humanized variable domain of a light chain and/or humanized variable domain of a heavy chain. In some embodiments, a humanized antibody contains a light chain as well as at least the variable domain of a heavy chain. In some embodiments, a humanized antibody contains a heavy chain as well as at least the variable domain of a light chain.

The terms "dual variable domain binding protein" and "dual variable domain immunoglobulin" refer to a binding protein that has two variable domains in each of its two binding arms (e.g., a pair of HC/LC) (see PCT Publication No. WO 02/02773), each of which is able to bind to an antigen. In an embodiment, each variable domain binds different antigens or epitopes. In another embodiment, each variable domain binds the same antigen or epitope. In another embodiment, a dual variable domain binding protein has two identical antigen binding arms, with identical specificity and identical CDR sequences, and is bivalent for each antigen to which it binds. In an embodiment, the DVD binding proteins may be monospecific, i.e., capable of binding one antigen or multispecific, i.e., capable of binding two or more antigens. DVD binding proteins comprising two heavy chain DVD polypeptides and two light chain DVD polypeptides are referred to as a DVD-Ig™. In an embodiment, each half of a four chain DVD binding protein comprises a heavy chain DVD polypeptide, and a light chain DVD polypeptide, and two antigen binding sites. In an embodiment, each binding site comprises a heavy chain variable domain and a light chain variable domain with a total of 6 CDRs involved in antigen binding per antigen binding site.

The term "antiidiotypic antibody" refers to an antibody raised against the amino acid sequence of the antigen combining site of another antibody. Antiidiotypic antibodies may be administered to enhance an immune response against an antigen.

The term "biological activity" refers to any one or more biological properties of a molecule (whether present naturally as found in vivo, or provided or enabled by recombinant means). Biological properties include, but are not limited to, binding a receptor, inducing cell proliferation, inhibiting cell growth, inducing other cytokines, inducing apoptosis, and enzymatic activity.

The term "neutralizing" refers to counteracting the biological activity of an antigen when a binding protein specifically binds to the antigen. In an embodiment, the neutralizing binding protein binds to an antigen (e.g., a cytokine) and reduces its biologically activity by at least about 20%, 40%, 60%, 80%, 85% or more.

"Specificity" refers to the ability of a binding protein to selectively bind an antigen.

"Affinity" is the strength of the interaction between a binding protein and an antigen, and is determined by the sequence of the CDRs of the binding protein as well as by the nature of the antigen, such as its size, shape, and/or charge. Binding proteins may be selected for affinities that provide desired therapeutic end-points while minimizing negative side-effects. Affinity may be measured using methods known to one skilled in the art (US 20090311253).

The term "potency" refers to the ability of a binding protein to achieve a desired effect, and is a measurement of its therapeutic efficacy. Potency may be assessed using methods known to one skilled in the art (US 20090311253).

The term "cross-reactivity" refers to the ability of a binding protein to bind a target other than that against which it was raised. Generally, a binding protein will bind its target tissue(s)/antigen(s) with an appropriately high affinity, but will display an appropriately low affinity for non-target normal tissues. Individual binding proteins are generally selected to meet two criteria. (1) Tissue staining appropriate for the known expression of the antibody target. (2) Similar staining pattern between human and tox species (mouse and cynomolgus monkey) tissues from the same organ. These and other methods of assessing cross-reactivity are known to one skilled in the art (US 20090311253).

The term "biological function" refers the specific in vitro or in vivo actions of a binding protein. Binding proteins may target several classes of antigens and achieve desired therapeutic outcomes through multiple mechanisms of action. Binding proteins may target soluble proteins, cell surface antigens, as well as extracellular protein deposits. Binding proteins may agonize, antagonize, or neutralize the activity of their targets. Binding proteins may assist in the clearance of the targets to which they bind, or may result in cytotoxicity when bound to cells. Portions of two or more antibodies may be incorporated into a multivalent format to achieve distinct functions in a single binding protein molecule. The in vitro assays and in vivo models used to assess biological function are known to one skilled in the art (US 20090311253).

A "stable" binding protein is one in which the binding protein essentially retains its physical stability, chemical stability and/or biological activity upon storage. A multivalent binding protein that is stable in vitro at various temperatures for an extended period of time is desirable. Methods of stabilizing binding proteins and assessing their stability at various temperatures are known to one skilled in the art (US 20090311253).

The term "solubility" refers to the ability of a protein to remain dispersed within an aqueous solution. The solubility of a protein in an aqueous formulation depends upon the proper distribution of hydrophobic and hydrophilic amino acid residues, and therefore, solubility can correlate with the production of correctly folded proteins. A person skilled in the art will be able to detect an increase or decrease in solubility of a binding protein using routine HPLC techniques and methods known to one skilled in the art (US 20090311253).

Binding proteins may be produced using a variety of host cells or may be produced in vitro, and the relative yield per effort determines the "production efficiency." Factors influencing production efficiency include, but are not limited to, host cell type (prokaryotic or eukaryotic), choice of expression vector, choice of nucleotide sequence, and methods employed. The materials and methods used in binding protein production, as well as the measurement of production efficiency, are known to one skilled in the art (US 20090311253).

The term "immunogenicity" means the ability of a substance to induce an immune response. Administration of a therapeutic binding protein may result in a certain incidence of an immune response. Potential elements that might induce immunogenicity in a multivalent format may be analyzed during selection of the parental antibodies, and steps to reduce such risk can be taken to optimize the parental antibodies prior to incorporating their sequences into a multivalent binding protein format. Methods of reducing the immunogenicity of antibodies and binding proteins are known to one skilled in the art (US 20090311253).

The terms "label" and "detectable label" mean a moiety attached to a member of a specific binding pair, such as an antibody or its analyte to render a reaction (e.g., binding) between the members of the specific binding pair, detectable. The labeled member of the specific binding pair is referred to as "detectably labeled." Thus, the term "labeled binding protein" refers to a protein with a label incorporated that provides for the identification of the binding protein. In an embodiment, the label is a detectable marker that can produce a signal that is detectable by visual or instrumental means, e.g., incorporation of a radiolabeled amino acid or attachment to a polypeptide of biotinyl moieties that can be detected by marked avidin (e.g., streptavidin containing a fluorescent marker or enzymatic activity that can be detected by optical or colorimetric methods). Examples of labels for polypeptides include, but are not limited to, the following: radioisotopes or radionuclides (e.g., $^{3}H$, $^{14}C$, $^{35}S$, $^{90}Y$, $^{99}Tc$, $^{111}In$, $^{125}I$, $^{131}I$, $^{177}Lu$, $^{166}Ho$, or $^{153}Sm$); chromogens, fluorescent labels (e.g., FITC, rhodamine, lanthanide phosphors), enzymatic labels (e.g., horseradish peroxidase, luciferase, alkaline phosphatase); chemiluminescent markers; biotinyl groups; predetermined polypeptide epitopes recognized by a secondary reporter (e.g., leucine zipper pair sequences, binding sites for secondary antibodies, metal binding domains, epitope tags); and magnetic agents, such as gadolinium chelates. Representative examples of labels commonly employed for immunoassays include moieties that produce light, e.g., acridinium compounds, and moieties that produce fluorescence, e.g., fluorescein. In this regard, the moiety itself may not be detectably labeled but may become detectable upon reaction with yet another moiety.

The term "conjugate" refers to a binding protein, such as an antibody, that is chemically linked to a second chemical moiety, such as a therapeutic or cytotoxic agent. The term "agent" includes a chemical compound, a mixture of chemical compounds, a biological macromolecule, or an extract made from biological materials. In an embodiment, the therapeutic or cytotoxic agents include, but are not limited to, pertussis toxin, taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. When employed in the context of an immunoassay, the conjugate antibody may be a detectably labeled antibody used as the detection antibody.

The terms "crystal" and "crystallized" refer to a binding protein (e.g., an antibody), or antigen binding portion thereof, that exists in the form of a crystal. Crystals are one form of the solid state of matter, which is distinct from other forms such as the amorphous solid state or the liquid crystalline state. Crystals are composed of regular, repeating, three-dimensional arrays of atoms, ions, molecules (e.g., proteins such as antibodies), or molecular assemblies (e.g., antigen/antibody complexes). These three-dimensional arrays are arranged according to specific mathematical relationships that are well-understood in the field. The fundamental unit, or building block, that is repeated in a crystal is called the asymmetric unit. Repetition of the asymmetric unit in an arrangement that conforms to a given, well-defined crystallographic symmetry provides the "unit cell" of the crystal. Repetition of the unit cell by regular translations in all three dimensions provides the crystal. See Giege, R. and Ducruix, A. Barrett, CRYSTALLIZATION OF NUCLEIC ACIDS AND PROTEINS, A PRACTICAL APPROACH, 2nd ea., pp. 20 1-16, Oxford University Press, New York, N.Y., (1999).

The term "vector" refers to a nucleic acid molecule capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Other vectors include RNA vectors. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, other forms of expression vectors are also included, such as viral vectors (e.g., replication defective retroviruses, adenoviruses and adeno-associated viruses), which serve equivalent functions. A group of pHybE vectors (U.S. Patent Application Ser. No. 61/021,282) were used for parental antibody and DVD-binding protein cloning. V1, derived from pJP183; pHybE-hCg1,z,non-a V2, was used for cloning of antibody and DVD heavy chains with a wild-type constant region. V2, derived from pJP191; pHybE-hCk V3, was used for cloning of antibody and DVD light chains with a kappa constant region. V3, derived from pJP192; pHybE-hCl V2, was used for cloning of antibody and DVDs light chains with a lambda constant region. V4, built with a lambda signal peptide and a kappa constant region, was used for cloning of DVD light chains with a lambda-kappa hybrid V domain. V5, built with a kappa signal peptide and a lambda constant region, was used for cloning of DVD light chains with a kappa-lambda hybrid V domain. V7, derived from pJP183; pHybE-hCg1,z,non-a V2, was used for cloning of antibody and DVD heavy chains with a (234,235 AA) mutant constant region.

The terms "recombinant host cell" or "host cell" refer to a cell into which exogenous DNA has been introduced. Such terms refer not only to the particular subject cell, but to the progeny of such a cell. Because certain modifications may occur in succeeding generations due to either mutation or environmental influences, such progeny may not, in fact, be identical to the parent cell, but are still included within the scope of the term "host cell" as used herein. In an embodiment, host cells include prokaryotic and eukaryotic cells. In an embodiment, eukaryotic cells include protist, fungal, plant and animal cells. In another embodiment, host cells include but are not limited to the prokaryotic cell line *E. Coli*; mammalian cell lines CHO, HEK 293, COS, NS0, SP2 and PER.C6; the insect cell line Sf9; and the fungal cell *Saccharomyces cerevisiae*.

The term "transfection" encompasses a variety of techniques commonly used for the introduction of exogenous nucleic acid (e.g., DNA) into a host cell, e.g., electroporation, calcium-phosphate precipitation, DEAE-dextran transfection and the like.

The term "cytokine" refers to a protein released by one cell population that acts on another cell population as an intercellular mediator. The term "cytokine" includes proteins from natural sources or from recombinant cell culture and biologically active equivalents of the native sequence cytokines.

The term "biological sample" means a quantity of a substance from a living thing or formerly living thing. Such substances include, but are not limited to, blood, (e.g., whole blood), plasma, serum, urine, amniotic fluid, synovial fluid, endothelial cells, leukocytes, monocytes, other cells, organs, tissues, bone marrow, lymph nodes and spleen.

The term "component" refers to an element of a composition. In relation to a diagnostic kit, for example, a component may be a capture antibody, a detection or conjugate antibody, a control, a calibrator, a series of calibrators, a sensitivity panel, a container, a buffer, a diluent, a salt, an enzyme, a co-factor for an enzyme, a detection reagent, a pretreatment reagent/solution, a substrate (e.g., as a solution), a stop solution, and the like that can be included in a kit for assay of a test sample. Thus, a "component" can include a polypeptide or other analyte as above, that is immobilized on a solid support, such as by binding to an anti-analyte (e.g., anti-polypeptide) antibody. Some components can be in solution or lyophilized for reconstitution for use in an assay.

"Control" refers to a composition known to not analyte ("negative control") or to contain analyte ("positive control"). A positive control can comprise a known concentration of analyte. "Control," "positive control," and "calibrator" may be used interchangeably herein to refer to a composition comprising a known concentration of analyte. A "positive control" can be used to establish assay performance characteristics and is a useful indicator of the integrity of reagents (e.g., analytes).

"Predetermined cutoff" and "predetermined level" refer generally to an assay cutoff value that is used to assess diagnostic/prognostic/therapeutic efficacy results by comparing the assay results against the predetermined cutoff/level, where the predetermined cutoff/level already has been linked or associated with various clinical parameters (e.g., severity of disease, progression/nonprogression/improvement, etc.). While the present disclosure may provide exemplary predetermined levels, it is well-known that cutoff values may vary depending on the nature of the immunoassay (e.g., antibodies employed, etc.). It further is well within the ordinary skill of one in the art to adapt the disclosure herein for other immunoassays to obtain immunoassay-specific cutoff values for those other immunoassays based on this disclosure. Whereas the precise value of the predetermined cutoff/level may vary between assays, correlations as described herein (if any) may be generally applicable.

"Pretreatment reagent," e.g., lysis, precipitation and/or solubilization reagent, as used in a diagnostic assay as described herein is one that lyses any cells and/or solubilizes any analyte that is/are present in a test sample. Pretreatment is not necessary for all samples, as described further herein. Among other things, solubilizing the analyte (e.g., polypeptide of interest) may entail release of the analyte from any endogenous binding proteins present in the sample. A pretreatment reagent may be homogeneous (not requiring a separation step) or heterogeneous (requiring a separation step). With use of a heterogeneous pretreatment reagent there is removal of any precipitated analyte binding proteins from the test sample prior to proceeding to the next step of the assay.

"Quality control reagents" in the context of immunoassays and kits described herein, include, but are not limited to, calibrators, controls, and sensitivity panels. A "calibrator" or "standard" typically is used (e.g., one or more, such as a plurality) in order to establish calibration (standard) curves for interpolation of the concentration of an analyte, such as an antibody or an analyte. Alternatively, a single calibrator, which is near a predetermined positive/negative cutoff, can be used. Multiple calibrators (i.e., more than one calibrator or a varying amount of calibrator(s)) can be used in conjunction so as to comprise a "sensitivity panel."

The term "specific binding partner" is a member of a specific binding pair. A specific binding pair comprises two different molecules that specifically bind to each other through chemical or physical means. Therefore, in addition to antigen and antibody specific binding, other specific binding pairs can include biotin and avidin (or streptavidin), carbohydrates and lectins, complementary nucleotide sequences, effector and receptor molecules, cofactors and enzymes, enzyme inhibitors and enzymes, and the like. Furthermore, specific binding pairs can include members that are analogs of the original specific binding members, for example, an analyte-analog. Immunoreactive specific binding members include antigens, antigen fragments, and antibodies, including monoclonal and polyclonal antibodies as well as complexes, fragments, and variants (including fragments of variants) thereof, whether isolated or recombinantly produced.

The term "Fc region" defines the C-terminal region of an immunoglobulin heavy chain, which may be generated by papain digestion of an intact antibody. The Fc region may be a native sequence Fc region or a variant Fc region. The Fc region of an immunoglobulin generally comprises two constant domains, a CH2 domain and a CH3 domain, and optionally comprises a CH4 domain. Replacements of amino acid residues in the Fc portion to alter antibody effector function are known in the art (e.g., U.S. Pat. Nos. 5,648,260 and 5,624,821). The Fc region mediates several important effector functions, e.g., cytokine induction, antibody dependent cell mediated cytotoxicity (ADCC), phagocytosis, complement dependent cytotoxicity (CDC), and half-life/clearance rate of antibody and antigen-antibody complexes. In some cases these effector functions are desirable for a therapeutic immunoglobulin but in other cases might be unnecessary or even deleterious, depending on the therapeutic objectives.

The term "antigen-binding portion" of a binding protein means one or more fragments of a binding protein (e.g., an antibody) that retain the ability to specifically bind to an antigen. The antigen-binding portion of a binding protein can be performed by fragments of a full-length antibody, as well as bispecific, dual specific, or multi-specific formats; specifically binding to two or more different antigens. Examples of binding fragments encompassed within the term "antigen-binding portion" of an binding protein include (i) an Fab fragment, a monovalent fragment consisting of the VL, VH, CL and CH1 domains; (ii) an F(ab')$_2$ fragment, a bivalent fragment comprising two Fab fragments linked by a disulfide bridge at the hinge region; (iii) an Fd fragment consisting of the VH and CH1 domains; (iv) an Fv fragment consisting of the VL and VH domains of a single arm of an antibody, (v) a dAb fragment, which comprises a single variable domain; and (vi) an isolated complementarity determining region (CDR). Furthermore, although the two domains of the Fv fragment, VL and VH, encoded by separate genes, they can be joined, using recombinant methods, by a synthetic linker that enables them to be made as a single protein chain in which the VL and VH regions pair to form monovalent molecules (known as single chain Fv (scFv). Such single chain antibodies are also intended to be encompassed within the term "antigen-binding portion" of an antibody. Other forms of single chain antibodies, such as diabodies are also encompassed. In addition, single chain antibodies also include "linear antibodies" comprising a pair of tandem Fv segments (VH-CH1-VH-CH1) which, together with complementary light chain polypeptides, form a pair of antigen binding regions.

The term "multivalent binding protein" means a binding protein comprising two or more antigen binding sites. In an embodiment, the multivalent binding protein is engineered to have three or more antigen binding sites, and is not a naturally occurring antibody. The term "multispecific binding protein" refers to a binding protein capable of binding two or more related or unrelated targets. In an embodiment, the dual variable domain (DVD) binding proteins provided herein comprise two or more antigen binding sites and are tetravalent or multivalent binding proteins.

The term "linker" means an amino acid residue or a polypeptide comprising two or more amino acid residues joined by peptide bonds that are used to link two polypeptides (e.g., two VH or two VL domains). Such linker polypeptides are well known in the art (see, e.g., Holliger et al. (1993) Proc. Natl. Acad. Sci. USA 90:6444-6448; Poljak et al. (1994) Structure 2:1121-1123).

The terms "Kabat numbering", "Kabat definitions" and "Kabat labeling" are used interchangeably herein. These terms, which are recognized in the art, refer to a system of numbering amino acid residues which are more variable (i.e., hypervariable) than other amino acid residues in the heavy and light chain variable regions of an antibody, or an antigen binding portion thereof (Kabat et al. (1971) Ann. N.Y. Acad. Sci. 190:382-391 and, Kabat et al. (1991) Sequences of Proteins of Immunological Interest, Fifth Edition, U.S. Department of Health and Human Services, NIH Publication No. 91-3242). For the heavy chain variable region, the hypervariable region ranges from amino acid positions 31 to 35 for CDR1, amino acid positions 50 to 65 for CDR2, and amino acid positions 95 to 102 for CDR3. For the light chain variable region, the hypervariable region ranges from amino acid positions 24 to 34 for CDR1, amino acid positions 50 to 56 for CDR2, and amino acid positions 89 to 97 for CDR3.

The term "CDR" means a complementarity determining region within an immunoglobulin variable region sequence. There are three CDRs in each of the variable regions of the heavy chain and the light chain, which are designated CDR1, CDR2 and CDR3, for each of the heavy and light chain variable regions. The term "CDR set" refers to a group of three CDRs that occur in a single variable region capable of binding the antigen. The exact boundaries of these CDRs have been defined differently according to different systems. The system described by Kabat (Kabat et al. (1987) and (1991)) not only provides an unambiguous residue numbering system applicable to any variable region of an antibody, but also provides precise residue boundaries defining the three CDRs. These CDRs may be referred to as Kabat CDRs. Chothia and coworkers (Chothia and Lesk (1987) J. Mol. Biol. 196:901-917; Chothia et al. (1989) Nature 342:877-883) found that certain sub-portions within Kabat CDRs adopt nearly identical peptide backbone conformations, despite having great diversity at the level of amino acid sequence. These sub-portions were designated as L1, L2 and L3 or H1, H2 and H3 where the "L" and the "H" designates the light chain and the heavy chain regions, respectively. These regions may be referred to as Chothia CDRs, which have boundaries that overlap with Kabat CDRs. Other boundaries defining CDRs overlapping with the Kabat CDRs have been described by Padlan (1995) FASEB J. 9:133-139 and MacCallum (1996) J. Mol. Biol. 262(5):732-45). Still other CDR boundary definitions may not strictly follow one of the herein systems, but will nonetheless overlap with the Kabat CDRs, although they may be shortened or lengthened in light of prediction or experimental findings that particular residues or groups of residues or even entire CDRs do not significantly impact antigen binding. The methods used herein may utilize CDRs defined according to any of these systems, although certain embodiments use Kabat or Chothia defined CDRs.

The term "epitope" means a region of an antigen that is bound by a binding protein, e.g., a polypeptide and/or other determinant capable of specific binding to an immunoglobulin or T-cell receptor. In certain embodiments, epitope determinants include chemically active surface groupings of molecules such as amino acids, sugar side chains, phosphoryl, or sulfonyl, and, in certain embodiments, may have specific three dimensional structural characteristics, and/or specific charge characteristics. In an embodiment, an epitope comprises the amino acid residues of a region of an antigen (or fragment thereof) known to bind to the complementary site on the specific binding partner. An antigenic fragment can contain more than one epitope. In certain embodiments, a binding protein specifically binds an antigen when it recognizes its target antigen in a complex mixture of proteins and/or macromolecules. Binding proteins "bind to the same epitope" if the antibodies cross-compete (one prevents the binding or modulating effect of the other). In addition, structural definitions of epitopes (overlapping, similar, identical) are informative; and functional definitions encompass structural (binding) and functional (modulation, competition) parameters. Different regions of proteins may perform different functions. For example specific regions of a cytokine interact with its cytokine receptor to bring about receptor activation whereas other regions of the protein may be required for stabilizing the cytokine. To abrogate the negative effects of cytokine signaling, the cytokine may be targeted with a binding protein that binds specifically to the receptor interacting region(s), thereby preventing the binding of its receptor. Alternatively, a binding protein may target the regions responsible for cytokine stabilization, thereby designating the protein for degradation. The methods of visualizing and modeling epitope recognition are known to one skilled in the art (US 20090311253).

"Pharmacokinetics" refers to the process by which a drug is absorbed, distributed, metabolized, and excreted by an organism. To generate a multivalent binding protein molecule with a desired pharmacokinetic profile, parent monoclonal antibodies with similarly desired pharmacokinetic profiles are selected. The PK profiles of the selected parental monoclonal antibodies can be easily determined in rodents using methods known to one skilled in the art (US 20090311253).

"Bioavailability" refers to the amount of active drug that reaches its target following administration. Bioavailability is function of several of the previously described properties, including stability, solubility, immunogenicity and pharmacokinetics, and can be assessed using methods known to one skilled in the art (US 20090311253).

The term "surface plasmon resonance" means an optical phenomenon that allows for the analysis of real-time biospecific interactions by detection of alterations in protein concentrations within a biosensor matrix, for example using the BIAcore® system (BIAcore International AB, a GE Healthcare company, Uppsala, Sweden and Piscataway, N.J.). For further descriptions, see Jönsson et al. (1993) Ann. Biol. Clin. 51:19-26. The term "$K_{on}$" means the on rate constant for association of a binding protein (e.g., an antibody or DVD-Ig protein) to the antigen to form the, e.g., DVD-Ig/antigen complex. The term "$K_{on}$" also means "association rate constant", or "ka", as is used interchangeably herein. This value indicating the binding rate of a binding protein to its target antigen or the rate of complex formation between a binding protein, e.g., an antibody, and antigen also is shown by the equation below:

Antibody ("$Ab$")+Antigen ("$Ag$")→$Ab$–$Ag$

The term "$K_{off}$" means the off rate constant for dissociation, or "dissociation rate constant", of a binding protein (e.g., an antibody or DVD-Ig protein) from the, e.g., DVD-Ig protein/antigen complex as is known in the art. This value indicates the dissociation rate of a binding protein, e.g., an antibody, from its target antigen or separation of Ab-Ag complex over time into free antibody and antigen as shown by the equation below:

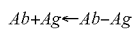

$$Ab+Ag \leftarrow Ab-Ag$$

The terms "$K_d$" and "equilibrium dissociation constant" means the value obtained in a titration measurement at equilibrium, or by dividing the dissociation rate constant ($K_{off}$) by the association rate constant ($K_{on}$). The association rate constant, the dissociation rate constant and the equilibrium dissociation constant, are used to represent the binding affinity of a binding protein (e.g., an antibody or DVD-Ig protein) to an antigen. Methods for determining association and dissociation rate constants are well known in the art. Using fluorescence-based techniques offers high sensitivity and the ability to examine samples in physiological buffers at equilibrium. Other experimental approaches and instruments such as a BIAcore® (biomolecular interaction analysis) assay, can be used (e.g., instrument available from BIAcore International AB, a GE Healthcare company, Uppsala, Sweden). Additionally, a KinExA® (Kinetic Exclusion Assay) assay, available from Sapidyne Instruments (Boise, Id.), can also be used.

The term "variant" means a polypeptide that differs from a given polypeptide in amino acid sequence by the addition (e.g., insertion), deletion, or conservative substitution of amino acids, but that retains the biological activity of the given polypeptide (e.g., a variant IL-17 antibody can compete with anti-IL-17 antibody for binding to IL-17). A conservative substitution of an amino acid, i.e., replacing an amino acid with a different amino acid of similar properties (e.g., hydrophilicity and degree and distribution of charged regions) is recognized in the art as typically involving a minor change. These minor changes can be identified, in part, by considering the hydropathic index of amino acids, as understood in the art (see, e.g., Kyte et al. (1982) J. Mol. Biol. 157: 105-132). The hydropathic index of an amino acid is based on a consideration of its hydrophobicity and charge. It is known in the art that amino acids of similar hydropathic indexes in a protein can be substituted and the protein still retains protein function. In one aspect, amino acids having hydropathic indexes of ±2 are substituted. The hydrophilicity of amino acids also can be used to reveal substitutions that would result in proteins retaining biological function. A consideration of the hydrophilicity of amino acids in the context of a peptide permits calculation of the greatest local average hydrophilicity of that peptide, a useful measure that has been reported to correlate well with antigenicity and immunogenicity (see, e.g., U.S. Pat. No. 4,554,101). Substitution of amino acids having similar hydrophilicity values can result in peptides retaining biological activity, for example immunogenicity, as is understood in the art. In one aspect, substitutions are performed with amino acids having hydrophilicity values within ±2 of each other. Both the hydrophobicity index and the hydrophilicity value of amino acids are influenced by the particular side chain of that amino acid. Consistent with that observation, amino acid substitutions that are compatible with biological function are understood to depend on the relative similarity of the amino acids, and particularly the side chains of those amino acids, as revealed by the hydrophobicity, hydrophilicity, charge, size, and other properties. The term "variant" also includes polypeptide or fragment thereof that has been differentially processed, such as by proteolysis, phosphorylation, or other post-translational modification, yet retains its biological activity or antigen reactivity, e.g., the ability to bind to IL-17. The term "variant" encompasses fragments of a variant unless otherwise defined. A variant may be 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, or 75% identical to the wildtype sequence.

I. Generation of Binding Proteins

Binding proteins capable of binding IL-13 and/or IL-17 and methods of making the same are provided. The binding protein can be generated using various techniques. Expression vectors, host cell and methods of generating the binding protein are provided and are well known in the art.

A. Generation of Parent Monoclonal Antibodies

The variable domains of the DVD binding protein can be obtained from parent antibodies, including polyclonal Abs and mAbs capable of binding antigens of interest. These antibodies may be naturally occurring or may be generated by recombinant technology. The person of ordinary skill in the art is well familiar with many methods for producing antibodies, including, but not limited to using hybridoma techniques, selected lymphocyte antibody method (SLAM), use of a phage, yeast, or RNA-protein fusion display or other library, immunizing a non-human animal comprising at least some of the human immunoglobulin locus, and preparation of chimeric, CDR-grafted, and humanized antibodies. See, e.g., US Patent Publication No. 20090311253 A1. Variable domains may also be prepared using affinity maturation techniques.

B. Criteria for Selecting Parent Monoclonal Antibodies

An embodiment is provided comprising selecting parent antibodies with at least one or more properties desired in the DVD binding protein molecule. In an embodiment, the desired property is one or more antibody parameters, such as, for example, antigen specificity, affinity to antigen, potency, biological function, epitope recognition, stability, solubility, production efficiency, immunogenicity, pharmacokinetics, bioavailability, tissue cross reactivity, or orthologous antigen binding. See, e.g., US Patent Publication No. 20090311253.

C. Construction of Binding Protein Molecules

The binding protein may be designed such that two different light chain variable domains (VL) from the two different parent monoclonal antibodies are linked in tandem directly or via a linker by recombinant DNA techniques, followed by the light chain constant domain CL. Similarly, the heavy chain comprises two different heavy chain variable domains (VH) linked in tandem, directly or via a linker, followed by the constant domain CH1 and Fc region (FIG. 1).

The variable domains can be obtained using recombinant DNA techniques from parent antibodies generated by any one of the methods described herein. In an embodiment, the variable domain is a murine heavy or light chain variable domain. In another embodiment, the variable domain is a CDR grafted or a humanized variable heavy or light chain domain. In an embodiment, the variable domain is a human heavy or light chain variable domain.

The linker sequence may be a single amino acid or a polypeptide sequence. In an embodiment, the choice of linker sequences is based on crystal structure analysis of several Fab molecules. There is a natural flexible linkage between the variable domain and the CH1/CL constant domain in Fab or antibody molecular structure. This natural linkage comprises approximately 10-12 amino acid residues, contributed by 4-6 residues from the C-terminus of a V domain and 4-6 residues from the N-terminus of a CL/CH1 domain. DVD binding proteins were generated using N-terminal 5-6 amino acid residues, or 11-12 amino acid residues, of CL or CH1 as a linker in the light chain and heavy chains, respectively. The N-terminal residues of CL or CH1 domains, particularly the first 5-6 amino acid residues, can adopt a loop conformation without strong secondary structures, and therefore can act as flexible linkers between the two variable domains. The N-terminal residues of CL or CH1 domains are natural extension of the variable domains, as they are part of the Ig sequences, and therefore their use minimizes to a large extent any immunogenicity potentially arising from the linkers and junctions.

In a further embodiment, of any of the heavy chain, light chain, two chain, or four chain embodiments, includes at least one linker comprising AKTTPKLEEGEFSEAR (SEQ ID NO: 1); AKTTPKLEEGEFSEARV (SEQ ID NO: 2); AKTTPKLGG (SEQ ID NO: 3); SAKTTPKLGG (SEQ ID NO: 4); SAKTTP (SEQ ID NO: 5); RADAAP (SEQ ID NO: 6); RADAAPTVS (SEQ ID NO: 7); RADAAAAGGPGS (SEQ ID NO: 8); RADAAAA(G$_4$S)$_4$ (SEQ ID NO: 9); SAKTTPKLEEGEFSEARV (SEQ ID NO: 10); ADAAP (SEQ ID NO: 11); ADAAPTVSIFPP (SEQ ID NO: 12); TVAAP (SEQ ID NO: 13); TVAAPSVFIFPP (SEQ ID NO: 14); QPKAAP (SEQ ID NO: 15); QPKAAPSVTLFPP (SEQ ID NO: 16); AKTTPP (SEQ ID NO: 17); AKTTPPSVTPLAP (SEQ ID NO: 18); AKTTAP (SEQ ID NO: 19); AKTTAPSVYPLAP (SEQ ID NO: 20); ASTKGP (SEQ ID NO: 21); ASTKGPSVFPLAP (SEQ ID NO: 22), GGGGSGGGGSGGGGS (SEQ ID NO: 23); GENKVEYAPALMALS (SEQ ID NO: 24); GPAKELTPLKEAKVS (SEQ ID NO: 25); or GHEAAAVMQVQYPAS (SEQ ID NO: 26); TVAAPSVFIFPPTVAAPSVFIFPP (SEQ ID NO: 27); ASTKGPSVFPLAPASTKGPSVFPLAP (SEQ ID NO: 28); or G/S based sequences (e.g., G4S repeats; SEQ ID NO: 29). In an embodiment, X2 is an Fc region. In another embodiment, X2 is a variant Fc region.

Other linker sequences may include any sequence of any length of a CL/CH1 domain but not all residues of a CL/CH1 domain; for example the first 5-12 amino acid residues of a CL/CH1 domain; the light chain linkers can be from CK or Cλ; and the heavy chain linkers can be derived from CH1 of any isotype, including Cγ1, Cγ2, Cγ3, Cγ4, Cα1, Cα2, Cδ, Cε, and Cμ. Linker sequences may also be derived from other proteins such as Ig-like proteins (e.g., TCR, FcR, KIR); G/S based sequences (e.g., G4S repeats; SEQ ID NO: 29); hinge region-derived sequences; and other natural sequences from other proteins.

In an embodiment, a constant domain is linked to the two linked variable domains using recombinant DNA techniques. In an embodiment, a sequence comprising linked heavy chain variable domains is linked to a heavy chain constant domain and a sequence comprising linked light chain variable domains is linked to a light chain constant domain. In an embodiment, the constant domains are human heavy chain constant domains and human light chain constant domains respectively. In an embodiment, the DVD heavy chain is further linked to an Fc region. The Fc region may be a native sequence Fc region or a variant Fc region. In another embodiment, the Fc region is a human Fc region. In another embodiment, the Fc region includes Fc region from IgG1, IgG2, IgG3, IgG4, IgA, IgM, IgE, or IgD.

In another embodiment, two heavy chain DVD polypeptides and two light chain DVD polypeptides are combined to form a DVD binding protein. Tables 1A-1C list amino acid sequences of VH and VL regions of exemplary antibodies useful for treating disease. In an embodiment, a DVD-Ig protein comprising at least two of the VH and/or VL regions listed in Tables 1A-1C, in any orientation, is provided. In some embodiments, VD1 and VD2 are independently chosen. Therefore, in some embodiments, VD1 and VD2 comprise the same SEQ ID NO and, in other embodiments, VD1 and VD2 comprise different SEQ ID NOS. The VH and VL domain sequences provided below comprise complementarity determining regions (CDRs) and framework sequences that are either known in the art or readily discernible using methods known in the art. In some embodiments, one or more of these CDRs and/or framework sequences are replaced, without loss of function, by other CDRs and/or framework sequences from binding proteins that are known in the art to bind to the same antigen.

TABLE 1A

List of Amino Acid Sequences of VH and VL Regions of Antibodies for Generating Binding Proteins, Including Multivalent Binding Proteins (CDR sequences in bold)

| SEQ ID No. | ABT Unique ID | Protein | region | Sequence 12345678901234567890123456789012345678901234567890 |
|---|---|---|---|---|
| 30 | AB397VH | VH-IL13 | (seq. 1) | EVTLRESGPGLVKPTQTLTLTCTLYGFSLSTSDMGVDWIRQPPGKGLEWLAHIWWDDVKRYNPALKSRLTISKDTSKNQVVLKLTSVDPVDTATYYCARTVSSGYIYYAMDYWGQGTLVTVSS |
| 31 | AB397VL | VL-IL13 | (seq. 1) | DIQMTQSPSSLSASVGDRVTISCRASQDIRNYLNWYQQKPGKAPKLLIFYTSKLHSGVPSRFSGSGSGTDYTLTISSLQPEDIATYYCQQGLTPPLTFGGGTKVEIKR |
| 32 | AB398VH | VH-IL13 | (seq. 2) | EVQLVQSGAEVKKPGASVKVSCKASGYTFTTYGVSWVRQAPGQGLEWMGEIYPGNYNTYYNEKFRGRVTMTTDTSTSTAYMELRSLRSDDTAVYYCARWRTSYFSDYGYFDYWGQGTTVTVSS |
| 33 | AB398VL | VL-IL13 | (seq. 2) | DVVMTQSPLSLPVTLGQPASISCRSSQSLVHSHGNTYLHWYQQRPGQSPRLLIYTVSNRFSGVPDRFSGSGSGTDFTLKISRVEAEDVGVYYCSQSTHVPYTFGGGTKVEIKR |
| 34 | AB399VH | VH-IL13 | (seq. 3) | EVQLVQSGAEVKKPGASVKVSCKASGYTFTSYWMHWVRQAPGQGLEWIGNINPKGGSNIYNEKFQGRVTMTRDTSISTAYMELSRLRSDDTAVYYCARLDYFGDSFDLWGQGTTVTVSS |
| 35 | AB399VL | VL-IL13 | (seq. 3) | DIQMTQSPSSLSASVGDRVTITCRASQGIRNYLNWYQQKPGKAPKLLIYYASNLEVGVPSRFSGSGSGTDYTLTISSLQPEDFATYYCQQDNRFPYTFGGGTKVEIKR |
| 36 | AB273VH | VH-IL17 | (seq. 1) | EVQLVQSGAEVKKPGSSVKVSCKASGYTFTDYEIHWVRQAPGQGLEWMGVNDPESGGTFYNQKFDGRVTLTADESTSTAYMELSSLRSEDTAVYYCTRYSKWDSFDGMDYWGQGTTVTVSS |

TABLE 1A -continued

List of Amino Acid Sequences of VH and VL Regions of Antibodies for Generating Binding Proteins, Including Multivalent Binding Proteins
(CDR sequences in bold)

| SEQ ID No. | ABT Unique ID | Protein region | Sequence 123456789012345678901234567890 |
|---|---|---|---|
| 37 | AB273VL | VL-IL17 (seq. 1) | DIQMTQSPSSLSASVGDRVTITCRASSGIISYIDWFQQKP GKAPKRLIYATFDLASGVPSRFSGSGSGTDYTLTISSLQP EDFATYYCRQVGSYPETFGQGTKLEIKR |
| 38 | AB274VH | VH-IL17 (seq. 2) | EVQLVQSGAEVKKPGSSVKVSCKASGGSFGGYGIGWVRQA PGQGLEWMGGITPFFGFADYAQKFQGRVTITADESTTTAY MELSGLTSDDTAVYYCARDPNEFWNGYYSTHDFDSWGQGT TVTVSS |
| 39 | AB274VL | VL-IL17 (seq. 2) | EIVLTQSPDFQSVTPKEKVTITCRASQDIGSELHWYQQKP DQPPKLLIKYASHSTSGVPSRFSGSGSGTDFTLTINGLEA EDAGTYYCHQTDSLPYTFGPGTKVDIKR |
| 40 | AB275VH | VH-IL17 (seq. 3) | EVQLVQSGAEVKKPGESVKISCKASGGSFRSYGISWVRQA PGQGLEWMGGITHFFGITDYAQKFQGRVTITADESTTTAY MELSGLTSDDTAVYYCAREPNDFWNGYYDTHDFDSWGQGT TVTVSS |
| 41 | AB275VL | VL-IL17 (seq. 3) | EIVLTQSPDFQSVTPKEKVTITCRASQNIGSELHWYQQKP DQSPKLLIKYASHSISGVPSRFSGSGSGTDFTLTINGLEA EDAATYYCHQSDTLPHTFGQGTKVDIKR |

TABLE 1B

Individual IL-17 VH Sequences from Affinity Matured Clones for Generating Binding Proteins, Including Multivalent Binding Proteins
IL-17 VH Sequences

| SEQ ID No. | Protein region | | Sequence 123456789012345678901234567890 |
|---|---|---|---|
| 42 | h10f7VH. 1a.g1m VH | | EVQLVQSGAEVKKPGSSVKVSCKASGYTFTDYEIHWVRQAPGQGLEWIGVNDPESGGTFY NQKFDGRATLTADKSTSTAYMELSSLRSED TAVYYCTRYYRYESFYGMDYWGQGTTVTVS S |
| | h10f7VH. 1a.g1m VH | CDR-H1 Residues 31-35 of SEQ ID NO.: 42 | DYEIH |
| | h10f7VH. 1a.g1m VH | CDR-H2 Residues 50-66 of SEQ ID NO.: 42 | VNDPESGGTFYNQKFDG |
| | h10f7VH. 1a.g1m VH | CDR-H3 Residues 99-110 of SEQ ID NO.: 42 | YYRYESFYGMDY |
| 43 | J439M1S3 R5#10 VH | | EVQLVQSGAEVKKPGSSVKVSCKASGYTFDDYEIHWVRQAPGQGLEWMGVNDPESGGTFY NQKFDGRATLTADKSTSTAYMELSSLRSED TAVYYCTRYDKWDSFYGMDYWGQGTTVTVS S |
| | J439M1S3 R5#10 VH | CDR-H1 Residues 31-35 of SEQ ID NO.: 43 | DYEIH |
| | J439M1S3 R5#10 VH | CDR-H2 Residues 50-66 of SEQ ID NO.: 43 | VNDPESGGTFYNQKFDG |
| | J439M1S3 R5#10 VH | CDR-H3 Residues 99-110 of SEQ ID NO.: 43 | YDKWDSFYGMDY |
| 44 | J439M1S3 R5#11 VH | | EVQLVQSGAEVKKPGSSVKVSCKASGYTFTDYEIHWVRQAPGQGLEWMGVNDPESGGTFY NQKFDGRVTLTADESTSTAYMELSSLRSED TAVYYCTRYSKWDSFDGMDYWGQGTTVTVS S |
| | J439M1S3 R5#11 VH | CDR-H1 Residues 31-35 of SEQ ID NO.: 44 | DYEIH |
| | J439M1S3 R5#11 VH | CDR-H2 Residues 50- | VNDPESGGTFYNQKFDG |

TABLE 1B -continued

Individual IL-17 VH Sequences from Affinity Matured Clones for
Generating Binding Proteins, Including Multivalent Binding Proteins
IL-17 VH Sequences

| SEQ ID No. | Protein region | | Sequence 12345678901234567890123456789 0 |
|---|---|---|---|
| | R5#11 VH J439M1S3 R5#11 VH | CDR-H3 | 66 of SEQ ID NO.: 44 Residues 99-110 of SEQ ID NO.: 44 | YSKWDSFDGMDY |
| 45 | J439M1S2 (H)3 #A6 VH | | EVQLVQSGAEVKKPGSSVKVSCKASGYTFTDYEIHWVRQAPGQGLEWIGVNDPDSGGTLYNQKFDGRVTLTADESTSTAYMELSSLRSEDTAVYYCTRYDKWYSFEGMDIWGQGTTVTVSS |
| | 439M1S2 (H)3 #A6 VH | CDR-H1 | Residues 31-35 of SEQ ID NO.: 45 | DYEIH |
| | 439M1S2 (H)3 #A6 VH | CDR-H2 | Residues 50-66 of SEQ ID NO.: 45 | VNDPDSGGTLYNQKFDG |
| | 439M1S2 (H)3 #A6 VH | CDR-H3 | Residues 99-110 of SEQ ID NO.: 45 | YDKWYSFEGNDI |
| 46 | J439M1S2 (H)3 #A11 VH | | EVQLVQSGAEVKKPGSSVKVSCKASGYTFTDYEIHWVRQAPGQGLEWMGVNDPESGGTFYNQKFDGRVTLSADESTSTAYMELSSLRSEDTAVYYCTRYDKYWSFEGMDYWGQGTTVTVSS |
| | J439M1S2 (H)3 #A11 VH | CDR-H1 | Residues 31-35 of SEQ ID NO.: 46 | DYEIH |
| | J439M1S2 (H)3 #A11 VH | CDR-H2 | Residues 50-66 of SEQ ID NO.: 46 | VNDPESGGTFYNQKFDG |
| | J439M1S2 (H)3 #A11 VH | CDR-H3 | Residues 99-110 of SEQ ID NO.: 46 | YDKYWSFEGNDY |
| 47 | J439M1S2 (H)3 #A16 VH | | EVQLVQSGAEVKKPGSSVKVSCKASGYTFSDYEIHWVRQAPGQGLEWMGVNDPESGGTFYNQKFDGRVTLTADESTSTAYMELSSLRSEDTAVYYCTRYDKWYSFEGMDIWGQGTTVTVSS |
| | J439M1S2 (H)3 #A16 VH | CDR-H1 | Residues 31-35 of SEQ ID NO.: 47 | DYEIH |
| | J439M1S2 (H)3 #A16 VH | CDR-H2 | Residues 50-66 of SEQ ID NO.: 47 | VNDPESGGTFYNQKFDG |
| | J439M1S2 (H)3 #A16 VH | CDR-H3 | Residues 99-110 of SEQ ID NO.: 47 | DKWYSFEGMDI |
| 48 | J439M1S2 (H)3 #B13 VH | | EVQLVQSGAEVKKPGSSVKVSCKASGYTFSDYEIHWVRQAPGQGLEWMGVNDPESGGTFYNQKFDGRVTLTADESTSTAYMELSSLRSEDTAVYYCTRYDKYWSFEGMDYWGQGTTVTVSS |
| | J439M1S2 (H)3 #B13 VH | CDR-H1 | Residues 31-35 of SEQ ID NO.: 48 | DYEIH |
| | J439M1S2 (H)3 #B13 VH | CDR-H2 | Residues 50-66 of SEQ ID NO.: 48 | VNDPESGGTFYNQKFDG |
| | J439M1S2 (H)3 #B13 VH | CDR-H3 | Residues 99-110 of SEQ | DKYWSFEGMDY |

TABLE 1B -continued

Individual IL-17 VH Sequences from Affinity Matured Clones for Generating Binding Proteins, Including Multivalent Binding Proteins
IL-17 VH Sequences

| SEQ ID No. | Protein region | | Sequence 123456789012345678901234567890 |
|---|---|---|---|
| | #B13 VH | | ID NO.: 48 |
| 49 | J439M1S2 (H)3 #B20 VH | | EVQLVQSGAEVKKPGSSVKVSCKASGYTFT DYEIHWVRQAPGQGLEWMGVNDPESGGTFY NQKFDGRVTLTADESTSTAYMELSSLRSED TAVYYCTRYDKWYSFEGMDIWGQGTTVTVS S |
| | J439M1S2 (H)3 #B20 VH | CDR-H1 | Residues 31-35 of SEQ ID NO.: 49 | DYEIH |
| | J439M1S2 (H)3 #B20 VH | CDR-H2 | Residues 50-66 of SEQ ID NO.: 49 | VNDPESGGTFYNQKFDG |
| | J439M1S2 (H)3 #B20 VH | CDR-H3 | Residues 99-110 of SEQ ID NO.: 49 | DKWYSFEGMDI |

TABLE 1C

Individual IL-17 VL Sequences from Affinity Matured Clones for Generating Binding Proteins, Including Multivalent Binding Proteins IL-17 VL Sequences

| SEQ ID No. | Protein region | | Sequence 123456789012345678901234567890 |
|---|---|---|---|
| 50 | J439M1S3 R5#10 VL | | DIQMTQSPSSLSASVGDRVTITCSASSGSI SYIDWFQQKPGKAPKRLIYATFELASGVPS RFSGSGSGTDFTLTISSLQPEDFATYYCHQ LGSYPDTFGQGTKLEIK |
| | J439M1S3 R5#10 VL | CDR-L1 | Residues 24-34 of SEQ ID NO.: 50 | SASSGSISYID |
| | J439M1S3 R5#10 VL | CDR-L2 | Residues 50-56 of SEQ ID NO.: 50 | ATFELAS |
| | J439M1S3 R5#10 VL | CDR-L3 | Residues 89-97 of SEQ ID NO.: 50 | HQLGSYPDT |
| 51 | J439M1S3 R5#11 VL | | DIQMTQSPSSLSASVGDRVTITCRASSGII SYIDWFQQKPGKAPKRLIYATFDLASGVPS RFSGSGSGTDYTLTISSLQPEDFATYYCRQ VGSYPETFGQGTKLEIK |
| | J439M1S3 R5#11 VL | CDR-L1 | Residues 24-34 of SEQ ID NO.: 51 | RASSGIISYID |
| | J439M1S3 R5#11 VL | CDR-L2 | Residues 50-56 of SEQ ID NO.: 51 | ATFDLAS |
| | J439M1S3 R5#11 VL | CDR-L3 | Residues 89-97 of SEQ ID NO.: 51 | RQVGSYPET |
| 52 | J427M2S3 #12 VL | | DIQMTQSPSSLSASVGDRVTITCSASSGII SSIDWFQQKPGKAPKRLIYATFALQSGVPS RFSGSGSGTDFTLTISSLQPEDFATYYCSQ MSSYPHTFGQGTKLEIK |

TABLE 1C-continued

Individual IL-17 VL Sequences from Affinity Matured Clones for Generating Binding Proteins, Including Multivalent Binding Proteins IL-17 VL Sequences

| SEQ ID No. | Protein | region | | Sequence 123456789012345678901234567890 |
|---|---|---|---|---|
| | J427M2S3 #12 VL | CDR-L1 | Residues 24-34 of SEQ ID NO.: 52 | SASSGIISSID |
| | J427M2S3 #12 VL | CDR-L2 | Residues 50-56 of SEQ ID NO.: 52 | ATFALQS |
| | J427M2S3 #12 VL | CDR-L3 | Residues 89-97 of SEQ ID NO.: 52 | SQMSSYPHT |
| 53 | J427M2S3 #27 VL | | Residues 24-34 of SEQ ID NO.: 53 | DIQMTQSPSSLSASVGDRVTITCSASSDIS SYLNWFQQKPGKSPKRLIYRTSELQSGVPS RFSGSGSGTDFTLTISSLQPEDFATYYCQQ WSSYPWTFGQGTKLEIK |
| | J427M2S3 #27 VL | CDR-L1 | Residues 50-56 of SEQ ID NO.: 53 | SASSDISSYLN |
| | J427M2S3 #27 VL | CDR-L2 | Residues 89-97 of SEQ ID NO.: 53 | RTSELQS |
| | J427M2S3 #27 VL | CDR-L3 | | QQWSSYPWT |
| 54 | J439M1S2 (H)3#A6 VL | | | DIQMTQSPSSLSASVGDRVTITCSASQGIR SYIDWFQQKPGKSPKRLIYATFDLASGVPS RFSGSGSGTDYTLTISSLQPEDFATYYCRQ VGNYPGTFGQGTKLEIK |
| | J439M1S2 (H)3#A6 VL | CDR-L1 | Residues 24-34 of SEQ ID NO.: 54 | SASQGIRSYID |
| | J439M1S2 (H)3#A6 VI | CDR-L2 | Residues 50-56 of SEQ ID NO.: 54 | ATFDLAS |
| | J439M1S2 (H)3#A6 VL | CDR-L3 | Residues 89-97 of SEQ ID NO.: 54 | RQVGNYPGT |

Detailed description of specific DVD binding proteins capable of binding specific targets, and methods of making the same, is provided in the Examples section below.

D. Production of Binding Proteins

The binding proteins provided herein may be produced by any of a number of techniques known in the art. For example, expression from host cells, wherein expression vector(s) encoding the DVD heavy and DVD light chains is (are) transfected into a host cell by standard techniques. Although it is possible to express the DVD binding proteins provided herein in either prokaryotic or eukaryotic host cells, DVD binding proteins are expressed in eukaryotic cells, for example, mammalian host cells, because such eukaryotic cells (and in particular mammalian cells) are more likely than prokaryotic cells to assemble and secrete a properly folded and immunologically active DVD binding protein.

In an exemplary system for recombinant expression of DVD proteins, a recombinant expression vector encoding both the DVD heavy chain and the DVD light chain is introduced into dhfr-CHO cells by calcium phosphate-mediated transfection. Within the recombinant expression vector, the DVD heavy and light chain genes are each operatively linked to CMV enhancer/AdMLP promoter regulatory elements to drive high levels of transcription of the genes. The recombinant expression vector also carries a DHFR gene, which allows for selection of CHO cells that have been transfected with the vector using methotrexate selection/amplification. The selected transformant host cells are cultured to allow for expression of the DVD heavy and light chains and intact DVD protein is recovered from the culture medium. Standard molecular biology techniques are used to prepare the recombinant expression vector, transfect the host cells, select for transformants, culture the host cells and recover the DVD protein from the culture medium. A method of synthesizing a DVD protein provided herein by culturing a host cell provided herein in a suitable culture medium until a DVD protein is synthesized is also provided. The method can further comprise isolating the DVD protein from the culture medium.

An important feature of DVD binding protein is that it can be produced and purified in a similar way as a conventional antibody. The production of DVD binding protein results in a homogeneous, single major product with desired dual-specific activity, without the need for sequence modification of the constant region or chemical modifications. Other previously described methods to generate "bi-specific", "multi-specific", and "multi-specific multivalent" full length binding proteins can lead to the intracellular or secreted production of a mixture of assembled inactive, mono-specific, multi-specific, multivalent, full length binding proteins, and multivalent full length binding proteins with a combination of different binding sites.

Surprisingly, the design of the "dual-specific multivalent full length binding proteins" provided herein leads to a dual variable domain light chain and a dual variable domain heavy chain that assemble primarily to the desired "dual-specific multivalent full length binding proteins".

At least 50%, at least 75% and at least 90% of the assembled, and expressed dual variable domain immunoglobulin molecules are the desired dual-specific tetravalent protein, and therefore possess enhanced commercial utility. Thus, a method to express a dual variable domain light chain and a dual variable domain heavy chain in a single cell leading to a single primary product of a "dual-specific tetravalent full length binding protein" is provided.

Methods of expressing a dual variable domain light chain and a dual variable domain heavy chain in a single cell leading to a "primary product" of a "dual-specific tetravalent full length binding protein", where the "primary product" is more than 50%, such as more than 75% and more than 90%, of all assembled protein, comprising a dual variable domain light chain and a dual variable domain heavy chain are provided.

II. Uses of Binding Proteins

Given their ability to bind to two or more antigens the binding proteins provided herein can be used to detect the antigens (e.g., in a biological sample, such as serum or plasma), using a conventional immunoassay, such as an enzyme linked immunosorbent assays (ELISA), a radioimmunoassay (RIA), or tissue immunohistochemistry. The binding protein is directly or indirectly labeled with a detectable substance to facilitate detection of the bound or unbound antibody. Suitable detectable substances include various enzymes, prosthetic groups, fluorescent materials, luminescent materials and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin. An example of a luminescent material is luminol and examples of suitable radioactive materials include $^{3}H$, $^{14}C$, $^{35}S$, $^{90}Y$, $^{99}Tc$, $^{111}In$, $^{125}I$, $^{131}I$, $^{177}Lu$, $^{166}Ho$, and $^{153}Sm$.

In an embodiment, the binding proteins provided herein are capable of neutralizing the activity of their antigen targets both in vitro and in vivo. Accordingly, such binding proteins can be used to inhibit antigen activity, e.g., in a cell culture containing the antigens, in human subjects or in other mammalian subjects having the antigens with which a binding protein provided herein cross-reacts. In another embodiment, a method for reducing antigen activity in a subject suffering from a disease or disorder in which the antigen activity is detrimental is provided. A binding protein provided herein can be administered to a human subject for therapeutic purposes.

The term "a disorder in which antigen activity is detrimental" is intended to include diseases and other disorders in which the presence of the antigen in a subject suffering from the disorder has been shown to be or is suspected of being either responsible for the pathophysiology of the disorder or a factor that contributes to a worsening of the disorder. Accordingly, a disorder in which antigen activity is detrimental is a disorder in which reduction of antigen activity is expected to alleviate the symptoms and/or progression of the disorder. Such disorders may be evidenced, for example, by an increase in the concentration of the antigen in a biological fluid of a subject suffering from the disorder (e.g., an increase in the concentration of antigen in serum, plasma, synovial fluid, etc., of the subject). Non-limiting examples of disorders that can be treated with the binding proteins provided herein include those disorders discussed below and in the section pertaining to pharmaceutical compositions comprising the binding proteins.

DVD binding proteins are useful as therapeutic agents to simultaneously block two different targets to enhance efficacy/safety and/or increase patient coverage.

Additionally, DVD binding proteins provided herein can be employed for tissue-specific delivery (target a tissue marker and a disease mediator for enhanced local PK thus higher efficacy and/or lower toxicity), including intracellular delivery (targeting an internalizing receptor and an intracellular molecule), delivering to inside brain (targeting transferrin receptor and a CNS disease mediator for crossing the blood-brain barrier). DVD binding protein can also serve as a carrier protein to deliver an antigen to a specific location via binding to a non-neutralizing epitope of that antigen and also to increase the half-life of the antigen. Furthermore, DVD binding protein can be designed to either be physically linked to medical devices implanted into patients or target these medical devices (see Burke et al. (2006) Advanced Drug Deliv. Rev. 58(3): 437-446; Hildebrand et al. (2006) Surface and Coatings Technol. 200(22-23): 6318-6324; Drug/device combinations for local drug therapies and infection prophylaxis, Wu (2006) Biomaterials 27(11):2450-2467; Mediation of the cytokine network in the implantation of orthopedic devices, Marques (2005) Biodegradable Systems in Tissue Engineer. Regen. Med. 377-397). Briefly, directing appropriate types of cell to the site of medical implant may promote healing and restoring normal tissue function. Alternatively, inhibition of mediators (including but not limited to cytokines), released upon device implantation by a DVD coupled to or target to a device is also provided.

A. Use of Binding Proteins in Various Diseases

Binding protein molecules provided herein are useful as therapeutic molecules to treat various diseases, e.g., wherein the targets that are recognized by the binding proteins are detrimental. Such binding proteins may bind one or more targets involved in a specific disease. Inhibition of IL-13 and/or IL-17 has also been shown to enhance anti-viral vaccines in animal models and may be beneficial in the treatment of HIV and other infectious diseases, for example, the human rhinovirus, other enteroviruses, coronavirus, herpes viruses, influenza virus, parainfluenza virus, respiratory syncytial virus or adenovirus.

Without limiting the disclosure, further information on certain disease conditions is provided.

1. Human Autoimmune and Inflammatory Response

IL-13 and/or IL-17 have been implicated in general autoimmune and inflammatory responses, including, for example, asthma, allergies, allergic lung disease, allergic rhinitis, atopic dermatitis, chronic obstructive pulmonary disease (COPD), fibrosis, cystic fibrosis (CF), fibrotic lung disease, idiopathic pulmonary fibrosis, liver fibrosis, lupus, hepatitis B-related liver diseases and fibrosis, sepsis, systemic lupus erythematosus (SLE), glomerulonephritis, inflammatory skin diseases, psoriasis, diabetes, insulin dependent diabetes mellitus, inflammatory bowel disease (IBD), ulcerative colitis (UC), Crohn's disease (CD), rheumatoid arthritis (RA), osteoarthritis (OA), multiple sclerosis (MS), graft-versus-host disease (GVHD), transplant rejection, ischemic heart disease (IHD), celiac disease, contact hypersensitivity, alcoholic liver disease, Behcet's disease, atherosclerotic vascular disease, occular surface inflammatory diseases, or Lyme disease.

The binding proteins provided herein can be used to treat neurological disorders. In an embodiment, the binding proteins provided herein or antigen-binding portions thereof, are used to treat neurodegenerative diseases, and conditions involving neuronal regeneration and spinal cord injury.

2. Asthma

Allergic asthma is characterized by the presence of eosinophilia, goblet cell metaplasia, epithelial cell alterations, airway hyperreactivity (AHR), and Th2 and Th1 cytokine expression, as well as elevated serum IgE levels. Corticosteroids are the most important anti-inflammatory treatment for asthma today, however their mechanism of action is non-specific and safety concerns exist, especially in the juvenile patient population. The development of more specific and targeted therapies is therefore warranted. There is increasing evidence that IL-13 in mice mimics many of the features of asthma, including AHR, mucus hypersecretion and airway fibrosis, independently of eosinophilic inflammation (Finotto et al. (2005) Internat. Immunol. 17(8): 993-1007; Padilla et al. (2005) J. Immunol. 174(12): 8097-8105).

IL-13 has been implicated as having a pivotal role in causing pathological responses associated with asthma. The development of anti-IL-13 mAb therapy to reduce the effects of IL-13 in the lung is an exciting new approach that offers considerable promise as a novel treatment for asthma. However other mediators of differential immunological pathways are also involved in asthma pathogenesis, and blocking these mediators, in addition to IL-13, may offer additional therapeutic benefit. Such target pairs include, but are not limited to, IL-13 and a pro-inflammatory cytokine, such as IL-17. There is growing evidence that IL-17 is involved in the pathogenesis of asthma. IL-17 induces the neutrophils into the airways and also enhances T-helper 2 (Th2) cell-mediated eosinophilic airway inflammation in asthma. Recent studies have demonstrated that inhibitors and other diverse regulators of IL-17 reduce antigen-induced airway inflammation, bronchial hyperresponsiveness, and Th2 cytokine levels in animal models of asthma (for a review see Park and Lee (2010) Respiratory Res., 11:78).

Animal models such as an OVA-induced asthma mouse model, where both inflammation and AHR can be assessed, are known in the art and may be used to determine the ability of various binding protein molecules to treat asthma. Animal models for studying asthma are disclosed in Coffman, et al. (2005) J. Exp. Med. 201(12):1875-1879; Lloyd et al. (2001) Adv. Immunol. 77: 263-295; Boyce et al. (2005) J. Exp. Med. 201(12):1869-1873; and Snibson et al. (2005) J. Brit. Soc. Allergy Clin. Immunol. 35(2):146-52. In addition to routine safety assessments of these target pairs specific tests for the degree of immunosuppression may be warranted and helpful in selecting the best target pairs (see Luster et al. (1994) Toxicol. 92(1-3):229-43; Descotes et al. (1992) Dev. Biol. Standard. 77:99-102; Hart et al. (2001) J. Allergy Clin. Immunol. 108(2):250-257).

3. Rheumatoid Arthritis

Rheumatoid arthritis (RA), a systemic disease, is characterized by a chronic inflammatory reaction in the synovium of joints and is associated with degeneration of cartilage and erosion of juxta-articular bone. Many pro-inflammatory cytokines, chemokines, and growth factors are expressed in diseased joints. Recent studies indicate that the involvement of T cells in RA is mediated to a significant extent by IL-17. Animal studies have shown that markedly increased IL-17 expression was detected in mice that develop articular lesions resembling human RA. Beneficial effects of IL-17 blockade were also observed various animal models of the disease (for a review see Witowski et al. (2004) Cell. Mol. Life. Sci. 61: 567-579). Whether a binding protein molecule will be useful for the treatment of rheumatoid arthritis can be assessed using pre-clinical animal RA models such as the collagen-induced arthritis mouse model. Other useful models are also well known in the art (see Brand (2005) Comp. Med. 55(2):114-22). Based on the cross-reactivity of the parental antibodies for human and mouse orthologues (e.g., reactivity for human and mouse TNF, human and mouse IL-15, etc.) validation studies in the mouse CIA model may be conducted with "matched surrogate antibody" derived binding protein molecules; briefly, a binding protein based on two (or more) mouse target specific antibodies may be matched to the extent possible to the characteristics of the parental human or humanized antibodies used for human binding protein construction (e.g., similar affinity, similar neutralization potency, similar half-life, etc.).

4. Systemic Lupus Erythematosus (SLE)

The immunopathogenic hallmark of SLE is the polyclonal B cell activation, which leads to hyperglobulinemia, autoantibody production and immune complex formation. Significant increased levels of IL-13 and IL-17 have been detected in patients with systemic lupus erythematosus (Morimoto et al. (2001) Autoimmunity, 34(1):19-25; Wong et al. (2008) Clin Immunol. 127(3):385-93). IL-17 represents an important cytokine in the pathogenesis of SLE. Increased IL-17 production has been shown in patients with SLE as well as in animals with lupus-like diseases. Animal models have demonstrated that blockade of IL-17 decreases lupus manifestations (for a review see Nalbandian et al. (2009) 157(2): 209-215). Based on the cross-reactivity of the parental antibodies for human and mouse othologues (e.g., reactivity for human and mouse CD20, human and mouse interferon alpha, etc.) validation studies in a mouse lupus model may be conducted with "matched surrogate antibody" derived binding protein molecules. Briefly, a binding protein based two (or more) mouse target specific antibodies may be matched to the extent possible to the characteristics of the parental human or humanized antibodies used for human binding protein construction (e.g., similar affinity, similar neutralization potency, similar half-life, etc.).

5. Multiple Sclerosis

Multiple sclerosis (MS) is a complex human autoimmune-type disease with a predominantly unknown etiology. Immunologic destruction of myelin basic protein (MBP) throughout the nervous system is the major pathology of multiple sclerosis. Of major consideration are immunological mechanisms that contribute to the development of autoimmunity. In particular, antigen expression, cytokine and leukocyte interactions, and regulatory T-cells, which help balance/modulate other T-cells such as Th1 and Th2 cells, are important areas for therapeutic target identification. In MS, increased expression of IL-17 has been detected both in brain lesions and in mononuclear cells isolated from blood and cerebrospinal fluid. IL-17-producing cells are extremely enriched in active MS lesions, suggesting that neutralization of this cytokine has the potential of being beneficial (for a review see Witowski et al. (2004) Cell. Mol. Life. Sci. 61: 567-579).

Several animal models for assessing the usefulness of the binding proteins to treat MS are known in the art (see Steinman et al. (2005) Trends Immunol. 26(11):565-71; Lublin et al. (1985) Springer Semin. Immunopathol.8(3):197-208; Genain et al. (1997) J. Mol. Med. 75(3):187-97; Tuohy et al. (1999) J. Exp. Med. 189(7):1033-42; Owens et al. (1995) Neurol. Clin. 13(1):51-73; and Hart et al. (2005) J. Immunol. 175(7):4761-8.) Based on the cross-reactivity of the parental antibodies for human and animal species othologues validation studies in the mouse EAE model may be conducted with "matched surrogate antibody" derived binding protein molecules. Briefly, a binding protein based on two (or more) mouse target specific antibodies may be matched to the extent possible to the characteristics of the parental human or humanized antibodies used for human binding protein construction (e.g., similar affinity, similar neutralization potency, similar half-life, etc.). The same concept applies to animal models in other non-rodent species, where a "matched surrogate antibody" derived binding protein would be selected for the anticipated pharmacology and possibly safety studies. In addition to routine safety assessments of these target pairs specific tests for the degree of immunosuppression may be warranted and helpful in selecting the best target pairs (see Luster et al. (1994) Toxicol. 92(1-3): 229-43; Descotes et al. (1992) Devel. Biol. Standard. 77: 99-102; Jones (2000) IDrugs 3(4):442-6).

6. Sepsis

Overwhelming inflammatory and immune responses are essential features of septic shock and play a central part in the pathogenesis of tissue damage, multiple organ failure, and death induced by sepsis. Cytokines have been shown to be mediators of septic shock. These cytokines have a direct toxic effect on tissues; they also activate phospholipase A2. These and other effects lead to increased concentrations of platelet-activating factor, promotion of nitric oxide synthase activity, promotion of tissue infiltration by neutrophils, and promotion of neutrophil activity. IL-17 levels and clinical prognosis of sepsis have been shown to be negatively correlated. Neutralization of IL-17A can significantly improve the survival rate of patients with sepsis (see Flierl et al. (2008) FASEB J. 22: 2198-2205).

One embodiment pertains to binding proteins capable of binding one or more targets involved in sepsis, such as, for example IL-13 and IL-17. The efficacy of such binding proteins for treating sepsis can be assessed in preclinical animal models known in the art (see Buras et al. (2005) Nat. Rev. Drug Discov. 4(10):854-65 and Calandra et al. (2000) Nat. Med. 6(2):164-70).

7. Neurological Disorders a. Neurodegenerative Diseases

Neurodegenerative diseases are either chronic in which case they are usually age-dependent or acute (e.g., stroke, traumatic brain injury, spinal cord injury, etc.). They are characterized by progressive loss of neuronal functions (e.g., neuronal cell death, axon loss, neuritic dystrophy, demyelination), loss of mobility and loss of memory. These chronic neurodegenerative diseases represent a complex interaction between multiple cell types and mediators. Treatment strategies for such diseases are limited and mostly constitute either blocking inflammatory processes with non-specific anti-inflammatory agents (e.g., corticosteroids, COX inhibitors) or agents to prevent neuron loss and/or synaptic functions. These treatments fail to stop disease progression. Specific therapies targeting more than one disease mediator may provide even better therapeutic efficacy for chronic neurodegenerative diseases than observed with targeting a single disease mechanism (see Deane et al. (2003) Nature Med. 9:907-13; and Masliah et al. (2005) Neuron. 46:857).

The binding protein molecules provided herein can bind one or more targets involved in chronic neurodegenerative diseases such as Alzheimers. The efficacy of binding protein molecules can be validated in pre-clinical animal models such as the transgenic mice that over-express amyloid precursor protein or RAGE and develop Alzheimer's disease-like symptoms. In addition, binding protein molecules can be constructed and tested for efficacy in the animal models and the best therapeutic binding protein can be selected for testing in human patients. Binding protein molecules can also be employed for treatment of other neurodegenerative diseases such as Parkinson's disease.

b. Neuronal Regeneration and Spinal Cord Injury

Despite an increase in knowledge of the pathologic mechanisms, spinal cord injury (SCI) is still a devastating condition and represents a medical indication characterized by a high medical need. Most spinal cord injuries are contusion or compression injuries and the primary injury is usually followed by secondary injury mechanisms (inflammatory mediators e.g., cytokines and chemokines) that worsen the initial injury and result in significant enlargement of the lesion area, sometimes more than 10-fold. IL-17 is a mediator of secondary degeneration, which contributes to neuroinflammation and hinders functional recovery. Studies using IL-17 KO mice have demonstrated that IL-17 contributes to neuroinflammatory responses and pain hypersensitivity following neuropathic injury (Kim and Moalem-Taylor (2010) J. Pain. 12(3):370-83). IL-17 deficiency improves locomotor recovery and tissue sparing after spinal cord contusion injury in mice (Hill at al. (2011) Neurosci Lett. 487(3):363-7).

The efficacy of binding protein molecules can be validated in pre-clinical animal models of spinal cord injury. In addition, these binding protein molecules can be constructed and tested for efficacy in the animal models and the best therapeutic binding protein can be selected for testing in human patients. In general, antibodies do not cross the blood brain barrier (BBB) in an efficient and relevant manner. However, in certain neurologic diseases, e.g., stroke, traumatic brain injury, multiple sclerosis, etc., the BBB may be compromised and allows for increased penetration of binding proteins and antibodies into the brain. In other neurological conditions, where BBB leakage is not occurring, one may employ the targeting of endogenous transport systems, including carrier-mediated transporters such as glucose and amino acid carriers and receptor-mediated transcytosis-mediating cell structures/receptors at the vascular endothelium of the BBB, thus enabling trans-BBB transport of the binding protein. Structures at the BBB enabling such transport include but are not limited to the insulin receptor, transferrin receptor, LRP and RAGE. In addition, strategies enable the use of binding proteins also as shuttles to transport potential drugs into the CNS including low molecular weight drugs, nanoparticles and nucleic acids (Coloma et al. (2000) Pharm Res. 17(3):266-74; Boado et al. (2007) Bioconjug. Chem. 18(2):447-55).

8. Oncological Disorders

Monoclonal antibody therapy has emerged as an important therapeutic modality for cancer (von Mehren et al. (2003) Annu. Rev. Med. 54:343-69). The use of dual-specific antibody that targets two separate tumor mediators will likely give additional benefit compared to a mono-specific therapy. IL-17 has been suggested to support tumor growth, probably by stimulating angiogenesis. IL-13 plays an important role in the regulation of anti-tumor immunity and tumor growth. Studies indicate that IL-13 is central to a novel immunoregulatory pathway in which NKT cells suppress tumor immunosurveillance. (For a review see Kolls et al. (2003) Am. J. Respir. Cell Mol. Biol. 28: 9-11, and Terabe et al. (2004) Cancer Immunol Immunother. 53(2):79-85.)

In an embodiment, diseases that can be treated or diagnosed with the compositions and methods provided herein include, but are not limited to, primary and metastatic cancers, including carcinomas of breast, colon, rectum, lung, oropharynx, hypopharynx, esophagus, stomach, pancreas, liver, gallbladder and bile ducts, small intestine, urinary tract (including kidney, bladder and urothelium), female genital tract (including cervix, uterus, and ovaries as well as choriocarcinoma and gestational trophoblastic disease), male genital tract (including prostate, seminal vesicles, testes and germ cell tumors), endocrine glands (including the thyroid, adrenal, and pituitary glands), and skin, as well as hemangiomas, melanomas, sarcomas (including those arising from bone and soft tissues as well as Kaposi's sarcoma), tumors of the brain, nerves, eyes, and meninges (including astrocytomas, gliomas, glioblastomas, retinoblastomas, neuromas, neuroblastomas, Schwannomas, and meningiomas), solid tumors arising from hematopoietic malignancies such as leukemias, and lymphomas (both Hodgkin's and non-Hodgkin's lymphomas).

In an embodiment, the antibodies provided herein or antigen-binding portions thereof, are used to treat cancer or in the prevention of metastases from the tumors described herein either when used alone or in combination with radiotherapy and/or other chemotherapeutic agents.

9. Gene Therapy

In a specific embodiment, nucleic acid sequences encoding a binding protein provided herein or another prophylactic or therapeutic agent provided herein are administered to treat, prevent, manage, or ameliorate a disorder or one or more symptoms thereof by way of gene therapy. Gene therapy refers to therapy performed by the administration to a subject of an expressed or expressible nucleic acid. In this embodiment, the nucleic acids produce their encoded antibody or prophylactic or therapeutic agent provided herein that mediates a prophylactic or therapeutic effect.

Any of the methods for gene therapy available in the art can be used in the methods provided herein. For general reviews of the methods of gene therapy, see Goldspiel et al. (1993) Clin. Pharmacy 12:488-505; Wu and Wu (1991) Biotherapy 3:87-95; Tolstoshev (1993) Ann. Rev. Pharmacol. Toxicol. 32:573-596; Mulligan (1993) Science 260:926-932; Morgan and Anderson (1993) Ann. Rev. Biochem. 62:191-217; and May (1993) TIBTECH 11(5):155-215. Methods commonly known in the art of recombinant DNA technology which can be used are described in Ausubel et al. (eds.), Current Protocols in Molecular Biology, John Wiley &Sons, NY (1993); and Kriegler, Gene Transfer and Expression, A Laboratory Manual, Stockton Press, NY (1990). Detailed description of various methods of gene therapy are disclosed in US Patent Publication No. US20050042664.

III. Pharmaceutical Compositions

Pharmaceutical compositions comprising one or more binding proteins, either alone or in combination with prophylactic agents, therapeutic agents, and/or pharmaceutically acceptable carriers are provided. The pharmaceutical compositions comprising binding proteins provided herein are for use in, but not limited to, diagnosing, detecting, or monitoring a disorder, in preventing, treating, managing, or ameliorating a disorder or one or more symptoms thereof, and/or in research. The formulation of pharmaceutical compositions, either alone or in combination with prophylactic agents, therapeutic agents, and/or pharmaceutically acceptable carriers, are known to one skilled in the art (US Patent Publication No. 20090311253 A1).

Methods of administering a prophylactic or therapeutic agent provided herein include, but are not limited to, parenteral administration (e.g., intradermal, intramuscular, intraperitoneal, intravenous and subcutaneous), epidural administration, intratumoral administration, mucosal administration (e.g., intranasal and oral routes) and pulmonary administration (e.g., aerosolized compounds administered with an inhaler or nebulizer). The formulation of pharmaceutical compositions for specific routes of administration, and the materials and techniques necessary for the various methods of administration are available and known to one skilled in the art (US Patent Publication No. 20090311253 A1).

Dosage regimens may be adjusted to provide the optimum desired response (e.g., a therapeutic or prophylactic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. The term "dosage unit form" refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms provided herein are dictated by and directly dependent on (a) the unique characteristics of the active compound and the particular therapeutic or prophylactic effect to be achieved, and (b) the limitations inherent in the art of compounding such an active compound for the treatment of sensitivity in individuals.

An exemplary, non-limiting range for a therapeutically or prophylactically effective amount of a binding protein provided herein is 0.1-20 mg/kg, for example, 1-10 mg/kg. It is to be noted that dosage values may vary with the type and severity of the condition to be alleviated. It is to be further understood that for any particular subject, specific dosage regimens may be adjusted over time according to the individual need and the professional judgment of the person administering or supervising the administration of the compositions, and that dosage ranges set forth herein are exemplary only and are not intended to limit the scope or practice of the claimed composition.

IV. Combination Therapy

A binding protein provided herein also can also be administered with one or more additional therapeutic agents useful in the treatment of various diseases, the additional agent being selected by the skilled artisan for its intended purpose. For example, the additional agent can be a therapeutic agent art-recognized as being useful to treat the disease or condition being treated by the antibody provided herein. The combination can also include more than one additional agent, e.g., two or three additional agents.

Combination therapy agents include, but are not limited to, antineoplastic agents, radiotherapy, chemotherapy such as DNA alkylating agents, cisplatin, carboplatin, anti-tubulin agents, paclitaxel, docetaxel, taxol, doxorubicin, gemcitabine, gemzar, anthracyclines, adriamycin, topoisomerase I inhibitors, topoisomerase II inhibitors, 5-fluorouracil (5-FU), leucovorin, irinotecan, receptor tyrosine kinase inhibitors (e.g., erlotinib, gefitinib), COX-2 inhibitors (e.g., celecoxib), kinase inhibitors, and siRNAs.

Combinations to treat autoimmune and inflammatory diseases are non-steroidal anti-inflammatory drug(s) also referred to as NSAIDS which include drugs like ibuprofen. Other combinations are corticosteroids including prednisolone; the well known side-effects of steroid use can be reduced or even eliminated by tapering the steroid dose required when treating patients in combination with the binding proteins provided herein. Non-limiting examples of therapeutic agents for rheumatoid arthritis with which an antibody provided herein, or antibody binding portion thereof, can be combined include the following: cytokine suppressive anti-inflammatory drug(s) (CSAIDs); antibodies to or antagonists of other human cytokines or growth factors, for example, TNF, LT, IL-1, IL-2, IL-3, IL-4, IL-5, IL-6, IL-7, IL-8, IL-15, IL-16, IL-18, IL-21, IL-23, interferons, EMAP-II, GM-CSF, FGF, and PDGF. Binding proteins provided herein, or antigen binding portions thereof, can be combined with antibodies to cell surface molecules such as CD2, CD3, CD4, CD8, CD25, CD28, CD30, CD40, CD45, CD69, CD80 (B7.1), CD86 (B7.2), CD90, CTLA or their ligands including CD154 (gp39 or CD40L).

Combinations of therapeutic agents may interfere at different points in the autoimmune and subsequent inflammatory cascade. Examples include a binding protein disclosed herein and a TNF antagonist like a chimeric, humanized or human TNF antibody, Adalimumab, (PCT Publication No. WO 97/29131), CA2 (Remicade™), CDP 571, a soluble p55 or p75 TNF receptor, or derivative thereof (p75TNFR1gG (Enbrel™) or p55TNFR1gG (Lenercept)), a TNFα converting enzyme (TACE) inhibitor; or an IL-1 inhibitor (an Interleukin-1-converting enzyme inhibitor, IL-1RA, etc.). Other combinations include a binding protein disclosed herein and Interleukin 11. Yet another combination include key players of the autoimmune response which may act parallel to, dependent on or in concert with IL-12 function; especially relevant are IL-18 antagonists including an IL-18 antibody, a soluble IL-18 receptor, or an IL-18 binding protein. It has been shown that IL-12 and IL-18 have overlapping but distinct functions and a combination of antagonists to both may be most effective. Yet another combination is a binding protein disclosed herein and a non-depleting anti-CD4 inhibitor. Yet other combinations include a binding protein disclosed herein and an antagonist of the co-stimulatory pathway CD80 (B7.1) or CD86 (B7.2) including an antibody, a soluble receptor, or an antagonistic ligand.

The binding proteins provided herein may also be combined with an agent, such as methotrexate, 6-MP, azathioprine sulphasalazine, mesalazine, olsalazine chloroquinine/hydroxychloroquine, pencillamine, aurothiomalate (intramuscular and oral), azathioprine, cochicine, a corticosteroid (oral, inhaled and local injection), a beta-2 adrenoreceptor agonist (salbutamol, terbutaline, salmeteral), a xanthine (theophylline, aminophylline), cromoglycate, nedocromil, ketofen, ipratropium, oxitropium, cyclosporin, FK506, rapamycin, mycophenolate mofetil, leflunomide, an NSAID, for example, ibuprofen, a corticosteroid such as prednisolone, a phosphodiesterase inhibitor, an adensosine agonist, an antithrombotic agent, a complement inhibitor, an adrenergic agent, an agent which interferes with signalling by proinflammatory cytokines such as TNF-α or IL-1 (e.g., IRAK, NIK, IKK, p38 or a MAP kinase inhibitor), an IL-1β converting enzyme inhibitor, a TNFα converting enzyme (TACE) inhibitor, a T-cell signalling inhibitor such as a kinase inhibitor, a metalloproteinase inhibitor, sulfasalazine, azathioprine, a 6-mercaptopurine, an angiotensin converting enzyme inhibitor, a soluble cytokine receptor or derivative thereof (e.g., a soluble p55 or p75 TNF receptor or the derivative p75TNFRIgG (Enbrel™) or p55TNFRIgG (Lenercept), sIL-1RI, sIL-1RII, sIL-6R), an antiinflammatory cytokine (e.g., IL-4, IL-10, IL-11, IL-13 and TGFβ), celecoxib, folic acid, hydroxychloroquine sulfate, rofecoxib, etanercept, infliximab, naproxen, valdecoxib, sulfasalazine, methylprednisolone, meloxicam, methylprednisolone acetate, gold sodium thiomalate, aspirin, triamcinolone acetonide, propoxyphene napsylate/apap, folate, nabumetone, diclofenac, piroxicam, etodolac, diclofenac sodium, oxaprozin, oxycodone hcl, hydrocodone bitartrate/apap, diclofenac sodium/misoprostol, fentanyl, anakinra, human recombinant, tramadol hcl, salsalate, sulindac, cyanocobalamin/fa/pyridoxine, acetaminophen, alendronate sodium, prednisolone, morphine sulfate, lidocaine hydrochloride, indomethacin, glucosamine sulf/chondroitin, amitriptyline hcl, sulfadiazine, oxycodone hcl/acetaminophen, olopatadine hcl, misoprostol, naproxen sodium, omeprazole, cyclophosphamide, rituximab, IL-1 TRAP, MRA, CTLA4-IG, IL-18 BP, anti-IL-18, Anti-IL15, BIRB-796, SCIO-469, VX-702, AMG-548, VX-740, Roflumilast, IC-485, CDC-801, or Mesopram. Combinations include methotrexate or leflunomide and in moderate or severe rheumatoid arthritis cases, cyclosporine.

In one embodiment, the binding protein or antigen-binding portion thereof, is administered in combination with one of the following agents for the treatment of rheumatoid arthritis: a small molecule inhibitor of KDR, a small molecule inhibitor of Tie-2; methotrexate; prednisone; celecoxib; folic acid; hydroxychloroquine sulfate; rofecoxib; etanercept; infliximab; leflunomide; naproxen; valdecoxib; sulfasalazine; methylprednisolone; ibuprofen; meloxicam; methylprednisolone acetate; gold sodium thiomalate; aspirin; azathioprine; triamcinolone acetonide; propxyphene napsylate/apap; folate; nabumetone; diclofenac; piroxicam; etodolac; diclofenac sodium; oxaprozin; oxycodone hcl; hydrocodone bitartrate/apap; diclofenac sodium/misoprostol; fentanyl; anakinra, human recombinant; tramadol hcl; salsalate; sulindac; cyanocobalamin/fa/pyridoxine; acetaminophen; alendronate sodium; prednisolone; morphine sulfate; lidocaine hydrochloride; indomethacin; glucosamine sulfate/chondroitin; cyclosporine; amitriptyline hcl; sulfadiazine; oxycodone hcl/acetaminophen; olopatadine hcl; misoprostol; naproxen sodium; omeprazole; mycophenolate mofetil; cyclophosphamide; rituximab; IL-1 TRAP; MRA; CTLA4-IG; IL-18 BP; IL-12/23; anti-IL 18; anti-IL 15; BIRB-796; SCIO-469; VX-702; AMG-548; VX-740; Roflumilast; IC-485; CDC-801; or mesopram.

Non-limiting examples of therapeutic agents for inflammatory bowel disease with which a binding protein provided herein can be combined include the following: budenoside; epidermal growth factor; a corticosteroid; cyclosporin, sulfasalazine; aminosalicylates; 6-mercaptopurine; azathioprine; metronidazole; a lipoxygenase inhibitor; mesalamine; olsalazine; balsalazide; an antioxidant; a thromboxane inhibitor; an IL-1 receptor antagonist; an anti-IL-1β mAb; an anti-IL-6 mAb; a growth factor; an elastase inhibitor; a pyridinyl-imidazole compound; an antibody to or antagonist of other human cytokines or growth factors, for example, TNF, LT, IL-1, IL-2, IL-6, IL-7, IL-8, IL-15, IL-16, IL-17, IL-18, EMAP-II, GM-CSF, FGF, or PDGF. Antibodies provided herein, or antigen binding portions thereof, can be combined with an antibody to a cell surface molecule such as CD2, CD3, CD4, CD8, CD25, CD28, CD30, CD40, CD45, CD69, CD90 or their ligands. The antibodies provided herein, or antigen binding portions thereof, may also be combined with an agent, such as methotrexate, cyclosporin, FK506, rapamycin, mycophenolate mofetil, leflunomide, an NSAID, for example, ibuprofen, a corticosteroid such as prednisolone, a phosphodiesterase inhibitor, an adenosine agonist, an antithrombotic agent, a complement inhibitor, an adrenergic agent, an agent which interferes with signalling by proinflammatory cytokines such as TNFα or IL-1 (e.g., an IRAK, NIK, IKK, p38 or MAP kinase inhibitor), an IL-1β converting enzyme inhibitor, a TNFα converting enzyme inhibitor, a T-cell signalling inhibitor such as a kinase inhibitor, a metalloproteinase inhibitor, sulfasalazine, azathioprine, a 6-mercaptopurine, an angiotensin converting enzyme inhibitor, a soluble cytokine receptor or derivative thereof (e.g., a soluble p55 or p75 TNF receptor, sIL-1RI, sIL-1RII, sIL-6R) or an antiinflammatory cytokine (e.g., IL-4, IL-10, IL-11, IL-13 or TGFβ) or a bcl-2 inhibitor.

Examples of therapeutic agents for Crohn's disease in which a binding protein can be combined include the following: a TNF antagonist, for example, an anti-TNF antibody, Adalimumab (PCT Publication No. WO 97/29131; HUMIRA), CA2 (REMICADE), CDP 571, a TNFR-Ig construct, (p75TNFRIgG (ENBREL) or a p55TNFRIgG (LENERCEPT)) inhibitor or a PDE4 inhibitor. Antibodies provided herein, or antigen binding portions thereof, can be combined with a corticosteroid, for example, budenoside and dexamethasone. Binding proteins provided herein or antigen binding portions thereof, may also be combined with an agent such as sulfasalazine, 5-aminosalicylic acid and olsalazine, or an agent that interferes with the synthesis or action of a proinflammatory cytokine such as IL-1, for example, an IL-1β converting enzyme inhibitor or IL-1 ra. Antibodies provided herein or antigen binding portion thereof may also be used with a T cell signaling inhibitor, for example, a tyrosine kinase inhibitor or an 6-mercaptopurine. Binding proteins provided herein, or antigen binding portions thereof, can be combined with IL-11. Binding proteins provided herein, or antigen binding portions thereof, can be combined with mesalamine, prednisone, azathioprine, mercaptopurine, infliximab, methylprednisolone sodium succinate, diphenoxylate/atrop sulfate, loperamide hydrochloride, methotrexate, omeprazole, folate, ciprofloxacin/dextrose-water, hydrocodone bitartrate/apap, tetracycline hydrochloride, fluocinonide, metronidazole, thimerosal/boric acid, cholestyramine/sucrose, ciprofloxacin hydrochloride, hyoscyamine sulfate, meperidine hydrochloride, midazolam hydrochloride, oxycodone hcl/acetaminophen, promethazine hydrochloride, sodium phosphate, sulfamethoxazole/trimethoprim, celecoxib, polycarbophil, propoxyphene napsylate, hydrocortisone, multivitamins, balsalazide disodium, codeine phosphate/apap, colesevelam hcl, cyanocobalamin, folic acid, levofloxacin, methylprednisolone, natalizumab or interferon-gamma Non-limiting examples of therapeutic agents for multiple sclerosis with which binding proteins provided herein can be combined include the following: a corticosteroid; prednisolone; methylprednisolone; azathioprine; cyclophosphamide; cyclosporine; methotrexate; 4-aminopyridine; tizanidine; interferon-β1a (AVONEX; Biogen); interferon-β1b (BETASERON; Chiron/Berlex); interferon α-n3) (Interferon Sciences/Fujimoto), interferon-α (Alfa Wassermann/J&J), interferon β1A-1F (Serono/Inhale Therapeutics), Peginterferon α 2b (Enzon/Schering-Plough), Copolymer 1 (Cop-1; COPAXONE; Teva Pharmaceutical Industries, Inc.); hyperbaric oxygen; intravenous immunoglobulin; clabribine; an antibody to or antagonist of other human cytokines or growth factors and their receptors, for example, TNF, LT, IL-1, IL-2, IL-6, IL-7, IL-8, IL-23, IL-15, IL-16, IL-18, EMAP-II, GM-CSF, FGF, or PDGF. Binding proteins provided herein can be combined with an antibody to a cell surface molecule such as CD2, CD3, CD4, CD8, CD19, CD20, CD25, CD28, CD30, CD40, CD45, CD69, CD80, CD86, CD90 or their ligands. Binding proteins provided herein, may also be combined with an agent, such as methotrexate, cyclosporine, FK506, rapamycin, mycophenolate mofetil, leflunomide, an NSAID, for example, ibuprofen, a corticosteroid such as prednisolone, a phosphodiesterase inhibitor, an adensosine agonist, an antithrombotic agent, a complement inhibitor, an adrenergic agent, an agent which interferes with signalling by a proinflammatory cytokine such as TNFα or IL-1 (e.g., IRAK, NIK, IKK, p38 or a MAP kinase inhibitor), an IL-1β converting enzyme inhibitor, a TACE inhibitor, a T-cell signaling inhibitor such as a kinase inhibitor, a metalloproteinase inhibitor, sulfasalazine, azathioprine, a 6-mercaptopurine, an angiotensin converting enzyme inhibitor, a soluble cytokine receptor or derivatives thereof (e.g., a soluble p55 or p75 TNF receptor, sIL-1RI, sIL-1RII, sIL-6R), an antiinflammatory cytokine (e.g., IL-4, IL-10, IL-13 or TGFβ) or a bcl-2 inhibitor.

Examples of therapeutic agents for multiple sclerosis in which binding proteins provided herein can be combined include interferon-13, for example, IFNβ1a and IFNβ1b; copaxone, corticosteroids, caspase inhibitors, for example inhibitors of caspase-1, IL-1 inhibitors, TNF inhibitors, and antibodies to CD40 ligand and CD80.

Non-limiting examples of therapeutic agents for asthma with which binding proteins provided herein can be combined include the following: albuterol, salmeterol/fluticasone, montelukast sodium, fluticasone propionate, budesonide, prednisone, salmeterol xinafoate, levalbuterol hcl, albuterol sulfate/ipratropium, prednisolone sodium phosphate, triamcinolone acetonide, beclomethasone dipropionate, ipratropium bromide, azithromycin, pirbuterol acetate, prednisolone, theophylline anhydrous, methylprednisolone sodium succinate, clarithromycin, zafirlukast, formoterol fumarate, influenza virus vaccine, methylprednisolone, amoxicillin trihydrate, flunisolide, allergy injection, cromolyn sodium, fexofenadine hydrochloride, flunisolide/ menthol, amoxicillin/clavulanate, levofloxacin, inhaler assist device, guaifenesin, dexamethasone sodium phosphate, moxifloxacin hcl, doxycycline hyclate, guaifenesin/d-methorphan, p-ephedrine/cod/chlorphenir, gatifloxacin, cetirizine hydrochloride, mometasone furoate, salmeterol xinafoate, benzonatate, cephalexin, pe/hydrocodone/chlorphenir, cetirizine hcl/pseudoephed, phenylephrine/cod/promethazine, codeine/promethazine, cefprozil, dexamethasone, guaifenesin/pseudoephedrine, chlorpheniramine/hydrocodone, nedocromil sodium, terbutaline sulfate, epinephrine, methylprednisolone, metaproterenol sulfate.

Non-limiting examples of therapeutic agents for COPD with which binding proteins provided herein can be combined include the following: albuterol sulfate/ipratropium, ipratropium bromide, salmeterol/fluticasone, albuterol, salmeterol xinafoate, fluticasone propionate, prednisone, theophylline anhydrous, methylprednisolone sodium succinate, montelukast sodium, budesonide, formoterol fumarate, triamcinolone acetonide, levofloxacin, guaifenesin, azithromycin, beclomethasone dipropionate, levalbuterol hcl, flunisolide, ceftriaxone sodium, amoxicillin trihydrate, gatifloxacin, zafirlukast, amoxicillin/clavulanate, flunisolide/ menthol, chlorpheniramine/hydrocodone, metaproterenol sulfate, methylprednisolone, mometasone furoate, p-ephedrine/cod/chlorphenir, pirbuterol acetate, p-ephedrine/loratadine, terbutaline sulfate, tiotropium bromide, (R,R)-formoterol, TgAAT, Cilomilast, Roflumilast.

Non-limiting examples of therapeutic agents for psoriasis with which binding proteins provided herein can be combined include the following: small molecule inhibitor of KDR, small molecule inhibitor of Tie-2, calcipotriene, clobetasol propionate, triamcinolone acetonide, halobetasol propionate, tazarotene, methotrexate, fluocinonide, betamethasone diprop augmented, fluocinolone acetonide, acitretin, tar shampoo, betamethasone valerate, mometasone furoate, ketoconazole, pramoxine/fluocinolone, hydrocortisone valerate, flurandrenolide, urea, betamethasone, clobetasol propionate/emoll, fluticasone propionate, azithromycin, hydrocortisone, moisturizing formula, folic acid, desonide, pimecrolimus, coal tar, diflorasone diacetate, etanercept folate, lactic acid, methoxsalen, hc/bismuth subgal/znox/resor, methylprednisolone acetate, prednisone, sunscreen, halcinonide, salicylic acid, anthralin, clocortolone pivalate, coal extract, coal tar/salicylic acid, coal tar/salicylic acid/sulfur, desoximetasone, diazepam, emollient, fluocinonide/emollient, mineral oil/castor oil/na lact, mineral oil/peanut oil, petroleum/isopropyl myristate, psoralen, salicylic acid, soap/tribromsalan, thimerosal/boric acid, celecoxib, infliximab, cyclosporine, alefacept, efalizumab, tacrolimus, pimecrolimus, PUVA, UVB, sulfasalazine.

Examples of therapeutic agents for SLE (Lupus) in which binding proteins provided herein can be combined include the following: NSAIDS, for example, diclofenac, naproxen, ibuprofen, piroxicam, indomethacin; COX2 inhibitors, for example, Celecoxib, rofecoxib, valdecoxib; anti-malarials, for example, hydroxychloroquine; Steroids, for example, prednisone, prednisolone, budenoside, dexamethasone; Cytotoxics, for example, azathioprine, cyclophosphamide, mycophenolate mofetil, methotrexate; inhibitors of PDE4 or purine synthesis inhibitor, for example Cellcept. Binding proteins provided herein may also be combined with agents such as sulfasalazine, 5-aminosalicylic acid, olsalazine, Imuran and agents which interfere with synthesis, production or action of proinflammatory cytokines such as IL-1, for example, caspase inhibitors like IL-1β converting enzyme inhibitors and IL-1 ra. Binding proteins provided herein may also be used with T cell signaling inhibitors, for example, tyrosine kinase inhibitors; or molecules that target T cell activation molecules, for example, CTLA-4-IgG or anti-B7 family antibodies, anti-PD-1 family antibodies. Binding proteins provided herein, can be combined with IL-11 or anti-cytokine antibodies, for example, fonotolizumab (anti-IFNg antibody), or anti-receptor receptor antibodies, for example, anti-IL-6 receptor antibody and antibodies to B-cell surface molecules. Antibodies provided herein or antigen binding portion thereof may also be used with LJP 394 (abetimus), agents that deplete or inactivate B-cells, for example, Rituximab (anti-CD20 antibody), lymphostat-B (anti-BlyS antibody), TNF antagonists, for example, anti-TNF antibodies, Adalimumab (PCT Publication No. WO 97/29131; HUMIRA), CA2 (REMICADE), CDP 571, TNFR-Ig constructs, (p75TNFRIgG (ENBREL) and p55TNFRIgG (LENERCEPT)) and bcl-2 inhibitors, because bcl-2 overexpression in transgenic mice has been demonstrated to cause a lupus like phenotype (see Marquina The pharmaceutical compositions provided herein may include a "therapeutically effective amount" or a "prophylactically effective amount" of a binding protein provided herein. A "therapeutically effective amount" refers to an amount effective, at dosages and for periods of time necessary, to achieve the desired therapeutic result. A therapeutically effective amount of the binding protein may be determined by a person skilled in the art and may vary according to factors such as the disease state, age, sex, and weight of the individual, and the ability of the binding protein to elicit a desired response in the individual. A therapeutically effective amount is also one in which any toxic or detrimental effects of the antibody, or antibody binding portion, are outweighed by the therapeutically beneficial effects. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

V. Diagnostics

The disclosure herein also provides diagnostic applications including, but not limited to, diagnostic assay methods, diagnostic kits containing one or more binding proteins, and adaptation of the methods and kits for use in automated and/or semi-automated systems. The methods, kits, and adaptations provided may be employed in the detection, monitoring, and/or treatment of a disease or disorder in an individual. This is further elucidated below.

A. Method of Assay

The present disclosure also provides a method for determining the presence, amount or concentration of an analyte, or fragment thereof, in a test sample using at least one binding protein as described herein. Any suitable assay as is known in the art can be used in the method. Examples include, but are not limited to, immunoassays and/or methods employing mass spectrometry.

Immunoassays provided by the present disclosure may include sandwich immunoassays, radioimmunoassay (RIA), enzyme immunoassay (EIA), enzyme-linked immunosorbent assay (ELISA), competitive-inhibition immunoassays, fluorescence polarization immunoassay (FPIA), enzyme multiplied immunoassay technique (EMIT), bioluminescence resonance energy transfer (BRET), and homogenous chemiluminescent assays, among others.

A chemiluminescent microparticle immunoassay, in particular one employing the ARCHITECT® automated analyzer (Abbott Laboratories, Abbott Park, Ill.), is an example of an immunoassay.

Methods employing mass spectrometry are provided by the present disclosure and include, but are not limited to MALDI (matrix-assisted laser desorption/ionization) or by SELDI (surface-enhanced laser desorption/ionization).

Methods for collecting, handling, processing, and analyzing biological test samples using immunoassays and mass spectrometry would be well-known to one skilled in the art, are provided for in the practice of the present disclosure (US 2009-0311253 A1).

B. Kit

A kit for assaying a test sample for the presence, amount or concentration of an analyte, or fragment thereof, in a test sample is also provided. The kit comprises at least one component for assaying the test sample for the analyte, or fragment thereof, and instructions for assaying the test sample for the analyte, or fragment thereof. The at least one component for assaying the test sample for the analyte, or fragment thereof, can include a composition comprising a binding protein, as disclosed herein, and/or an anti-analyte binding protein (or a fragment, a variant, or a fragment of a variant thereof), which is optionally immobilized on a solid phase.

Optionally, the kit may comprise a calibrator or control, which may comprise isolated or purified analyte. The kit can comprise at least one component for assaying the test sample for an analyte by immunoassay and/or mass spectrometry. The kit components, including the analyte, binding protein, and/or anti-analyte binding protein, or fragments thereof, may be optionally labeled using any art-known detectable label. The materials and methods for the creation provided for in the practice of the present disclosure would be known to one skilled in the art (US 2009-0311253 A1).

C. Adaptation of Kit and Method

The kit (or components thereof), as well as the method of determining the presence, amount or concentration of an analyte in a test sample by an assay, such as an immunoassay as described herein, can be adapted for use in a variety of automated and semi-automated systems (including those wherein the solid phase comprises a microparticle), as described, for example, in U.S. Pat. Nos. 5,089,424 and 5,006,309, and as commercially marketed, for example, by Abbott Laboratories (Abbott Park, Ill.) as ARCHITECT®.

Other platforms available from Abbott Laboratories include, but are not limited to, AxSYM®, IMx® (see, for example, U.S. Pat. No. 5,294,404, PRISM®, EIA (bead), and Quantum™ II, as well as other platforms. Additionally, the assays, kits and kit components can be employed in other formats, for example, on electrochemical or other hand-held or point-of-care assay systems. The present disclosure is, for example, applicable to the commercial Abbott Point of Care (i-STAT®, Abbott Laboratories) electrochemical immunoassay system that performs sandwich immunoassays. Immunosensors and their methods of manufacture and operation in single-use test devices are described, for example in, U.S. Pat. Nos. 5,063,081, 7,419,821, and 7,682,833; and US Publication Nos. 20040018577, 20060160164 and US 20090311253.

It will be readily apparent to those skilled in the art that other suitable modifications and adaptations of the methods described herein are obvious and may be made using suitable equivalents without departing from the scope of the embodiments disclosed herein. Having now described certain embodiments in detail, the same will be more clearly understood by reference to the following examples, which are included for purposes of illustration only and are not intended to be limiting.

EXAMPLES

Example 1.

Generation of an Anti-IL-17 Humanized Monoclonal Antibody h10F7

Example 1.2

Affinity Maturation of the Humanized Anti-Human IL-17 Antibody h10F7

A humanized anti-human IL-17 antibody was previously disclosed. This antibody was subsequently affinity matured to improve its overall affinity to human, cynomolgus monkey, and mouse IL-17. Several libraries were made according to specifications below:

H1+H2 Library:
Limited mutagenesis at 7 residues at 30, 31, 33, 35, 53, 56, 57, and 58.
Toggle between human germline and h10F7 sequences at positions 27, 48, 51, 52, 54, 67, and 69.

H3 Library:
Limited mutagenesis at 95-100c and 102.
Toggle between human germline and h10F7 sequences at 93.

LC Library 1:
Limited mutagenesis at 30, 31, 32, 34, 50, 53, 89, 91, 92, 93, and 96.
Toggle between human germline and h10F7 sequence at positions 4, 24, 27, 29, 33, 36, 43, 47, 52, and 55.

LC library 2: constructed with an additional residue at position G28 in CDR1 to increase identity to human antibodies.
Limited mutagenesis at 28, 30, 31, 32, 34, 50, 53, 89, 91, 92, 93, and 96.
Toggle between human germline and h10F7 sequence at positions 24, 27, 29, 33, 37, 44, 48, 52, and 55.
One framework germ-lining mutation in FR1 (position 4) to be tested first as scFv. "M" will be preferred over "L" if binding is not affected.

rHC library: recombine outputs of H1+H2 and H3 libraries.

rHCLC library: recombine outputs of H1+H2, H3, and LC1 or LC2 libraries. (Choose LC2 over LC1 if LC2 output binding appears to be at least as good as WT, otherwise recombine LC1 output).

All four libraries were selected separately for the ability to bind human, cynomolgus monkey and mouse IL-17 in the presence of decreasing concentrations of biotinylated antigens. All mutated CDR sequences recovered from library selections were recombined into additional libraries and the recombined libraries were subjected to more stringent selection conditions before individual antibodies are identified.

The table below provides a list of amino acid sequences of VH and VL of the h10F7 antibody which were subjected to the affinity maturation selection protocol. Amino acid residues of individual CDRs of each VH and VL sequence are indicated in bold.

TABLE 2

Amino acid residues observed in affinity matured anti-IL-17 antibody h10F7

(SEQ ID NO: 55)

```
h10f7 Heavy chain variable region
h10f7VH.1   12345678901234567890123456789012345678901234567890012a345678901
            EVQLVQSGAEVKKPGSSVKVSCKASGYTFTDYEIHWVRQAPGQGLEWIGVNDPESGGIFYNQ
                                         DE          M I D   SL
                                         S                   IY
                                         A                   M
                                         E
                                         N
                                         P 2345678901234567890012abc345678901234567890abcd1234567890123
            KFDGRATLTADKSTSTAYMELSSLRSEDTAVYYCTRYYRYESFYGMDYWGQGTTVIVSS
               V I                          DKWDGLE   I
               I                            SMFW YN   C
                                            W Y SD    E
                                            F V L     L
```

TABLE 2 -continued

Amino acid residues observed in affinity
matured anti-IL-17 antibody h10F7

```
                              E  N  S     S
                              N  M  Q     F
                              F  A  H
                                 R  A
                                 F
                                 M
                                 K
                                 H
```

(SEQ ID NO: 56)
h10f7 Light chain variable region
H10f7Vk.1a  <u>12345</u>678901234567890123456789012345678901234567<u>89012345678901</u>
            DIQLTQSPSSLSASVGDRVTITCSASS-SISYIYWFQQKPGKSPKRWIYATFELASGVPSR
```
              M        R  QGIRRCLD  Y     A   L  R  SD  Q
                       K  SVSNSVN            E  A
                          DLVGD  F            D  Y
                          Q NTN  S            S  G
                          A FPP  Q            G  Q
                          I GLI  G            T  W
                          V LDF                Q  L
                          T PCA                P  H
                          E K                   M
                            M
```

234567890123456789012345678<u>9012345</u>67890123456a
            FSGSGSGTDYTLTISSLQPEDFATYYCHQRSSYPWTFGQGTKLEIK
```
                             R VGN  E
                             Q WTI  L
                             L LMR  G
                             N MNF  F
                             Y KRT  Y
                             S FKY  P
                             V PAL  I
                             A GDM  D
                               S W  R
                               Q K  H
                               I H  Q
                               T G  N
                               D C
```

Tables 1B and 1C in section I.C above, provide individual VH and VL sequences from converted clones. These affinity matured sequences were converted to full length IgG.

TABLE 3 h10F7 affinity matured scFv clones converted to full length IgG

| ScFv clone name | HC plasmid | LC plasmid | Full length IgG (protein) name |
| --- | --- | --- | --- |
| J427 M2S3 #12 | pHybE-h10F7VH.1a.g1m (SEQ ID NO: 42) | pHybE-hCk V3 J427 M2S3 #12 (SEQ ID NO: 52) | h10F7-M12 |
| J427 M2S3 #27 | pHybE-h10F7VH.1a.g1m (SEQ ID NO: 42) | pHybE-hCk V3 J427 M2S3 #27 (SEQ ID NO: 53) | h10F7-M27 |
| J439M1S3R5#10 | pHybE-hCg1, z, non-a, mut (234, 235) V2 J439M1S3R5#10 (SEQ ID NO: 43) | pHybE-hCk V3 J439M1S3R5#10 (SEQ ID NO: 50) | h10F7-M10 |
| J439M1S3R5#11 | pHybE-hCg1, z, non-a, mut (234, 235) V2 J439M1S3R5#11 (SEQ ID NO: 44) | pHybE-hCk V3 J439M1S3R5#11 (SEQ ID NO: 51) | h10F7-M11 |
| J439M1S2(H)3 #A6 | pHybE-hCg1, z, non-a, mut (234, 235) V2 J439M1S2(H)3 #A6 (SEQ ID NO: 45) | pHybE-hCk V3 J439M1S2(H)3#A6 (SEQ ID NO: 54) | h10F7-A6 |
| J439M1S2(H)3 #A11 | pHybE-hCg1, z, non-a, mut (234, 235) V2 J439M1S2(H)3 #A11 (SEQ ID NO: 46) | pHybE-hCk V3 J439M1S3R5#11 (SEQ ID NO: 51) | h10F7-A11 |

TABLE 3-continued h10F7 affinity matured scFv clones converted to full length IgG

| ScFv clone name | HC plasmid | LC plasmid | Full length IgG (protein) name |
|---|---|---|---|
| J439M1S2(H)3 #A16 | pHybE-hCg1, z, non-a, mut (234, 235) V2 J439M1S2(H)3 #A16 (SEQ ID NO: 47) | pHybE-hCk V3 J439M1S2(H)3#A6 (SEQ ID NO: 54) | h10F7-A16 |
| J439M1S2(H)3 #B13 | pHybE-hCg1, z, non-a, mut (234, 235) V2 J439M1S2(H)3 #B13 (SEQ ID NO: 48) | pHybE-hCk V3 J439M1S3R5#11 (SEQ ID NO: 51) | h10F7-B13 |
| J439M1S2(H)3 #B20 | pHybE-hCg1, z, non-a, mut (234, 235) V2 J439M1S2(H)3 #B20 (SEQ ID NO: 49) | pHybE-hCk V3 J439M1S3R5#11 (SEQ ID NO: 51) | h10F7-B20 |

Example 2

Generation and Characterization of Anti-IL-13 and Anti-IL-17 Dual Variable Domain (DVD) Binding Proteins Four-chain dual variable domain (DVD) binding proteins using parent antibodies with known amino acid sequences were generated by synthesizing polynucleotide fragments encoding DVD binding protein variable heavy and DVD binding protein variable light chain sequences and cloning the fragments into a pHybC-D2 vector according to art known methods. The DVD binding protein constructs were cloned into and expressed in 293 cells and purified according to art known methods. DVD VH and VL chains for the DVD binding proteins are provided below.

Example 2.1

DVD Binding Proteins that Bind IL-13 and IL-17

TABLE 4

| DVD Variable Domain Name | Outer Variable Domain Name | Linker | Inner Variable Domain | SEQ ID VD1 - X1 - VD2 Formula |
|---|---|---|---|---|
| DVD2148H | AB397VH | HG-short | AB273VH | 30 - 21 - 36 |
| DVD2148L | AB397VL | LK-short | AB273VL | 31 - 13 - 37 |
| DVD2149H | AB273H | HG-short | AB397VH | 36 - 21 - 30 |
| DVD2149L | AB273L | LK-short | AB397VL | 37 - 13 - 31 |
| DVD2150H | AB397VH | HG-short | AB273VH | 30 - 21 - 36 |
| DVD2150L | AB397VL | LK-long | AB273VL | 31 - 14 - 37 |
| DVD2151H | AB273VH | HG-short | AB397VH | 36 - 21 - 30 |
| DVD2151L | AB273VL | LK-long | AB397VL | 37 - 14 - 31 |
| DVD2152H | AB397VH | HG-long | AB273VH | 30 - 22 - 36 |
| DVD2152L | AB397VL | LK-short | AB273VL | 31 - 13 - 37 |
| DVD2153H | AB273VH | HG-long | AB397VH | 36 - 22 - 30 |
| DVD2153L | AB273VL | LK-short | AB397VL | 37 - 13 - 31 |
| DVD2154H | AB397VH | HG-short | AB274VH | 30 - 21 - 38 |
| DVD2154L | AB397VL | LK-short | AB274VL | 31 - 13 - 39 |
| DVD2155H | AB274VH | HG-short | AB397VH | 38 - 21 - 30 |
| DVD2155L | AB274VL | LK-short | AB397VL | 39 - 13 - 31 |
| DVD2156H | AB397VH | HG-short | AB274VH | 30 - 21 - 38 |
| DVD2156L | AB397VL | LK-long | AB274VL | 31 - 14 - 39 |
| DVD2157H | AB274VH | HG-short | AB397VH | 38 - 21 - 30 |
| DVD2157L | AB274VL | LK-long | AB397VL | 39 - 14 - 31 |
| DVD2158H | AB397VH | HG-long | AB274VH | 30 - 22 - 38 |
| DVD2158L | AB397VL | LK-short | AB274VL | 31 - 13 - 39 |
| DVD2159H | AB274VH | HG-long | AB397VH | 38 - 22 - 30 |
| DVD2159L | AB274VL | LK-short | AB397VL | 39 - 13 - 31 |
| DVD2160H | AB397VH | HG-short | AB275VH | 30 - 21 - 40 |
| DVD2160L | AB397VL | LK-short | AB275VL | 31 - 13 - 40 |
| DVD2161H | AB275VH | HG-short | AB397VH | 40 - 21 - 30 |
| DVD2161L | AB275VL | LK-short | AB397VL | 41 - 13 - 31 |
| DVD2162H | AB397VH | HG-short | AB275VH | 30 - 21 - 40 |
| DVD2162L | AB397VL | LK-long | AB275VL | 31 - 14 - 41 |
| DVD2163H | AB275VH | HG-short | AB397VH | 40 - 21 - 30 |
| DVD2163L | AB275VL | LK-long | AB397VL | 41 - 14 - 31 |
| DVD2164H | AB397VH | HG-long | AB275VH | 30 - 22 - 40 |
| DVD2164L | AB397VL | LK-short | AB275VL | 31 - 13 - 41 |
| DVD2165H | AB275VH | HG-long | AB397VH | 40 - 22 - 30 |
| DVD2165L | AB275VL | LK-short | AB397VL | 41 - 13 - 31 |
| DVD2166H | AB398VH | HG-short | AB273VH | 32 - 21 - 36 |
| DVD2166L | AB398VL | LK-short | AB273VL | 33 - 13 - 37 |
| DVD2167H | AB273VH | HG-short | AB398VH | 36 - 21 - 32 |
| DVD2167L | AB273VL | LK-short | AB398VL | 37 - 13 - 33 |
| DVD2168H | AB398VH | HG-short | AB273VH | 32 - 21 - 36 |
| DVD2168L | AB398VL | LK-long | AB273VL | 33 - 14 - 37 |
| DVD2169H | AB273VH | HG-short | AB398VH | 36 - 21 - 32 |
| DVD2169L | AB273VL | LK-long | AB398VL | 37 - 14 - 33 |
| DVD2170H | AB398VH | HG-long | AB273VH | 32 - 22 - 36 |
| DVD2170L | AB398VL | LK-short | AB273VL | 33 - 13 - 37 |
| DVD2171H | AB273VH | HG-long | AB398VH | 36 - 22 - 32 |
| DVD2171L | AB273VL | LK-short | AB398VL | 37 - 13 - 33 |
| DVD2172H | AB398VH | HG-short | AB274VH | 32 - 21 - 38 |
| DVD2172L | AB398VL | LK-short | AB274VL | 33 - 13 - 39 |
| DVD2173H | AB274VH | HG-short | AB398VH | 38 - 21 - 32 |
| DVD2173L | AB274VL | LK-short | AB398VL | 39 - 13 - 33 |
| DVD2174H | AB398VH | HG-short | AB274VH | 32 - 21 - 38 |
| DVD2174L | AB398VL | LK-long | AB274VL | 33 - 14 - 39 |
| DVD2175H | AB274VH | HG-short | AB398VH | 38 - 21 - 32 |
| DVD2175L | AB274VL | LK-long | AB398VL | 39 - 14 - 33 |
| DVD2176H | AB398VH | HG-long | AB274VH | 32 - 22 - 38 |
| DVD2176L | AB398VL | LK-short | AB274VL | 33 - 13 - 39 |
| DVD2177H | AB274VH | HG-long | AB398VH | 38 - 22 - 32 |
| DVD2177L | AB274VL | LK-short | AB398VL | 39 - 13 - 33 |
| DVD2178H | AB398VH | HG-short | AB275VH | 32 - 21 - 40 |
| DVD2178L | AB398VL | LK-short | AB275VL | 33 - 13 - 41 |
| DVD2179H | AB275VH | HG-short | AB398VH | 40 - 21 - 32 |
| DVD2179L | AB275VL | LK-short | AB398VL | 41 - 13 - 33 |
| DVD2180H | AB398VH | HG-short | AB275VH | 32 - 21 - 40 |
| DVD2180L | AB398VL | LK-long | AB275VL | 33 - 14 - 41 |
| DVD2181H | AB275VH | HG-short | AB398VH | 40 - 21 - 32 |
| DVD2181L | AB275VL | LK-long | AB398VL | 41 - 14 - 43 |
| DVD2182H | AB398VH | HG-long | AB275VH | 32 - 22 - 40 |
| DVD2182L | AB398VL | LK-short | AB275VL | 33 - 13 - 41 |
| DVD2183H | AB275VH | HG-long | AB398VH | 40 - 22 - 32 |
| DVD2183L | AB275VL | LK-short | AB398VL | 41 - 13 - 33 |
| DVD2184H | AB399VH | HG-short | AB273VH | 34 - 21 - 36 |
| DVD2184L | AB399VL | LK-short | AB273VL | 35 - 13 - 37 |
| DVD2185H | AB273VH | HG-short | AB399VH | 36 - 21 - 34 |
| DVD2185L | AB273VL | LK-short | AB399VL | 37 - 13 - 35 |
| DVD2186H | AB399VH | HG-short | AB273VH | 34 - 21 - 36 |

TABLE 4-continued

| DVD Variable Domain Name | Outer Variable Domain Name | Linker | Inner Variable Domain | SEQ ID VD1 - X1 - VD2 Formula |
|---|---|---|---|---|
| DVD2186L | AB399VL | LK-long | AB273VL | 35 - 14 - 37 |
| DVD2187H | AB273VH | HG-short | AB399VH | 36 - 21 - 34 |
| DVD2187L | AB273VL | LK-long | AB399VL | 37 - 14 - 35 |
| DVD2188H | AB399VH | HG-short | AB273VH | 34 - 22 - 36 |
| DVD2188L | AB399VL | LK-short | AB273VL | 35 - 13 - 37 |
| DVD2189H | AB273VH | HG-long | AB399VH | 36 - 22 - 34 |
| DVD2189L | AB273VL | LK-short | AB399VL | 37 - 13 - 35 |
| DVD2190H | AB399VH | HG-short | AB274VH | 34 - 21 - 38 |
| DVD2190L | AB399VL | LK-short | AB274VL | 35 - 13 - 39 |
| DVD2191H | AB274VH | HG-short | AB399VH | 8 - 21 - 34 |
| DVD2191L | AB274VL | LK-short | AB399VL | 39 - 13 - 35 |
| DVD2192H | AB399VH | HG-short | AB274VH | 34 - 21 - 38 |
| DVD2192L | AB399VL | LK-long | AB274VL | 35 - 14 - 39 |
| DVD2193H | AB274VH | HG-short | AB399VH | 38 - 21 - 34 |
| DVD2193L | AB274VL | LK-long | AB399VL | 39 - 14 - 35 |
| DVD2194H | AB399VH | HG-long | AB274VH | 34 - 22 - 38 |
| DVD2194L | AB399VL | LK-short | AB274VL | 35 - 13 - 39 |
| DVD2195H | AB274VH | HG-long | AB399VH | 38 - 22 - 34 |
| DVD2195L | AB274VL | LK-short | AB399VL | 39 - 13 - 35 |
| DVD2196H | AB399VH | HG-short | AB275VH | 34 - 21 - 40 |
| DVD2196L | AB399VL | LK-short | AB275VL | 35 - 13 - 41 |
| DVD2197H | AB275VH | HG-short | AB399VH | 40 - 21 - 34 |
| DVD2197L | AB275VL | LK-short | AB399VL | 41 - 13 - 35 |
| DVD2198H | AB399VH | HG-short | AB275VH | 34 - 21 - 40 |
| DVD2198L | AB399VL | LK-long | AB275VL | 35 - 14 - 41 |
| DVD2199H | AB275VH | HG-short | AB399VH | 40 - 21 - 34 |
| DVD2199L | AB275VL | LK-long | AB399VL | 41 - 14 - 35 |
| DVD2200H | AB399VH | HG-long | AB275VH | 34 - 22 - 40 |
| DVD2200L | AB399VL | LK-short | AB275VL | 35 - 13 - 41 |
| DVD2201H | AB275VH | HG-long | AB399VH | 40 - 22 - 34 |
| DVD2201L | AB275VL | LK-short | AB399VL | 41 - 13 - 35 |

Table 5 contains the yield data for parent antibodies and DVD-Ig constructs expressed as milligrams per liter in 293 cells.

TABLE 5

Transient Expression in Yields of Parent Antibodies and DVD-Ig Constructs in 293 Cells

| Parent Antibody or DVD-Ig ID | N-terminal Variable Domain (VD) | C-terminal Variable Domain (VD) | Expression yield (mg/L) |
|---|---|---|---|
| AB273 | IL-17 (SEQ 1) | | 16.6 |
| AB274 | IL-17 (SEQ 2) | | 44.6 |
| AB275 | IL-17 (SEQ 3) | | 44.2 |
| AB397 | IL-13 (SEQ 1) | | 73.6 |
| AB398 | IL-13 (SEQ 2) | | 96.0 |
| AB399 | IL-13 (SEQ 3) | | 83.8 |
| DVD2148 | IL-13 (SEQ 1) | IL-17 (SEQ 1) | 14.4 |
| DVD2149 | IL-17 (SEQ 1) | IL-13 (SEQ 1) | 0.6 |
| DVD2150 | IL-13 (SEQ 1) | IL-17 (SEQ 1) | 6.2 |
| DVD2151 | IL-17 (SEQ 1) | IL-13 (SEQ 1) | 0.4 |
| DVD2152 | IL-13 (SEQ 1) | IL-17 (SEQ 1) | 25.6 |
| DVD2153 | IL-17 (SEQ 1) | IL-13 (SEQ 1) | 1.0 |
| DVD2154 | IL-13 (SEQ 1) | IL-17 (SEQ 2) | 35.0 |
| DVD2155 | IL-17 (SEQ 2) | IL-13 (SEQ 1) | 30.8 |
| DVD2156 | IL-13 (SEQ 1) | IL-17 (SEQ 2) | 37.2 |
| DVD2157 | IL-17 (SEQ 2) | IL-13 (SEQ 1) | 29.2 |
| DVD2158 | IL-13 (SEQ 1) | IL-17 (SEQ 2) | 57.2 |
| DVD2159 | IL-17 (SEQ 2) | IL-13 (SEQ 1) | 37.4 |
| DVD2160 | IL-13 (SEQ 1) | IL-17 (SEQ 3) | 65.8 |
| DVD2161 | IL-17 (SEQ 3) | IL-13 (SEQ 1) | 47.2 |
| DVD2162 | IL-13 (SEQ 1) | IL-17 (SEQ 3) | 38.2 |
| DVD2163 | IL-17 (SEQ 3) | IL-13 (SEQ 1) | 33.6 |
| DVD2164 | IL-13 (SEQ 1) | IL-17 (SEQ 3) | 64.4 |
| DVD2165 | IL-17 (SEQ 3) | IL-13 (SEQ 1) | 48.5 |
| DVD2166 | IL-13 (SEQ 2) | IL-17 (SEQ 1) | 13.7 |
| DVD2167 | IL-17 (SEQ 1) | IL-13 (SEQ 2) | 8.9 |
| DVD2168 | IL-13 (SEQ 2) | IL-17 (SEQ 1) | 7.8 |
| DVD2169 | IL-17 (SEQ 1) | IL-13 (SEQ 2) | 1.9 |
| DVD2170 | IL-13 (SEQ 2) | IL-17 (SEQ 1) | 10.4 |
| DVD2171 | IL-17 (SEQ 2) | IL-13 (SEQ 2) | 4.3 |
| DVD2172 | IL-13 (SEQ 2) | IL-17 (SEQ 2) | 26.5 |
| DVD2173 | IL-17 (SEQ 2) | IL-13 (SEQ 2) | 16.5 |
| DVD2174 | IL-13 (SEQ 2) | IL-17 (SEQ 2) | 28.3 |
| DVD2175 | IL-17 (SEQ 2) | IL-13 (SEQ 2) | 10.7 |
| DVD2176 | IL-13 (SEQ 2) | IL-17 (SEQ 2) | 21.5 |
| DVD2177 | IL-17 (SEQ 2) | IL-13 (SEQ 2) | 18.4 |
| DVD2178 | IL-13 (SEQ 2) | IL-17 (SEQ 3) | 9.5 |
| DVD2179 | IL-17 (SEQ 3) | IL-13 (SEQ 2) | 8.9 |
| DVD2180 | IL-13 (SEQ 2) | IL-17 (SEQ 3) | 8.5 |
| DVD2181 | IL-17 (SEQ 3) | IL-13 (SEQ 2) | 2.8 |
| DVD2182 | IL-13 (SEQ 2) | IL-17 (SEQ 3) | 14.0 |
| DVD2183 | IL-17 (SEQ 3) | IL-13 (SEQ 2) | 9.2 |
| DVD2184 | IL-13 (SEQ 3) | IL-17 (SEQ 1) | 0.2 |
| DVD2185 | IL-17 (SEQ 1) | IL-13 (SEQ 3) | 26.9 |
| DVD2186 | IL-13 (SEQ 3) | IL-17 (SEQ 1) | 0.0 |
| DVD2187 | IL-17 (SEQ 1) | IL-13 (SEQ 3) | 2.3 |
| DVD2188 | IL-13 (SEQ 3) | IL-17 (SEQ 1) | 0.0 |
| DVD2189 | IL-17 (SEQ 1) | IL-13 (SEQ 3) | 1.3 |
| DVD2190 | IL-13 (SEQ 3) | IL-17 (SEQ 2) | 31.5 |
| DVD2191 | IL-17 (SEQ 2) | IL-13 (SEQ 3) | 42.7 |
| DVD2192 | IL-13 (SEQ 3) | IL-17 (SEQ 2) | 2.6 |
| DVD2193 | IL-17 (SEQ 2) | IL-13 (SEQ 3) | 18.3 |
| DVD2194 | IL-13 (SEQ 3) | IL-17 (SEQ 2) | 0.0 |
| DVD2195 | IL-17 (SEQ 2) | IL-13 (SEQ 3) | 21.6 |
| DVD2196 | IL-13 (SEQ 3) | IL-17 (SEQ 3) | 27.4 |
| DVD2197 | IL-17 (SEQ 3) | IL-13 (SEQ 3) | 72.2 |
| DVD2198 | IL-13 (SEQ 3) | IL-17 (SEQ 3) | 0.1 |
| DVD2199 | IL-17 (SEQ 3) | IL-13 (SEQ 3) | 8.1 |
| DVD2200 | IL-13 (SEQ 3) | IL-17 (SEQ 3) | 1.1 |
| DVD2201 | IL-17 (SEQ 3) | IL-13 (SEQ 3) | 11.4 |

All DVD-Ig molecules expressed well in 293 cells. DVD-Ig molecules could be easily purified over a protein A column. In most cases, >5 mg/L purified DVD-Ig protein could be obtained easily from supernatants of 293 cells.

Example 3

Assays Used to Determine the Functional Activity of Parent Antibodies and DVD-Ig Proteins Example 3.1

IL-13 Bioassay and Neutralization Assay

A549 cells were plated at $1.5–2 \times 10^5$ cells per well in a 100 µL volume and incubated overnight at 37° C., 5% $CO_2$. Following a 16-20 hour overnight incubation, the original 100 µl media seeding volume was removed and 100 µL of 400 ng/mL (2× concentrated) rhTNF-α was added to all wells. The plates were placed at 37° C., 5% $CO_2$ until the addition of IL-13 and antibody or DVD-Ig protein. A 20 µg/mL working stock of antibody or DVD-Ig protein (4× concentrated) was prepared in complete F12 medium. An eight point serial dilution was performed (5 µg/mL-0.0003 µg/mL) in complete F12 in Marsh dilution plates. Sixty uL/well of each antibody or DVD-Ig protein dilution was added in quadruplicate to a 96 well v-bottom (Costar#3894) plate and 60 µL of a 4× concentrated (20 ng/mL) solution of IL-13 was added to all wells except the cell only control. Following a 1 hour incubation, 100 µL of the above IL-13/Antibody or DVD-Ig protein complex was added to the A549 cells. All well volumes were equal to 200 µL. The final concentration of recombinant IL-13 was 5 ng/mL and rhTNF-α was 200 ng/mL. All plate reagents were then 1× concentrated. After a 16-20 hour incubation, the well contents (200 μL) were transferred into a 96-well round bottom plate (Costar#3799) and placed in a −20° C. freezer. The supernatants were tested for hTARC levels by ELISA in the Assay Lab. Neutralization potency was determined by calculating percent inhibition relative to the 5 ng/mL IL-13 alone control value. Reported IC$_{50}$ values (sigmoidal curve dose responses) were calculated using GraphPad Prism.

is inhibited by neutralizing anti-IL-17 antibodies (See, e.g., J. Imm. 155:5483-5486 (1995) or Cytokine 9:794-800 (1997)).

HS27 cells were maintained in assay medium (DMEM high glucose medium (Gibco #11965) with 10% fetal bovine serum (Gibco#26140), 4 mM L-glutamine, 1 mM sodium pyruvate, penicillin G (100 U/500 ml) and streptomycin (100 μg/500 ml)). Cells were grown in T150 flasks until they were

TABLE 6

IL-13 Neutralization Assay With IL-13 Parent Antibody and DVD-Ig Protein

| Parent Antibody or DVD-Ig ID | N-terminal Variable Domain (VD) | C-terminal Variable Domain (VD) | N-Terminal VD IL13 Neutralization Assay IC50 nM | C-Terminal VD IL13 Neutralization AssayIC50 nM |
|---|---|---|---|---|
| AB397 | IL-13 (SEQ 1) | | 0.033 | |
| AB398 | IL-13 (SEQ 2) | | 0.082 | |
| AB399 | IL-13 (SEQ 3) | | 0.043 | |
| DVD2148 | IL-13 (SEQ 1) | IL-17 (SEQ 1) | 0.054 | NA |
| DVD2149 | IL-17 (SEQ 1) | IL-13 (SEQ 1) | NA | 1.426 |
| DVD2150 | IL-13 (SEQ 1) | IL-17 (SEQ 1) | 0.099 | NA |
| DVD2151 | IL-17 (SEQ 1) | IL-13 (SEQ 1) | NA | 0.526 |
| DVD2152 | IL-13 (SEQ 1) | IL-17 (SEQ 1) | 0.112 | NA |
| DVD2153 | IL-17 (SEQ 1) | IL-13 (SEQ 1) | NA | 2.442 |
| DVD2154 | IL-13 (SEQ 1) | IL-17 (SEQ 2) | 0.430 | NA |
| DVD2155 | IL-17 (SEQ 2) | IL-13 (SEQ 1) | NA | 1.180 |
| DVD2156 | IL-13 (SEQ 1) | IL-17 (SEQ 2) | 0.129 | NA |
| DVD2157 | IL-17 (SEQ 2) | IL-13 (SEQ 1) | NA | 0.244 |
| DVD2158 | IL-13 (SEQ 1) | IL-17 (SEQ 2) | 0.131 | NA |
| DVD2159 | IL-17 (SEQ 2) | IL-13 (SEQ 1) | NA | 0.876 |
| DVD2160 | IL-13 (SEQ 1) | IL-17 (SEQ 3) | 0.178 | NA |
| DVD2161 | IL-17 (SEQ 3) | IL-13 (SEQ 1) | NA | 0.812 |
| DVD2162 | IL-13 (SEQ 1) | IL-17 (SEQ 3) | 0.126 | NA |
| DVD2163 | IL-17 (SEQ 3) | IL-13 (SEQ 1) | NA | 0.195 |
| DVD2164 | IL-13 (SEQ 1) | IL-17 (SEQ 3) | 0.146 | NA |
| DVD2165 | IL-17 (SEQ 3) | IL-13 (SEQ 1) | NA | 0.355 |
| DVD2166 | IL-13 (SEQ 2) | IL-17 (SEQ 1) | 0.089 | NA |
| DVD2167 | IL-17 (SEQ 1) | IL-13 (SEQ 2) | NA | 1.700 |
| DVD2168 | IL-13 (SEQ 2) | IL-17 (SEQ 1) | 0.119 | NA |
| DVD2169 | IL-17 (SEQ 1) | IL-13 (SEQ 2) | NA | 0.309 |
| DVD2170 | IL-13 (SEQ 2) | IL-17 (SEQ 1) | 0.106 | NA |
| DVD2171 | IL-17 (SEQ 1) | IL-13 (SEQ 2) | NA | 0.506 |
| DVD2172 | IL-13 (SEQ 2) | IL-17 (SEQ 2) | 0.111 | NA |
| DVD2173 | IL-17 (SEQ 2) | IL-13 (SEQ 2) | NA | 2.136 |
| DVD2174 | IL-13 (SEQ 2) | IL-17 (SEQ 2) | 0.085 | NA |
| DVD2175 | IL-17 (SEQ 2) | IL-13 (SEQ 2) | NA | 0.115 |
| DVD2176 | IL-13 (SEQ 2) | IL-17 (SEQ 2) | 0.106 | NA |
| DVD2177 | IL-17 (SEQ 2) | IL-13 (SEQ 2) | NA | 0.155 |
| DVD2178 | IL-13 (SEQ 2) | IL-17 (SEQ 3) | 0.088 | NA |
| DVD2179 | IL-17 (SEQ 3) | IL-13 (SEQ 2) | NA | 0.916 |
| DVD2180 | IL-13 (SEQ 2) | IL-17 (SEQ 3) | 0.091 | NA |
| DVD2181 | IL-17 (SEQ 3) | IL-13 (SEQ 2) | NA | 0.040 |
| DVD2182 | IL-13 (SEQ 2) | IL-17 (SEQ 3) | 0.077 | NA |
| DVD2183 | IL-17 (SEQ 3) | IL-13 (SEQ 2) | NA | 0.086 |
| DVD2184 | IL-13 (SEQ 3) | IL-17 (SEQ 1) | 0.121 | NA |
| DVD2185 | IL-17 (SEQ 1) | IL-13 (SEQ 3) | NA | 1.254 |
| DVD2187 | IL-17 (SEQ 1) | IL-13 (SEQ 3) | NA | 0.811 |
| DVD2189 | IL-17 (SEQ 1) | IL-13 (SEQ 3) | NA | 0.172 |
| DVD2190 | IL-13 (SEQ 3) | IL-17 (SEQ 2) | 0.087 | NA |
| DVD2191 | IL-17 (SEQ 2) | IL-13 (SEQ 3) | NA | 0.165 |
| DVD2192 | IL-13 (SEQ 3) | IL-17 (SEQ 2) | 0.056 | NA |
| DVD2193 | IL-17 (SEQ 2) | IL-13 (SEQ 3) | NA | 0.028 |
| DVD2195 | IL-17 (SEQ 2) | IL-13 (SEQ 3) | NA | 0.052 |
| DVD2196 | IL-13 (SEQ 3) | IL-17 (SEQ 3) | 0.029 | NA |
| DVD2197 | IL-17 (SEQ 3) | IL-13 (SEQ 3) | NA | 0.081 |
| DVD2199 | IL-17 (SEQ 3) | IL-13 (SEQ 3) | NA | 0.088 |
| DVD2200 | IL-13 (SEQ 3) | IL-17 (SEQ 3) | 0.096 | NA |
| DVD2201 | IL-17 (SEQ 3) | IL-13 (SEQ 3) | NA | 0.092 |

All DVD-Ig proteins containing VDs from AB397, AB398, or AB399 in either the N-terminal or C-terminal position showed neutralization in the A549 IL-13 neutralization assay.

Example 3.2

IL-17 Bioassay and Neutralization Assay

The human HS27 cell line (ATCC #CRL-1634) secretes IL-6 in response to IL-17. The IL-17-induced IL-6 secretion about 80-90% confluent the day of the assay. Human IL-17 (R&D Systems, #317-IL/CF) was reconstituted in sterile PBS without Ca$^{2+}$ and Mg$^{2+}$, stored frozen, freshly thawed for use and diluted to 40 ng/ml (4×) in assay medium. Serial dilutions of antibodies were made in a separate plate (4× concentrations), mixed with an equal volume of 40 ng/ml (4×) of human IL-17 and incubated at 37° C. for 1 hour. HS27 cells (typically about 20,000 cells in 50 μl assay medium) were added to each well of a 96-well flat-bottom tissue culture plate (Costar #3599), followed by the addition of 50 μl of the pre-incubated antibody or DVD-Ig protein plus IL-17 mix. The final concentration of IL-17 was 10 ng/ml. Cells were incubated for about 24 hours at 37° C. The media supernatants were then collected. The level of IL-17 neutralization was measured by determination of IL-6 amounts in supernatant using a commercial Meso Scale Discovery kit according to manufacturer's instructions. IC50 values were obtained using logarithm of antibody or DVD-Ig protein vs. IL-6 amount variable slope fit.

Example 3.3

Affinity Determination Using BIACORE Technology

TABLE 8

Reagents Used in Biacore Analyses

| Assay | Antigen | Vendor Designation | Vendor | Catalog # |
|---|---|---|---|---|
| IL-17 | Recombinant Human IL-17 | R&D systems | 317-IL |

TABLE 7

IL-17 Neutralization Assay With IL-17 Parent Antibody and DVD-Ig Protein

| Parent Antibody or DVD-Ig ID | N-terminal Variable Domain (VD) | C-terminal Variable Domain (VD) | N-Terminal VD IL17 Neutralization Assay IC50 nM | C-Terminal VD IL17 Neutralization Assay IC50 nM |
|---|---|---|---|---|
| AB273 | IL-17 (SEQ 1) | | | 0.0198 |
| AB274 | IL-17 (SEQ 2) | | | 0.003 |
| AB275 | IL-17 (SEQ 3) | | | 0.0052 |
| DVD2148 | IL-13 (SEQ 1) | IL-17 (SEQ 1) | NA | 0.0116 |
| DVD2149 | IL-17 (SEQ 1) | IL-13 (SEQ 1) | 0.0028 | NA |
| DVD2150 | IL-13 (SEQ 1) | IL-17 (SEQ 1) | NA | 0.004 |
| DVD2151 | IL-17 (SEQ 1) | IL-13 (SEQ 1) | 0.0179 | NA |
| DVD2152 | IL-13 (SEQ 1) | IL-17 (SEQ 1) | NA | 0.0069 |
| DVD2153 | IL-17 (SEQ 1) | IL-13 (SEQ 1) | 0.0049 | NA |
| DVD2154 | IL-13 (SEQ 1) | IL-17 (SEQ 2) | NA | 0.3508 |
| DVD2155 | IL-17 (SEQ 2) | IL-13 (SEQ 1) | 0.0078 | NA |
| DVD2156 | IL-13 (SEQ 1) | IL-17 (SEQ 2) | NA | 0.0155 |
| DVD2157 | IL-17 (SEQ 2) | IL-13 (SEQ 1) | 0.0066 | NA |
| DVD2158 | IL-13 (SEQ 1) | IL-17 (SEQ 2) | NA | 0.0998 |
| DVD2159 | IL-17 (SEQ 2) | IL-13 (SEQ 1) | 0.0081 | NA |
| DVD2160 | IL-13 (SEQ 1) | IL-17 (SEQ 3) | NA | 0.7034 |
| DVD2161 | IL-17 (SEQ 3) | IL-13 (SEQ 1) | 0.0144 | NA |
| DVD2162 | IL-13 (SEQ 1) | IL-17 (SEQ 3) | NA | 0.0213 |
| DVD2163 | IL-17 (SEQ 3) | IL-13 (SEQ 1) | 0.0151 | NA |
| DVD2164 | IL-13 (SEQ 1) | IL-17 (SEQ 3) | NA | 0.1354 |
| DVD2165 | IL-17 (SEQ 3) | IL-13 (SEQ 1) | 0.0133 | NA |
| DVD2166 | IL-13 (SEQ 2) | IL-17 (SEQ 1) | NA | 0.0164 |
| DVD2167 | IL-17 (SEQ 1) | IL-13 (SEQ 2) | 0.0029 | NA |
| DVD2168 | IL-13 (SEQ 2) | IL-17 (SEQ 1) | NA | 0.0025 |
| DVD2169 | IL-17 (SEQ 1) | IL-13 (SEQ 2) | 0.0021 | NA |
| DVD2170 | IL-13 (SEQ 2) | IL-17 (SEQ 1) | NA | 0.0053 |
| DVD2171 | IL-17 (SEQ 1) | IL-13 (SEQ 2) | 0.0011 | NA |
| DVD2172 | IL-13 (SEQ 2) | IL-17 (SEQ 2) | NA | 0.6781 |
| DVD2173 | IL-17 (SEQ 2) | IL-13 (SEQ 2) | 0.008 | NA |
| DVD2174 | IL-13 (SEQ 2) | IL-17 (SEQ 2) | NA | 0.0126 |
| DVD2175 | IL-17 (SEQ 2) | IL-13 (SEQ 2) | 0.0089 | NA |
| DVD2176 | IL-13 (SEQ 2) | IL-17 (SEQ 2) | NA | 0.1164 |
| DVD2177 | IL-17 (SEQ 2) | IL-13 (SEQ 2) | 0.0101 | NA |
| DVD2178 | IL-13 (SEQ 2) | IL-17 (SEQ 3) | NA | 0.6911 |
| DVD2179 | IL-17 (SEQ 3) | IL-13 (SEQ 2) | 0.0097 | NA |
| DVD2180 | IL-13 (SEQ 2) | IL-17 (SEQ 3) | NA | 0.0567 |
| DVD2181 | IL-17 (SEQ 3) | IL-13 (SEQ 2) | 0.0097 | NA |
| DVD2182 | IL-13 (SEQ 2) | IL-17 (SEQ 3) | NA | 0.266 |
| DVD2183 | IL-17 (SEQ 3) | IL-13 (SEQ 2) | 0.0125 | NA |
| DVD2184 | IL-13 (SEQ 3) | IL-17 (SEQ 1) | NA | 0.4054 |
| DVD2185 | IL-17 (SEQ 1) | IL-13 (SEQ 3) | 0.0013 | NA |
| DVD2187 | IL-17 (SEQ 1) | IL-13 (SEQ 3) | 0.0016 | NA |
| DVD2189 | IL-17 (SEQ 1) | IL-13 (SEQ 3) | 0.0017 | NA |
| DVD2190 | IL-13 (SEQ 3) | IL-17 (SEQ 2) | NA | 0.061 |
| DVD2191 | IL-17 (SEQ 2) | IL-13 (SEQ 3) | 0.013 | NA |
| DVD2192 | IL-13 (SEQ 3) | IL-17 (SEQ 2) | NA | 0.015 |
| DVD2193 | IL-17 (SEQ 2) | IL-13 (SEQ 3) | 0.014 | NA |
| DVD2195 | IL-17 (SEQ 2) | IL-13 (SEQ 3) | 0.0181 | NA |
| DVD2196 | IL-13 (SEQ 3) | IL-17 (SEQ 3) | NA | 0.0551 |
| DVD2197 | IL-17 (SEQ 3) | IL-13 (SEQ 3) | 0.005 | NA |
| DVD2199 | IL-17 (SEQ 3) | IL-13 (SEQ 3) | 0.0102 | NA |
| DVD2200 | IL-13 (SEQ 3) | IL-17 (SEQ 3) | NA | 0.0072 |
| DVD2201 | IL-17 (SEQ 3) | IL-13 (SEQ 3) | 0.0116 | NA |

All DVD-Ig proteins containing VDs from AB273, AB274, or AB275 in either the N-terminal or C-terminal position showed neutralization in the HS27 IL-17 neutralization assay.

TABLE 8-continued

Reagents Used in Biacore Analyses

| Assay | Antigen | Vendor Designation | Vendor | Catalog # |
|---|---|---|---|---|
| | IL-13 | Recombinant Human IL-13 | R&D systems | 213-IL |

BIACORE Methods:

The BIACORE assay (Biacore, Inc, Piscataway, N.J.) determined the affinity of antibodies or DVD-Ig with kinetic measurements of on-rate and off-rate constants. Binding of antibodies or DVD-Ig proteins to a target antigen (for example, a purified recombinant target antigen) was determined by surface plasmon resonance-based measurements with a Biacore®1000 or 3000 instrument (Biacore® AB, Uppsala, Sweden) using running HBS-EP (10 mM HEPES [pH 7.4], 150 mM NaCl, 3 mM EDTA, and 0.005% surfactant P20) at 25° C. All chemicals were obtained from Biacore® AB (Uppsala, Sweden) or otherwise from a different source as described in the text. For example, approximately 5000 RU of goat anti-mouse IgG, (Fcγ), fragment specific polyclonal antibody (Pierce Biotechnology Inc, Rockford, Ill.) diluted in 10 mM sodium acetate (pH 4.5) was directly immobilized across a CM5 research grade biosensor chip using a standard amine coupling kit according to manufacturer's instructions and procedures at 25 μg/ml. Unreacted moieties on the biosensor surface were blocked with ethanolamine. Modified carboxymethyl dextran surface in flowcell 2 and 4 was used as a reaction surface. Unmodified carboxymethyl dextran without goat anti-mouse IgG in flow cell 1 and 3 was used as the reference surface. For kinetic analysis, rate equations derived from the 1:1 Langmuir binding model were fitted simultaneously to association and dissociation phases of all eight injections (using global fit analysis) with the use of Biaevaluation 4.0.1 software. Purified antibodies or DVD-Ig proteins were diluted in HEPES-buffered saline for capture across goat anti-mouse IgG specific reaction surfaces. Antibodies or DVD-Ig proteins to be captured as a ligand (25 μg/ml) were injected over reaction matrices at a flow rate of 5 μl/minute. The association and dissociation rate constants, $k_{on}$ ($M^{-1}s^{-1}$) and $k_{off}$ ($s^{-1}$) were determined under a continuous flow rate of 25 μl/minute. Rate constants were derived by making kinetic binding measurements at different antigen concentrations ranging from 10-200 nM. The equilibrium dissociation constant (M) of the reaction between antibodies or DVD-Ig proteins and the target antigen was then calculated from the kinetic rate constants by the following formula: $K_D=k_{off}/k_{on}$. Binding was recorded as a function of time and kinetic rate constants were calculated. In this assay, on-rates as fast as $10^6 M^{-1}s^{-1}$ and off-rates as slow as $10^{-6}$ $s^{-1}$ were measured.

TABLE 9

BIACORE Analysis of Parental Antibodies and DVD-Ig Proteins

| Parent Antibody or DVD-Ig ID | N-terminal Variable Domain (VD) | C-terminal Variable Domain (VD) | $k_{on}$ (M-1s-1) | $k_{off}$ (s-1) | $k_D$ (M) |
|---|---|---|---|---|---|
| AB273 | IL-17 (SEQ 1) | | 2.00E+06 | <1.0e-6 | <5.0E-13 |
| AB274 | IL-17 (SEQ 2) | | 1.10E+06 | 8.20E-06 | 7.40E-12 |
| AB275 | IL-17 (SEQ 3) | | 1.90E+06 | 6.50E-05 | 3.40E-11 |
| AB397 | IL-13 (SEQ 1) | | 9.20E+05 | 1.20E-04 | 1.30E-10 |
| AB398 | IL-13 (SEQ 2) | | 6.30E+05 | 2.80E-05 | 4.50E-11 |
| AB399 | IL-13 (SEQ 3) | | 3.40E+05 | 6.40E-05 | 1.90E-11 |
| AB397 | IL-13 (SEQ 1) | | 9.20E+05 | 1.20E-04 | 1.30E-10 |
| AB274 | IL-17 (SEQ 2) | | 1.10E+06 | 8.20E-06 | 7.40E-12 |
| DVD2155 | IL-17 (SEQ 2) | | 2.70E+06 | 6.90E-06 | 2.60E-12 |
| DVD2155 | | IL-13 (SEQ 1) | 2.30E+05 | 3.80E-05 | 1.60E-10 |
| AB397 | IL-13 (SEQ 1) | | 9.20E+05 | 1.20E-04 | 1.30E-10 |
| AB274 | IL-17 (SEQ 2) | | 1.10E+06 | 8.20E-06 | 7.40E-12 |
| DVD2157 | IL-17 (SEQ 2) | | 1.50E+06 | 2.60E-05 | 1.80E-11 |
| DVD2157 | | IL-13 (SEQ 1) | 3.30E+05 | 6.90E-05 | 2.10E-10 |
| AB397 | IL-13 (SEQ 1) | | 9.20E+05 | 1.20E-04 | 1.30E-10 |
| AB274 | IL-17 (SEQ 2) | | 1.10E+06 | 8.20E-06 | 7.40E-12 |
| DVD2158 | IL-13 (SEQ 1) | | 1.60E+06 | 1.40E-04 | 8.60E-11 |
| DVD2158 | | IL-17 (SEQ 2) | 2.00E+04 | <1.0e-6 | <5.0E-11 |
| DVD2159 | IL-17 (SEQ 2) | | 2.50E+06 | 1.20E-05 | 4.90E-12 |
| DVD2159 | | IL-13 (SEQ 1) | 2.60E+05 | 5.30E-05 | 2.00E-10 |
| AB397 | IL-13 (SEQ 1) | | 9.20E+05 | 1.20E-04 | 1.30E-10 |
| AB275 | IL-17 (SEQ 3) | | 1.90E+06 | 6.50E-05 | 3.40E-11 |
| DVD2161 | IL-17 (SEQ 3) | | 1.60E+06 | 4.50E-05 | 2.70E-11 |
| DVD2161 | | IL-13 (SEQ 1) | 1.10E+05 | 4.10E-05 | 3.80E-10 |
| AB397 | IL-13 (SEQ 1) | | 9.20E+05 | 1.20E-04 | 1.30E-10 |
| AB275 | IL-17 (SEQ 3) | | 1.90E+06 | 6.50E-05 | 3.40E-11 |
| DVD2164 | IL-13 (SEQ 1) | | 1.50E+06 | 1.70E-04 | 1.10E-10 |
| DVD2164 | | IL-17 (SEQ 3) | 1.80E+04 | 3.10E-05 | 1.70E-09 |
| DVD2165 | IL-17 (SEQ 3) | | 2.30E+06 | 3.20E-05 | 1.40E-11 |
| DVD2165 | | IL-13 (SEQ 1) | 2.60E+05 | 5.70E-05 | 2.20E-10 |
| AB398 | IL-13 (SEQ 2) | | 6.30E+05 | 2.80E-05 | 4.50E-11 |
| AB273 | IL-17 (SEQ 1) | | 2.00E+06 | <1.0e-6 | <5.0E-13 |
| DVD2166 | IL-13 (SEQ 2) | | 7.60E+05 | 2.60E-05 | 3.40E-11 |
| DVD2166 | | IL-17 (SEQ 1) | 1.30E+05 | 9.40E-06 | 7.50E-11 |
| DVD2167 | IL-17 (SEQ 1) | | 2.70E+06 | <1.0e-6 | <3.7E-13 |
| DVD2167 | | IL-13 (SEQ 2) | 2.10E+04 | <1.0e-6 | <4.8e-11 |
| AB398 | IL-13 (SEQ 2) | | 6.30E+05 | 2.80E-05 | 4.50E-11 |
| AB273 | IL-17 (SEQ 1) | | 2.00E+06 | <1.0e-6 | <5.0E-13 |

TABLE 9-continued

BIACORE Analysis of Parental Antibodies and DVD-Ig Proteins

| Parent Antibody or DVD-Ig ID | N-terminal Variable Domain (VD) | C-terminal Variable Domain (VD) | $k_{on}$ (M−1s−1) | $k_{off}$ (s−1) | $k_D$ (M) |
|---|---|---|---|---|---|
| DVD2168 | IL-13 (SEQ 2) | | 6.80E+05 | 3.70E−05 | 5.40E−11 |
| DVD2168 | | IL-17 (SEQ 1) | 4.00E+05 | <1.0e−6 | <2.5E−12 |
| AB398 | IL-13 (SEQ 2) | | 6.30E+05 | 2.80E−05 | 4.50E−11 |
| AB273 | IL-17 (SEQ 1) | | 2.00E+06 | <1.0e−6 | <5.0E−13 |
| DVD2171 | IL-17 (SEQ 1) | | 1.90E+06 | 2.10E−05 | 1.10E−11 |
| DVD2171 | | IL-13 (SEQ 2) | 2.00E+05 | <1.0e−6 | <5e−12 |
| AB398 | IL-13 (SEQ 2) | | 6.30E+05 | 2.80E−05 | 4.50E−11 |
| AB274 | IL-17 (SEQ 2) | | 1.10E+06 | 8.20E−06 | 7.40E−12 |
| DVD2172 | IL-13 (SEQ 2) | | 8.90E+05 | 2.90E−05 | 3.30E−11 |
| DVD2172 | | IL-17 (SEQ 2) | 6.80E+03 | 1.70E−04 | 2.60E−08 |
| DVD2173 | IL-13 (SEQ 2) | | 2.50E+06 | 9.00E−06 | 3.60E−12 |
| DVD2173 | | IL-13 (SEQ 2) | 3.10E+05 | 3.70E−05 | 1.20E−10 |
| AB398 | IL-13 (SEQ 2) | | 6.30E+05 | 2.80E−05 | 4.50E−11 |
| AB274 | IL-17 (SEQ 2) | | 1.10E+06 | 8.20E−06 | 7.40E−12 |
| DVD2174 | IL-13 (SEQ 2) | | 7.90E+05 | 2.80E−05 | 3.60E−11 |
| DVD2174 | | IL-17 (SEQ 2) | 1.80E+05 | 1.80E−05 | 9.80E−11 |
| DVD2175 | IL-17 (SEQ 2) | | 2.70E+06 | 5.40E−06 | 2.10E−12 |
| DVD2175 | | IL-13 (SEQ 2) | 5.20E+04 | <1.0e−6 | <1.9e−11 |
| AB398 | IL-13 (SEQ 2) | | 6.30E+05 | 2.80E−05 | 4.50E−11 |
| AB274 | IL-17 (SEQ 2) | | 1.10E+06 | 8.20E−06 | 7.40E−12 |
| DVD2177 | IL-17 (SEQ 2) | | 2.50E+06 | 1.00E−05 | 4.30E−12 |
| DVD2177 | | IL-13 (SEQ 2) | 1.10E+05 | <1.0e−6 | <9.1e−12 |
| AB398 | IL-13 (SEQ 2) | | 6.30E+05 | 2.80E−05 | 4.50E−11 |
| AB275 | IL-17 (SEQ 3) | | 1.90E+06 | 6.50E−05 | 3.40E−11 |
| DVD2179 | IL-17 (SEQ 3) | | 1.70E+06 | 6.40E−05 | 3.90E−11 |
| DVD2179 | | IL-13 (SEQ 2) | 2.80E+05 | 1.00E−06 | 3.60E−12 |
| AB398 | IL-13 (SEQ 2) | | 6.30E+05 | 2.80E−05 | 4.50E−11 |
| AB275 | IL-17 (SEQ 3) | | 1.90E+06 | 6.50E−05 | 3.40E−11 |
| DVD2181 | IL-17 (SEQ 3) | | 2.60E+06 | 4.20E−05 | 1.60E−11 |
| DVD2181 | | IL-13 (SEQ 2) | 8.20E+04 | <1.0e−6 | <1.2e−11 |
| AB398 | IL-13 (SEQ 2) | | 6.30E+05 | 2.80E−05 | 4.50E−11 |
| AB275 | IL-17 (SEQ 3) | | 1.90E+06 | 6.50E−05 | 3.40E−11 |
| DVD2183 | IL-17 (SEQ 3) | | 2.30E+06 | 3.60E−05 | 1.50E−11 |
| DVD2183 | | IL-13 (SEQ 2) | 2.40E+05 | <1.0e−6 | <4.2e−12 |
| AB399 | IL-13 (SEQ 3) | | 3.40E+06 | 6.40E−05 | 1.90E−11 |
| AB273 | IL-17 (SEQ 1) | | 2.00E+06 | <1.0e−6 | <5.0E−13 |
| DVD2185 | IL-17 (SEQ 1) | | 1.70E+06 | 1.50E−05 | 8.90E−12 |
| DVD2185 | | IL-13 (SEQ 3) | 1.10E+05 | <1.0e−6 | <9.1e−12 |
| AB399 | IL-13 (SEQ 3) | | 3.40E+06 | 6.40E−05 | 1.90E−11 |
| AB273 | IL-17 (SEQ 1) | | 2.00E+06 | <1.0e−6 | <5.0E−13 |
| DVD2187 | IL-17 (SEQ 1) | | 2.60E+06 | <1.0e−6 | <3.8E−13 |
| DVD2187 | | IL-13 (SEQ 3) | 2.90E+05 | 2.10E−05 | 7.20E−11 |
| AB399 | IL-13 (SEQ 3) | | 3.40E+06 | 6.40E−05 | 1.90E−11 |
| AB273 | IL-17 (SEQ 1) | | 2.00E+06 | <1.0e−6 | <5.0E−13 |
| DVD2189 | IL-17 (SEQ 1) | | 2.50E+06 | <1.0e−6 | <4.0E−13 |
| DVD2189 | | IL-13 (SEQ 3) | 4.10E+05 | 3.90E−05 | 9.40E−11 |
| AB399 | IL-13 (SEQ 3) | | 3.40E+06 | 6.40E−05 | 1.90E−11 |
| AB274 | IL-17 (SEQ 2) | | 1.10E+06 | 8.20E−06 | 7.40E−12 |
| DVD2190 | IL-13 (SEQ 3) | | 2.60E+06 | 5.70E−05 | 2.10E−11 |
| DVD2190 | | IL-17 (SEQ 2) | 8.90E+04 | 3.40E−06 | 3.80E−11 |
| DVD2191 | IL-17 (SEQ 2) | | 2.50E+06 | 1.20E−05 | 4.60E−12 |
| DVD2191 | | IL-13 (SEQ 3) | 2.60E+05 | 4.40E−05 | 1.70E−10 |
| AB399 | IL-13 (SEQ 3) | | 3.40E+06 | 6.40E−05 | 1.90E−11 |
| AB274 | IL-17 (SEQ 2) | | 1.10E+06 | 8.20E−06 | 7.40E−12 |
| DVD2192 | IL-13 (SEQ 3) | | 1.50E+06 | 5.10E−05 | 3.50E−11 |
| DVD2192 | | IL-17 (SEQ 2) | 2.60E+05 | <1.0e−6 | <3.8E−12 |
| DVD2193 | IL-17 (SEQ 2) | | 1.90E+06 | 2.20E−05 | 1.20E−11 |
| DVD2193 | | IL-13 (SEQ 3) | 5.90E+05 | 3.90E−05 | 6.60E−11 |
| AB399 | IL-13 (SEQ 3) | | 3.40E+06 | 6.40E−05 | 1.90E−11 |
| AB274 | IL-17 (SEQ 2) | | 1.10E+06 | 8.20E−06 | 7.40E−12 |
| DVD2195 | IL-17 (SEQ 2) | | 2.40E+06 | 4.80E−06 | 2.00E−12 |
| DVD2195 | | IL-13 (SEQ 3) | 2.60E+06 | 3.70E−05 | 1.40E−11 |
| AB399 | IL-13 (SEQ 3) | | 3.40E+06 | 6.40E−05 | 1.90E−11 |
| AB275 | IL-17 (SEQ 3) | | 1.90E+06 | 6.50E−05 | 3.40E−11 |
| DVD2196 | IL-13 (SEQ 3) | | 2.20E+06 | 6.40E−05 | 2.90E−11 |
| DVD2196 | | IL-17 (SEQ 3) | 1.10E+05 | <1.0e−6 | <9.1E−12 |
| DVD2197 | IL-17 (SEQ 3) | | 1.60E+06 | 6.20E−05 | 3.80E−11 |
| DVD2197 | | IL-13 (SEQ 3) | 3.10E+05 | 4.40E−05 | 1.40E−10 |
| AB399 | IL-13 (SEQ 3) | | 3.40E+06 | 6.40E−05 | 1.90E−11 |
| AB275 | IL-17 (SEQ 3) | | 1.90E+06 | 6.50E−05 | 3.40E−11 |
| DVD2199 | IL-17 (SEQ 3) | | 2.30E+06 | 4.40E−05 | 1.90E−11 |
| DVD2199 | | IL-13 (SEQ 3) | 1.30E+06 | 3.40E−05 | 2.60E−11 |
| AB399 | IL-13 (SEQ 3) | | 3.40E+06 | 6.40E−05 | 1.90E−11 |
| AB275 | IL-17 (SEQ 3) | | 1.90E+06 | 6.50E−05 | 3.40E−11 |

TABLE 9-continued

BIACORE Analysis of Parental Antibodies and DVD-Ig Proteins

| Parent Antibody or DVD-Ig ID | N-terminal Variable Domain (VD) | C-terminal Variable Domain (VD) | $k_{on}$ (M−1s−1) | $k_{off}$ (s−1) | $k_D$ (M) |
|---|---|---|---|---|---|
| DVD2200 | IL-13 (SEQ 3) | | 1.30E+06 | 6.00E−05 | 4.50E−11 |
| DVD2200 | | IL-17 (SEQ 3) | 1.80E+05 | 4.60E−06 | 2.50E−11 |
| DVD2201 | IL-17 (SEQ 3) | | 1.60E+06 | 6.30E−05 | 4.00E−11 |
| DVD2201 | | IL-13 (SEQ 3) | 2.40E+06 | 5.70E−05 | 2.40E−11 |

Binding of all DVD-Ig proteins characterized by Biacore technology was maintained and comparable to that of parent antibodies. All variable domains bound with similar high affinity as the parent antibodies.

Example 4

Characterization of Antibodies and DVD-Ig Proteins

The ability of purified DVD-Ig protein to inhibit a functional activity was determined, e.g., using the cytokine bioassay as described in Example 3. The binding affinities of the DVD-Ig protein to recombinant human antigen were determined using surface plasmon resonance (Biacore®) measurement as described in Example 4. The $IC_{50}$ values from the bioassays and the affinity of the antibodies and DVD-Ig proteins were ranked. The DVD-Ig protein that fully maintain the activity of the parent mAbs were selected as candidates for future development. The top 2-3 most favorable DVD-Ig proteins were further characterized.

Example 4.1

Pharmacokinetic Analysis of Humanized Antibodies or DVD-Ig Protein

Pharmacokinetic studies are carried out in Sprague-Dawley rats and cynomolgus monkeys. Male and female rats and cynomolgus monkeys are dosed intravenously or subcutaneously with a single dose of 4 mg/kg mAb or DVD-Ig protein and samples are analyzed using antigen capture ELISA, and pharmacokinetic parameters are determined by noncompartmental analysis. Briefly, ELISA plates are coated with goat anti-biotin antibody (5 mg/ml, 4° C., overnight), blocked with Superblock (Pierce), and incubated with biotinylated human antigen at 50 ng/ml in 10% Superblock TTBS at room temperature for 2 hours. Serum samples are serially diluted (0.5% serum, 10% Superblock in TTBS) and incubated on the plate for 30 minutes at room temperature. Detection is carried out with HRP-labeled goat anti human antibody and concentrations are determined with the help of standard curves using the four parameter logistic fit. Values for the pharmacokinetic parameters are determined by non-compartmental model using WinNonlin software (Pharsight Corporation, Mountain View, Calif.). Humanized mAbs with good pharmacokinetics profile (T½ is 8-13 days or better, with low clearance and excellent bioavailability 50-100%) are selected.

Example 4.2

Physicochemical and In Vitro Stability Analysis of Humanized Monoclonal Antibodies and DVD-Ig Proteins Size Exclusion Chromatography Antibodies or DVD-Ig proteins were diluted to 2.5 mg/mL with water and 20 mL was analyzed on a Shimadzu HPLC system using a TSK gel G3000 SWXL column (Tosoh Bioscience, cat# k5539-05k). Samples were eluted from the column with 211 mM sodium sulfate, 92 mM sodium phosphate, pH 7.0, at a flow rate of 0.3 mL/minutes. The HPLC system operating conditions were as follows:

Mobile phase: 211 mM $Na_2SO_4$, 92 mM $Na_2HPO_4*7H_2O$, pH 7.0

Gradient: Isocratic

Flow rate: 0.3 mL/minute

Detector wavelength: 280 nm

Autosampler cooler temp: 4° C.

Column oven temperature: Ambient

Run time: 50 minutes

Table 10 contains purity data of parent antibodies and DVD-Ig proteins expressed as percent monomer (unaggregated protein of the expected molecular weight) as determined by the above protocol.

TABLE 10

Purity of Parent Antibodies and DVD-Ig Proteins as Determined by Size Exclusion Chromatography

| Parent Antibody or DVD-Ig ID | N-terminal Variable Domain (VD) | C-terminal Variable Domain (VD) | % Monomer (purity) |
|---|---|---|---|
| AB273 | | IL-17 (SEQ 1) | 100 |
| AB274 | | IL-17 (SEQ 2) | 70.7 |
| AB275 | | IL-17 (SEQ 3) | 94.5 |
| AB397 | | IL-13 (SEQ 1) | 93 |
| AB398 | | IL-13 (SEQ 2) | 92.8 |
| AB399 | | IL-13 (SEQ 3) | 98.8 |
| DVD2148 | IL-13 (SEQ 1) | IL-17 (SEQ 1) | 69.6 |
| DVD2150 | IL-13 (SEQ 1) | IL-17 (SEQ 1) | 68.7 |
| DVD2152 | IL-13 (SEQ 1) | IL-17 (SEQ 1) | 63.5 |
| DVD2153 | IL-17 (SEQ 1) | IL-13 (SEQ 1) | 79 |
| DVD2154 | IL-13 (SEQ 1) | IL-17 (SEQ 2) | 78.3 |
| DVD2155 | IL-17 (SEQ 2) | IL-13 (SEQ 1) | 93.2 |
| DVD2156 | IL-13 (SEQ 1) | IL-17 (SEQ 2) | 75.1 |
| DVD2157 | IL-17 (SEQ 2) | IL-13 (SEQ 1) | 92.5 |
| DVD2158 | IL-13 (SEQ 1) | IL-17 (SEQ 2) | 81.4 |
| DVD2159 | IL-17 (SEQ 2) | IL-13 (SEQ 1) | 94.9 |
| DVD2160 | IL-13 (SEQ 1) | IL-17 (SEQ 3) | 73.1 |
| DVD2161 | IL-17 (SEQ 3) | IL-13 (SEQ 1) | 85.6 |
| DVD2162 | IL-13 (SEQ 1) | IL-17 (SEQ 3) | 66 |
| DVD2163 | IL-17 (SEQ 3) | IL-13 (SEQ 1) | 70 |
| DVD2164 | IL-13 (SEQ 1) | IL-17 (SEQ 3) | 84 |
| DVD2165 | IL-17 (SEQ 3) | IL-13 (SEQ 1) | 84 |
| DVD2166 | IL-13 (SEQ 2) | IL-17 (SEQ 1) | 82.5 |
| DVD2167 | IL-17 (SEQ 1) | IL-13 (SEQ 2) | 94 |
| DVD2168 | IL-13 (SEQ 2) | IL-17 (SEQ 1) | 94 |
| DVD2169 | IL-17 (SEQ 1) | IL-13 (SEQ 2) | 68.5 |
| DVD2170 | IL-13 (SEQ 2) | IL-17 (SEQ 1) | 73 |
| DVD2171 | IL-17 (SEQ 1) | IL-13 (SEQ 2) | 83 |
| DVD2172 | IL-13 (SEQ 2) | IL-17 (SEQ 2) | 82 |
| DVD2173 | IL-17 (SEQ 2) | IL-13 (SEQ 2) | 91 |
| DVD2174 | IL-13 (SEQ 2) | IL-17 (SEQ 2) | 83 |
| DVD2175 | IL-17 (SEQ 2) | IL-13 (SEQ 2) | 88 |
| DVD2176 | IL-13 (SEQ 2) | IL-17 (SEQ 2) | 78 |
| DVD2177 | IL-17 (SEQ 2) | IL-13 (SEQ 2) | 94 |
| DVD2178 | IL-13 (SEQ 2) | IL-17 (SEQ 3) | 65 |
| DVD2179 | IL-17 (SEQ 3) | IL-13 (SEQ 2) | 81 |
| DVD2180 | IL-13 (SEQ 2) | IL-17 (SEQ 3) | 69 |
| DVD2181 | IL-17 (SEQ 3) | IL-13 (SEQ 2) | 88 |

TABLE 10-continued

Purity of Parent Antibodies and DVD-Ig Proteins as Determined by Size Exclusion Chromatography

| Parent Antibody or DVD-Ig ID | N-terminal Variable Domain (VD) | C-terminal Variable Domain (VD) | % Monomer (purity) |
|---|---|---|---|
| DVD2182 | IL-13 (SEQ 2) | IL-17 (SEQ 3) | 62 |
| DVD2183 | IL-17 (SEQ 3) | IL-13 (SEQ 2) | 89 |
| DVD2185 | IL-17 (SEQ 1) | IL-13 (SEQ 2) | 99.9 |
| DVD2187 | IL-17 (SEQ 1) | IL-13 (SEQ 3) | 84 |
| DVD2189 | IL-17 (SEQ 1) | IL-13 (SEQ 3) | 84 |
| DVD2190 | IL-13 (SEQ 3) | IL-17 (SEQ 2) | 99 |
| DVD2191 | IL-17 (SEQ 2) | IL-13 (SEQ 3) | 98 |
| DVD2192 | IL-13 (SEQ 3) | IL-17 (SEQ 2) | 99 |
| DVD2193 | IL-17 (SEQ 2) | IL-13 (SEQ 3) | 99 |
| DVD2195 | IL-17 (SEQ 2) | IL-13 (SEQ 3) | 96 |
| DVD2196 | IL-13 (SEQ 3) | IL-17 (SEQ 3) | 99 |
| DVD2197 | IL-17 (SEQ 3) | IL-13 (SEQ 3) | 96 |
| DVD2199 | IL-17 (SEQ 3) | IL-13 (SEQ 3) | 93 |
| DVD2200 | IL-13 (SEQ 3) | IL-17 (SEQ 3) | 92 |
| DVD2201 | IL-17 (SEQ 3) | IL-13 (SEQ 3) | 99 |

DVD-Ig proteins showed an excellent SEC profile with most DVD-Ig proteins showing >90% monomer. This DVD-Ig protein profile was similar to that observed for parent antibodies.

SDS-PAGE

Antibodies and DVD-Ig proteins are analyzed by sodium dodecyl sulfate—polyacrylamide gel electrophoresis (SDS-PAGE) under both reducing and non-reducing conditions. Adalimumab lot AFP04C is used as a control. For reducing conditions, the samples are mixed 1:1 with 2× tris glycine SDS-PAGE sample buffer (Invitrogen, cat# LC2676, lot#1323208) with 100 mM DTT, and heated at 60° C. for 30 minutes. For non-reducing conditions, the samples are mixed 1:1 with sample buffer and heated at 100° C. for 5 minutes. The reduced samples (10 mg per lane) are loaded on a 12% pre-cast tris-glycine gel (Invitrogen, cat# EC6005box, lot#6111021), and the non-reduced samples (10 mg per lane) are loaded on an 8%-16% pre-cast tris-glycine gel (Invitrogen, cat# EC6045box, lot#6111021). SeeBlue Plus 2 (Invitrogen, cat#LC5925, lot#1351542) is used as a molecular weight marker. The gels are run in a XCell SureLock mini cell gel box (Invitrogen, cat#E10001) and the proteins are separated by first applying a voltage of 75 to stack the samples in the gel, followed by a constant voltage of 125 until the dye front reached the bottom of the gel. The running buffer used is 1× tris glycine SDS buffer, prepared from a 10× tris glycine SDS buffer (ABC, MPS-79-080106)). The gels are stained overnight with colloidal blue stain (Invitrogen cat#46-7015, 46-7016) and destained with Milli-Q water until the background is clear. The stained gels are then scanned using an Epson Expression scanner (model 1680, S/N DASX003641).

Sedimentation Velocity Analysis

Antibodies or DVD-Ig proteins are loaded into the sample chamber of each of three standard two-sector carbon epon centerpieces. These centerpieces have a 1.2 cm optical path length and are built with sapphire windows. PBS is used for a reference buffer and each chamber contained 140 μL. All samples are examined simultaneously using a 4-hole (AN-60Ti) rotor in a Beckman ProteomeLab XL-I analytical ultracentrifuge (serial #PL106C01).

Run conditions are programmed and centrifuge control is performed using ProteomeLab (v5.6). The samples and rotor are allowed to thermally equilibrate for one hour prior to analysis (20.0±0.1° C.). Confirmation of proper cell loading is performed at 3000 rpm and a single scan is recorded for each cell. The sedimentation velocity conditions are the following:

Sample Cell Volume: 420 mL
Reference Cell Volume: 420 mL
Temperature: 20° C.
Rotor Speed: 35,000 rpm
Time: 8:00 hours
UV Wavelength: 280 nm
Radial Step Size: 0.003 cm
Data Collection: One data point per step without signal averaging.
Total Number of Scans: 100

LC-MS Molecular Weight Measurement of Intact Antibodies

Molecular weight of intact antibodies and DVD-Ig proteins are analyzed by LC-MS. Each antibody or DVD-Ig protein is diluted to approximately 1 mg/mL with water. An 1100 HPLC (Agilent) system with a protein microtrap (Michrom Bioresources, Inc, cat#004/25109/03) is used to desalt and introduce 5 mg of the sample into an API Qstar pulsar i mass spectrometer (Applied Biosystems). A short gradient is used to elute the samples. The gradient is run with mobile phase A (0.08% FA, 0.02% TFA in HPLC water) and mobile phase B (0.08% FA and 0.02% TFA in acetonitrile) at a flow rate of 50 mL/minute. The mass spectrometer is operated at 4.5 kvolts spray voltage with a scan range from 2000 to 3500 mass to charge ratio.

LC-MS Molecular Weight Measurement of Antibody and DVD-Ig Protein Light and Heavy Chains Molecular weight measurement of antibody and DVD-Ig protein light chain (LC), heavy chain (HC) and deglycosylated HC are analyzed by LC-MS. Antibodies and DVD-Ig proteins are diluted to 1 mg/mL with water and the sample is reduced to LC and HC with a final concentration of 10 mM DTT for 30 minutes at 37° C. To deglycosylate the antibodies and DVD-Ig proteins, 100 mg of the antibody or DVD-Ig protein is incubated with 2 mL of PNGase F, 5 mL of 10% N-octylglucoside in a total volume of 100 mL overnight at 37° C. After deglycosylation the sample is reduced with a final concentration of 10 mM DTT for 30 minutes at 37° C. An Agilent 1100 HPLC system with a C4 column (Vydac, cat#214TP5115, S/N 060206537204069) is used to desalt and introduce the sample (5 mg) into an API Qstar pulsar i mass spectrometer (Applied Biosystems). A short gradient is used to elute the sample. The gradient is run with mobile phase A (0.08% FA, 0.02% TFA in HPLC water) and mobile phase B (0.08% FA and 0.02% TFA in acetonitrile) at a flow rate of 50 mL/minute. The mass spectrometer is operated at 4.5 kvolts spray voltage with a scan range from 800 to 3500 mass to charge ratio.

Peptide Mapping

The antibody or DVD-Ig protein is denatured for 15 minutes at room temperature with a final concentration of 6 M guanidine hydrochloride in 75 mM ammonium bicarbonate. The denatured samples are reduced with a final concentration of 10 mM DTT at 37° C. for 60 minutes, followed by alkylation with 50 mM iodoacetic acid (IAA) in the dark at 37° C. for 30 minutes. Following alkylation, the sample is dialyzed overnight against four liters of 10 mM ammonium bicarbonate at 4° C. The dialyzed sample is diluted to 1 mg/mL with 10 mM ammonium bicarbonate, pH 7.8 and 100 mg of antibody or DVD-Ig protein is either digested with trypsin (Promega, cat#V5111) or Lys-C (Roche, cat#11 047 825 001) at a 1:20 (w/w) trypsin/Lys-C:antibody or DVD-Ig protein ratio at 37° C. for 4 hours. Digests are quenched with 1 mL of 1 N HCl. For peptide mapping with mass spectrometer detection, 40 mL of the digests are separated by reverse phase high performance liquid chromatography (RPHPLC) on a C18 column (Vydac, cat#218TP51, S/N NE9606 10.3.5) with an Agilent 1100 HPLC system. The peptide separation is run with a gradient using mobile phase A (0.02% TFA and 0.08% FA in HPLC grade water) and mobile phase B (0.02% TFA and 0.08% FA in acetonitrile) at a flow rate of 50 mL/minutes. The API QSTAR Pulsar i mass spectromer is operated in positive mode at 4.5 kvolts spray voltage and a scan range from 800 to 2500 mass to charge ratio.

Disulfide Bond Mapping

To denature the antibody, 100 mL of the antibody or DVD-Ig protein is mixed with 300 mL of 8 M guanidine HCl in 100 mM ammonium bicarbonate. The pH is checked to ensure that it is between 7 and 8 and the samples are denatured for 15 minutes at room temperature in a final concentration of 6 M guanidine HCl. A portion of the denatured sample (100 mL) is diluted to 600 mL with Milli-Q water to give a final guanidine-HCl concentration of 1 M. The sample (220 mg) is digested with either trypsin (Promega, cat #V5111, lot#22265901) or Lys-C (Roche, cat#11047825001, lot#12808000) at a 1:50 trypsin or 1:50 Lys-C: antibody or DVD-Ig protein (w/w) ratios (4.4 mg enzyme: 220 mg sample) at 37° C. for approximately 16 hours. An additional 5 mg of trypsin or Lys-C is added to the samples and digestion is allowed to proceed for an additional 2 hours at 37° C. Digestions are stopped by adding 1 mL of TFA to each sample. Digested samples are separated by RPHPLC using a C18 column (Vydac, cat#218TP51 S/N NE020630-4-1A) on an Agilent HPLC system. The separation is run with the same gradient used for peptide mapping using mobile phase A (0.02% TFA and 0.08% FA in HPLC grade water) and mobile phase B (0.02% TFA and 0.08% FA in acetonitrile) at a flow rate of 50 mL/minute. The HPLC operating conditions are the same as those used for peptide mapping. The API QSTAR Pulsar i mass spectromer is operated in positive mode at 4.5 kvolts spray voltage and a scan range from 800 to 2500 mass-to-charge ratio. Disulfide bonds are assigned by matching the observed MWs of peptides with the predicted MWs of tryptic or Lys-C peptides linked by disulfide bonds.

Free Sulfhydryl Determination

The method used to quantify free cysteines in an antibody or DVD-Ig protein is based on the reaction of Ellman's reagent, 5,50-dithio-bis(2-nitrobenzoic acid) (DTNB), with sulfhydryl groups (SH) which gives rise to a characteristic chromophoric product, 5-thio-(2-nitrobenzoic acid) (TNB). The reaction is illustrated in the formula:

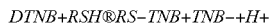

$$DTNB+RSH\circledR RS-TNB+TNB-+H+$$

The absorbance of the TNB− is measured at 412 nm using a Cary 50 spectrophotometer. An absorbance curve is plotted using dilutions of 2 mercaptoethanol (b-ME) as the free SH standard and the concentrations of the free sulfhydryl groups in the protein are determined from absorbance at 412 nm of the sample.

The b-ME standard stock is prepared by a serial dilution of 14.2 M b-ME with HPLC grade water to a final concentration of 0.142 mM. Then standards in triplicate for each concentration are prepared. Antibody or DVD-Ig protein is concentrated to 10 mg/mL using an amicon ultra 10,000 MWCO centrifugal filter (Millipore, cat# UFC801096, lot# L3KN5251) and the buffer is changed to the formulation buffer used for adalimumab (5.57 mM sodium phosphate monobasic, 8.69 mM sodium phosphate dibasic, 106.69 mM NaCl, 1.07 mM sodium citrate, 6.45 mM citric acid, 66.68 mM mannitol, pH 5.2, 0.1% (w/v) Tween). The samples are mixed on a shaker at room temperature for 20 minutes. Then 180 mL of 100 mM Tris buffer, pH 8.1 is added to each sample and standard followed by the addition of 300 mL of 2 mM DTNB in 10 mM phosphate buffer, pH 8.1. After thorough mixing, the samples and standards are measured for absorption at 412 nm on a Cary 50 spectrophotometer. The standard curve is obtained by plotting the amount of free SH and $OD_{412}$ nm of the b-ME standards. Free SH content of samples are calculated based on this curve after subtraction of the blank.

Weak Cation Exchange Chromatography

Antibody or DVD-Ig protein is diluted to 1 mg/mL with 10 mM sodium phosphate, pH 6.0. Charge heterogeneity is analyzed using a Shimadzu HPLC system with a WCX-10 Pro-Pac analytical column (Dionex, cat#054993, S/N 02722). The samples are loaded on the column in 80% mobile phase A (10 mM sodium phosphate, pH 6.0) and 20% mobile phase B (10 mM sodium phosphate, 500 mM NaCl, pH 6.0) and eluted at a flow rate of 1.0 mL/minute.

Oligosaccharide Profiling

Oligosaccharides released after PNGase F treatment of antibody or DVD-Ig protein are derivatized with 2-aminobenzamide (2-AB) labeling reagent. The fluorescent-labeled oligosaccharides are separated by normal phase high performance liquid chromatography (NPHPLC) and the different forms of oligosaccharides are characterized based on retention time comparison with known standards.

The antibody or DVD-Ig protein is first digested with PNGaseF to cleave N-linked oligosaccharides from the Fc portion of the heavy chain. The antibody or DVD-Ig protein (200 mg) is placed in a 500 mL Eppendorf tube along with 2 mL PNGase F and 3 mL of 10% N-octylglucoside. Phosphate buffered saline is added to bring the final volume to 60 mL. The sample is incubated overnight at 37° C. in an Eppendorf thermomixer set at 700 RPM. Adalimumab lot AFP04C is also digested with PNGase F as a control.

After PNGase F treatment, the samples are incubated at 95° C. for 5 minutes in an Eppendorf thermomixer set at 750 RPM to precipitate out the proteins, then the samples are placed in an Eppendorf centrifuge for 2 minutes at 10,000 RPM to spin down the precipitated proteins. The supernatent containing the oligosaccharides are transferred to a 500 mL Eppendorf tube and dried in a speed-vac at 65° C.

The oligosaccharides are labeled with 2AB using a 2AB labeling kit purchased from Prozyme (cat# GKK-404, lot#132026). The labeling reagent is prepared according to the manufacturer's instructions. Acetic acid (150 mL, provided in kit) is added to the DMSO vial (provided in kit) and mixed by pipeting the solution up and down several times. The acetic acid/DMSO mixture (100 mL) is transferred to a vial of 2-AB dye (just prior to use) and mixed until the dye is fully dissolved. The dye solution is then added to a vial of reductant (provided in kit) and mixed well (labeling reagent). The labeling reagent (5 mL) is added to each dried oligosaccharide sample vial, and mixed thoroughly. The reaction vials are placed in an Eppendorf thermomixer set at 65° C. and 700-800 RPM for 2 hours of reaction.

After the labeling reaction, the excess fluorescent dye is removed using GlycoClean S Cartridges from Prozyme (cat# GKI-4726). Prior to adding the samples, the cartridges are washed with 1 mL of milli-Q water followed with 5 ishes of 1 mL 30% acetic acid solution. Just prior to adding the samples, 1 mL of acetonitrile (Burdick and Jackson, cat# AH015-4) is added to the cartridges.

After all of the acetonitrile passed through the cartridge, the sample is spotted onto the center of the freshly washed disc and allowed to adsorb onto the disc for 10 minutes. The disc is washed with 1 mL of acetonitrile followed by five ishes of 1 mL of 96% acetonitrile. The cartridges are placed over a 1.5 mL Eppendorf tube and the 2-AB labeled oligosaccharides are eluted with 3 ishes (400 mL each ish) of milli Q water.

The oligosaccharides are separated using a Glycosep N HPLC (cat# GKI-4728) column connected to a Shimadzu HPLC system. The Shimadzu HPLC system consisted of a system controller, degasser, binary pumps, autosampler with a sample cooler, and a fluorescent detector.

Stability at Elevated Temperatures

The buffer of antibody or DVD-Ig protein is either 5.57 mM sodium phosphate monobasic, 8.69 mM sodium phosphate dibasic, 106.69 mM NaCl, 1.07 mM sodium citrate, 6.45 mM citric acid, 66.68 mM mannitol, 0.1% (w/v) Tween, pH 5.2; or mM histidine, 10 mM methionine, 4% mannitol, pH 5.9 using Amicon ultra centrifugal filters. The final concentration of the antibodies or DVD-Ig proteins is adjusted to 2 mg/mL with the appropriate buffers. The antibody or DVD-Ig protein solutions are then filter sterized and 0.25 mL aliquots are prepared under sterile conditions. The aliquots are left at either −80° C., 5° C., 25° C., or 40° C. for 1, 2 or 3 weeks. At the end of the incubation period, the samples are analyzed by size exclusion chromatography and SDS-PAGE.

The stability samples are analyzed by SDS-PAGE under both reducing and non-reducing conditions. The procedure used is the same as described herein. The gels are stained overnight with colloidal blue stain (Invitrogen cat#46-7015, 46-7016) and destained with Milli-Q water until the background is clear. The stained gels are then scanned using an Epson Expression scanner (model 1680, S/N DASX003641). To obtain more sensitivity, the same gels are silver stained using silver staining kit (Owl Scientific) and the recommended procedures given by the manufacturer is used.

Dynamic Scanning Fluorimetry

The DVD-Igs proteins were dialysed in 10 mM citrate 10 mM phosphate buffer, pH 6.0 to get a final concentration of 1 mg/ml. Triplicates were run for each DVD-Ig protein. For each sample, 27 µl of the DVD-Ig protein was added in a well of a 96 well plate and mixed with 3 µl of 4× diluted SYPRO Orange dye (Invitrogen). The dye is supplied in DMSO at a concentration of 5000× and was diluted to the working concentration of 4× in water. The plate was centrifuged for 30 seconds to ensure that both the dye and the protein settle to the bottom of the wells and complete mixing was ensured by gentle aspiration by a pipette tip. The plate was then sealed with an adhesive film.

A real time PCR (Applied Biosciences, 7500 Series) was used for measuring the change in fluorescence intensities with temperature. The plate was heated from 25° C. to 95° C. at a temperature ramp rate of approximately 0.5° C./minute and emission fluorescence was collected using TAMRA filter. The data was exported to Microsoft Excel and plotted as temperature vs fluorescence for each DVD-Ig protein. Onset of melting was noted as the temperature where the thermogram rises above the baseline fluorescence. SYPRO Orange is a hydrophobic dye and preferentially binds to the exposed hydrophobic residues in an unfolded protein molecule. Hence the onset of unfolding temperature, as measured by an increase in fluorescence, is an indication of the thermal stability of the DVD-Ig protein. The unfolding temperature for the DVD-Ig proteins can be found in Table 11.

TABLE 11

Thermal Stability of DVD-Ig Proteins as Determined by Dynamic Scanning Fluorimetry

| Parent Antibody or DVD-Ig ID | N-terminal Variable Domain (VD) | C-terminal Variable Domain (VD) | T onset (deg C.) |
|---|---|---|---|
| DVD2148 | IL-13 (SEQ 1) | IL-17 (SEQ 1) | 62 |
| DVD2150 | IL-13 (SEQ 1) | IL-17 (SEQ 1) | 61 |
| DVD2152 | IL-13 (SEQ 1) | IL-17 (SEQ 1) | 60.5 |
| DVD2154 | IL-13 (SEQ 1) | IL-17 (SEQ 2) | 61.5 |
| DVD2155 | IL-17 (SEQ 2) | IL-13 (SEQ 1) | |
| DVD2156 | IL-13 (SEQ 1) | IL-17 (SEQ 2) | 59 |
| DVD2157 | IL-17 (SEQ 2) | IL-13 (SEQ 1) | 50.5 |
| DVD2158 | IL-13 (SEQ 1) | IL-17 (SEQ 2) | 63 |
| DVD2159 | IL-17 (SEQ 2) | IL-13 (SEQ 1) | 49.5 |
| DVD2160 | IL-13 (SEQ 1) | IL-17 (SEQ 3) | 64 |
| DVD2161 | IL-17 (SEQ 3) | IL-13 (SEQ 1) | 48 |
| DVD2162 | IL-13 (SEQ 1) | IL-17 (SEQ 3) | 60.5 |
| DVD2163 | IL-17 (SEQ 3) | IL-13 (SEQ 1) | 48 |
| DVD2164 | IL-13 (SEQ 1) | IL-17 (SEQ 3) | 61.5 |
| DVD2165 | IL-17 (SEQ 3) | IL-13 (SEQ 1) | 50 |
| DVD2166 | IL-13 (SEQ 2) | IL-17 (SEQ 1) | 62.5 |
| DVD2167 | IL-17 (SEQ 1) | IL-13 (SEQ 2) | 50.5 |
| DVD2168 | IL-13 (SEQ 2) | IL-17 (SEQ 1) | 46 |
| DVD2170 | IL-13 (SEQ 2) | IL-17 (SEQ 1) | 61.5 |
| DVD2172 | IL-13 (SEQ 2) | IL-17 (SEQ 2) | 63.5 |
| DVD2173 | IL-17 (SEQ 2) | IL-13 (SEQ 2) | 55.5 |
| DVD2174 | IL-13 (SEQ 2) | IL-17 (SEQ 2) | 64.5 |
| DVD2175 | IL-17 (SEQ 2) | IL-13 (SEQ 2) | 53 |
| DVD2176 | IL-13 (SEQ 2) | IL-17 (SEQ 2) | 64 |
| DVD2177 | IL-17 (SEQ 2) | IL-13 (SEQ 2) | 52.5 |
| DVD2178 | IL-13 (SEQ 2) | IL-17 (SEQ 3) | 64 |
| DVD2179 | IL-17 (SEQ 3) | IL-13 (SEQ 2) | 49.5 |
| DVD2180 | IL-13 (SEQ 2) | IL-17 (SEQ 3) | 62 |
| DVD2182 | IL-13 (SEQ 2) | IL-17 (SEQ 3) | 63 |
| DVD2183 | IL-17 (SEQ 3) | IL-13 (SEQ 2) | 48 |
| DVD2185 | IL-17 (SEQ 1) | IL-13 (SEQ 3) | 54.5 |
| DVD2190 | IL-13 (SEQ 3) | IL-17 (SEQ 2) | 48 |
| DVD2191 | IL-17 (SEQ 2) | IL-13 (SEQ 3) | 54.5 |
| DVD2193 | IL-17 (SEQ 2) | IL-13 (SEQ 3) | 51 |
| DVD2195 | IL-17 (SEQ 2) | IL-13 (SEQ 3) | 51.5 |
| DVD2196 | IL-13 (SEQ 3) | IL-17 (SEQ 3) | 48.5 |
| DVD2197 | IL-17 (SEQ 3) | IL-13 (SEQ 3) | 49 |
| DVD2199 | IL-17 (SEQ 3) | IL-13 (SEQ 3) | 45 |
| DVD2201 | IL-17 (SEQ 3) | IL-13 (SEQ 3) | 46 |

Most DVD-Ig proteins showed an unfolding temperature>50. This DVD-Ig protein profile is similar to that observed for parent antibodies.

Solubility Determination

DVD-Ig protein candidates were dialyzed in 15 mM His, pH 6.0. This was followed by concentrating them up to 50 µl in centricons with a 30K cutoff. Solubility was visually confirmed by absence of precipitation after storage at 4° C. and quantitatively determined by UV absorbance measurement at 280 nm.

TABLE 12

Solubility of DVD-Ig Proteins

| Parent Antibody or DVD-Ig ID | N-terminal Variable Domain (VD) | C-terminal Variable Domain (VD) | Visual observation | Solubility (mg/mL) |
|---|---|---|---|---|
| DVD2148 | IL-13 (SEQ 1) | IL-17 (SEQ 1) | Clear | >53.0 |
| DVD2150 | IL-13 (SEQ 1) | IL-17 (SEQ 1) | Clear | >28.6 |
| DVD2152 | IL-13 (SEQ 1) | IL-17 (SEQ 1) | Clear | >57.3 |
| DVD2154 | IL-13 (SEQ 1) | IL-17 (SEQ 2) | Clear | >79.2 |
| DVD2155 | IL-17 (SEQ 2) | IL-13 (SEQ 1) | Ppt | |
| DVD2156 | IL-13 (SEQ 1) | IL-17 (SEQ 2) | Clear | >98.9 |
| DVD2157 | IL-17 (SEQ 2) | IL-13 (SEQ 1) | Clear | >23.2 |
| DVD2158 | IL-13 (SEQ 1) | IL-17 (SEQ 2) | Clear | >121.6 |
| DVD2159 | IL-17 (SEQ 2) | IL-13 (SEQ 1) | Ppt | 13.3 |
| DVD2160 | IL-13 (SEQ 1) | IL-17 (SEQ 3) | Clear | >122.3 |
| DVD2161 | IL-17 (SEQ 3) | IL-13 (SEQ 1) | Ppt | 10.5 |
| DVD2162 | IL-13 (SEQ 1) | IL-17 (SEQ 3) | Clear | >85.2 |
| DVD2163 | IL-17 (SEQ 3) | IL-13 (SEQ 1) | Clear | >8.6 |
| DVD2164 | IL-13 (SEQ 1) | IL-17 (SEQ 3) | Clear | >99.1 |

TABLE 12-continued

Solubility of DVD-Ig Proteins

| Parent Antibody or DVD-Ig ID | N-terminal Variable Domain (VD) | C-terminal Variable Domain (VD) | Visual observation | Solubility (mg/mL) |
|---|---|---|---|---|
| DVD2165 | IL-17 (SEQ 3) | IL-13 (SEQ 1) | opalascent | — |
| DVD2166 | IL-13 (SEQ 2) | IL-17 (SEQ 1) | Clear | >13.8 |
| DVD2167 | IL-17 (SEQ 1) | IL-13 (SEQ 2) | Clear | — |
| DVD2168 | IL-13 (SEQ 2) | IL-17 (SEQ 1) | Clear | — |
| DVD2170 | IL-13 (SEQ 2) | IL-17 (SEQ 1) | Ppt | 12.1 |
| DVD2172 | IL-13 (SEQ 2) | IL-17 (SEQ 2) | Clear | >58.9 |
| DVD2173 | IL-17 (SEQ 2) | IL-13 (SEQ 2) | phase separation | 39.3 |
| DVD2174 | IL-13 (SEQ 2) | IL-17 (SEQ 2) | Clear | >75.4 |
| DVD2175 | IL-17 (SEQ 2) | IL-13 (SEQ 2) | Ppt | |
| DVD2176 | IL-13 (SEQ 2) | IL-17 (SEQ 2) | Clear | >43.5 |
| DVD2177 | IL-17 (SEQ 2) | IL-13 (SEQ 2) | Clear | >9.8 |
| DVD2178 | IL-13 (SEQ 2) | IL-17 (SEQ 3) | Clear | >69.8 |
| DVD2179 | IL-17 (SEQ 3) | IL-13 (SEQ 2) | Ppt | 12.1 |
| DVD2180 | IL-13 (SEQ 2) | IL-17 (SEQ 3) | phase separation | 61.7 |
| DVD2182 | IL-13 (SEQ 2) | IL-17 (SEQ 3) | Clear | >57.5 |
| DVD2183 | IL-17 (SEQ 3) | IL-13 (SEQ 2) | Ppt | |
| DVD2185 | IL-17 (SEQ 1) | IL-13 (SEQ 3) | phase separation | |
| DVD2190 | IL-13 (SEQ 3) | IL-17 (SEQ 2) | Clear | >62.4 |
| DVD2191 | IL-17 (SEQ 2) | IL-13 (SEQ 3) | phase separation | 44 |
| DVD2193 | IL-17 (SEQ 2) | IL-13 (SEQ 3) | Ppt | |
| DVD2195 | IL-17 (SEQ 2) | IL-13 (SEQ 3) | Clear | |
| DVD2196 | IL-13 (SEQ 3) | IL-17 (SEQ 3) | Clear | >59.8 |
| DVD2197 | IL-17 (SEQ 3) | IL-13 (SEQ 3) | Ppt | 31 |
| DVD2199 | IL-17 (SEQ 3) | IL-13 (SEQ 3) | opalescent | |
| DVD2201 | IL-17 (SEQ 3) | IL-13 (SEQ 3) | opalescent | |

Most DVD-Ig proteins showed clear appearance and could be concentrated to greater than 25 mg/ml. This DVD-Ig protein profile is similar to that observed for parent antibodies.

INCORPORATION BY REFERENCE

The contents of all cited references (including literature references, patents, patent applications, and websites) that may be cited throughout this application are hereby expressly incorporated by reference in their entirety for any purpose, as are the references cited therein. The disclosure will employ, unless otherwise indicated, conventional techniques of immunology, molecular biology and cell biology, which are well known in the art.

The present disclosure also incorporates by reference in their entirety techniques well known in the field of molecular biology and drug delivery. These techniques include, but are not limited to, techniques described in the following publications:

Ausubel et al. (eds.), CURRENT PROTOCOLS IN MOLECULAR BIOLOGY, John Wiley &Sons, NY (1993);

Ausubel, F. M. et al. eds., SHORT PROTOCOLS IN MOLECULAR BIOLOGY (4th Ed. 1999) John Wiley & Sons, NY. (ISBN 0-471-32938-X);

CONTROLLED DRUG BIOAVAILABILITY, DRUG PRODUCT DESIGN AND PERFORMANCE, Smolen and Ball (eds.), Wiley, New York (1984);

Giege, R. and Ducruix, A. Barrett, CRYSTALLIZATION OF NUCLEIC ACIDS AND PROTEINS, a Practical Approach, 2nd ea., pp. 20 1-16, Oxford University Press, New York, N.Y., (1999);

Goodson, in MEDICAL APPLICATIONS OF CONTROLLED RELEASE, vol. 2, pp. 115-138 (1984);

Hammerling, et al., in: MONOCLONAL ANTIBODIES AND T-CELL HYBRIDOMAS 563-681 (Elsevier, N.Y., 1981;

Harlow et al., ANTIBODIES: A LABORATORY MANUAL, (Cold Spring Harbor Laboratory Press, 2nd ed. 1988);

Kabat et al., SEQUENCES OF PROTEINS OF IMMUNOLOGICAL INTEREST (National Institutes of Health, Bethesda, Md. (1987) and (1991);

Kabat, E. A., et al. (1991) SEQUENCES OF PROTEINS OF IMMUNOLOGICAL INTEREST, Fifth Edition, U.S. Department of Health and Human Services, NIH Publication No. 91-3242;

Kontermann and Dubel eds., ANTIBODY ENGINEERING (2001) Springer-Verlag. New York. 790 pp. (ISBN 3-540-41354-5).

Kriegler, Gene Transfer and Expression, A Laboratory Manual, Stockton Press, NY (1990); Lu and Weiner eds., CLONING AND EXPRESSION VECTORS FOR GENE FUNCTION ANALYSIS (2001) BioTechniques Press. Westborough, Mass. 298 pp. (ISBN 1-881299-21-X). MEDICAL APPLICATIONS OF CONTROLLED RELEASE, Langer and Wise (eds.), CRC Pres., Boca Raton, Fla. (1974);

Old, R. W. & S. B. Primrose, PRINCIPLES OF GENE MANIPULATION: AN INTRODUCTION TO GENETIC ENGINEERING (3d Ed. 1985) Blackwell Scientific Publications, Boston. Studies in Microbiology; V.2:409 pp. (ISBN 0-632-01318-4).

Sambrook, J. et al. eds., MOLECULAR CLONING: A LABORATORY MANUAL (2d Ed. 1989) Cold Spring Harbor Laboratory Press, NY. Vols. 1-3. (ISBN 0-87969-309-6). SUSTAINED AND CONTROLLED RELEASE DRUG DELIVERY SYSTEMS, J. R. Robinson, ed., Marcel Dekker, Inc., New York, 1978

Winnacker, E. L. FROM GENES TO CLONES: INTRODUCTION TO GENE TECHNOLOGY (1987) VCH Publishers, NY (translated by Horst Ibelgaufts). 634 pp. (ISBN 0-89573-614-4).

EQUIVALENTS

The disclosure may be embodied in other specific forms without departing from the spirit or essential characteristics thereof. The foregoing embodiments are therefore to be considered in all respects illustrative rather than limiting of the disclosure. Scope of the disclosure is thus indicated by the appended claims rather than by the foregoing description, and all changes that come within the meaning and range of equivalency of the claims are therefore intended to be embraced herein.

We claim:

1. A binding protein comprising first and second polypeptide chains, each independently comprising VD1-(X1)n-VD2-C-(X2)n, wherein
    VD1 is a first antibody variable domain;
    VD2 is a second antibody variable domain;
    C is an antibody constant domain;
    X1 is a linker;
    X2 is an antibody Fc region; and
    n is 0 or 1;
wherein the VD1 domains on the first and second polypeptide chains form a first functional target binding site and the VD2 domains on the first and second polypeptide chains form a second functional target binding site, and wherein the binding protein binds IL-13 and IL-17, wherein
    (a) the variable domains that form a functional target binding site for IL-13 comprise the amino acid sequences of SEQ ID NO: 32 and SEQ ID NO:33, and
    (b) the variable domains that form a functional target binding site for IL-17 comprise the amino acid sequences of
        SEQ ID NO: 36 and SEQ ID NO: 37,
        SEQ ID NO: 38 and SEQ ID NO: 39,
        SEQ ID NO: 40 and SEQ ID NO: 41,
        SEQ ID NO: 42 and SEQ ID NO: 52,
        SEQ ID NO: 42 and SEQ ID NO: 53,
        SEQ ID NO: 43 and SEQ ID NO: 50,
        SEQ ID NO: 44 and SEQ ID NO: 51,
        SEQ ID NO: 45 and SEQ ID NO: 54,
        SEQ ID NO: 46 and SEQ ID NO: 51,
        SEQ ID NO: 47 and SEQ ID NO: 54,
        SEQ ID NO: 48 and SEQ ID NO: 51, or
        SEQ ID NO: 49 and SEQ ID NO: 51.

2. The binding protein according to claim 1, wherein the first polypeptide chain comprises a first VD1-(X1)n-VD2-C-(X2)n, wherein
    VD1 is a first antibody heavy chain variable domain;
    VD2 is a second antibody heavy chain variable domain;
    C is an antibody heavy chain constant domain;
    X1 is a linker;
    X2 is an antibody Fc region; and
    n is 0 or 1,
wherein the second polypeptide chain comprises a second VD1-(X1)n-VD2-C, wherein
    VD1 is a first antibody light chain variable domain;
    VD2 is a second antibody light chain variable domain;
    C is an antibody light chain constant domain;
    X1 is a linker;
    n is 1 for (X1)n; and
    n is 0 for (X2)n,
wherein the VD1 domains on the first and second polypeptide chains form a first functional target binding site and the VD2 domains on the first and second polypeptide chains form a second functional target binding site.

3. The binding protein according to claim 1, wherein X1 comprises the amino acid sequence of any one of SEQ ID NOs: 1-29 or a G4S (SEQ ID NO: 29) repeating sequence.

4. The binding protein according to claim 1, wherein the Fc region is a variant sequence Fc region.

5. The binding protein according to claim 1, wherein the Fc region is an Fc region from IgG1, IgG2, IgG3, IgG4, IgA, IgM, IgE, or IgD.

6. The binding protein according to claim 1, comprising two first polypeptide chains and two second polypeptide chains.

7. A pharmaceutical composition comprising the binding protein according to claim 1 and a pharmaceutically acceptable carrier.

8. The pharmaceutical composition according to claim 7, further comprising at least one additional therapeutic agent.

9. A kit for assaying a test sample for the presence, amount, or concentration of IL13 and/or IL17 in the sample, said kit comprising:
    (a) instructions for assaying the test sample for IL13 and/or IL17; and
    (b) at least one binding protein according to claim 1.

10. A binding protein conjugate comprising the binding protein according to claim 1 and an immunoadhesion molecule, an imaging agent, a therapeutic agent, or a cytotoxic agent.

11. The binding protein conjugate according to claim 10, wherein the imaging agent is a radiolabel, an enzyme, a fluorescent label, a luminescent label, a bioluminescent label, a magnetic label, or biotin.

12. The binding protein conjugate according to claim 11, wherein said radiolabel is $^{3}$H, $^{14}$C, $^{35}$S, $^{90}$Y, $^{99}$Tc, $^{111}$In, $^{125}$I, $^{131}$I, $^{177}$Lu, $^{166}$Ho, or $^{153}$Sm.

13. The binding protein conjugate according to claim 10, wherein said therapeutic or cytotoxic agent is an anti-metabolite, an alkylating agent, an antibiotic, a growth factor, a cytokine, an anti-angiogenic agent, an anti-mitotic agent, an anthracycline, toxin, or an apoptotic agent.

14. The binding protein according to claim 1, wherein the binding protein is a crystallized binding protein.

15. A binding protein comprising first and second polypeptide chains, each independently comprising VD1-(X1)n-VD2-C-(X2)n, wherein
   VD1 is a first antibody variable domain;
   VD2 is a second antibody variable domain;
   C is an antibody constant domain;
   X1 is a linker;
   X2 is an antibody Fc region; and
   n is 0 or 1;
wherein the VD1 domains on the first and second polypeptide chains form a first functional target binding site and the VD2 domains on the first and second polypeptide chains form a second functional target binding site, and wherein the binding protein binds IL-13 and IL-17, wherein
   (a) the variable domains that form a functional target binding site for IL-13 comprise the amino acid sequences of SEQ ID NO: 32 and SEQ ID NO:33, and
   (b) the variable domains that form a functional target binding site for IL-17 comprise an amino acid sequence selected from the group consisting of SEQ ID NOs: 36, 37, 38, 39, 40, 41, 42, 43, 44, 45, 46, 47, 48, 49, 50, 51, 52, 53, and 54.

16. An IL-13 and IL-17 binding protein, wherein the binding protein comprises the amino acid sequences of any one of:
   (a) DVD2166H (comprising SEQ ID NOs: 32 and 36) and DVD2166L (comprising SEQ ID NOs: 33 and 37);
   (b) DVD2167H (comprising SEQ ID NOs: 36 and 32) and DVD2167L (comprising SEQ ID NOs: 37 and 33);
   (c) DVD2168H (comprising SEQ ID NOs: 32 and 36) and DVD2168L (comprising SEQ ID NOs: 33 and 37);
   (d) DVD2169H (comprising SEQ ID NOs: 36 and 32) and DVD2169L (comprising SEQ ID NOs: 37 and 33);
   (e) DVD2170H (comprising SEQ ID NOs: 32 and 36) and DVD2170L (comprising SEQ ID NOs: 33 and 37);
   (f) DVD2171H (comprising SEQ ID NOs: 36 and 32) and DVD2171L (comprising SEQ ID NOs: 37 and 33);
   (g) DVD2172H (comprising SEQ ID NOs: 32 and 38) and DVD2172L (comprising SEQ ID NOs: 33 and 39);
   (h) DVD2173H (comprising SEQ ID NOs: 38 and 32) and DVD2173L (comprising SEQ ID NOs: 39 and 33);
   (i) DVD2174H (comprising SEQ ID NOs: 32 and 38) and DVD2174L (comprising SEQ ID NOs: 33 and 39);
   (j) DVD2175H (comprising SEQ ID NOs: 38 and 32) and DVD2175L (comprising SEQ ID NOs: 39 and 33);
   (k) DVD2176H (comprising SEQ ID NOs: 32 and 38) and DVD2176L (comprising SEQ ID NOs: 33 and 39);
   (l) DVD2177H (comprising SEQ ID NOs: 38 and 32) and DVD2177L (comprising SEQ ID NOs: 39 and 33);
   (m) DVD2178H (comprising SEQ ID NOs: 32 and 40) and DVD2178L (comprising SEQ ID NOs: 33 and 41);
   (n) DVD2179H (comprising SEQ ID NOs: 40 and 32) and DVD2179L (comprising SEQ ID NOs: 41 and 33);
   (o) DVD2180H (comprising SEQ ID NOs: 32 and 40) and DVD2180L (comprising SEQ ID NOs: 33 and 41);
   (p) DVD2181H (comprising SEQ ID NOs: 40 and 32) and DVD2181L (comprising SEQ ID NOs: 41 and 33);
   (q) DVD2182H (comprising SEQ ID NOs: 32 and 40) and DVD2182L (comprising SEQ ID NOs: 33 and 41); and
   (r) DVD2183H (comprising SEQ ID NOs: 40 and 32) and DVD2183L (comprising SEQ ID NOs: 41 and 33).

* * * * *